US012280104B2

(12) United States Patent
Brown et al.

(10) Patent No.: US 12,280,104 B2
(45) Date of Patent: Apr. 22, 2025

(54) COMPOSITION AND METHODS FOR MRNA VACCINES AGAINST NOVEL OMICRON CORONAVIRUS INFECTIONS

(71) Applicant: RNAimmune, Inc., Gaithersburg, MD (US)

(72) Inventors: David Brown, Gaithersburg, MD (US); Yong-Sik Bong, Frederick, MD (US); Neeti Ananthaswamy, Potomac, MD (US); Naihsuan C. Guy, Gaithersburg, MD (US); Dong Shen, Baltimore, MD (US)

(73) Assignee: RNAIMMUNE, INC., Gaithersburg, MD (US)

( * ) Notice: Subject to any disclaimer, the term of this patent is extended or adjusted under 35 U.S.C. 154(b) by 0 days.

(21) Appl. No.: 18/385,879

(22) Filed: Oct. 31, 2023

(65) Prior Publication Data

US 2024/0156947 A1 May 16, 2024

Related U.S. Application Data

(60) Provisional application No. 63/381,901, filed on Nov. 1, 2022.

(51) Int. Cl.

| | |
|---|---|
| ***A61K 39/215*** | (2006.01) |
| ***A61K 9/51*** | (2006.01) |
| ***A61K 45/06*** | (2006.01) |
| ***A61P 31/14*** | (2006.01) |
| ***C07K 14/005*** | (2006.01) |
| *A61K 39/00* | (2006.01) |

(52) U.S. Cl.

CPC .......... *A61K 39/215* (2013.01); *A61K 9/5123* (2013.01); *A61K 45/06* (2013.01); *A61P 31/14* (2018.01); *C07K 14/005* (2013.01); *A61K 2039/6018* (2013.01); *A61K 2039/6031* (2013.01)

(58) Field of Classification Search

None

See application file for complete search history.

(56) References Cited

U.S. PATENT DOCUMENTS

| | | | |
|---|---|---|---|
| 10,973,909 | B1 | 4/2021 | Csiszovszki et al. |
| 2017/0340725 | A1 | 11/2017 | Ciaramella et al. |
| 2019/0240317 | A1 | 8/2019 | Ciaramella et al. |
| 2019/0351048 | A1 | 11/2019 | Rauch |
| 2021/0316002 | A1 | 10/2021 | Ellis |
| 2021/0388032 | A1 | 12/2021 | Langedijk et al. |
| 2022/0040292 | A1 | 2/2022 | Tang et al. |
| 2022/0064631 | A1* | 3/2022 | Barna ................ C12N 15/1093 |
| 2023/0108926 | A1 | 4/2023 | Tang et al. |
| 2023/0117167 | A1 | 4/2023 | Mueller et al. |

FOREIGN PATENT DOCUMENTS

| | | | | |
|---|---|---|---|---|
| CN | 115160413 | A | * 10/2022 | ............. A61K 39/12 |
| JP | 2004-536598 | A | 12/2004 | |
| JP | 2009-509516 | A | 3/2009 | |
| JP | 2015-513897 | A | 5/2015 | |
| WO | WO-2017/049245 | A2 | 3/2017 | |
| WO | WO-2019/226940 | A1 | 11/2019 | |
| WO | WO-2021/159118 | A2 | 8/2021 | |
| WO | WO-2021/247779 | A1 | 12/2021 | |
| WO | WO-2022/072910 | A1 | 4/2022 | |
| WO | WO-2023/018831 | A2 | 2/2023 | |
| WO | WO-2023/079507 | A1 | 5/2023 | |
| WO | WO-2023/091766 | A2 | 5/2023 | |
| WO | WO-2024/094881 | A1 | 5/2024 | |

OTHER PUBLICATIONS

English translation of CN115160413A, description section only, Espacenet on Mar. 5, 2024, 12 pages (Year: 2024).*
Nicholson and Pasquinelli, Trends in Cell Biology, Mar. 2019, 29(3):191-200 (Year: 2019).*
Shi et al., Transl. Res., Oct. 2022, 248:11-21 (Year: 2022).*
CDC COVID-19 Treatment Guidelines, Dec. 2023, pp. 18-21, available from https://files.covid19treatmentguidelines.nih.gov/guidelines/section/section_53.pdf (Year: 2023).*
Kon et al., Curr. Opin. Biotechnol., Feb. 2022, 73:329-336 (Year: 2022).*
PCT/US2023/036540, Oct. 31, 2023, Rnaimmune, Inc.
Chan et al., "A familial cluster of pneumonia associated with the 2019 novel coronavirus indicating person-to-person transmission: a study of a family cluster", Lancet, 2020, vol. 395, pp. 514-523, Epub Jan. 24, 2020.
Genbank, Accession: QHD43416.1, Surface Glycoprotein [Wuhan searfood market pneumonia virus], Jan. 23, 2020, www.ncbi.nlm.nih.gov/protein/1791269090?sat=48&satkey=1085346.
Genbank_CP006842, Corynebacterium glyciniphilum AJ3170, complete genome GenBank Accession No. CP006842, Apr. 8, 2015, www.ncbi.nlm.nih.gov/nuccore/CP006842.
Huang et al, "Clinical features of patients infected with 2019 novel coronavirus in Wuhan, China", Lancet, Feb. 15, 2020, vol. 395, pp. 497-506.
Liu et al., "Potential inhibitors against 2019-nCoV coronavirus M protease from clinically approved medicines", J. Genet Genomics, Feb. 20, 2020, vol. 47(2), pp. 119-121.

(Continued)

*Primary Examiner* — Stacy B Chen

(74) *Attorney, Agent, or Firm* — Foley & Lardner LLP

(57) ABSTRACT

Provided herein is a ribonucleic acid (RNA) encoding a spike (S) protein or an immunogenic fragment thereof of a severe acute respiratory syndrome coronavirus 2 (SARS-CoV-2) comprising at least one non-naturally occurring amino acid mutation. In some embodiments, the S protein is derived from an Omicron variant. Additionally provided are relevant polynucleotides, vectors, cells, compositions, kits, production methods and methods of use.

30 Claims, 12 Drawing Sheets

Specification includes a Sequence Listing.

(56) References Cited

OTHER PUBLICATIONS

Ljungberg et al., "Self-Replicating Alphavirus RNA Vaccines," Expert Rev Vaccines, 14(2):177-94 (Feb. 2015).

Lu et al., "Genomic characterisation and epidemiology of 2019 novel coronavirus: implications for virus origins and receptor binding", Lancet, 2020, vol. 395, pp. 565-574, epub 2020.

Menachery et al., "A SARS-like cluster of circulating bat coronaviruses shows potential for human emergence", Nat Med. 2015, vol. 21(12), pp. 1508-1513.

Midoux et al., "Lipid-based mRNA Vaccine Delivery Systems," Expert Rev. Vaccines 14(2):221-234 (2015).

NCBI_NC_045512.2, Wuhan seafood market pneumonia virus isolate Wuhan-Hu-1, complete genome, NCBI accession No. NC_045512.2, Jan. 28, 2020, www.ncbi.nlm.nih.gov/nuccore/1798174254?sat=4&satkey=350670880.

Non-Final Office Action on U.S. Appl. No. 17/170,876 DTD Oct. 17, 2023.

Notice of Allowance on U.S. Appl. No. 17/170,876 DTD Feb. 7, 2024.

SEQ ID# 1, U.S. Appl. No. 17/794,862, prior art year of search 2023, https://dav.uspto.gov/webapp/applicationViewer.html?casenumber=17170876, 3 pages.

Zhou et al., "A pneumonia outbreak associated with a new coronavirus of probably bat origin", Nature, 2020, vol. 579, pp. 270-273, Epub Feb. 3, 2020.

International Search Report and Written Opinion on PCT/US2023/036540 DTD Feb. 27, 2024, 16 pages.

Lancet, Jan. 2020, and vol. 395 and pp. 565-574, <Https://Doi.Org/10.1016/S0140-6736 (20) 30251-8> (Document Showing a Well-known Technique). 10 pgs.

Zhang YZ et al. and Wuhan seafood market pneumoniavirus isolate Wuhan-Hu-1, complete genome and Database DDBJ/EMBL/GenBank[online], Jan. 14, 2020, AccessionNo.MN908947, and <https://www.ncbi.nlm.nih.gov/nuccore/1796487982?sat=47&satkey=151862760> [Date of search 2025.01.28] (Document showing a well-known technique). 10 pgs.

* cited by examiner

Antibody: SARS-CoV-2 Spike Protein (RBD) Monoclonal Antibody (HL257) (MA5-36253)

Antibody: SARS-CoV-2 Spike Antibody, Omicron Reactive, Mouse MAb (40592-MM117-100)

| Mouse ID | IgG concentration (ug/ml) |
|---|---|
| 5272 | 109.35 |
| 5273 | 169.30 |
| 5274 | 182.81 |
| 5275 | 516.09 |
| 5276 | 137.86 |

| | 614D | Delta | Omicron | BA2 |
|---|---|---|---|---|
| Bottom | 2.746 | 0.5178 | -15.76 | -31.27 |
| Top | 102.4 | 101.9 | 102.2 | 102.6 |
| LogIC50 | -0.8185 | -0.4760 | -0.06900 | 0.3339 |
| IC50 | 0.1519 | 0.3342 | 0.8531 | 2.157 |
| Span | 99.64 | 101.4 | 117.9 | 133.9 |

| | 614D | Delta | BA.1 | BA.2 |
|---|---|---|---|---|
| IC50 (ug/ml) | 0.338 | 0.746 | 1.903 | 4.812 |

SEQUENCE LISTING

Sequence total quantity: 59
SEQ ID NO: 1 moltype = AA length = 1273
FEATURE Location/Qualifiers
source 1..1273
mol_type = protein
organism = Severe acute respiratory syndrome coronavirus 2
SEQUENCE: 1
MFVFLVLLPL VSSQCVNLTT RTQLPPAYTN SFTRGVYYPD KVFRSSVLHS TQDLFLPFFS 60
NVTWFHAIHV SGTNGTKRFD NPVLPFNDGV YFASTEKSNI IRGWIFGTTL DSKTQSLLIV 120
NNATNVVIKV CEFQFCNDPF LGVYYHKNNK SWMESEFRVY SSANNCTFEY VSQPFLMDLE 180
GKQGNFKNLR EFVFKNIDGY FKIYSKHTPI NLVRDLPQGF SALEPLVDLP IGINITRFQT 240
LLALHRSYLT PGDSSSGWTA GAAAYYVGYL QPRTFLLKYN ENGTITDAVD CALDPLSETK 300
CTLKSFTVEK GIYQTSNFRV QPTESIVRFP NITNLCPFGE VFNATRFASV YAWNRKRISN 360
CVADYSVLYN SASFSTFKCY GVSPTKLNDL CFTNVYADSF VIRGDEVRQI APGQTGKIAD 420
YNYKLPDDFT GCVIAWNSNN LDSKVGGNYN YLYRLFRKSN LKPFERDIST EIYQAGSTPC 480
NGVEGFNCYF PLQSYGFQPT NGVGYQPYRV VVLSFELLHA PATVCGPKKS TNLVKNKCVN 540
FNFNGLTGTG VLTESNKKFL PFQQFGRDIA DTTDAVRDPQ TLEILDITPC SFGGVSVITP 600
GTNTSNQVAV LYQDVNCTEV PVAIHADQLT PTWRVYSTGS NVFQTRAGCL IGAEHVNNSY 660
ECDIPIGAGI CASYQTQTNS PRRARSVASQ SIIAYTMSLG AENSVAYSNN SIAIPTNFTI 720
SVTTEILPVS MTKTSVDCTM YICGDSTECS NLLLQYGSFC TQLNRALTGI AVEQDKNTQE 780
VFAQVKQIYK TPPIKDFGGF NFSQILPDPS KPSKRSFIED LLFNKVTLAD AGFIKQYGDC 840
LGDIAARDLI CAQKFNGLTV LPPLLTDEMI AQYTSALLAG TITSGWTFGA GAALQIPFAM 900
QMAYRFNGIG VTQNVLYENQ KLIANQFNSA IGKIQDSLSS TASALGKLQD VVNQNAQALN 960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT 1273

SEQ ID NO: 2 moltype = AA length = 1273
FEATURE Location/Qualifiers
source 1..1273
mol_type = protein
organism = synthetic construct
SEQUENCE: 2
MFVFLVLLPL VSSQCVNLTT RTQLPPAYTN SFTRGVYYPD KVFRSSVLHS TQDLFLPFFS 60
NVTWFHAIHV SGTNGTKRFD NPVLPFNDGV YFASTEKSNI IRGWIFGTTL DSKTQSLLIV 120
NNATNVVIKV CEFQFCNDPF LGVYYHKNNK SWMESEFRVY SSANNCTFEY VSQPFLMDLE 180
GKQGNFKNLR EFVFKNIDGY FKIYSKHTPI NLVRDLPQGF SALEPLVDLP IGINITRFQT 240
LLALHRSYLT PGDSSSGWTA GAAAYYVGYL QPRTFLLKYN ENGTITDAVD CALDPLSETK 300
CTLKSFTVEK GIYQTSNFRV QPTESIVRFP NITNLCPFGE VFNATRFASV YAWNRKRISN 360
CVADYSVLYN SASFSTFKCY GVSPTKLNDL CFTNVYADSF VIRGDEVRQI APGQTGKIAD 420
YNYKLPDDFT GCVIAWNSNN LDSKVGGNYN YLYRLFRKSN LKPFERDIST EIYQAGSTPC 480
NGVEGFNCYF PLQSYGFQPT NGVGYQPYRV VVLSFELLHA PATVCGPKKS TNLVKNKCVN 540
FNFNGLTGTG VLTESNKKFL PFQQFGRDIA DTTDAVRDPQ TLEILDITPC SFGGVSVITP 600
GTNTSNQVAV LYQGVNCTEV PVAIHADQLT PTWRVYSTGS NVFQTRAGCL IGAEHVNNSY 660
ECDIPIGAGI CASYQTQTNS PSRAGSVASQ SIIAYTMSLG AENSVAYSNN SIAIPTNFTI 720
SVTTEILPVS MTKTSVDCTM YICGDSTECS NLLLQYGSFC TQLNRALTGI AVEQDKNTQE 780
VFAQVKQIYK TPPIKDFGGF NFSQILPDPS KPSKRSPIED LLFNKVTLAD AGFIKQYGDC 840
LGDIAARDLI CAQKFNGLTV LPPLLTDEMI AQYTSALLAG TITSGWTFGA GPALQIPFPM 900
QMAYRFNGIG VTQNVLYENQ KLIANQFNSA IGKIQDSLSS TPSALGKLQD VVNQNAQALN 960
TLVKQLSSNF GAISSVLNDI LSRLDPPEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT 1273

SEQ ID NO: 3 moltype = DNA length = 3822
FEATURE Location/Qualifiers
source 1..3822
mol_type = other DNA
organism = synthetic construct
SEQUENCE: 3
atgtttgttt ttcttgtttt attgccacta gtctctagtc agtgtgttaa tcttacaacc 60
agaactcaat tacccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780

-continued

```
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg gtgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
ccttcgcggg caggtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280
acacaattaa accgtgcttt aactggaata gctgttgaac aagacaaaaa cacccaagaa 2340
gtttttgcac aagtcaaaca aatttacaaa acaccaccaa ttaaagattt tggtggtttt 2400
aatttttcac aaatattacc agatccatca aaaccaagca agaggtcacc tattgaagat 2460
ctacttttca acaaagtgac acttgcagat gctggcttca tcaaacaata tggtgattgc 2520
cttggtgata ttgctgctag agacctcatt tgtgcacaaa agtttaacgg ccttactgtt 2580
ttgccacctt tgctcacaga tgaaatgatt gctcaataca cttctgcact gttagcgggt 2640
acaatcactt ctggttggac ctttggtgca ggtcctgcat tacaaatacc atttcctatg 2700
caaatggctt ataggtttaa tggtattgga gttacacaga atgttctcta tgagaaccaa 2760
aaattgattg ccaaccaatt taatagtgct attggcaaaa ttcaagactc actttcttcc 2820
acaccaagtg cacttggaaa acttcaagat gtggtcaacc aaaatgcaca agctttaaac 2880
acgcttgtta aacaacttag ctccaatttt ggtgcaattt caagtgtttt aaatgatatc 2940
ctttcacgtc ttgacccacc tgaggctgaa gtgcaaattg ataggttgat cacaggcaga 3000
cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120
gatttttgtg gaaagggcta tcatcttatg tccttccctc agtcagcacc tcatggtgta 3180
gtcttcttgc atgtgactta tgtccctgca caagaaaaga acttcacaac tgctcctgcc 3240
atttgtcatg atggaaaagc acactttcct cgtgaaggtg tctttgtttc aaatggcaca 3300
cactggtttg taacacaaag gaatttttat gaaccacaaa tcattactac agacaacaca 3360
tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcaaatta cattacacat aa 3822
```

```
SEQ ID NO: 4           moltype = RNA  length = 3822
FEATURE                Location/Qualifiers
source                 1..3822
                       mol_type = other RNA
                       organism = synthetic construct
SEQUENCE: 4
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
```

```
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg gtgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
ccttcgcggg caggtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcacc tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtcctgcat tacaaatacc atttcctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acaccaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacccacc tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gattttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                     3822
```

```
SEQ ID NO: 5            moltype = AA  length = 1268
FEATURE                 Location/Qualifiers
source                  1..1268
                        mol_type = protein
                        organism = synthetic construct
SEQUENCE: 5
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVSQIAPGQT GNIADYNYKL  420
PDDFTGCVIA WNSNNLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNSSYECDIP  660
IGAGICASYQ TQTKSHSRAG SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SPIEDLLFNK VTLADAGFIK QYGDCLGDIA  840
ARDLICAQKF NGLTVLPPLL TDEMIAQYTS ALLAGTITSG WTFGAGPALQ IPFPMQMAYR  900
FNGIGVTQNV LYENQKLIAN QFNSAIGKIQ DSLSSTPSAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                         1268
```

```
SEQ ID NO: 6            moltype = DNA  length = 3809
FEATURE                 Location/Qualifiers
source                  1..3809
                        mol_type = other DNA
                        organism = synthetic construct
SEQUENCE: 6
```

-continued

```
atgttcgtat tcctagtact actaccccta gtaagcagcc agtgcgtaaa cctaatcacc  60
cggacccaga gctacaccaa cagcttcacc cggggcgtat actaccccga caaggtattc  120
cggagcagcg tactacacag cacccaggac ctattcctac ccttcttcag caacgtaacc  180
tggttccacg ccatcagcgg caccaacggc accaagcggt tcgacaaccc cgtactaccc  240
ttcaacgacg gcgtatactt cgccagcacc gagaagagca acatcatccg gggctggatc  300
ttcggcacca ccctagacag caagacccag agcctactaa tcgtaaacaa cgccaccaac  360
gtagtaatca aggtatgcga gttccagttc tgcaacgacc ccttcctaga cgtatactac  420
cacaagaaca acaagagctg gatggagagc gagttccggg tatacagcag cgccaacaac  480
tgcaccttcg agtacgtaag ccagcccttc ctaatggacc tagagggcaa gcagggcaac  540
ttcaagaacc tacgggagtt cgtattcaag aacatcgacg gctacttcaa gatctacagc  600
aagcacaccc ccatcaacct aggccgggac ctaccccagg gcttcagcgc cctagagccc  660
ctagtagacc tacccatcgg catcaacatc acccggttcc agaccctact agccctacac  720
cggagctacc taacccccgg cgacagcagc agcggctgga ccgccggcgc cgccgcctac  780
tacgtaggct acctacagcc ccggaccttc ctactaaagt acaacgagaa cggcaccatc  840
accgacgccg tagactgcgc cctagacccc ctaagcgaga ccaagtgcac cctaaagagc  900
ttcaccgtag agaagggcat ctaccagacc agcaacttcc gggtacagcc caccgagagc  960
atcgtacggt tccccaacat caccaaccta tgccccttcg acgaggtatt caacgccacc  1020
cggttcgcca gcgtatacgc ctggaaccgg aagcggatca gcaactgcgt agccgactac  1080
agcgtactat acaacttcgc ccccttcttc gccttcaagt gctacggcgt aagccccacc  1140
aagctaaacg acctatgctt caccaacgta tacgccgaca gcttcgtaat ccggggcaac  1200
gaggtaagcc agatcgcccc cggccagacc ggcaacatcg ccgactacaa ctacaagcta  1260
cccgacgact tcaccggctg cgtaatcgcc tggaacagca acaacctaga cagcaaggta  1320
ggcggcaact acaactaccg gtaccggcta ttccggaaga gcaacctaaa gcccttcgag  1380
cgggacatca gcaccgagat ctaccaggcc ggcaacaagc cctgcaacgg cgtagccggc  1440
gtaaactgct acttccccct acagagctac ggcttccggc ccacctacgg cgtaggccac  1500
cagccctacc gggtggtggt gctaagcttc gagctactac acgcccccgc caccgtgtgc  1560
ggccccaaga agagcaccaa cctagtgaag aacaagtgcg tgaacttcaa cttcaacggc  1620
ctaaccggca ccggcgtgct aaccgagagc aacaagaagt tcctaccctt ccagcagttc  1680
ggccgggaca tcgccgacac caccgacgcc gtgcgggacc cccagaccct agagatccta  1740
gacatcaccc cctgcagctt cggcggcgtg agcgtgatca cccccggcac caacaccagc  1800
aaccaggtgg ccgtgctata ccagggcgtg aactgcaccg aggtgcccgt ggccatccac  1860
gccgaccagc taacccccac ctggcgggtg tacagcaccg gcagcaacgt gttccagacc  1920
cgggccggct gcctaatcgg cgccgagtac gtgaacagca gctacgagtg cgacatcccc  1980
atcggcgccg gcatctgcgc cagctaccag acccagacca agagccacag ccgggccggc  2040
agcgtggcca gccagagcat catcgcctac accatgagcc taggcgccga gaacagcgtg  2100
gcctacagca acaacagcat cgccatcccc accaacttca ccatcagcgt gaccaccgag  2160
atcctacccg tgagcatgac caagaccagc gtggactgca ccatgtacat ctgcggcgac  2220
agcaccgagt gcagcaacct actactacag tacggcagct tctgcaccca gctaaagcgg  2280
gccctaaccg gcatcgccgt ggagcaggac aagaacaccc aggaggtgtt cgcccaggtg  2340
aagcagatct acaagacccc ccccatcaag tacttcggcg gcttcaactt cagccagatc  2400
ctacccgacc ccagcaagcc cagcaagcgg agccccatcg aggacctact attcaacaag  2460
gtgaccctag ccgacgccgg cttcatcaag cagtacggcg actgcctagg cgacatcgcc  2520
gcccgggacc taatctgcgc ccagaagttc aacggcctaa ccgtgctacc cccccctacta  2580
accgacgaga tgatcgccca gtacaccagc gccctactag ccggcaccat caccagcggc  2640
tggaccttcg gcgccggccc cgccctacag atccccttcc ccatgcagat ggcctaccgg  2700
ttcaacggca tcggcgtgac ccagaacgtg ctatacgaga accagaagct aatcgccaac  2760
cagttcaaca gcgccatcgg caagatccag gacagcctaa gcagcacccc cagcgcccta  2820
ggcaagctac aggacgtggt gaaccacaac gcccaggccc taaacaccct agtgaagcag  2880
ctaagcagca agttcggcgc catcagcagc gtgctaaacg acatcctaag ccggctagac  2940
cccccccgagg ccgaggtgca gatcgaccgg ctaatcaccg gccggctaca gagcctacag  3000
acctacgtga cccagcagct aatccgggcc gccgagatcc gggccagcgc caacctagcc  3060
gccaccaaga tgagcgagtg cgtgctaggc cagagcaagc gggtggactt ctgcggcaag  3120
ggctaccacc taatgagctt cccccagagc gccccccacg gcgtggtgtt cctacacgtg  3180
acctacgtgc ccgcccagga gaagaacttc accaccgccc ccgccatctg ccacgacggc  3240
aaggcccact tcccccggga gggcgtgttc gtgagcaacg gcacccactg gttcgtgacc  3300
cagcggaact tctacgagcc ccagatcatc accaccgaca acaccttcgt gagcggcaac  3360
tgcgacgtgg tgatcggcat cgtgaacaac accgtgtacg acccccctaca gcccgagcta  3420
gacagcttca aggaggagct agacaagtac ttcaagaacc acaccagccc cgacgtggac  3480
ctaggcgaca tcagcggcat caacgccagc gtggtgaaca tccagaagga gatcgaccgg  3540
ctaaacgagg tggccaagaa cctaaacgag agcctaatcg acctacagga gctaggcaag  3600
tacgagcagt acatcaagtg gccctggtac atctggctag gcttcatcgc cggcctaatc  3660
gccatcgtga tggtgaccat catgctatgc tgcatgacca gctgctgcag ctgcctaaag  3720
ggctgctgca gctgcggcag ctgctgcaag ttcgacgagg acgacagcga gcccgtgcta  3780
aagggcgtga agctacacta cacctaaaa                                   3809

SEQ ID NO: 7            moltype = DNA  length = 3809
FEATURE                 Location/Qualifiers
source                  1..3809
                        mol_type = other DNA
                        organism = synthetic construct
SEQUENCE: 7
atgttcgtgt tcctggtgct gctgcctctc gtgtctagcc agtgcgtcaa cctgatcacc  60
cggacccagt cttataccaa cagcttcaca aggggcgtct actatcctga caaggtattc  120
agaagctccg tgctgcatag cacccaagac ctgttcctgc ctttcttctc taacgtgacg  180
tggttccacg ccatcagtgg aaccaatggc accaaaagat ttgataatcc cgtgctgcct  240
tttaatgacg gcgtctactt cgcctctaca gagaagtcta acattatccg ggctggatc  300
ttcggcacca ccctggacag caaaacccag agcctgctga tcgtgaacaa cgcaaccaac  360
gtggttatca aagtgtgtga gttccagttc tgtaatgatc cttttctgga cgtgtattac  420
cacaagaata ataagagctg gatggaatct gagttcagag tgtacagtag cgccaataac  480
```

-continued

```
tgcaccttcg agtacgtctc tcagcctttt ctgatggacc tggaaggcaa gcagggcaac  540
ttcaagaacc tgagagaatt cgtgttcaaa aacatcgacg gctacttcaa gatctactcc  600
aagcacaccc caatcaacct gggcagagat ctgcctcaag gcttcagcgc cctggaaccc  660
ctagtggact taccaatcgg catcaacatc accagattcc agaccctgct agctctgcat  720
agatcttatc tgacaccagg cgacagcagc agcggctgga ccgccggcgc tgctgcttac  780
tacgtgggct acctgcagcc tagaaccttc ctgctgaagt acaacgaaaa cggcaccatc  840
accgacgccg tggactgtgc cctggaccct ctgagcgaaa ccaaatgcac actgaagtcc  900
ttcaccgtgg aaaagggcat ctaccagaca agcaacttca gggtgcagcc tacagagtct  960
atcgtgcggt ttccaaacat cacaaacctc tgtcctttcg acgaggtgtt caacgccaca  1020
agattcgcca gcgtgtacgc ctggaatcgg aagcggatca gcaactgcgt ggccgactac  1080
agcgtgctgt acaacttcgc ccctttttc gcttttaagt gctacggcgt gagccctacc  1140
aagctgaacg acctgtgctt cacaaacgtg tacgccgaca gcttcgtgat cagaggcaat  1200
gaggtatccc agatcgcccc tggccagaca ggcaacatag ccgattacaa ctacaagctg  1260
cctgatgact tcacaggctg cgtgatcgcc tggaactcta acaacctcga tagcaaggtg  1320
ggcggaaact acaactacag gtaccggctg ttccggaagt ctaacctgaa gccttttgag  1380
agagacatct ctacagaaat ctaccaggcc gggaacaaac cctgcaacgg agtggccggg  1440
gtgaattgct acttccctct gcaaagctac ggcttccggc ccacatacgg cgtcggccac  1500
cagccctaca gagtggtcgt gctctctttt gagctgctgc acgcccctgc taccgtgtgt  1560
ggccccaaga agtctaccaa cctggttaag aacaagtgtg tgaacttcaa cttcaacggg  1620
ctgaccggca ccggagtgct gaccgaaagc aataagaagt tcctgccctt tcagcaattt  1680
ggcagagata ttgctgacac cacagacgcc gtgcgcgacc cccagactct ggaaatcctg  1740
gatatcaccc catgtagctt cggcggcgtt agcgtgatca cccccggaac caatacctcc  1800
aatcaggtgg ccgtgctcta ccagggcgtg aactgtaccg aggtgcctgt ggccatccac  1860
gcagatcagc tgactcctac atggcgggtg tactccaccg gctccaatgt gttccagaca  1920
cgggctggct gcctgatcgg cgccgagtac gtgaatagca gctatgagtg cgacattcct  1980
attggagccg gcatctgcgc ctcttatcaa acacagacaa agagccacag cagagccggc  2040
agcgtggcca gccagagcat catcgcctac accatgagcc tgggtgccga gaacagcgtg  2100
gcatacagca acaacagcat cgccatcccc acaaacttca cgatcagtgt gaccaccgag  2160
atcctgcctg tgtccatgac aaagacatcc gtggattgca ccatgtacat ctgcggcgat  2220
tctacagaat gctcaaatct gctgctgcaa tatggcagct tctgcaccca actgaaaaga  2280
gccctgacag gaatcgctgt cgagcaggat aagaacaccc aggaggtgtt tgcccaggtg  2340
aaacagatct ataagacccc tccaatcaag tactttggcg gattcaactt cagccagatt  2400
ctccccgatc caagcaagcc cagcaagaga agccctatcg aggatctgct gttcaacaag  2460
gtgacgctgg ccgacgccgg cttcatcaag cagtacggag actgcctggg cgacatcgcc  2520
gccagagatc tgatctgtgc ccagaagttc aacgggctta ctgtgctgcc acctctgctg  2580
acggatgaaa tgatcgctca gtacacaagc gctctgctgg ccggcacaat cacctctggc  2640
tggactttcg gagccggccc cgctctgcag atcccttttcc ctatgcagat ggcctacaga  2700
ttcaacggca tcggagtgac ccagaacgtg ctgtacgaga accagaagct gatagctaac  2760
cagtttaata gcgccatcgg caaaatccag gacagcctga gcagcacccc tagcgctctg  2820
ggaaagctgc aggacgtggt gaaccacaat gcccaggccc tgaacaccct ggtgaagcag  2880
ctctcctcta aatttggcgc catttcctcc gtgctgaatg atatcctgag cagactggac  2940
cctcccgagg ccgaagtgca aatcgacagg ctgatcaccg gcagactaca gagcctgcaa  3000
acctacgtta cccagcagct gatcagagcc gccgagatca gagccagcgc caacctcgcc  3060
gccaccaaaa tgagcgaatg tgttctgggg cagtccaaga gagtggattt ctgcggcaag  3120
ggataccacc tgatgtcttt cccccagagc gctcctcatg gcgtcgtatt cctgcacgtg  3180
acctacgtgc ccgcccagga gaaaaacttc accactgccc ctgccatctg ccacgacggc  3240
aaggcccact tccctcggga aggcgttttc gtgtcaaacg gcacccactg gttcgtgacc  3300
cagagaaact tctacgaacc tcagattatc acaaccgaca acaccttcgt gtccggcaac  3360
tgtgacgtcg tgatcggaat cgtgaacaat accgtgtacg accccctgca gcctgagctg  3420
gacagcttca aggaggaact ggacaagtac ttcaagaatc acacatctcc tgacgtggac  3480
ctaggcgaca tctcaggcat caacgcttcg gttgtgaaca tccagaaaga gatcgaccgg  3540
ctgaacgagg tggccaagaa cctgaacgag agcctgatcg acctgcagga gctgggaaaa  3600
tacgagcagt acatcaagtg gccttggtac atctggctgg gctttatcgc cggcctgatc  3660
gccatcgtga tggtgaccat catgctgtgc tgcatgacca gctgctgtag ctgtctgaag  3720
ggctgttgca gctgcggctc ttgctgcaag ttcgacgagg acgactccga gcctgtgctg  3780
aaaggcgtga agctgcacta cacataaaa                                    3809
```

```
SEQ ID NO: 8            moltype = AA  length = 1268
FEATURE                 Location/Qualifiers
source                  1..1268
                        mol_type = protein
                        organism = synthetic construct
SEQUENCE: 8
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVSQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRSAG SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SPIEDLLFNK VTLADAGFIK QYGDCLGDIA  840
ARDLICAQKF NGLTVLPPLL TDEMIAQYTS ALLAGTITSG WTFGAGPALQ IPFPMQMAYR  900
FNGIGVTQNV LYENQKLIAN QFNSAIGKIQ DSLSSTPSAL GKLQDVVNHN AQALNTLVKQ  960
```

-continued

```
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                           1268

SEQ ID NO: 9            moltype = DNA  length = 3809
FEATURE                 Location/Qualifiers
source                  1..3809
                        mol_type = other DNA
                        organism = synthetic construct
SEQUENCE: 9
atgttcgtat tcctagtact actaccccta gtaagcagcc agtgcgtaaa cctaatcacc  60
cggacccaga gctacaccaa cagcttcacc cggggcgtat actaccccga caaggtattc  120
cggagcagcg tactacacag cacccaggac ctattcctac ccttcttcag caacgtaacc  180
tggttccacg ccatcagcgg caccaacggc accaagcggt tcgacaaccc cgtactaccc  240
ttcaacgacg gcgtatactt cgccagcacc gagaagagca acatcatccg gggctggatc  300
ttcggcacca ccctagacag caagacccag agcctactaa tcgtaaacaa cgccaccaac  360
gtagtaatca aggtatgcga gttccagttc tgcaacgacc ccttcctaga cgtatactac  420
cacaagaaca acaagagctg gatggagagc gagttccggg tatacagcag cgccaacaac  480
tgcaccttcg agtacgtaag ccagcccttc ctaatggacc tagagggcaa gcagggcaac  540
ttcaagaacc tacgggagtt cgtattcaag aacatcgacg gctacttcaa gatctacagc  600
aagcacaccc ccatcaacct aggccgggac ctaccccagg gcttcagcgc cctagagccc  660
ctagtagacc tacccatcgg catcaacatc acccggttcc agaccctact agccctacac  720
cggagctacc taacccccgg cgacagcagc agcggctgga ccgccggcgc cgccgcctac  780
tacgtaggct acctacagcc ccggaccttc ctactaaagt acaacgagaa cggcaccatc  840
accgacgccg tagactgcgc cctagacccc ctaagcgaga ccaagtgcac cctaaagagc  900
ttcaccgtag agaagggcat ctaccagacc agcaacttcc gggtacagcc caccgagagc  960
atcgtacggt tccccaacat caccaaccta tgccccttcg acgaggtatt caacgccacc  1020
cggttcgcca gcgtatacgc ctggaaccgg aagcggatca gcaactgcgt agccgactac  1080
agcgtactat acaacttcgc cccctttcttc gccttcaagt gctacggcgt aagccccacc  1140
aagctaaacg acctatgctt caccaacgta tacgccgaca gcttcgtaat ccggggcaac  1200
gaggtaagcc agatcgcccc cggccagacc ggcaacatcg ccgactacaa ctacaagcta  1260
cccgacgact tcaccggctg cgtaatcgcc tggaacagca acaagctaga cagcaaggta  1320
ggcggcaact acaactaccg gtaccggcta ttccggaaga gcaacctaaa gcccttcgag  1380
cgggacatca gcaccgagat ctaccaggcc ggcaacaagc cctgcaacgg cgtagccggc  1440
gtaaactgct acttcccccct acagagctac ggcttccggc ccacctacgg cgtgggccac  1500
cagccctacc gggtggtggt gctaagcttc gagctactac acgcccccgc caccgtgtgc  1560
ggccccaaga agagcaccaa cctagtgaag aacaagtgcg tgaacttcaa cttcaacggc  1620
ctaaccggca ccggcgtgct aaccgagagc aacaagaagt tcctaccctt ccagcagttc  1680
ggccgggaca tcgccgacac caccgacgcc gtgcgggacc cccagaccct agagatccta  1740
gacatcaccc cctgcagctt cggcggcgtg agcgtgatca cccccggcac caacaccagc  1800
aaccaggtgg ccgtgctata ccagggcgtg aactgcaccg aggtgcccgt ggccatccac  1860
gccgaccagc taacccccac ctggcgggtg tacagcaccg gcagcaacgt gttccagacc  1920
cgggccggct gcctaatcgg cgccgagtac gtgaacaaca gctacgagtg cgacatcccc  1980
atcggcgccg gcatctgcgc cagctaccag acccagacca agagccaccg gagcgccggc  2040
agcgtggcca gccagagcat catcgcctac accatgagcc taggcgccga gaacagcgtg  2100
gcctacagca acaacagcat cgccatcccc accaacttca ccatcagcgt gaccaccgag  2160
atcctacccg tgagcatgac caagaccagc gtggactgca ccatgtacat ctgcggcgac  2220
agcaccgagt gcagcaacct actactacag tacggcagct tctgcaccca gctaaagcgg  2280
gccctaaccg gcatcgccgt ggagcaggac aagaacaccc aggaggtgtt cgcccaggtg  2340
aagcagatct acaagacccc ccccatcaag tacttcggcg gcttcaactt cagccagatc  2400
ctacccgacc ccagcaagcc cagcaagcgg agcgccatcg aggacctact attcaacaag  2460
gtgaccctag ccgacgccgg cttcatcaag cagtacggcg actgcctagg cgacatcgcc  2520
gcccgggacc taatctgcgc ccagaagttc aacggcctaa ccgtgctacc cccctacta  2580
accgacgaga tgatcgccca gtacaccagc gccctactag ccggcaccat caccagcggc  2640
tggaccttcg gcgccggccc cgccctacag atccccttcc ccatgcagat ggcctaccgg  2700
ttcaacggca tcggcgtgac ccagaacgtg ctatacgaga accagaagct aatcgccaac  2760
cagttcaaca gcgccatcgg caagatccag gacagcctaa gcagcacccc cagcgcccta  2820
ggcaagctac aggacgtggt gaaccacaac gcccaggccc taaacaccct agtgaagcag  2880
ctaagcagca agttcggcgc catcagcagc gtgctaaacg acatcctaag ccggctagac  2940
ccccccgagg ccgaggtgca gatcgaccgg ctaatcaccg gccggctaca gagcctacag  3000
acctacgtga cccagcagct aatccgggcc gccgagatcc gggccagcgc caacctagcc  3060
gccaccaaga tgagcgagtg cgtgctaggc cagagcaagc gggtggactt ctgcggcaag  3120
ggctaccacc taatgagctt cccccagagc gccccccacg gcgtggtgtt cctacacgtg  3180
acctacgtgc ccgcccagga gaagaacttc accaccgccc ccgccatctg ccacgacggc  3240
aaggcccact tcccccggga gggcgtgttc gtgagcaacg gcacccactg gttcgtgacc  3300
cagcggaact tctacgagcc ccagatcatc accaccgaca acaccttcgt gagcggcaac  3360
tgcgacgtgg tgatcggcat cgtgaacaac accgtgtacg accccctaca gcccgagcta  3420
gacagcttca aggaggagct agacaagtac ttcaagaacc acaccagccc cgacgtggac  3480
ctaggcgaca tcagcggcat caacgccagc gtggtgaaca tccagaagga gatcgaccgg  3540
ctaaacgagg tggccaagaa cctaaacgag agcctaatcg acctacagga gctaggcaag  3600
tacgagcagt acatcaagtg gccctggtac atctggctag gcttcatcgc cggcctaatc  3660
gccatcgtga tggtgaccat catgctatgc tgcatgacca gctgctgcag ctgcctaaag  3720
ggctgctgca gctgcggcag ctgctgcaag ttcgacgagg acgacagcga gcccgtgcta  3780
aagggcgtga agctacacta cacctaaaa                                    3809

SEQ ID NO: 10           moltype = DNA  length = 3808
```

-continued

```
FEATURE                 Location/Qualifiers
source                  1..3808
                        mol_type = other DNA
                        organism = synthetic construct
SEQUENCE: 10
atgttcgtgt tcctggtgct gttaccccctg gtctctagcc aatgtgtgaa cctgatcacc  60
cggacccaga gctacaccaa cagcttcacc agaggcgtgt actaccctga caaggtgttc  120
agaagctcag tgctgcattc tacccaagac ctgttcctgc cttttttttag caatgtgaca  180
tggttccacg ccatcagtgg aacaaacggc accaagcggt ttgacaaccc cgtgctgcct  240
tttaacgacg gcgtgtactt cgccagcaca gaaaagtcta acattatccg ggctggatc  300
ttcggcacaa cactggatag caaaacgcag agcctgttaa tcgtgaacaa cgccacaaat  360
gtcgtgatca aggtgtgcga gtttcagttt tgtaacgacc ctttcctgga tgtgtactac  420
cacaagaaca acaagagctg gatggaatcc gaattcagag tgtactctag cgccaacaac  480
tgcaccttcg agtacgtaag ccagcccttt ctgatggacc ttgagggcaa acagggaaac  540
ttcaagaacc tgcgggaatt cgtgttcaag aacatcgacg gctacttcaa gatctatagc  600
aagcacaccc ctatcaacct gggaagagac ctgccccagg gcttctccgc cctggaacct  660
ctggtcgatc tgcccatcgg catcaatatc acaagatttc agaccctact ggccctgcat  720
agatcctacc tgaccccccgg cgatagctca tctggctgga ccgccggcgc cgctgcctac  780
tacgtcggat acctgcaacc tagaaccttt ctgctgaagt acaatgagaa cggcaccatt  840
accgatgccg tggattgcgc attggacccc ctgagcgaga caaagtgtac actgaagtct  900
ttcaccgtgg aaaaaggcat ctaccagacc agcaacttca gggtgcaacc aacagaatcc  960
atcgtgaggt tccctaacat aactaatctg tgtcctttcg acgaggtgtt caacgccaca  1020
agatttgctt ctgtttatgc ctggaaccgg aagagaatct cgaactgcgt ggctgactac  1080
tccgtgctgt ataacttcgc tcccttcttc gccttcaagt gctacggcgt ttctccgacc  1140
aaactgaatg acctctgctt cacaaacgta tacgcggaca gcttcgtgat caggggcaac  1200
gaggtgagtc agatcgctcc tggccagacc gggaacatcg ccgattacaa ttataagctg  1260
cctgacgact tcaccggctg tgtgatcgct tggaacagca ataagctgga ctctaaggtg  1320
ggcggcaact acaactaccg gtatcggctg ttcagaaaga gcaacctgaa gcccttcgag  1380
agagacatca gcaccgagat ctaccaggcc ggtaataagc cttgtaacgg cgtggctggc  1440
gtcaattgct actttcctct gcaaagctac ggcttccggc ctacctacgg cgtgggccac  1500
cagccttaca gagtggtggt gctgtctttc gagctgctcc acgcccctgc caccgtttgc  1560
ggccccaaga agtccaccaa cctggtcaag aacaagtgcg tgaacttcaa cttcaacgga  1620
ctgaccggca caggagtgct gaccgagagc aacaaaaagt tcctgccttt ccagcagttc  1680
ggcagagata tcgcagacac cactgacgcc gtgcgggacc cgcagacact ggaaatcctg  1740
gacatcaccc cctgcagctt cggcggagtt agcgttatca cacctggcac aaataccagc  1800
aaccaggtgg ccgtgctgta ccagggtgtg aattgcaccg aggtgcccgt ggctatccac  1860
gccgaccagc tgacccctac atggcgggtg tacagcaccg gtagcaatgt ctttcaaacc  1920
agagcgggat gtctgattgg agctgaatac gtgaacaatt cttatgaatg cgatatccct  1980
atcggcgccg gcatctgtgc ctcttaccag acccagacca agtctcacag aagcgccggc  2040
agcgtggcca gccagagcat catcgcctac accatgagcc ttggcgccga gaactccgtg  2100
gcctacagca acaacagcat cgccatccca acaaacttca ccatcagcgt caccaccgag  2160
atcctgccag tcagcatgac aaaaaccagc gtggactgca ccatgtacat ctgcggagat  2220
tccaccgaat gcagcaatct gctactccag tacggcagct tctgcacaca gctgaagaga  2280
gccctgaccg gcatcgccgt ggaacaggat aagaacacac aggaggtttt cgctcaggtg  2340
aagcaaatct ataagacacc ccccatcaag tacttcggag gcttcaactt ctctcagata  2400
ctgcctgacc ctagcaagcc ttccaaacgg tccgctatcg aggacctgct gttcaacaag  2460
gtgaccctgg ctgatgccgg gttcatcaag cagtacggcg actgcctggg cgacatcgcc  2520
gctagagact tgatttgtgc ccagaaattt aacggactga cagtgttgcc ccctctgctg  2580
acagatgaga tgatcgccca gtacaccagt gccctgctgg ccggcactat tacaagcggt  2640
tggacattcg gcgcgggccc tgccctgcag atcccttttc ctatgcagat ggcctataga  2700
ttcaatggca tcggcgtgac ccagaacgta ctgtacgaga accaaaagct gatcgccaat  2760
cagtttaaca gcgccatcgg caagatccag gatagcctga gctctacccc cagcgccctg  2820
gggaaactgc aggacgtggt gaaccacaac gcccaagccc tgaacactct ggtgaaacag  2880
ctgtcctcga agttcggcgc catcagctcc gtgctgaacg acatcctcag cagactggac  2940
cctcctgagg ccgaggtgca aatcgacaga ctgatcacag gccggctgca gagcctgcag  3000
acatacgtga cccagcagct gatcagagcc gccgagattc gggccagcgc taatctggcc  3060
gccacgaaga tgagtgaatg cgtgctgggc cagtctaaga gagtggattt ctgcggcaag  3120
ggctatcacc tgatgagctt tcctcagagc gcccctcacg gcgtggtctt tctgcacgtg  3180
acctacgtgc ccgctcagga gaagaacttt accacagccc ctgctatctg ccacgacggc  3240
aaggctcact tccctagaga aggcgtgttc gtgtccaacg gcacccactg gttcgtgacc  3300
cagagaaact tctacgagcc acagatcatc accacagaca acaccttcgt gtcgggcaac  3360
tgtgatgtgg tgatcggcat cgtcaacaac accgtctacg accctctgca gccagagctg  3420
gacagcttca aagaggaact ggacaaatac ttcaagaatc acaccagccc ggacgtggac  3480
ctgggcgaca tctccggcat taacgcctct gtggttaaca tccagaagga aatcgataga  3540
ctgaatgagg tggcaaagaa cctgaacgag agcctgatcg acctgcagga gctgggaaag  3600
tacgaacagt acatcaagtg gccttggtac atctggctgg gattcatcgc cggcctgatc  3660
gccatcgtga tggtgaccat catgctgtgc tgcatgacca gctgctgtag ttgcctgaag  3720
ggctgctgca gctgcggatc ttgctgtaag ttcgacgagg atgacagcga gcccgtgctc  3780
aaaggcgtca agctgcacta cacctaaa                                   3808

SEQ ID NO: 11           moltype = AA  length = 1271
FEATURE                 Location/Qualifiers
source                  1..1271
                        mol_type = protein
                        organism = synthetic construct
SEQUENCE: 11
MFVFLVLLPL VSSQCVNLRT RTQLPPAYTN SFTRGVYYPD KVFRSSVLHS TQDLFLPFFS  60
NVTWFHAIHF SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
```

-continued

```
QGNFKNLREF VFKNIDGYFK IYSKHTPINL VRDLPQGFSV LEPLVDLPIG INITRFQTLL  240
ALHRSYLTPG DSSSGLTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGNIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSPIEDLL FNKVTLADAG FIKQYGDCLG  840
DIAARDLICA QKFNGLTVLP PLLTDEMIAQ YTSALLAGTI TSGWTFGAGP ALQIPFPMQM  900
AYRFNGIGVT QNVLYENQKL IANQFNSAIG KIQDSLSSTP SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                      1271

SEQ ID NO: 12          moltype = DNA  length = 3815
FEATURE                Location/Qualifiers
source                 1..3815
                       mol_type = other DNA
                       organism = synthetic construct
SEQUENCE: 12
atgttcgtat tcctagtact actaccccta gtaagcagcc agtgcgtaaa cctaatcacc  60
cggacccaga gctacaccaa cagcttcacc cggggcgtat actaccccga caaggtattc  120
cggagcagcg tactacacag cacccaggac ctattcctac ccttcttcag caacgtaacc  180
tggttccacg ccatccacgt aagcggcacc aacggcacca agcggttcga caaccccgta  240
ctacccttca acgacggcgt atacttcgcc agcaccgaga agagcaacat catccggggc  300
tggatcttcg gcaccaccct agacagcaag acccagagcc tactaatcgt aaacaacgcc  360
accaacgtag taatcaaggt atgcgagttc cagttctgca acgacccctt cctagacgta  420
tactaccaca agaacaacaa gagctggatg gagagcgagt tccgggtata cagcagcgcc  480
aacaactgca ccttcgagta cgtaagccag cccttcctaa tggacctaga gggcaagcag  540
ggcaacttca agaacctacg ggagttcgta ttcaagaaca tcgacggcta cttcaagatc  600
tacagcaagc acacccccat caacctaggc cgggacctac cccagggctt cagcgcccta  660
gagcccctag tagacctacc catcggcatc aacatcaccc ggttccagac cctactagcc  720
ctacaccgga gctacctaac ccccggcgac agcagcagcg gctggaccgc cggcgccgcc  780
gcctactacg taggctacct acagccccgg accttcctac taaagtacaa cgagaacggc  840
accatcaccg acgccgtaga ctgcgcccta gacccccctaa gcgagaccaa gtgcacccta  900
aagagcttca ccgtagagaa gggcatctac cagaccagca acttccgggt acagcccacc  960
gagagcatcg tacggttccc caacatcacc aacctatgcc ccttcgacga ggtattcaac  1020
gccacccggt tcgccagcgt atacgcctgg aaccggaagc ggatcagcaa ctgcgtagcc  1080
gactacagcg tactatacaa cttcgccccc ttcttcgcct tcaagtgcta cggcgtaagc  1140
cccaccaagc taaacgacct atgcttcacc aacgtatacg ccgacagctt cgtaatccgg  1200
ggcaacgagg tacggcagat cgcccccggc cagaccggca acatcgccga ctacaactac  1260
aagctacccg acgacttcac cggctgcgta atcgcctgga acagcaacaa gctagacagc  1320
aaggtaggcg gcaactacaa ctaccagtac cggctattcc ggaagagcaa cctaaagccc  1380
ttcgagcggg acatcagcac cgagatctac caggccggca acaagccctg caacggcgta  1440
gccggcttca actgctactt ccccctacgg agctacggct tccggcccac ctacggcgtg  1500
ggccaccagc cctaccgggt ggtggtgcta agcttcgagc tactacacgc ccccgccacc  1560
gtgtgcggcc ccaagaagag caccaaccta gtgaagaaca agtgcgtgaa cttcaacttc  1620
aacggcctaa ccggcaccgg cgtgctaacc gagagcaaca agaagttcct acccttccag  1680
cagttcggcc gggacatcgc cgacaccacc gacgccgtgc gggaccccca gaccctagag  1740
atcctagaca tcacccccctg cagcttcggc ggcgtgagcg tgatcacccc cggcaccaac  1800
accagcaacc aggtggccgt gctataccag ggcgtgaact gcaccgaggt gcccgtggcc  1860
atccacgccg accagctaac ccccacctgg cgggtgtaca gcaccggcag caacgtgttc  1920
cagacccggg ccggctgcct aatcggcgcc gagtacgtga acaacagcta cgagtgcgac  1980
atccccatcg gcgccggcat ctgcgccagc taccagaccc agaccaagag ccacagccgg  2040
gccggcagcg tggccagcca gagcatcatc gcctacacca tgagcctagg cgccgagaac  2100
ctagtggcct acagcaacaa cagcatcgcc atccccacca acttcaccat cagcgtgacc  2160
accgagatcc tacccgtgag catgaccaag accagcgtgg actgcaccat gtacatctgc  2220
ggcgacagca ccgagtgcag caacctacta ctacagtacg gcagcttctg cacccagcta  2280
aagcgggccc taaccggcat cgccgtggag caggacaaga acacccagga ggtgttcgcc  2340
caggtgaagc agatctacaa gacccccccc atcaagtact tcggcggctt caacttcagc  2400
cagatcctac ccgaccccag caagcccagc aagcggagcc ccatcgagga cctactattc  2460
aacaaggtga ccctagccga cgccggcttc atcaagcagt acggcgactg cctaggcgac  2520
atcgccgccc gggacctaat ctgcgcccag aagttcaacg gcctaaccgt gctacccccc  2580
ctactaaccg acgagatgat cgcccagtac accagcgccc tactagccgg caccatcacc  2640
agcggctgga ccttcggcgc cggccccgcc ctacagatcc ccttccccat gcagatggcc  2700
taccggttca acggcatcgg cgtgacccag aacgtgctat acgagaacca gaagctaatc  2760
gccaaccagt tcaacagcgc catcggcaag atccaggaca gcctaagcag cacccccagc  2820
gccctaggca agctacagga cgtggtgaac cacaacgccc aggccctaaa caccctagtg  2880
aagcagctaa gcagcaagtt cggcgccatc agcagcgtgc taaacgacat cctaagccgg  2940
ctagaccccc ccgaggccga ggtgcagatc gaccggctaa tcaccggccg gctacagagc  3000
ctacagacct acgtgaccca gcagctaatc cgggccgccg agatccgggc cagcgccaac  3060
ctagccgcca ccaagatgag cgagtgcgtg ctaggccaga gcaagcgggt ggacttctgc  3120
ggcaagggct accacctaat gagcttcccc cagagcgccc cccacggcgt ggtgttccta  3180
```

-continued

```
cacgtgacct acgtgcccgc ccaggagaag aacttcacca ccgcccccgc catctgccac  3240
gacggcaagg cccacttccc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgaccc cctacagccc  3420
gagctagaca gcttcaagga ggagctagac aagtacttca agaaccacac cagccccgac  3480
gtggacctag gcgacatcag cggcatcaac gccagcgtgg tgaacatcca gaaggagatc  3540
gaccggctaa acgaggtggc caagaaccta aacgagagcc taatcgacct acaggagcta  3600
ggcaagtacg agcagtacat caagtggccc tggtacatct ggctaggctt catcgccggc  3660
ctaatcgcca tcgtgatggt gaccatcatg ctatgctgca tgaccagctg ctgcagctgc  3720
ctaaagggct gctgcagctg cggcagctgc tgcaagttcg acgaggacga cagcgagccc  3780
gtgctaaagg gcgtgaagct acactacacc taaaa                             3815

SEQ ID NO: 13           moltype = DNA  length = 3815
FEATURE                 Location/Qualifiers
source                  1..3815
                        mol_type = other DNA
                        organism = synthetic construct
SEQUENCE: 13
atgtttgtgt tcctggtgct gctgccactg gtgagctcac agtgcgtgaa tctgatcaca  60
cggacccaat cctacaccaa cagcttcaca agaggagtgt attaccctga caaggtgttt  120
agaagcagcg tgctgcatag cacccaagat ctgttcctgc ccttcttcag caatgtaacc  180
tggttccacg ccatccacgt gagcggcaca aacggcacca agcggttcga caacccccgtc  240
ctgcctttca atgacggcgt ttattttgct tccaccgaga agagtaacat cataaggggc  300
tggatctttg gcaccactct ggacagcaag acccagtccc tgctgatcgt gaacaacgcc  360
acaaacgtgg tgatcaaggt gtgtgaattc cagttttgca acgacccttt cctggacgtg  420
tattaccata agaacaataa atcttggatg gaaagcgagt tcagagtgta cagctctgcc  480
aacaactgca cattcgaata cgtgagccag ccttttctga tggacctgga aggaaagcag  540
ggcaacttca agaatctgag agaattcgta ttcaagaata tcgacggcta cttcaagatc  600
tacagcaagc acacccccat caacctggga agagacctgc cccaaggctt cagcgccctg  660
gaacccttgg tcgacctgcc catcggcatc aacatcacaa gattccaaac cctgctggcc  720
ctgcacagat cctacctgac acctggcgat tctagctctg gctggacagc cggagccgct  780
gcttattacg tgggatatct gcaacctcga acattcctgc tgaagtacaa tgaaaatgga  840
accatcacag atgccgtgga ttgcgctctg gaccctctct ctgaaacaaa atgcaccctg  900
aagtctttca ccgtggaaaa aggcatctac cagaccagta acttcagagt gcagcccacc  960
gaatccatcg tgcggttccc taacatcact aacctgtgtc ctttcgatga ggtgttcaac  1020
gccacccggt tcgcctctgt gtacgcctgg aatagaaaga ggatctctaa ctgcgttgca  1080
gactactctg tgctgtacaa cttcgcccca tttttcgcct tcaagtgcta cggagtgagc  1140
cctaccaaac taaacgatct gtgcttcacc aacgtgtacg ccgacagctt tgtgatcaga  1200
ggcaacgagg ttaggcagat cgcccctggc cagacgggca atatcgccga ttacaactac  1260
aagctgcctg atgacttcac cgggtgtgtg attgcttgga acagcaacaa actggatagc  1320
aaggtgggcg gcaactacaa ctaccagtat agactgtttc ggaaaagcaa cctgaaaccc  1380
tttgagagag acatcagcac cgagatctac caggccggca acaagccttg taatggagtg  1440
gccggattta actgctactt ccctctgaga tcttacggct tccgccccac ctacggtgtg  1500
ggccaccagc cctaccgggt cgtggtgctg agctttgagt tactgcacgc ccctgccaca  1560
gtctgtggcc ctaaaaagtc caccaatctg gtgaagaaca agtgcgtgaa cttcaacttc  1620
aatggcctga ccggcacagg agtgctgacc gagtctaaca aaaagttcct gccgttccag  1680
cagttcggca gagatatcgc cgacaccacc gacgccgtgc gggaccctca gaccctggaa  1740
atcctggaca tcaccccttg ttcatttgga ggcgtgtccg tgatcacgcc tggcaccaac  1800
accagcaacc aggtggctgt gctgtaccag ggcgtgaact gcacagaggt gcctgtggct  1860
atccacgccg accagttgac ccctacctgg cgggtgtaca gcacaggcag caatgtattc  1920
cagactagag ccggctgcct gatcggagcc gaatacgtga acaacagcta tgagtgtgac  1980
atccccatcg gcgccggcat ctgcgcctcc taccagacac agaccaagag ccacagccgg  2040
gccggcagcg ttgctagcca gtctatcatt gcctacacca tgagcctcgg cgccgagaac  2100
ctggtcgcct acagcaacaa tagcatcgcc atccctacca actttacgat cagcgtgacc  2160
accgagatcc tgccagtgtc tatgacgaaa accagcgtgg attgcacaat gtacatctgt  2220
ggcgactcta ccgagtgcag caacctgctg ctccaatacg ggagcttttg tacacagctg  2280
aagcgggcgc tgacagggat tgctgtggaa caggacaaga acacacagga ggtgttcgct  2340
caggtgaagc aaatctacaa gaccccacct atcaaatact tcggcggatt caacttttct  2400
cagatcctgc ctgaccctag caaacctagc aagcgatccc caatcgagga cctgctgttc  2460
aacaaggtga ccctggccga tgccggcttc atcaagcagt acggcgactg cctgggcgat  2520
atcgccgcca gagacctgat ttgcgctcag aaattcaacg gcctgacagt gctgcctcct  2580
ctgctgaccg atgagatgat cgcccagtac accagcgccc tgctggccgg aacaatcacc  2640
agcggctgga ccttcggcgc aggccctgcc ctgcaaatcc cattccccat gcagatggcc  2700
tacagattca acggcatcgg tgtcacccag aacgtgctgt acgagaacca aaagctgatc  2760
gccaaccagt tcaatagcgc cataggcaag atccaggaca gcctgagcag cacccccttct  2820
gccctgggca agctgcagga tgtggtaaac cacaacgccc aggctctgaa caccctggtg  2880
aagcagctga gctccaaatt tggcgctatc agcagcgttc tgaacgacat cctgtcaaga  2940
ctggaccctc ccgaggccga agtgcagatc gaccggctga tcacaggacg gctgcagagc  3000
ctgcaaacct acgtgaccca gcagttgatc agagccgctg aaatccgggc aagcgccaac  3060
ctcgccgcca ccaaaatgag cgaatgtgtg ctgggccaga gcaagagagt tgacttctgc  3120
ggaaagggct accacctgat gagcttcccc cagagtgctc cccacggcgt ggtgtttctg  3180
cacgtgacat atgtgcctgc ccaggagaag aatttcacca ccgcccctgc catctgccac  3240
gacggaaagg cccacttccc tcgcgagggc gtgttcgtga gcaatggcac tcactggttc  3300
gtaactcaaa gaaacttcta cgagcctcag atcatcacca ccgacaacac cttcgtgagc  3360
ggaaactgcg acgtagtgat cggaatcgtc aacaacacag tctacgaccc cctgcagcct  3420
gagctggaca gcttcaaaga ggagctggac aagtacttca agaaccacac ctctcctgat  3480
gtggacctgg gcgacatctc gggcatcaac gccagcgtgg tgaacatcca gaaggaaatc  3540
gacagactta acgaggtggc aaagaacctg aacgagagcc tgatcgatct tcaggagctg  3600
ggcaagtacg aacagtacat caaatggccc tggtacatct ggctgggctt catcgccggc  3660
```

-continued

```
ctgatcgcca tcgtgatggt gacaatcatg ctgtgctgca tgacctcctg ctgcagctgc  3720
ctgaagggat gctgcagctg tggctcctgc tgtaagttcg atgaggacga ttcagaacca  3780
gtgctcaagg gcgttaaact gcactacaca taaaa                             3815

SEQ ID NO: 14          moltype = DNA  length = 3815
FEATURE                Location/Qualifiers
source                 1..3815
                       mol_type = other DNA
                       organism = synthetic construct
SEQUENCE: 14
atgttcgtgt tcctggtgct gctgcccctg gtgagcagcc agtgcgtgaa cctgatcacc  60
cggacccaga gctacaccaa cagcttcacc cggggcgtgt actaccccga caaggtgttc  120
cggagcagcg tgctgcacag cacccaggac ctgttcctgc ccttcttcag caacgtgacc  180
tggttccacg ccatccacgt gagcggcacc aacggcacca agcggttcga caaccccgtg  240
ctgcccttca acgacggcgt gtacttcgcc agcaccgaga agagcaacat catccggggc  300
tggatcttcg gcaccaccct ggacagcaag acccagagcc tgctgatcgt gaacaacgcc  360
accaacgtgg tgatcaaggt gtgcgagttc cagttctgca acgacccctt cctggacgtg  420
tactaccaca agaacaacaa gagctggatg gagagcgagt tccgggtgta cagcagcgcc  480
aacaactgca ccttcgagta cgtgagccag cccttcctga tggacctgga gggcaagcag  540
ggcaacttca agaacctgcg ggagttcgtg ttcaagaaca tcgacggcta cttcaagatc  600
tacagcaagc acacccccat caacctgggc cgggacctgc cccagggctt cagcgccctg  660
gagcccctgg tggacctgcc catcggcatc aacatcaccc ggttccagac cctgctggcc  720
ctgcaccgga gctacctgac ccccggcgac agcagcagcg gctggaccgc cggcgccgcc  780
gcctactacg tgggctacct gcagccccgg accttcctgc tgaagtacaa cgagaacggc  840
accatcaccg acgccgtgga ctgcgccctg gacccccctga gcgagaccaa gtgcaccctg  900
aagagcttca ccgtggagaa gggcatctac cagaccagca acttccgggt gcagcccacc  960
gagagcatcg tgcggttccc caacatcacc aacctgtgcc ccttcgacga ggtgttcaac  1020
gccacccggt tcgccagcgt gtacgcctgg aaccggaagc ggatcagcaa ctgcgtggcc  1080
gactacagcg tgctgtacaa cttcgccccc ttcttcgcct tcaagtgcta cggcgtgagc  1140
cccaccaagc tgaacgacct gtgcttcacc aacgtgtacg ccgacagctt cgtgatccgg  1200
ggcaacgagg tgcggcagat cgcccccggc cagaccggca acatcgccga ctacaactac  1260
aagctgcccg acgacttcac cggctgcgtg atcgcctgga acagcaacaa gctggacagc  1320
aaggtgggcg gcaactacaa ctaccagtac cggctgttcc ggaagagcaa cctgaagccc  1380
ttcgagcggg acatcagcac cgagatctac caggccggca acaagccctg caacggcgtg  1440
gccggcttca actgctactt cccctgcgg agctacggct tccggcccac ctacggcgtg  1500
ggccaccagc cctaccgggt ggtggtgctg agcttcgagc tgctgcacgc ccccgccacc  1560
gtgtgcggcc ccaagaagag caccaacctg gtgaagaaca agtgcgtgaa cttcaacttc  1620
aacggcctga ccggcaccgg cgtgctgacc gagagcaaca agaagttcct gcccttccag  1680
cagttcggcc gggacatcgc cgacaccacc gacgccgtgc gggaccccca gaccctggag  1740
atcctggaca tcacccctg cagcttcggc ggcgtgagcg tgatcacccc cggcaccaac  1800
accagcaacc aggtggccgt gctgtaccag ggcgtgaact gcaccgaggt gcccgtggcc  1860
atccacgccg accagctgac ccccacctgg cgggtgtaca gcaccggcag caacgtgttc  1920
cagacccggg ccggctgcct gatcggcgcc gagtacgtga acaacagcta cgagtgcgac  1980
atccccatcg gcgccggcat ctgcgccagc taccagaccc agaccaagag ccacagccgg  2040
gccggcagcg tggccagcca gagcatcatc gcctacacca tgagcctggg cgccgagaac  2100
ctggtggcct acagcaacaa cagcatcgcc atccccacca acttcaccat cagcgtgacc  2160
accgagatcc tgcccgtgag catgaccaag accagcgtgg actgcaccat gtacatctgc  2220
ggcgacagca ccgagtgcag caacctgctg ctgcagtacg gcagcttctg cacccagctg  2280
aagcgggccc tgaccggcat cgccgtggag caggacaaga acacccagga ggtgttcgcc  2340
caggtgaagc agatctacaa gaccccccc atcaagtact tcggcggctt caacttcagc  2400
cagatcctgc ccgaccccag caagcccagc aagcggagcc ccatcgagga cctgctgttc  2460
aacaaggtga ccctggccga cgccggcttc atcaagcagt acggcgactg cctgggcgac  2520
atcgccgccc gggacctgat ctgcgcccag aagttcaacg gcctgaccgt gctgcccccc  2580
ctgctgaccg acgagatgat cgcccagtac accagcgccc tgctggccgg caccatcacc  2640
agcggctgga ccttcggcgc cggcccgcc ctgcagatcc ccttccccat gcagatggcc  2700
taccggttca acggcatcgg cgtgacccag aacgtgctgt acgagaacca gaagctgatc  2760
gccaaccagt tcaacagcgc catcggcaag atccaggaca gcctgagcag cacccccagc  2820
gccctgggca agctgcagga cgtggtgaac cacaacgccc aggccctgaa caccctggtg  2880
aagcagctga gcagcaagtt cggcgccatc agcagcgtgc tgaacgacat cctgagccgg  2940
ctggaccccc ccgaggccga ggtgcagatc gaccggctga tcaccggccg gctgcagagc  3000
ctgcagacct acgtgaccca gcagctgatc cgggccgccg agatccgggc cagcgccaac  3060
ctggccgcca ccaagatgag cgagtgcgtg ctgggccaga gcaagcgggt ggacttctgc  3120
ggcaagggct accacctgat gagcttcccc cagagcgccc cccacggcgt ggtgttcctg  3180
cacgtgacct acgtgcccgc ccaggagaag aacttcacca ccgcccccgc catctgccac  3240
gacggcaagg cccacttccc ccgggagggc gtgttcgtga gcaacggcac ccactggttc  3300
gtgacccagc ggaacttcta cgagccccag atcatcacca ccgacaacac cttcgtgagc  3360
ggcaactgcg acgtggtgat cggcatcgtg aacaacaccg tgtacgaccc cctgcagccc  3420
gagctggaca gcttcaagga ggagctggac aagtacttca agaaccacac cagccccgac  3480
gtggacctgg gcgacatcag cggcatcaac gccagcgtgg tgaacatcca gaaggagatc  3540
gaccggctga acgaggtggc caagaacctg aacgagagcc tgatcgacct gcaggagctg  3600
ggcaagtacg agcagtacat caagtggccc tggtacatct ggctgggctt catcgccggc  3660
ctgatcgcca tcgtgatggt gaccatcatg ctgtgctgca tgaccagctg ctgcagctgc  3720
ctgaagggct gctgcagctg cggcagctgc tgcaagttcg acgaggacga cagcgagccc  3780
gtgctgaagg gcgtgaagct gcactacacc taaaa                             3815

SEQ ID NO: 15          moltype = DNA  length = 3814
FEATURE                Location/Qualifiers
source                 1..3814
                       mol_type = other DNA
```

-continued

```
                         organism = synthetic construct
SEQUENCE: 15
atgttcgtgt tcctggtgct gctgcctctg gtgtcctccc aatgtgttaa cctcaccaca  60
agaacgcagc tgcccccagc ctataccaac agcttcacga gaggcgtgta ctaccccgac  120
aaggtgttcc gtagctccgt gctgcacagc acccaagatc tgtttctgcc tttcttcagc  180
aatgtgacct ggttccacgt catcagcggc accaatggga ccaagcggtt tgataatcct  240
gtcctgccct ttaacgatgg agtgtatttc gccagtatcg aaaagtccaa catcatcaga  300
ggctggatct tcggcaccac cctggattct aagacacaaa gtctgctgat cgtgaacaac  360
gcaacaaatg tggtgatcaa ggtgtgtgaa ttccagttct gcaatgaccc tttcctagac  420
cacaagaaca acaagagctg gatggaaagc gaattccggg tgtacagctc tgccaacaac  480
tgtaccttcg aatacgtttc tcagcccttt ctgatggacc tggaaggcaa gcagggaaac  540
ttcaagaacc taagagaatt cgtgttcaag aacatcgatg gctacttcaa gatctacagc  600
aagcacacac ctatcatcgt gcgggaacct gaggacctgc ctcaaggctt cagcgccctg  660
gagcccctgg tggacctgcc tatcgggatc aacatcaccc ggttccagac cctgctcgcc  720
ctgcatagat cttatctgac accaggcgat tctagcagcg gctggaccgc cggcgccgct  780
gcctactacg tgggctacct gcagcctaga acctttctcc tgaagtacaa cgagaacggc  840
acaatcaccg acgccgtgga ctgcgccctg gaccctctgt ccgagacaaa gtgcaccctg  900
aagtctttca ccgtggaaaa gggcatctat cagacctcta acttccgggt gcagcctacc  960
gagagcatcg tgcgctttcc aaacatcacc aacctgtgcc ctttcgacga ggtgttcaat  1020
gccaccagat tcgcctccgt gtacgcctgg aacagaaaga ggatctccaa ctgcgtcgct  1080
gattacagcg tcctctacaa cctggcccct tttttcacct tcaagtgcta cggagtgtct  1140
cctaccaagc tgaacgacct ctgcttcacc aatgtgtatg ccgatagctt tgtgatccgg  1200
ggcgatgagg tgcggcagat cgctcctggg cagaccggca acattgctga ctacaactac  1260
aagctgcccg acgacttcac gggctgcgtg atcgcttgga atagcaacaa acttgacagc  1320
aaggtgtccg gaaattacaa ctacctgtac agactgttca ggaagtctaa cctgaagcct  1380
ttcgagcggg atatcagcac agagatctac caagctggca acaagccctg caacggcgtg  1440
gccggattca attgctactt cccactgaga tcctacagct tccgacctac gtacggcgtt  1500
ggccaccagc cttacagggt cgtggtgctg agcttcgagc tcctgcacgc ccctgccacc  1560
gtgtgcggcc caaagaagtc taccaatctt gttaaaaaca agtgcgtgaa cttcaacttc  1620
aacggtctga agggaaccgg cgtgctgacc gagtctaaca agaaattcct gccctttcag  1680
cagttcggga gagacattgc tgacaccacg gatgccgtga gagaccctca gacactggaa  1740
atcctggaca tcaccccttg tagctttggc ggagtgagcg tgatcacccc tggcacaaac  1800
accagcaatc aggttgctgt gctgtaccag ggcgtgaact gcaccgaggt gcctgtggcc  1860
atccacgccg atcagctgac ccctacctgg cgcgtttaca gcacaggctc taatgtcttt  1920
cagacaagag ccggctgtct gatcggcgcc gagtacgtaa ataatagcta tgaatgcgac  1980
atcccgatcg gcgcaggcat ttgtgccagc taccagaccc agaccaaaag ccacagcaga  2040
gccggatctg tggcttctca gtccatcatc gcctacacca tgagcctggg tgctgagaac  2100
tccgtggcct acagcaacaa ctctatcgcc atccccacca acttcacaat atccgtgacc  2160
accgaaattc tgcctgtgtc tatgaccaag accagcgtgg actgcaccat gtacatttgc  2220
ggcgactcta ctgagtgcag caacctgctg ctccaatacg gcagcttctg tacccagctc  2280
aaaagagccc tgaccggaat cgccgtggaa caggacaaga acacacagga ggtgttcgcc  2340
caggtgaagc aaatctacaa gacacctccc atcaaatact tcggcggctt taatttttct  2400
cagatcctgc ctgatccctc caagcctagc aaacggagcc ccatcgagga cctgctgttc  2460
aacaaggtga cactggctga cgccggattc atcaagcagt acggcgactg cctgggcgac  2520
atcgccgcaa gagacctgat ctgcgcccag aaattcaagg gcctgactgt gctgccgccg  2580
ctgctgaccg acgagatgat cgcccagtac acctccgccc tgctggccgg aaccatcaca  2640
tccggctgga ccttcggcgc tggcgctgcc ctgcagatcc ctttccctat gcagatggcc  2700
taccggttta acggaatcgg cgtgacacag aacgtgctgt acgagaatca aaagctgatc  2760
gccaaccagt ttaacagcgc tattggcaag attcaggact ccctgagctc tacccccctct  2820
gccctgggca agctgcagga cgtggtgaac cacaacgccc aggccctgaa caccctggtg  2880
aagcagctga gctccaagtt cggagctatc agctctgtcc tgaacgacat tttctccaga  2940
ctggaccctc cagaagccga ggtccagatc gatcggctga tcaccggcag actgcaaagc  3000
ctgcagacat atgtgacaca gcagctgatc agagccgccg aaatcagagc gagcgccaat  3060
ctggccgcca caaagatgag cgaatgcgtg ttgggccaaa gtaaaagagt ggatttctgc  3120
ggcaaaggat accacctgat gagcttccca cagagtgccc ctcacggcgt ggtgttcctg  3180
catgtgacct acgtgcccgc ccaggagaag aacttcacta cagcccctgc aatctgccac  3240
gacggcaagg cccacttccc cagagagggt gtgtttgtga gcaatggcac tcactggttc  3300
gtcacccaaa gaaacttcta cgagccccag atcatcacca cagacaacac attcgtgagc  3360
ggcaattgcg acgtggtgat cggaatcgtg aacaacacag tgtacgaccc cctgcagcca  3420
gagctggata gcttcaaaga ggaactggac aagtacttca agaaccacac ctctcctgac  3480
gtggaccttg gcgacatctc tggaatcaac gccagcgtgg tgaacatcca gaaggaaatc  3540
gacagactca acgaggtcgc caagaacctg aacgagagcc tgatcgatct gcaggagctg  3600
ggcaagtacg agcagtacat caaatggcct tggtacatct ggctgggctt catcgctggc  3660
cttatcgcca tcgtcatggt gacaatcatg ctgtgttgca tgacatcttg ttgcagctgt  3720
ctgaagggct gctgcagctg cggctcttgt tgtaaattcg acgaggatga tagcgagcct  3780
gtgctgaagg gagtgaaact gcactacacc taaa                              3814

SEQ ID NO: 16            moltype =   length =
SEQUENCE: 16
000

SEQ ID NO: 17            moltype = DNA  length = 132
FEATURE                  Location/Qualifiers
source                   1..132
                         mol_type = other DNA
                         organism = synthetic construct
SEQUENCE: 17
gctcgctttc ttgctgtcca atttctatta aaggttcctt tgttccctaa gtccaactac  60
taaactgggg gatattatga agggccttga gcatctggat tctgcctaat aaaaaacatt  120
```

```
tattttcatt gc                                                    132

SEQ ID NO: 18          moltype = RNA  length = 132
FEATURE                Location/Qualifiers
source                 1..132
                       mol_type = other RNA
                       organism = synthetic construct
SEQUENCE: 18
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                    132

SEQ ID NO: 19          moltype = DNA  length = 50
FEATURE                Location/Qualifiers
source                 1..50
                       mol_type = other DNA
                       organism = synthetic construct
SEQUENCE: 19
acatttgctt ctgacacaac tgtgttcact agcaacctca aacagacacc            50

SEQ ID NO: 20          moltype = RNA  length = 50
FEATURE                Location/Qualifiers
source                 1..50
                       mol_type = other RNA
                       organism = synthetic construct
SEQUENCE: 20
acatttgctt ctgacacaac tgtgttcact agcaacctca aacagacacc            50

SEQ ID NO: 21          moltype = DNA  length = 55
FEATURE                Location/Qualifiers
source                 1..55
                       mol_type = other DNA
                       organism = synthetic construct
SEQUENCE: 21
ggcgctcgag caggttcaga aggagatcaa aaacccccaa ggatcaaacg ccacc      55

SEQ ID NO: 22          moltype = RNA  length = 55
FEATURE                Location/Qualifiers
source                 1..55
                       mol_type = other RNA
                       organism = synthetic construct
SEQUENCE: 22
ggcgctcgag caggttcaga aggagatcaa aaacccccaa ggatcaaacg ccacc      55

SEQ ID NO: 23          moltype = DNA  length = 50
FEATURE                Location/Qualifiers
source                 1..50
                       mol_type = other DNA
                       organism = synthetic construct
SEQUENCE: 23
gggcgctcga gcaggttcag aaggagatca aaaaccccca aggatcaaac            50

SEQ ID NO: 24          moltype = RNA  length = 50
FEATURE                Location/Qualifiers
source                 1..50
                       mol_type = other RNA
                       organism = synthetic construct
SEQUENCE: 24
gggcgctcga gcaggttcag aaggagatca aaaaccccca aggatcaaac            50

SEQ ID NO: 25          moltype = DNA  length = 55
FEATURE                Location/Qualifiers
source                 1..55
                       mol_type = other DNA
                       organism = synthetic construct
SEQUENCE: 25
ggcgcacgag cagggagaga aggagatcaa aaacccccaa ggatcaaacg ccacc      55

SEQ ID NO: 26          moltype = RNA  length = 55
FEATURE                Location/Qualifiers
source                 1..55
                       mol_type = other RNA
                       organism = synthetic construct
SEQUENCE: 26
ggcgcacgag cagggagaga aggagatcaa aaacccccaa ggatcaaacg ccacc      55

SEQ ID NO: 27          moltype = RNA  length = 40
FEATURE                Location/Qualifiers
source                 1..40
```

-continued

```
                        mol_type = other RNA
                        organism = synthetic construct
SEQUENCE: 27
aaaaaaaaaa aaaaaaaaaa aaaaaaaaaa aaaaaaaaaa                          40

SEQ ID NO: 28           moltype = RNA  length = 121
FEATURE                 Location/Qualifiers
source                  1..121
                        mol_type = other RNA
                        organism = synthetic construct
SEQUENCE: 28
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                    121

SEQ ID NO: 29           moltype = DNA  length = 48
FEATURE                 Location/Qualifiers
source                  1..48
                        mol_type = other DNA
                        organism = synthetic construct
SEQUENCE: 29
cggcaataaa aagacagaat aaaacgcacg gtgttgggtc gtttgttc               48

SEQ ID NO: 30           moltype = RNA  length = 48
FEATURE                 Location/Qualifiers
source                  1..48
                        mol_type = other RNA
                        organism = synthetic construct
SEQUENCE: 30
cggcaataaa aagacagaat aaaacgcacg gtgttgggtc gtttgttc               48

SEQ ID NO: 31           moltype =   length =
SEQUENCE: 31
000

SEQ ID NO: 32           moltype =   length =
SEQUENCE: 32
000

SEQ ID NO: 33           moltype = DNA  length = 6601
FEATURE                 Location/Qualifiers
source                  1..6601
                        mol_type = other DNA
                        organism = synthetic construct
SEQUENCE: 33
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acctcgcgaa  420
tgcatctaga tatcggatcc cgggcccgtc gactgcagag gcctgcatgc aagctttaat  480
acgactcact ataaggacat ttgcttctga cacaactgtg ttcactagca acctcaaaca  540
gacaccgcca ccatgttcgt gttcctggtg ctgctgcctc tggtcagcag ccagtgcgtg  600
aacctgagaa caagaacaca gcttcctcca gcctacacaa actcttttac acggggcgtg  660
tactatcctg acaaggtgtt ccggtccagc gtgctgcact caacccaaga cctgttcctg  720
cccttcttca gcaacgtcac ctggttccac gccatccacg tgtctggcac caatggcaca  780
aagcgattcg ataaccccgt gctgcctttc aacgacggcg tgtactttgc ctccatcgag  840
aagtccaaca tcatccgggg ctggatcttc gggaccacac tggatagcaa gacccagtct  900
ctgctgatcg taaacaacgc caccaacgtg gtcatcaagg tgtgcgagtt ccagttctgc  960
aacgaccctt tcctcgatgt gtactaccac aagaacaaca agtcttggat ggaatcgggc  1020
gtgtatagca gcgccaacaa ctgcaccttc gaatacgtga gccagccttt cctgatggac  1080
ctggaaggca aacaaggcaa ttttaagaac ctgagagaat tcgtgttcaa aaatatagac  1140
ggctatttca agatctacag caagcacacc cctattaatc tggtgcggga tctgcctcag  1200
ggcttcagcg ccctcgaacc tctggtggac ctgccaatcg gcatcaacat tacaagattc  1260
cagacgctgc tcgctctgca cagatcttac ctgacccctg gcgacagcag cagcggctgg  1320
accgccggcg ccgccgctta ctacgtgggc tacctgcagc ctagaacctt tctgctgaag  1380
tacaacgaga acggcaccat cactgatgcc gtggattgcg ccctggaccc tctgtccgaa  1440
accaaatgta cactgaagtc ttttaccgtg gaaaaaggaa tctaccagac ttccaacttc  1500
cgggtgcagc cgaccgagag catcgtgcgg ttccctaaca tcacaaacct gtgccccttt  1560
ggcgaggtgt tcaacgccac aagatttgct agcgtgtacg cctggaatag aaagagaatc  1620
agcaactgcg tggccgatta cagcgtgctg tacaatagcg cctctttcag caccttcaaa  1680
tgctacggcg tgagccccac caagctgaac gatctgtgtt ttacaaacgt gtatgccgac  1740
tcattcgtaa tcaggggcga tgaggtgaga cagatcgctc ctggacagac aggcaaaatc  1800
gcggactaca actataagct gcctgatgac ttcacaggat gtgtgatcgc atggaactcc  1860
aataacctcg acagcaaggt gggcggaaat tacaattacc gctacagact gtttagaaag  1920
agcaatctga aacctttcga gagagacatc agcacagaga tctaccaggc cggcagcaag  1980
ccctgtaacg gcgtcgaggg cttcaactgc tacttccccc tgcagagcta cggcttccag  2040
```

-continued

```
cctaccaacg gcgtgggata ccagccttac agagtggtgg tgctgagctt cgagctgctg  2100
catgctcctg ctacagtgtg tggtcctaag aagagcacca acctggttaa gaacaagtgc  2160
gtgaatttta acttcaatgg actgaccgga accggcgtgc tgaccgaaag caacaagaaa  2220
ttcctgcctt ttcagcagtt tggcagagac atcgccgaca ccaccgacgc cgtgagagat  2280
ccacaaaccc tggaaatcct ggacatcaca ccttgctcat ttggaggggt gtcggtgatc  2340
acacctggca ccaacaccag caaccaggtg gccgtgctgt accagggagt gaattgtacc  2400
gaggtccccg tggccattca cgccgaccag ctgacccccta cctggcgggt gtactccacc  2460
ggctctaacg tattccagac cagagccggc tgtctgatcg gcgcagaaca cgtgaacaat  2520
agctacgagt gcgacatccc tatcggagcc gggatctgcg ctagctacca gacccagaca  2580
aactccagaa gcagagccgg aagcgtggcc agccagtcta tcatcgccta caccatgagc  2640
ctgggcgccg aaaacagcgt tgcctacagc aacaattcta tcgccatccc tacaaacttc  2700
accatctccg tgaccaccga gatcctgcct gtcagcatga caaagaccag cgtagactgc  2760
acaatgtaca tctgcggaga ttccaccgag tgtagtaacc tcctgctgca atacggatct  2820
ttctgtactc agctgaacag agccctgacc ggcatcgccg ttgaacagga caagaacacc  2880
caggaggttt tcgcccaggt taagcagatc tacaaaaccc ctcctatcaa ggacttcgga  2940
ggctttaact tctcccagat cctgcccgac cccagcaagc ccagcaagcg gagccccatc  3000
gaggacctgc tgttcaacaa ggtgaccctg gccgacgccg gcttcatcaa acagtacggc  3060
gattgcctgg gagacatcgc cgctagagat ctaatttgcg cccaaaagtt taacggcctg  3120
acagtgctgc ctccactgct gacagacgag atgatcgccc agtacacatc tgccctgctg  3180
gctggtacca tcacatctgg ctggaccttt ggcgccggcc ccgccctcca gatccctttc  3240
cccatgcaga tggcctaccg gttcaacggc atcggcgtga cccagaacgt gctgtacgaa  3300
aaccagaaac tgatcgccaa ccagttcaat agcgcgatcg gcaaaatcca ggatagcctc  3360
agctctacac ccagcgctct tggcaagctg caaaacgtgg tgaaccagaa tgcccaggcc  3420
cttaacaccc tggtgaagca gctatcctct aatttcggtg ccatcagcag cgtgctgaat  3480
gatatcctga gcagactgga cccccctgag gccgaagtgc agatcgacag actgatcacc  3540
ggaagactgc agagcctgca aacctacgtg acccagcaac tgatccgggc cgcagaaatc  3600
cgggcctccg ctaacctggc cgctaccaag atgagcgagt gcgtgctggg tcaaagcaag  3660
cgcgtggact tctgtggaaa aggctaccac ctgatgagct tccctcagag cgctccacac  3720
ggcgtggtgt tcctgcatgt gacttacgtg cctgcccagg aaaagaactt caccaccgcc  3780
cctgccattt gtcacgacgg caaggcccac ttcccccggg aaggcgtgtt tgtgtctaac  3840
ggaacacact ggtttgtgac tcaaagaaac ttctacgagc cacagatcat caccacagat  3900
aacaccttcg tcagcggcaa ctgcgacgtg gtgatcggca tcgtgaacaa tactgtgtac  3960
gacccccctgc agccagagct cgattctttc aaagaggaac tggataagta cttcaagaac  4020
cacacatccc ccgacgtcga cctgggcgat atcagcggca ttaacgccag cgtggtgaac  4080
atccagaagg aaatcgatag actgaacgag gtggcaaaga acctgaatga gtccctgatt  4140
gacctgcaag agctcgggaa gtacgagcag tatatcaagt ggccttggta catctggctg  4200
ggcttcatcg cgggcctgat cgccatcgtt atggtgacga tcatgctgtg ctgcatgacc  4260
agttgctgta gctgcctgaa gggctgctgc agctgcggca gctgttgcaa gttcgacgag  4320
gacgacagcg agcctgtgct gaagggcgtt aagctgcact acacctgagc tcgctttctt  4380
gctgtccaat ttctattaaa ggttcctttg ttccctaagt ccaactacta aactgggga  4440
tattatgaag ggccttgagc atctggattc tgcctaataa aaaacattta ttttcattgc  4500
caataggccg aaatcggcaa gcgcgatcgc aaaaaaaaaa aaaaaaaaaa aaaaaaaaaa  4560
aaaaaaaaaa aaaaaaaaaa gaaaaaaaaa aaaaaaaaaa aaaaaaaaaa aaaaaaaaaa  4620
aaaaaaaaaa aaaaaaaaaa agaattcctc gagatttaaa ttcgcgagta ctatgcatat  4680
gggcccaata ttaattaagc gctagcacgc gtttaaacag gcctcgaggc gcgcccgctt  4740
cctcgctcac tgactcgctg cgctcggtcg ttcggctgcg gcgagcggta tcagctcact  4800
caaaggcggt aatacggtta tccacagaat caggggataa cgcaggaaag aacatgtgag  4860
caaaaggcca gcaaaaggcc aggaaccgta aaaaggccgc gttgctggcg tttttccata  4920
ggctccgccc ccctgacgag catcacaaaa atcgacgctc aagtcagagg tggcgaaacc  4980
cgacaggact ataaagatac caggcgtttc cccctggaag ctccctcgtg cgctctcctg  5040
ttccgaccct gccgcttacc ggatacctgt ccgcctttct cccttcggga agcgtggcgc  5100
tttctcatag ctcacgctgt aggtatctca gttcggtgta ggtcgttcgc tccaagctgg  5160
gctgtgtgca cgaacccccc gttcagcccg accgctgcgc cttatccggt aactatcgtc  5220
ttgagtccaa cccggtaaga cacgacttat cgccactggc agcagccact ggtaacagga  5280
ttagcagagc gaggtatgta ggcggtgcta cagagttctt gaagtggtgg cctaactacg  5340
gctacactag aagaacagta tttggtatct gcgctctgct gaagccagtt accttcggaa  5400
aaagagttgg tagctcttga tccggcaaac aaaccaccgc tggtagcggt ggtttttttg  5460
tttgcaagca gcagattacg cgcagaaaaa aaggatctca agaagatcct ttgatctttt  5520
ctacggggtc tgacgctcag tggaacgaaa actcacgtta agggattttg gtcatgagat  5580
tatcaaaaag gatcttcacc tagatccttt taaattaaaa atgaagtttt aaatcaagcc  5640
caatctgaat aatgttacaa ccaattaacc aattctgatt agaaaaactc atcgagcatc  5700
aaatgaaact gcaatttatt catatcagga ttatcaatac catatttttg aaaaagccgt  5760
ttctgtaatg aaggagaaaa ctcaccgagg cagttccata ggatggcaag atcctggtat  5820
cggtctgcga ttccgactcg tccaacatca atacaaccta ttaatttccc ctcgtcaaaa  5880
ataaggttat caagtgagaa atcaccatga gtgacgactg aatccggtga gaatggcaaa  5940
agtttatgca tttctttcca gacttgttca acaggccagc cattacgctc gtcatcaaaa  6000
tcactcgcat caaccaaacc gttattcatt cgtgattgcg cctgagcgag acgaaatacg  6060
cgatcgctgt taaaaggaca attacaaaca ggaatcgaat gcaaccggcg caggaacact  6120
gccagcgcat caacaatatt ttcacctgaa tcaggatatt cttctaatac ctggaatgct  6180
gtttttccgg ggatcgcagt ggtgagtaac catgcatcat caggagtacg gataaaatgc  6240
ttgatggtcg gaagaggcat aaattccgtc agccagttta gtctgaccat ctcatctgta  6300
acatcattgg caacgctacc tttgccatgt ttcagaaaca actctggcgc atcgggcttc  6360
ccatacaagc gatagattgt cgcacctgat tgcccgacat tatcgcgagc ccatttatac  6420
ccatataaat cagcatccat gttggaattt aatcgcggcc tcgacgtttc ccgttgaata  6480
tggctcataa cacccccttgt attactgttt atgtaagcag acagttttat tgttcatgat  6540
gatatatttt tatcttgtgc aatgtaacat cagagatttt gagacacggg ccagagctgc  6600
a                                                                 6601
```

SEQ ID NO: 34          moltype = AA  length = 9

-continued

```
FEATURE                Location/Qualifiers
source                 1..9
                       mol_type = protein
                       organism = synthetic construct
SEQUENCE: 34
KHKHKHKHK                                                        9

SEQ ID NO: 35          moltype = AA  length = 10
FEATURE                Location/Qualifiers
source                 1..10
                       mol_type = protein
                       organism = synthetic construct
SEQUENCE: 35
HKHKHKHKHK                                                       10

SEQ ID NO: 36          moltype = AA  length = 10
FEATURE                Location/Qualifiers
source                 1..10
                       mol_type = protein
                       organism = synthetic construct
SEQUENCE: 36
KHKHKHKHKH                                                       10

SEQ ID NO: 37          moltype = AA  length = 11
FEATURE                Location/Qualifiers
source                 1..11
                       mol_type = protein
                       organism = synthetic construct
SEQUENCE: 37
HKHKHKHKHK H                                                     11

SEQ ID NO: 38          moltype = AA  length = 20
FEATURE                Location/Qualifiers
source                 1..20
                       mol_type = protein
                       organism = synthetic construct
REGION                 1..20
                       note = This sequence is one part of a branched amino acid
                        sequence
SEQUENCE: 38
KHKHHKHHKH HKHHKHHKHK                                            20

SEQ ID NO: 39          moltype = AA  length = 17
FEATURE                Location/Qualifiers
source                 1..17
                       mol_type = protein
                       organism = synthetic construct
REGION                 1..17
                       note = This sequence is one part of a branched amino acid
                        sequence
SEQUENCE: 39
KHHHKHHHKH HHKHHHK                                               17

SEQ ID NO: 40          moltype = AA  length = 18
FEATURE                Location/Qualifiers
source                 1..18
                       mol_type = protein
                       organism = synthetic construct
REGION                 1..18
                       note = This sequence is one part of a branched amino acid
                        sequence
SEQUENCE: 40
KHHHKHHHKH HHHKHHHK                                              18

SEQ ID NO: 41          moltype = AA  length = 18
FEATURE                Location/Qualifiers
source                 1..18
                       mol_type = protein
                       organism = synthetic construct
SITE                   1
                       note = D-Lysine
SITE                   5
                       note = D-Lysine
SITE                   9
                       note = D-Lysine
SITE                   14
                       note = D-Lysine
SITE                   18
                       note = D-Lysine
```

-continued

```
REGION                1..18
                      note = This sequence is one part of a branched amino acid
                       sequence
SEQUENCE: 41
KHHHKHHHKH HHHKHHHK                                              18

SEQ ID NO: 42         moltype = AA  length = 19
FEATURE               Location/Qualifiers
source                1..19
                      mol_type = protein
                      organism = synthetic construct
REGION                1..19
                      note = This sequence is one part of a branched amino acid
                       sequence
SEQUENCE: 42
HKHHHKHHHK HHHHKHHHK                                             19

SEQ ID NO: 43         moltype = AA  length = 20
FEATURE               Location/Qualifiers
source                1..20
                      mol_type = protein
                      organism = synthetic construct
REGION                1..20
                      note = This sequence is one part of a branched amino acid
                       sequence
SEQUENCE: 43
HHKHHHKHHH KHHHHKHHHK                                            20

SEQ ID NO: 44         moltype = AA  length = 21
FEATURE               Location/Qualifiers
source                1..21
                      mol_type = protein
                      organism = synthetic construct
REGION                1..21
                      note = This sequence is one part of a branched amino acid
                       sequence
SEQUENCE: 44
KHHHHKHHHH KHHHHKHHHH K                                          21

SEQ ID NO: 45         moltype = AA  length = 18
FEATURE               Location/Qualifiers
source                1..18
                      mol_type = protein
                      organism = synthetic construct
REGION                1..18
                      note = This sequence is one part of a branched amino acid
                       sequence
SEQUENCE: 45
KHHHKHHHKH HHKHHHHK                                              18

SEQ ID NO: 46         moltype = AA  length = 18
FEATURE               Location/Qualifiers
source                1..18
                      mol_type = protein
                      organism = synthetic construct
REGION                1..18
                      note = This sequence is one part of a branched amino acid
                       sequence
SEQUENCE: 46
KHHHKHHHHK HHHKHHHK                                              18

SEQ ID NO: 47         moltype = AA  length = 19
FEATURE               Location/Qualifiers
source                1..19
                      mol_type = protein
                      organism = synthetic construct
REGION                1..19
                      note = This sequence is one part of a branched amino acid
                       sequence
SEQUENCE: 47
KHHHKHHHHK HHHKHHHHK                                             19

SEQ ID NO: 48         moltype = AA  length = 4
FEATURE               Location/Qualifiers
source                1..4
                      mol_type = protein
                      organism = synthetic construct
SEQUENCE: 48
RRAR                                                             4
```

```
SEQ ID NO: 49          moltype = AA  length = 4
FEATURE                Location/Qualifiers
source                 1..4
                       mol_type = protein
                       organism = synthetic construct
SEQUENCE: 49
HHHK                                                                4

SEQ ID NO: 50          moltype =   length =
SEQUENCE: 50
000

SEQ ID NO: 51          moltype = DNA  length = 18
FEATURE                Location/Qualifiers
source                 1..18
                       mol_type = other DNA
                       organism = synthetic construct
SEQUENCE: 51
taatacgact cactataa                                                 18

SEQ ID NO: 52          moltype =   length =
SEQUENCE: 52
000

SEQ ID NO: 53          moltype = RNA  length = 40
FEATURE                Location/Qualifiers
source                 1..40
                       mol_type = other RNA
                       organism = synthetic construct
SEQUENCE: 53
aaaaaaaaaa aaaaaaaaaa aaaaaaaaaa aaaaaaaaaa                         40

SEQ ID NO: 54          moltype = RNA  length = 121
FEATURE                Location/Qualifiers
source                 1..121
                       mol_type = other RNA
                       organism = synthetic construct
SEQUENCE: 54
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                   121

SEQ ID NO: 55          moltype = AA  length = 1270
FEATURE                Location/Qualifiers
source                 1..1270
                       mol_type = protein
                       organism = synthetic construct
SEQUENCE: 55
MFVFLVLLPL VSSQCVNLIT RTQSYTNSFT RGVYYPDKVF RSSVLHSTQD LFLPFFSNVT  60
WFHAIHVSGT NGTKRFDNPV LPFNDGVYFA STEKSNIIRG WIFGTTLDSK TQSLLIVNNA  120
TNVVIKVCEF QFCNDPFLDV YYHENNKSRM ESELRVYSSA NNCTFEYVSQ PFLMDLEGKQ  180
GNFKNLREFV FKNIDGYFKI YSKHTPVNLG RDLPQGFSAL EPLVDLPIGI NITRFQTLLA  240
LHRSYLTPGD SSSSWTAGAA AYYVGYLQPR TFLLKYNENG TITDAVDCAL DPLSETKCTL  300
KSFTVEKGIY QTSNFRVQPT ESIVRFPNIT NLCPFHEVFN ATRFASVYAW NRKRISNCVA  360
DYSVLYNFAP FFAFKCYGVS PTKLNDLCFT NVYADSFVIR GNEVSQIAPG QTGNIADYNY  420
KLPDDFTGCV IAWNSNKLDS KVSGNYNYLY RLFRKSKLKP FERDISTEIY QAGNKPCNGV  480
AGFNCYFPLR SYGFRPTYGV GHQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHSR AGSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSPIEDLLF NKVTLADAGF IKQYGDCLGD  840
IAARDLICAQ KFNGLTVLPP LLTDEMIAQY TSALLAGTIT SGWTFGAGPA LQIPFPMQMA  900
YRFNGIGVTQ NVLYENQKLI ANQFNSAIGK IQDSLSSTPS ALGKLQDVVN HNAQALNTLV  960
KQLSSKFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                          1270

SEQ ID NO: 56          moltype = DNA  length = 3813
FEATURE                Location/Qualifiers
source                 1..3813
                       mol_type = other DNA
                       organism = synthetic construct
SEQUENCE: 56
atgttcgtgt tcctggtgct gctgcctctg gtgtcttctc agtgcgtgaa tctgatcacc  60
```

-continued

```
agaacccagt cttacaccaa ttctttcacc agaggcgtgt actaccctga taaggtgttc  120
agatcttctg tgctgcactc tacccaggat ctgttcctgc ctttcttctc taatgtgacc  180
tggttccacg ccatccacgt gtctggcacc aatggcacca agagattcga taatcctgtg  240
ctgcctttca atgatggcgt gtacttcgcc tctaccgaga agtctaatat catcagaggc  300
tggatcttcg gcaccaccct ggattctaag acccagtctc tgctgatcgt gaataatgcc  360
accaatgtgg tgatcaaggt gtgcgagttc cagttctgca atgatccttt cctggatgtg  420
tactaccacg agaataataa gagcagaatg gagtctgagc tgagagtgta ctcttctgcc  480
aataattgca ccttcgagta cgtgtctcag cctttcctga tggatctgga gggcaagcag  540
ggcaatttca agaatctgag agagttcgtg ttcaagaata tcgatggcta cttcaagatc  600
tactctaagc acacccctgt gaatctgggc agagatctgc ctcagggctt ctctgccctg  660
gagcctctgg tggatctgcc tatcggcatc aatatcacca gattccagac cctgctggcc  720
ctgcacagat cttacctgac ccctggcgat tcttcttctt cttggaccgc cggcgccgcc  780
gcctactacg tgggctacct gcagcctaga accttcctgc tgaagtacaa tgagaatggc  840
accatcaccg atgccgtgga ttgcgccctg gatcctctgt ctgagaccaa gtgcaccctg  900
aagtctttca ccgtggagaa gggcatctac cagacctcta atttcagagt gcagcctacc  960
gagtctatcg tgagattccc taatatcacc aatctgtgcc ctttccacga ggtgttcaat  1020
gccaccagat tcgcctctgt gtacgcctgg aatagaaaga gaatctctaa ttgcgtggcc  1080
gattactctg tgctgtacaa tttcgcccct ttcttcgcct tcaagtgcta cggcgtgtct  1140
cctaccaagc tgaatgatct gtgcttcacc aacgtgtacg ccgattcttt cgtgatcaga  1200
ggcaacgagg tgtctcagat cgcccctggc cagaccggca acatcgccga ttacaactac  1260
aagctgcctg atgatttcac cggctgcgtg atcgcctgga actctaacaa gctggattct  1320
aaggtgtctg gcaactacaa ctacctgtac agactgttca gaaagtctaa gctgaagcct  1380
ttcgagagag atatctctac cgagatctac caggccggca acaagccttg caacggcgtg  1440
gccggcttca actgctactt ccctctgcag tcttacggct tcagacctac ctacggcgtg  1500
ggccaccagc cttacagagt ggtggtgctg tctttcgagc tgctgcacgc ccctgccacc  1560
gtgtgcggcc ctaagaagtc taccaacctg gtgaagaaca agtgcgtgaa cttcaacttc  1620
aacggcctga ccggcaccgg cgtgctgacc gagtctaaca agaagttcct gcctttccag  1680
cagttcggca gagatatcgc cgataccacc gatgccgtga gagatcctca gaccctggag  1740
atcctggata tcaccccttg ctctttcggc ggcgtgtctg tgatcacccc tggcaccaac  1800
acctctaacc aggtggccgt gctgtaccag ggcgtgaact gcaccgaggt gcctgtggcc  1860
atccacgccg atcagctgac ccctacctgg agagtgtact ctaccggctc taacgtgttc  1920
cagaccagag ccggctgcct gatcggcgcc gagtacgtga acaactctta cgagtgcgat  1980
atccctatcg gcgccggcat ctgcgcctct taccagaccc agaccaagtc tcacagcaga  2040
gccggctctg tggcctctca gtctatcatc gcctacacca tgtctctggg cgccgagaac  2100
tctgtggcct actctaacaa ctctatcgcc atccctacca acttcaccat ctctgtgacc  2160
accgagatcc tgcctgtgtc tatgaccaag acctctgtgg attgcaccat gtacatctgc  2220
ggcgattcta ccgagtgctc taacctgctg ctgcagtacg gctctttctg cacccagctg  2280
aagagagccc tgaccggcat cgccgtggag caggataaga acacccagga ggtgttcgcc  2340
caggtgaagc agatctacaa gacccctcct atcaagtact tcggcggctt caacttctct  2400
cagatcctgc ctgatccttc taagccttct aagagatctc ctatcgagga tctgctgttc  2460
aacaaggtga ccctggccga tgccggcttc atcaagcagt acggcgattg cctgggcgat  2520
atcgccgcca gagatctgat ctgcgcccag aagttcaacg gcctgaccgt gctgcctcct  2580
ctgctgaccg atgagatgat cgcccagtac acctctgccc tgctggccgg caccatcacc  2640
tctggctgga ccttcggcgc cggccctgcc ctgcagatcc ctttccctat gcagatggcc  2700
tacagattca acggcatcgg cgtgacccag aacgtgctgt acgagaacca gaagctgatc  2760
gccaaccagt tcaactctgc catcggcaag atccaggatt ctctgtcttc taccccttct  2820
gccctgggca agctgcagga tgtggtgaac cacaacgccc aggccctgaa caccctggtg  2880
aagcagctgt cttctaagtt cggcgccatc tcttctgtgc tgaacgatat cctgagcaga  2940
ctggatcctc ctgaggccga ggtgcagatc gatagactga tcaccggcag actgcagtct  3000
ctgcagacct acgtgaccca gcagctgatc agagccgccg agatcagagc ctctgccaac  3060
ctggccgcca ccaagatgtc tgagtgcgtg ctgggccagt ctaagagagt ggatttctgc  3120
ggcaagggct accacctgat gtctttccct cagtctgccc ctcacggcgt ggtgttcctg  3180
cacgtgacct acgtgcctgc ccaggagaag aacttcacca ccgcccctgc catctgccac  3240
gatggcaagg cccacttccc tagagagggc gtgttcgtgt ctaacggcac ccactggttc  3300
gtgacccaga gaaacttcta cgagcctcag atcatcacca ccgataacac cttcgtgtct  3360
ggcaactgcg atgtggtgat cggcatcgtg aacaacaccg tgtacgatcc tctgcagcct  3420
gagctggatt ctttcaagga ggagctggat aagtacttca agaaccacac ctctcctgat  3480
gtggatctgg gcgatatctc tggcatcaac gcctctgtgg tgaacatcca gaaggagatc  3540
gatagactga acgaggtggc caagaacctg aacgagtctc tgatcgatct gcaggagctg  3600
ggcaagtacg agcagtacat caagtggcct tggtacatct ggctgggctt catcgccggc  3660
ctgatcgcca tcgtgatggt gaccatcatg ctgtgctgca tgacctcttg ctgctcttgc  3720
ctgaagggct gctgctcttg cggctcttgc tgcaagttcg atgaggatga ttctgagcct  3780
gtgctgaagg gcgtgaagct gcactacacc taa                             3813
```

```
SEQ ID NO: 57          moltype = AA  length = 1268
FEATURE                Location/Qualifiers
source                 1..1268
                       mol_type = protein
                       organism = synthetic construct
SEQUENCE: 57
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT TFASVYAWNR KRISNCVADY  360
SVLYNFAPFF AFKCYGVSPT KLNDLCFTNV YADSFVIRGN EVSQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
```

-continued

LTGTGVLTES NKKFLPFQQF GRDIADTTDA VRDPQTLEIL DITPCSFGGV SVITPGTNTS 600
NQVAVLYQGV NCTEVPVAIH ADQLTPTWRV YSTGSNVFQT RAGCLIGAEY VNNSYECDIP 660
IGAGICASYQ TQTKSHSRAG SVASQSIIAY TMSLGAENSV AYSNNSIAIP TNFTISVTTE 720
ILPVSMTKTS VDCTMYICGD STECSNLLLQ YGSFCTQLKR ALTGIAVEQD KNTQEVFAQV 780
KQIYKTPPIK YFGGFNFSQI LPDPSKPSKR SPIEDLLFNK VTLADAGFIK QYGDCLGDIA 840
ARDLICAQKF NGLTVLPPLL TDEMIAQYTS ALLAGTITSG WTFGAGPALQ IPFPMQMAYR 900
FNGIGVTQNV LYENQKLIAN QFNSAIGKIQ DSLSSTPSAL GKLQDVVNHN AQALNTLVKQ 960
LSSKFGAISS VLNDILSRLD PPEAEVQIDR LITGRLQSLQ TYVTQQLIRA AEIRASANLA 1020
ATKMSECVLG QSKRVDFCGK GYHLMSFPQS APHGVVFLHV TYVPAQEKNF TTAPAICHDG 1080
KAHFPREGVF VSNGTHWFVT QRNFYEPQII TTDNTFVSGN CDVVIGIVNN TVYDPLQPEL 1140
DSFKEELDKY FKNHTSPDVD LGDISGINAS VVNIQKEIDR LNEVAKNLNE SLIDLQELGK 1200
YEQYIKWPWY IWLGFIAGLI AIVMVTIMLC CMTSCCSCLK GCCSCGSCCK FDEDDSEPVL 1260
KGVKLHYT 1268

SEQ ID NO: 58 moltype = DNA length = 3807
FEATURE Location/Qualifiers
source 1..3807
mol_type = other DNA
organism = synthetic construct
SEQUENCE: 58
atgttcgtgt tcctggtgct gctgcctctg gtgtcttctc agtgcgtgaa tctgatcacc 60
agaacccagt cttacaccaa ttctttcacc agaggcgtgt actaccctga taaggtgttc 120
agatcttctg tgctgcactc tacccaggat ctgttcctgc ctttcttctc taatgtgacc 180
tggttccacg ccatctctgg caccaatggc accaagagat tcgataatcc tgtgctgcct 240
ttcaatgatg gcgtgtactt cgcctctacc gagaagtcta atatcatcag aggctggatc 300
ttcggcacca ccctggattc taagacccag tctctgctga tcgtgaataa tgccaccaat 360
gtggtgatca aggtgtgcga gttccagttc tgcaatgatc ctttcctgga tgtgtactac 420
cacaagaata ataagtcttg gatggagtct gagttcagag tgtactcttc tgccaataat 480
tgcaccttcg agtacgtgtc tcagcctttc ctgatggatc tggagggcaa gcagggcaat 540
ttcaagaatc tgagagagtt cgtgttcaag aatatcgatg gctacttcaa gatctactct 600
aagcacaccc ctatcaatct gggcagagat ctgcctcagg gcttctctgc cctggagcct 660
ctggtggatc tgcctatcgg catcaatatc accagattcc agaccctgct ggccctgcac 720
agatcttacc tgacccctgg cgattcttct tctggctgga ccgccggcgc cgccgcctac 780
tacgtgggct acctgcagcc tagaaccttc ctgctgaagt acaatgagaa tggcaccatc 840
accgatgccg tggattgcgc cctggatcct ctgtctgaga ccaagtgcac cctgaagtct 900
ttcaccgtgg agaagggcat ctaccagacc tctaatttca gagtgcagcc taccgagtct 960
atcgtgagat tccctaatat caccaatctg tgccctttcg atgaggtgtt caatgccacc 1020
accttcgcct ctgtgtacgc ctggaataga aagagaatct ctaattgcgt ggccgattac 1080
tctgtgctgt acaatttcgc ccctttcttc gccttcaagt gctacggcgt gtctcctacc 1140
aagctgaatg atctgtgctt caccaatgtg tacgccgatt ctttcgtgat cagaggcaac 1200
gaggtgtctc agatcgcccc tggccagacc ggcaacatcg ccgattacaa ctacaagctg 1260
cctgatgatt tcaccggctg cgtgatcgcc tggaactcta acaagctgga ttctaaggtg 1320
ggcggcaact acaactacag atacagactg ttcagaaagt ctaacctgaa gcctttcgag 1380
agagatatct ctaccgagat ctaccaggcc ggcaacaagc cttgcaacgg cgtggccggc 1440
gtgaactgct acttccctct gcagtcttac ggcttcagac ctacctacgg cgtgggccac 1500
cagccttaca gagtggtggt gctgtctttc gagctgctgc acgcccctgc caccgtgtgc 1560
ggccctaaga agtctaccaa cctggtgaag aacaagtgcg tgaacttcaa cttcaacggc 1620
ctgaccggca ccggcgtgct gaccgagtct aacaagaagt tcctgccttt ccagcagttc 1680
ggcagagata tcgccgatac caccgatgcc gtgagagatc ctcagaccct ggagatcctg 1740
gatatcaccc cttgctcttt cggcggcgtg tctgtgatca cccctggcac caacacctct 1800
aaccaggtgg ccgtgctgta ccagggcgtg aactgcaccg aggtgcctgt ggccatccac 1860
gccgatcagc tgacccctac ctggagagtg tactctaccg gctctaacgt gttccagacc 1920
agagccggct gcctgatcgg cgccgagtac gtgaacaact cttacgagtg cgatatccct 1980
atcggcgccg gcatctgcgc ctcttaccag acccagacca agtctcacag cagagccggc 2040
tctgtggcct ctcagtctat catcgcctac accatgtctc tgggcgccga gaactctgtg 2100
gcctactcta acaactctat cgccatccct accaacttca ccatctctgt gaccaccgag 2160
atcctgcctg tgtctatgac caagacctct gtggattgca ccatgtacat ctgcggcgat 2220
tctaccgagt gctctaacct gctgctgcag tacggctctt tctgcaccca gctgaagaga 2280
gccctgaccg gcatcgccgt ggagcaggat aagaacaccc aggaggtgtt cgcccaggtg 2340
aagcagatct acaagacccc tcctatcaag tacttcggcg gcttcaactt ctctcagatc 2400
ctgcctgatc cttctaagcc ttctaagaga tctcctatcg aggatctgct gttcaacaag 2460
gtgaccctgg ccgatgccgg cttcatcaag cagtacggcg attgcctggg cgatatcgcc 2520
gccagagatc tgatctgcgc ccagaagttc aacggcctga ccgtgctgcc tcctctgctg 2580
accgatgaga tgatcgccca gtacacctct gccctgctgg ccggcaccat cacctctggc 2640
tggaccttcg gcgccggccc tgccctgcag atccctttcc ctatgcagat ggcctacaga 2700
ttcaacggca tcggcgtgac ccagaacgtg ctgtacgaga accagaagct gatcgccaac 2760
cagttcaact ctgccatcgg caagatccag gattctctgt cttctacccc ttctgccctg 2820
ggcaagctgc aggatgtggt gaaccacaac gcccaggccc tgaacaccct ggtgaagcag 2880
ctgtcttcta agttcggcgc catctcttct gtgctgaacg atatcctgag cagactggat 2940
cctcctgagg ccgaggtgca gatcgataga ctgatcaccg gcagactgca gtctctgcag 3000
acctacgtga cccagcagct gatcagagcc gccgagatca gagcctctgc caacctggcc 3060
gccaccaaga tgtctgagtg cgtgctgggc cagtctaaga gagtggattt ctgcggcaag 3120
ggctaccacc tgatgtcttt ccctcagtct gccccctcacg gcgtggtgtt cctgcacgtg 3180
acctacgtgc ctgcccagga gaagaacttc accaccgccc ctgccatctg ccacgatggc 3240
aaggcccact tccctagaga gggcgtgttc gtgtctaacg gcacccactg gttcgtgacc 3300
cagagaaact tctacgagcc tcagatcatc accaccgata acaccttcgt gtctggcaac 3360
tgcgatgtgg tgatcggcat cgtgaacaac accgtgtacg atcctctgca gcctgagctg 3420
gattctttca aggaggagct ggataagtac ttcaagaacc acacctctcc tgatgtggat 3480
ctgggcgata tctctggcat caacgcctct gtggtgaaca tccagaagga gatcgataga 3540

-continued

```
ctgaacgagg tggccaagaa cctgaacgag tctctgatcg atctgcagga gctgggcaag  3600
tacgagcagt acatcaagtg gccttggtac atctggctgg gcttcatcgc cggcctgatc  3660
gccatcgtga tggtgaccat catgctgtgc tgcatgacct cttgctgctc ttgcctgaag  3720
ggctgctgct cttgcggctc ttgctgcaag ttcgatgagg atgattctga gcctgtgctg  3780
aagggcgtga agctgcacta cacctaa                                     3807

SEQ ID NO: 59          moltype = RNA  length = 300
FEATURE                Location/Qualifiers
source                 1..300
                       mol_type = other RNA
                       organism = synthetic construct
misc_difference        1..300
                       note = This sequence may encompass 10-300 nucleotides
SEQUENCE: 59
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
```

COMPOSITION AND METHODS FOR MRNA VACCINES AGAINST NOVEL OMICRON CORONAVIRUS INFECTIONS

CROSS-REFERENCE TO RELATED APPLICATION

This application claims priority under 35 U.S.C. § 119(e) to U.S. Provisional Application No. 63/381,901, filed Nov. 1, 2022, incorporated by reference in its entirety.

INCORPORATION BY REFERENCE OF SEQUENCE LISTING

The instant application contains a Sequence Listing which has been submitted electronically in XML format and is hereby incorporated by reference in its entirety. Said XML copy, created on Oct. 31, 2023, is named 129774-5061_SL.xml and is 117,587 bytes in size.

TECHNICAL FIELD

Prophylactic and therapeutic agents for vaccination, prevention and treatment of 2019-nCoV infections are provided.

BACKGROUND

Coronaviruses (CoVs) have repeatedly crossed species barriers and some have emerged as important human pathogens. During the past two decades, two coronaviruses infecting animals have evolved and caused outbreaks in humans: severe acute respiratory syndrome-related coronavirus (SARS-CoV, 2002, genus: Betacoronavirus, subgenus: Sarbecovirus), and Middle East respiratory syndrome-related coronavirus (MERS-CoV, 2012, genus: Betacoronavirus, subgenus: Merbecovirus). See, for example, Drosten et al., *New Engl J Med.* 2003; 348:1967-1976; and Zaki et al., *New Engl J Med.* 2012; 367:1814-1820.

The SARS-CoV-2 2019 (COVID-19) is a new strain of coronavirus that causes coronavirus disease. See, for example, Zhu et al., *N Engl J Med.* 2020, 382:727-733. Accordingly to the COVID-19 Weekly Epidemiological Update and Weekly Operational Update dated Jul. 26, 2021 and published by World Health Organization (WHO), there are close to 200 million confirmed cases and more than 4 million confirmed deaths worldwide. No cure is available for COVID-19, while steroid has been used for therapeutic management of hospitalized adults, and the Food and Drug Administration (FDA) has issued Emergency Use Authorizations (EUAs) for anti-SARS-CoV-2 antibodies in treating non-hospitalized individuals with COVID-19, such as sotrovimab, and the combination of casirivimab and imdevimab. See, for example, COVID-19 Treatment Guidelines Panel. Coronavirus Disease 2019 (COVID-19) Treatment Guidelines. National Institutes of Health. Available at www.covid19treatmentguidelines.nih.gov and last accessed on Jul. 27, 2021.

While steroid use and anti-SARS-CoV-2 antibodies have played an important role in preventing and treating COVID-19, these methods are challenged by viral evolution, particularly the emergence of the recently identified Omicron variant sublineages BA.4, BA.5, BA.2.75, BF.7, and BA.2.12.1, which have demonstrated pronounced antigenic resistance and increased immune-escape relative to other variants of concern (Gruell, et. al., Cell Host Microbe. 2022. 1931-3128(22)00318-3). Accordingly, there remains an urgent need for effective prevention and treatment of a SARS-CoV-2 infection. This disclosure satisfies this need and provides related advantages as well.

SUMMARY

Provided herein are spike (s) proteins or immunologic fragments thereof as well as a deoxyribonucleic acid (DNA) or a ribonucleic acid (RNA) encoding the spike (S) proteins or an immunogenic fragment of each thereof of a severe acute respiratory syndrome coronavirus 2 (SARS-CoV-2). The S protein or immunogenic fragment thereof comprises or consists essentially of, or yet further consists of at least one non-naturally occurring amino acid mutation, for example, as compared to an S protein of a SARS-CoV-2 Omicron variant, such as SEQ ID NO: 1. SEQ ID NO:1 is the S protein of a wild-type variant. In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), a glycine (G) as the amino acid corresponding to R685 of SEQ ID NO: 1 (R685G), a proline (P) as the amino acid corresponding to F817 of SEQ ID NO: 1 (F817P), a P as the amino acid corresponding to A892 of SEQ ID NO: 1 (A892P), a P as the amino acid corresponding to A899 of SEQ ID NO: 1 (A899P), a P as the amino acid corresponding to A942 of SEQ ID NO: 1 (A942P), a P as the amino acid corresponding to K986 of SEQ ID NO: 1 (K986P), or a P as the amino acid corresponding to V987 of SEQ ID NO: 1 (V987P). In some embodiments, the RNA encoding a spike (S) protein or an immunogenic fragment thereof does not comprise SEQ ID NO: 2. In one aspect, the RNA encodes an S protein or an immunogenic fragment thereof comprising SEQ ID NO: 5, 8, 11, 55, or 57. In one aspect, the RNA can further comprise elements operably linked to the RNA to assist in expression or replication of the RNA.

In one aspect, provided is a polynucleotide, such as a DNA encoding an RNA as disclosed herein. Also provided are complements of the encoding DNA that can further comprise elements operably linked to the DNA to assist in expression or replication of the DNA.

In a further aspect, provided is a vector comprising a polynucleotide as disclosed herein. In one embodiment, the vector is a plasmid or a viral vector. In yet a further aspect, provided is a cell comprising one or more of: an RNA as disclosed herein, a polynucleotide as disclosed herein, or a vector as disclosed herein. In one aspect, provided is a composition comprising, or alternatively consisting essentially of, or yet further consisting of a carrier, optionally a pharmaceutically acceptable carrier and one or more of: an RNA as disclosed herein, a polynucleotide as disclosed herein, a vector as disclosed herein, or a cell as disclosed herein.

Additionally provided is a method of producing a DNA or an RNA as disclosed herein. In some embodiments, the method comprises, or alternatively consists essentially of, or yet further consisting of culturing a cell as disclosed herein under conditions suitable for expressing the DNA and/or the RNA. In other embodiments, the method comprises, or alternatively consists essentially of, or yet further consists of contacting a polynucleotide or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP (such as N1-methyl pseudouridine trisphosphate) under conditions suitable for expressing the RNA. In further embodiments, a method as disclosed herein further comprises isolating the DNA or the RNA.

In one aspect, provided is a composition comprising, or alternatively consisting essentially of, or yet further consisting of a protein, a polypeptide, an RNA or DNA as disclosed herein and a carrier such as a pharmaceutically acceptable carrier. In some embodiments, the pharmaceutically acceptable carrier comprises, or alternatively consists essentially of, or yet further consists of a polymeric nanoparticle. In further embodiments, the polymeric nanoparticle comprises, or alternatively consists essentially of, or yet further consists of a Histidine-Lysine co-polymer (HKP). In some embodiments, the pharmaceutically acceptable carrier further comprises a lipid, optionally one or more of: a cationic lipid (such as Dlin-MC3-DMA, i.e., MC3), a helper lipid, a cholesterol, or a PEGylated lipid. In some embodiments, the pharmaceutically acceptable carrier comprises, or alternatively consists essentially of, or yet further consists of a lipid nanoparticle (LNP). In some embodiments, the LNP comprises one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof. In further embodiments, the LNP further comprises one or more of: a helper lipid, a cholesterol, or a PEGylated lipid. A further pharmaceutically acceptable carrier can be added to the nanoparticle composition, e.g., phosphate buffered saline and the like.

In further embodiments, the pharmaceutically acceptable carrier further comprises a dilute, an adjuvant, a binder, a stabilizer, a buffer, a salt, a lipophilic solvent, or a preservative. In some embodiments, the nanoparticle is a self-assembled nanoparticle. In a further aspect, provided is a composition comprising, or alternatively consisting essentially of, or yet further consisting of a self-assembled nanoparticle comprising an RNA as disclosed herein. In some embodiments, the nanoparticle encapsulates the RNA. In other embodiments, the nanoparticle is conveniently or non-covalently linked to the RNA.

In a further embodiments, provided is a method of producing the composition. In some embodiments, the method comprises, or alternatively consists essentially of, or yet further consists of contacting an RNA as disclosed herein with an HKP, thereby the RNA and the HKP are self-assembled into nanoparticles. Additionally or alternatively, the method comprises, or alternatively consists essentially of, or yet further consist of contacting an RNA as disclosed herein with a lipid, thereby the RNA and the lipid are self-assembled into nanoparticles. In further embodiment, the contacting step is performed in a microfluidic mixer, such as NanoAssemblr Ignite.

In another aspect, provided is a method of one or more of: (a) preventing a subject from having a symptomatic SARS-CoV-2 infection, (b) inducing an immune response to SARS-CoV-2 in a subject in need thereof, (c) reducing the binding of a SARS-CoV-2 or an S protein thereof with angiotensin converting enzyme 2 (ACE2) in a subject in need thereof, (d) treating a subject infected with SARS-CoV-2, or (e) reducing a SARS-CoV-2 viral load in a subject in need thereof. The method comprises, or alternatively consists essentially of, or yet further consists of administering to the subject one or more of: an RNA or DNA as disclosed herein, a polynucleotide as disclosed herein, a vector as disclosed herein, or a composition as disclosed herein.

In one aspect, provided is an inhalation system comprising, or alternatively consisting essentially of, or yet further consisting of an RNA or DNA as disclosed herein, a polynucleotide as disclosed herein, a vector as disclosed herein, or a composition as disclosed herein, and a nebulizer.

In another aspect, provided is a method of producing a spike (S) protein or an immunogenic fragment thereof of a severe acute respiratory syndrome coronavirus 2 (SARS-CoV-2). The method comprises, or alternatively consists essentially of, or yet further consists of culturing a cell as disclosed herein under conditions suitable for expressing the S protein or immunogenic fragment thereof. In further embodiments, the method herein further comprises isolating the S protein or immunogenic fragment thereof. Alternatively or in addition, the S protein or an immunogenic fragment thereof can be produced by administering a composition comprising the DNA and/or RNA to a subject.

Additionally, provided is a method for screening a candidate agent reducing or inhibiting the binding of SARS-CoV-2 and its receptor, such as ACE2, optionally in a subject or on a cell of the subject or both. The method comprises, or alternatively consist essentially of, or yet further consists of expressing a spike (S) protein or an immunogenic fragment thereof from an RNA as disclosed herein, and measuring the binding between the expressed S protein or immunogenic fragment thereof and the SARS-CoV-2 receptor, such as ACE2, with or without the presence of the candidate agent or with different concentrations of the candidate agent. In some embodiments, less binding between the expressed S protein or immunogenic fragment thereof and the SARS-CoV-2 receptor with the presence of the candidate agent compared to without the candidate agent, indicates that the candidate agent reduces or inhibits the binding of SARS-CoV-2 and its receptor. In some embodiments, decreased binding between the expressed S protein or immunogenic fragment thereof and the SARS-CoV-2 receptor while increasing the concentration of the candidate agent indicates the candidate agent reduces or inhibits the binding of SARS-CoV-2 and its receptor.

In yet a further aspect, provided is a method for selecting an RNA encoding a spike (S) protein or an immunogenic fragment thereof of a severe acute respiratory syndrome coronavirus 2 (SARS-CoV-2). The method comprises, or alternatively consists essentially of, or yet further consists of transducing the RNA into a cell, culturing the cell under conditions suitable for expressing the RNA, and measuring IFN-α or IFN-β or both secreted by the cell. In some embodiments, the method further comprises selecting the RNA if no secretion of IFN-α or IFN-β or both or less secretion of IFN-α or IFN-β or both compared to an RNA encoding a wild type S protein or an immunogenic fragment thereof.

Also provided is a kit for use in a method as described herein. In some embodiments, the kit comprises, or alternatively consists essentially of, or yet further consists of instructions for use and one or more of: an RNA as disclosed herein, a polynucleotide as disclosed herein, a vector as disclosed herein, a composition as disclosed herein, or an inhalation system as disclosed herein.

BRIEF DESCRIPTION OF THE FIGURES

FIG. 2B, polyA 60) or no PolyA tail (FIG. 2C).

As shown in FIG. 1, Omicron BA.1 showed stronger intensity to anti-Spike (WT) antibody than UK and Delta variants (panel A). The expression levels of each variant was evaluated by ACE2 binding (FIG. 2) because ACE2 has a similar affinity to spike proteins of different variants. Based on this observation, the results suggest that Omicron BA.1 has a stronger affinity to anti-Spike (WT) antibody. The expression of Omicron BA.1 is higher than both Delta and UK variants using either SARS-CoV-2 Spike Protein (RBD) Monoclonal Antibody (HL257) (FIG. 4A) or SARS-CoV-2 Spike Antibody, Omicron Reactive, Mouse Mab (FIG. 4B). The loading control of each sample is FIG. 4C. FIG. 4D shows the SARS-CoV-Spike Protein (RBD) monoclonal antibody (HL257) (MA5-36253), merged with control. FIG. 4E shows Antibody: SARS-CoV-2 Spike Antibody: Omicron Reactive, Mouse MAb (40592-MM117-100), merged with control.

DETAILED DESCRIPTION

Definitions

Figure 1:
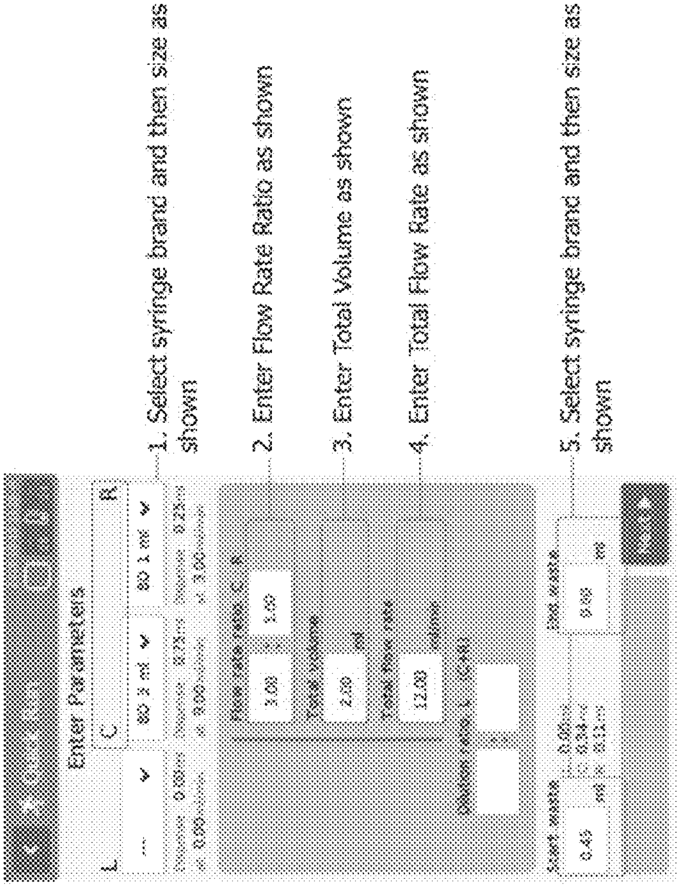
FIG. 1 provides a representative parameter setting of NanoAssemblr Ignite for producing an RNA in a RL-007 lipid. RL-007 is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). 0.13 mg/mL of mRNA was mixed in a 3:1 (v/v) ratio with RL-007.

As it would be understood, the section or subsection headings as used herein is for organizational purposes only and are not to be construed as limiting and/or separating the subject matter described.

It is to be understood that this disclosure is not limited to particular embodiments described, as such may, of course, vary. It is also to be understood that the terminology used herein is for the purpose of describing particular embodiments only, and is not intended to be limiting, since the scope of this disclosure will be limited only by the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach;

Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (Cold Spring Harbor Laboratory Press (2002)); Sohail (ed.) (2004) Gene Silencing by RNA Interference: Technology and Application (CRC Press); and Plotkin et al., Plotkin;s Human Vaccines, $7^{th}$ edition (Elsevier).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

As used herein, comparative terms as used herein, such as high, low, increase, decrease, reduce, or any grammatical variation thereof, can refer to certain variation from the reference. In some embodiments, such variation can refer to about 10%, or about 20%, or about 30%, or about 40%, or about 50%, or about 60%, or about 70%, or about 80%, or about 90%, or about 1 fold, or about 2 folds, or about 3 folds, or about 4 folds, or about 5 folds, or about 6 folds, or about 7 folds, or about 8 folds, or about 9 folds, or about 10 folds, or about 20 folds, or about 30 folds, or about 40 folds, or about 50 folds, or about 60 folds, or about 70 folds, or about 80 folds, or about 90 folds, or about 100 folds or more higher than the reference. In some embodiments, such variation can refer to about 1%, or about 2%, or about 3%, or about 4%, or about 5%, or about 6%, or about 7%, or about 8%, or about 0%, or about 10%, or about 20%, or about 30%, or about 40%, or about 50%, or about 60%, or about 70%, or about 75%, or about 80%, or about 85%, or about 90%, or about 95%, or about 96%, or about 97%, or about 98%, or about 99% of the reference.

As will be understood by one skilled in the art, for any and all purposes, all ranges disclosed herein also encompass any and all possible subranges and combinations of subranges thereof. Furthermore, as will be understood by one skilled in the art, a range includes each individual member.

"Optional" or "optionally" means that the subsequently described circumstance may or may not occur, so that the description includes instances where the circumstance occurs and instances where it does not.

As used herein, "and/or" refers to and encompasses any and all possible combinations of one or more of the associated listed items, as well as the lack of combinations when interpreted in the alternative ("or").

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The terms or "acceptable," "effective," or "sufficient" when used to describe the selection of any components, ranges, dose forms, etc. disclosed herein intend that said component, range, dose form, etc. is suitable for the disclosed purpose.

In some embodiments, the terms "first" "second" "third" "fourth" or similar in a component name are used to distinguish and identify more than one components sharing certain identity in their names. For example, "first RNA" and "second RNA" are used to distinguishing two RNAs.

Severe acute respiratory syndrome coronavirus 2 (SARS-CoV-2), also referred to as 2019 novel coronavirus (2019-nCoV) or human coronavirus 2019 (HCoV-19 or hCoV-19), is the virus that causes COVID-19 (coronavirus disease 2019), the respiratory illness responsible for the COVID-19 pandemic.

Each SARS-CoV-2 virion is 50-200 nanometers in diameter, comprising a linear, positive-sense, single-stranded RNA genome (about 30,000 bases long) and four structural proteins, known as the S (spike), E (envelope), M (membrane), and N (nucleocapsid) proteins. The N protein holds the RNA genome, and the S, E, and M proteins together create the viral envelope. Coronavirus S proteins are glycoproteins that are divided into two functional parts (S1 and S2). In SARS-CoV-2, the spike protein is the protein responsible for allowing the virus to attach to and fuse with the membrane of a host cell; specifically, its S1 subunit catalyzes attachment, the S2 subunit fusion. Studies have shown that SARS-CoV-2 has sufficient affinity to the receptor angiotensin converting enzyme 2 (ACE2) on human cells to use them as a mechanism of cell entry. Initial spike protein priming by transmembrane protease, serine 2 (TMPRSS2) is also shown as essential for entry of SARS-CoV-2. The host protein neuropilin 1 (NRP1) may aid the virus in host cell entry using ACE2. After a SARS-CoV-2 virion attaches to a target cell, the cell's TMPRSS2 cuts open the spike protein of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells.

Genetic variants of SARS-CoV-2 have been emerging and circulating around the world throughout the COVID-19 pandemic. The B.1.1.7 (Alpha), B.1.351 (Beta), B.1.617.2 (Delta), and P.1 (Gamma) variants circulating in the United States are classified as variants of concern. Other variants are also present, such as B.1.526 (Iota), B.1.427 (Epsilon), B.1.429 (Epsilon), B.1.617 (Kappa, Delta), B.1.525 (Eta), and P.2 (Zeta). The B.1.1.529 (Omicron) variant was first reported in South Africa and has spread worldwide. Omicron is classified as the fifth variant of concern by the World Health Organization. Omicron variants are divided into separate lineages including BA.1, BA.2, BA.3, BA.4, BA.5, BA.2.12.1, BA.2.75, and BF.7. Accordingly, the term "SARS-CoV-2" as used herein can refer to any one or more or all of the variants. In some embodiments, SARS-CoV-2 as used herein refers to an Omicron variant, which was first identified in South Africa. In further embodiments, SARS-CoV-2 Omicron variant comprises mutations in the gene encoding the S protein causing one or more of the following amino acid mutations in the S protein: T19I, Δ24-26, A27S, Δ69/70, G142D, K147E, W152R, F157L, I210V, V213G, G257S, G339D, G339H, R346T, S371F, S373P, S375F, T376A, D405N, R408S, K417N, N440K, G446S, L452R, L452Q, N460K, S477N, T478K, E484A, F486V, Q493R, Q498R, N501Y, Y505H, D614G, H655Y, N679K, P681H, S704L, N764K, D796Y, Q954H, and/or N969K. In some embodiments, the Omicron variant is a BA.2.12.1, BA.4, or BA.5 variant, comprising mutations in the gene encoding the S protein causing one or more of the following amino acid mutations in the S protein: T19I, Δ24-26, A27S, V213G, S371F, T376A, D405N, and/or R408S. In some embodiments, the Omicron variant is a BA.2.12.1 variant comprising mutations in the gene encoding the S protein causing one or more of the following amino acid mutations in the S protein: L452Q, S704L, T19I, Δ24-26, A27S, V213G, S371F, T376A, D405N, and/or R408S. In some embodiments, the Omicron variant is a BA.4 or BA.5 variant comprising mutations in the gene encoding the S protein causing one or more of the following amino acid mutations in the S protein: Δ69/70, L452R, Q493R, T19I, Δ24-26, A27S, V213G, S371F, T376A, D405N, and/or R408S. In some embodiments, the Omicron variant is a BA.2.75 variant comprising one or more of the following mutations in the S protein: T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K. In some embodiments, the Omicron variant is a BF.7 variant comprising one or more of the following mutations in the S protein: T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K. In some embodiments, the one or more mutations comprises, or alternatively consists essentially of, or yet further consists of one or more of: T19I, Δ24-26, A27S, A67V, Δ69/70, T95I, G142D, Δ143-145, N211I, Δ212, V213G, ins214EPE, G339D, S371F, S371L, S373P, S375F, T376A, D405N, R408S, K417N, N440K, G446S L452R, L452Q, S477N, T478K, E484A, F486V, Q493R, G496S, Q498R, N501Y, Y505H, D614G, T547K, H655Y, N679K, P681H, S704L, N764K, D796Y, N856K, Q954H, N969K, and/or L981F. In some embodiments, the one or more mutations comprises, or alternatively consists essentially of, or yet further consists of one or more of: T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, and/or N969K. In some embodiments, the one or more mutations comprises, or alternatively consists essentially of, or yet further consists of one or more of: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and/or N969K. In some embodiments, the one or more mutations comprises, or alternatively consists essentially of, or yet further consists of one or more of: A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K. In some embodiments, the one or more mutations comprises, or alternatively consists essentially of, or yet further consists of one or more of: T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K. In some embodiments, the one or more mutations comprises, or alternatively consists essentially of, or yet further consists of one or more of: T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K.

Subjects with a SARS-CoV-2 infection can experience a range of clinical manifestations, from an asymptomatic SARS-CoV-2 infection with no symptoms, to a symptomatic SARS-CoV-2 infection with critical illness. SARS-CoV-2 infection can be grouped into the following severity of illness categories; however, the criteria for each category may overlap or vary across clinical guidelines and clinical trials, and a patient's clinical status may change over time. Asymptomatic or presymptomatic SARS-CoV-2 infection occurs when a subject tests positive for SARS-CoV-2 using a virologic test, but exhibits no symptoms (e.g., fever, cough, sore throat, malaise, headache, muscle pain, nausea, vomiting, diarrhea, loss of taste and smell) consistent with a symptomatic SARS-CoV-2 infection. A symptomatic SARS-CoV-2 infection occurs when a subject exhibits mild, moderate, severe, or critical illness associated with SARS-CoV-2 infection, as defined by the U.S. National Institutes of Health. Subjects with mild illness associated with SARS-CoV-2 infection exhibit symptoms including, but not limited to, fever, cough, sore throat, malaise, headache, muscle pain, nausea, vomiting, diarrhea, loss of taste and smell, but do not have shortness of breath, dyspnea, or abnormal chest imaging. Subjects with moderate illness associated with SARS-CoV-2 infection show evidence of lower respiratory disease during clinical assessment or imaging and have an oxygen saturation ($SpO_2$)≥94% on room air at sea level. Subjects with severe illness associated with SARS-CoV-2 infection have $SpO_2$<94% on room air at sea level, a ratio of arterial partial pressure of oxygen to fraction of inspired oxygen ($PaO_2/FiO_2$)<300 mm Hg, a respiratory rate >30 breaths/min, or lung infiltrates >50%. Subjects with critical illness associated with SARS-CoV-2 infection have respiratory failure, septic shock, and/or multiple organ dysfunction.

Symptoms of a coronavirus infection include, but are not limited to, mild symptoms, such as fatigues, tingling, tingling or numbness in the hands and feet, dizziness, confusion, brain fog, body ache, chills, loss of appetite, nausea, vomiting, abdominal pain or discomfort, loss of smell, inability to taste, muscle weakness, photophobia, adenopathy, headaches, cough, dry cough, shortness of breath, sore throat, lower extremity weakness/numbness, diarrhea, low blood 02, sneezing, runny nose or post-nasal drip; severe symptoms, such as ventilatory use, high fever, severe cough, delirium, seizures, stroke, systematic inflammation, cytokine storm; and other symptoms, such as fever, swollen adenoids, pneumonia, bronchitis, and Dyspnea.

Viral infection of a coronavirus, such as SARS-COV-2, can be detected via a commercially available test known in the art, for example via polymerase chain reaction (PCR) or immunoassay may be used. In some embodiments, a method as disclosed herein further comprises detecting a coronavirus using a test known in the art. In one embodiment, active viral infection refers to an ongoing infection wherein the virus is replicating and producing new virus. Such active viral infection may be detected using polymerase chain reaction (PCR). Non-limiting examples of primers and probes suitable for use in the PCR include 2019-nCoV CDC Probe and Primer Kit for SARS-CoV-2 (BioSearch Technologies, Catalog No. KIT-nCoV-PP1-1000), 2019-nCoV Kit, 500 rxn (Integrated DNA Technologies (IDT), Catalog No. 10006606) and 2019-nCoV Kit, 1000 rxn (Integrated DNA Technologies (IDT), Catalog No. 10006770). Also see, www.cdc.gov/coronavirus/2019-ncov/lab/rt-pcr-panel-primer-probes.html and www.cdc.gov/coronavirus/2019-ncov/downloads/List-of-Acceptable-Commercial-Primers-Probes.pdf. Suitable protocols for performing such tests can be found at www.cdc.gov/coronavirus/2019-ncov/lab/virus-requests.html, www.fda.gov/media/134922/download, www.cdc.gov/coronavirus/2019-ncov/downloads/processing-sputum-specimens.pdf, www.fda.gov/media/134922/download, www.fda.gov/media/134919/download, www.fda.gov/media/134922/download, last accessed on Aug. 10, 2021. In some embodiments, diagnostic assays for COVID-19 based on detecting antibodies is combined with those disclosed herein, such as those discussed by Lisboa Bastos M et al. (Diagnostic accuracy of serological tests for covid-19: systematic review and meta-analysis. BMJ. 2020 Jul. 1; 370:m2516. doi: 10.1136/bmj.m2516).

Other commercially available tests include, but not limited to those listed in the Table below.

Commercially available tests for SARS-CoV-2 and COVID-19

| Company Name | Test Name |
|---|---|
| 3D Medicines | SARS-CoV-2 and Influenza A & B RT-qPCR Detection Kit |
| Abbott | SARS-CoV-2 IgG test |
| Abbott | ID Now COVID-19 |
| Abbott | Abbott RealTime SARS-CoV-2 EUA test |
| Anatolia Geneworks | Bosphore Novel Coronavirus (2019-nCoV) Detection Kit |
| ARUP Laboratories | COVID-19 |
| A*STAR, Tan Tock Seng Hospital of Singapore | A*STAR Fortitude 2.0 |
| Assure Tech | COVID-19 IgG/IgM Rapid Test Device |
| Atila BioSystems | iAMP COVID-19 Detection Kit |
| AusDiagnostics | AusDiagnostics SARS-CoV-2, influenza, RSV panel |
| Autobio Diagnostics | Anti-SARS-CoV-2 Rapid Test |
| Avellino Lab | Avellino SARS-CoV-2/COVID-19 (AvellinoCoV2) |
| Bako Diagnostics | BakoDx SARS-CoV-2 RNA test |
| Baptist Hospital Miami Pathology/Laboratory Medicine Lab | COVID-19 RT-PCR Test |
| Becton Dickinson | BD SARS-CoV-2 Reagents for BD MAX System |
| Becton Dickinson, BioGx | BioGX SARS-CoV-2 Reagents for the BD MAX System |
| Beijing Decombio Biotechnology | Novel Coronavirus IgM/IgG Combo Rapid Test-Cassette |
| Beijing Diagreat Biotechnologies | 2019-nCoV IgG, IgM Antibody Determination Kits 2019-nCoV IgG/IgM Antibody Rapid Test Kit |
| Beijing Kewei Clinical Diagnostic Reagent | Genonto RapidTest10 COVID-19 IgG/IgM Antibody Rapid Test Kit |
| Beijing O&D Biotech | Coronavirus disease (COVID-19) Total Antibody Rapid Test (Colloidal Gold) |
| Beroni Group | SARS-CoV-2 IgG/IgM Antibody Detection Kit |
| BGI | Real-Time Fluorescent RT-PCR kit for detecting SARS-2019-nCoV |
| Biodesix | SARS-CoV-2 Droplet Digital PCR (ddPCR) test |
| Biolidics | 2019-nCoV IgG/IgM Detection Kit (Colloidal Gold) |
| BioMedomics | COVID-19 IgM-IgG Rapid Test |
| BioMérieux | SARS-COV-2 R-GENE test |
| BioMérieux/BioFire Defense | BioFire COVID-19 test |
| Bioneer | AccuPower COVID-19 Real-Time RT-PCR Kit, AccuPower SARS-CoV-2 Real-Time RT-PCR Kit |
| Bio-Rad Laboratories | SARS-CoV-2 Total Ab test |
| BioReference Laboratories | Novel Coronavirus COVID-19 |
| Boston Children's Hospital Infectious Diseases Diagnostic Laboratory (IDDL) | Childrens-Altona-SARS-CoV-2 assay |
| BTNX | Rapid Response COVID-19 IgG/IgM Test Cassette |
| Cellex | qSARS-CoV-2 IgG/IgM Rapid Test |
| Centers for Disease Control and | CDC 2019-Novel Coronavirus (2019-nCoV) Real- |

-continued

Commercially available tests for SARS-CoV-2 and COVID-19

| Company Name | Test Name |
|---|---|
| Prevention (performed at qualified high-complexity CLIA laboratories designated by CDC) | Time RT-PCR Diagnostic Panel (CDC) |
| Cepheid | Xpert Xpress SARS-CoV-2 test |
| CerTest BioTec | ViaSure SARS-CoV-2 Real Time PCR Detection Kit |
| Chembio Diagnostics | DDP COVID-19 IgM/IgG System |
| Children's Hospital of Philadelphia Infectious Disease Diagnostics Laboratory | SARS-CoV-2 RT-PCR test |
| ChromaCode | HDPCR SARS-CoV-2 real-time PCR assay |
| CirrusDx Laboratories | CirrusDx SARS-CoV-2 Assay |
| Co-Diagnostics | Logix Smart Coronavirus Disease 2019 (COVID-19) Kit |
| Core Technology | CoreTest COVID-19 IgM/IgG Ab Test |
| Credo Diagnostics Biomedical | VitaPCR SARS-CoV2 Assay |
| DiaCarta | QuantiVirus SARS-CoV-2 test kit |
| Diagnostic Solutions Laboratory | COVID-19 Assay |
| DiaSorin Molecular | Simplexa COVID-19 Direct |
| Diatherix Eurofins | COVID-19 Panel |
| Diazyme Laboratories | Diazyme DZ-LITE SARS-CoV-2 IgG, IgM CLIA Kits |
| Eachy Biopharmaceuticals | AccuRapid SARS-CoV-2 IgM/IgG Test Kit (Lateral Flow Immunoassay) |
| Euroimmun/PerkinElmer | EuroRealTime SARS-CoV-2 |
| Euroimmun/PerkinElmer | Anti-SARS-CoV-2 ELISAs (IgA and IgG) |
| Exact Sciences | SARS-CoV-2 Test |
| Fosun Pharma USA | Fosun COVID-19 RT-PCR Detection Kit |
| Fulgent Genetics/MedScan Laboratory | COVID-19 |
| Genetic Signatures | Easy Screen SARS-CoV-2 detection kit |
| Genetron | Detection Kit for Novel Coronavirus (SARS-CoV-2) RNA (PCR-Fluorescence Probing) |
| GenMark Diagnostics | ePlex SARS-CoV-2 Test |
| Genomica/PharmMar Group | 2 kits: qCOVID-19, CLART COVID-19 |
| GenoSensor | GS COVID-19 RT-PCR Kit |
| Gnomegen | Gnomegen COVID-19 RT-Digital PCR Detection Kit |
| Gold Standard Diagnostics | SARS-CoV-2 IgG, IgM, IgA assays |
| Guangzhou Wondfo Biotech | SARS-CoV-2 Antibody Test |
| Hackensack University Medical Center (HUMC) Molecular Pathology Laboratory | CDI Enhanced COVID-19 Test |
| Hangzhou AllTest Biotech | AllTest 2019-nCoV IgG/IgM Rapid Test Cassette, AllTest COVID IgG/IgM Rapid Test Dipstick |
| Hangzhou Biotest Biotech | COVID-19 IgG/IgM Rapid Test Cassette |
| Hangzhou Clongene Biotech | Clungene COVID-19 IgM/IgG Rapid Test Cassette |
| Hangzhou Testsealabs Biotechnology | One Step SARS-CoV2 (COVID-19) IgG/IgM Test |
| Healgen Scientific | COVID-19 IgG/IgM Rapid Test Cassette(Whole Blood/Serum/Plasma) |
| Hologic | Panther Fusion SARS-CoV-2 assay |
| InBios International | Smart Detect SARS-CoV-2 rRT-PCR Kit |
| Innovita (Tangshan) Biological Technology | 2019-nCoV Ab Test (Colloidal Gold) |
| Integrated DNA Technologies/Danaher | IDT 2019-novel coronavirus kit |
| Integrity Laboratories | SARS-CoV-2 Assay |
| Ipsum Diagnostics | CoV-19 IDx assay |
| Jiangsu Macro & Micro-Test Med-Tech | SARS-CoV-2 IgM/IgG Rapid Assay Kit (Colloidal Gold) |
| JN Medsys | ProTect Covid-19 kit |
| Kogene Biotech | 2019 Novel Coronavirus Real-time PCR Kit |
| KorvaLabs | Curative-Korva SARS-Cov-2 Assay |
| Laboratory Corporation of America | LabCorp 2019 Novel Coronavirus test |
| LGC, Biosearch Technologies | 2019-nCoV CDC-qualified Probe and Primer Kits for SARS-CoV-2 |
| Lifeassay Diagnostics | Test-it COVID-19 IgM/IgG Lateral Flow Assay |
| Luminex | ARIES SARS-CoV-2 Assay |
| Luminex | NxTAGCoV Extended Panel Assay |
| Maccura Biotechnology | SARS-CoV-2 Fluorescent PCR Kit |
| Massachusetts General Hospital | MGH COVID-19 qPCR assay |
| Medical Systems Biotechnology | Coronavirus Disease 2019 Antibody (IgM/IgG) Combined Test Kit |
| Mesa Biotech | Accula SARS-CoV-2 test |
| Mount Sinai Labs | COVID-19 ELISA IgG Antibody Test |

-continued

| Commercially available tests for SARS-CoV-2 and COVID-19 | |
|---|---|
| Company Name | Test Name |
| Nanjing Liming Bio-products | SARS-CoV-2 IgM/IgG Antibody Rapid Test Kit |
| NanoResearch | NanoMedicina SARS-CoV-2 IgM/IgG Antibody Rapid Test |
| Nantong Diagnos Biotechnology | (2019-nCoV) New coronavirus Antibody Test (Colloidal Gold) |
| NeuMoDx Molecular | NeuMoDx SARS-CoV-2 Assay |
| Nirmidas Biotech | COVID-19 (SARS-CoV-2) IgM/IgG Antibody Detection Kit |
| Northwestern Medicine Diagnostic Molecular Laboratory | SARS-Cov-2 Assay |
| Novacyt/Primerdesign | COVID-19 Genesig Real-Time PCR assay |
| NY State Department of Health (performed at Wadsworth Center and New York City Department of Health and Mental Hygiene, Public Health Laboratories) | New York SARS-CoV-2 Real-time Reverse Transcriptase (RT)-PCR Diagnostic Panel |
| Orig3n | Orig3n 2019 Novel Coronavirus (COVID-19) Test |
| Ortho Clinical Diagnostics | Vitros Immunodiagnostic Products Anti-SARS-CoV-2 Total Reagent Pack and Calibrators |
| Osang Healthcare | GeneFinder COVID-19 Plus RealAmp Kit |
| PathoFinder | RealAccurate Quadruplex Corona-plus PCR Kit |
| PCL | COVID19 IgG/IgM Rapid Gold |
| PerkinElmer | PerkinElmer New Coronavirus Nucleic Acid Detection Kit |
| Phamatech | COVID19 IgG/IgM Rapid Test |
| Promedical | COVID-19 Rapid Test, Wondfo SARS-CoV-2 Antibody Test (Lateral Flow Method) |
| Qiagen | QiaStat-Dx Respiratory SARS-CoV-2 Panel |
| Quest Diagnostics | Coronavirus Disease 2019 (COVID-19) Test |
| Quidel | Lyra SARS-CoV-2 Assay |
| Rendu Biotechnology | 2019-nCoV detection kit |
| Roche | Cobas SARS-CoV-2 Test |
| Rutgers University Clinical Genomics Laboratory | ThermoFisher - Applied Biosystems TaqPath COVID-19 Combo Kit |
| ScienCell Research Laboratories | ScienCell SARS-CoV-2 Coronavirus Real-time RT-PCR (RT-qPCR) Detection Kit |
| SD Biosensor | Standard Q COVID-19 IgM/IgG Duo |
| Seegene | Allplex 2019-nCoV Assay |
| Sentinel Diagnostics | STAT-NAT COVID-19 HK kit, B kit |
| Shanghai Fosun Long March Medical Science/Shanghai Fosun Pharmaceutical | novel coronavirus nucleic acid detection kit |
| Shenzhen Landwind Medical | COVID-19 IgG/IgM Rapid Test Device |
| Snibe Diagnostics | Maglumi 2019-nCoV (SARS-CoV-2) IgM/IgG kits |
| SolGent | DiaPlexQ Novel Coronavirus (2019-nCoV) Detection kit |
| Specialty Diagnostic (SDI) Laboratories | SDI SARS-CoV-2 Assay |
| Stanford Health Care Clinical Virology Laboratory | SARS-CoV-2 PCR Assay |
| SureScreen Diagnostics | SureScreen COVID19 IgM/IgG Rapid Test Cassette |
| Suzhou Kangheshun Medical Technology | SARS-CoV-2 IgG/IgM Rapid Test Cassette |
| Systaaq Diagnostic Products | 2019-Novel Coronavirus (COVID-19) Real Time PCR Kit |
| Telepoint Medical Services | SARS-CoV-2 IgG/IgM Rapid Qualitative Test |
| Thermo Fisher Scientific | TaqPath COVID-19 Combo Kit, RT-PCR CE-IVD Kit |
| Tianjin Beroni Biotechnology | SARS-CoV-2 IgG/IgM Antibody Detection Kit |
| TIB Molbiol Syntheselabor | Sarbecovirus E-gene |
| Trax Management Services | Phoenix Dx 2019-CoV |
| United Biomedical | UBI SARS-CoV-2 ELISA |
| University of North Carolina Medical Center | UNC Health SARS-CoV-2 real-time RT-PCR test |
| Vela Diagnostics | ViroKey SARS-CoV-2 RT-PCR Test |
| Viracor Eurofins | Viracor SARS-CoV-2 assay |
| Vision Medicals | SARS-CoV-2 Clinical Sequencing assay |
| VivaChek Biotech (Hangzhou) | VivaDiag COVID-19 IgM/IgG Rapid Test |
| Yale New Haven Hospital Clinical Virology Laboratory | SARS-CoV-2 PCR test |
| YD Diagnostics | MolecuTech Real-Time COVID-19 |
| Zhejiang Orient Gene Biotech | COVID-19 IgG/IgM Rapid Test Cassette |
| Zhengzhou Fortune Bioscience | IgG/IgM Antibody Rapid Test Kits (Colloidal Gold Immunochromatography method) |
| Zhongshan Bio-Tech | SARS-CoV-2 IgM/IgG (GICA) |
| Zhuhai Encode Medical | Novel Coronavirus (COVID-19) IgG/IgM Rapid Test |

-continued

| Commercially available tests for SARS-CoV-2 and COVID-19 | |
|---|---|
| Company Name | Test Name |
| Engineering | Device |
| Zhuhai Livzon Diagnostics | Diagnostic Kit for IgM/IgG Antibody to Coronavirus (SARS-CoV-2) (Colloidal Gold) |

The term "protein", "peptide" and "polypeptide" are used interchangeably and in their broadest sense to refer to a compound of two or more subunit amino acids, amino acid analogs or peptidomimetics. The subunits (which are also referred to as residues) may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the terms "spike protein," "spike glycoprotein" or "S protein" are used interchangeably, referring to a glycoprotein projecting from the lipid bilayer of the surface of an enveloped virus, such as SARS-CoV-2. In some embodiments, an S protein refers to an S protein of a SARS-CoV-2. In further embodiments, an S protein or an equivalent thereof as used herein also refers to an S protein variant (for example, an S protein of a naturally occurring SARS-CoV-2 variant, such as an Omicron variant), an S protein mutant (for example, a mutated S protein as disclosed herein), an S protein fragment (such as an immunogenic fragment), or any combination thereof (such as, a naturally occurring variant engineered with additional mutation(s), or a fragment thereof).

In some embodiments, an S protein as used herein comprises, or consists essentially of, or yet further consists of an S1 polypeptide or an S2 polypeptide or both. In some embodiments, an S protein as used herein is a precursor protein comprising, or consisting essentially of, or yet further consisting of both S1 and S2. Such precursor can be processed into S1 and S2 by Cathepsin L (CTSL), Transmembrane Serine Protease (TMPRSS2) or furin to yield the mature S1 and S2 protein. In some embodiments, the S protein as used herein refers to a protein complex comprising, or consisting essentially of, or yet further consisting of a mature S1 protein and a mature S2 protein. In other embodiments, the S protein as used herein refers to an S1 protein. In yet other embodiments, the S protein as used herein refers to an S2 protein. In some embodiments, the precursor protein comprises, or consists essentially of, or yet further consists of the polypeptide as set forth in SEQ ID NO: 1 or an equivalent thereof. In some embodiments, the S1 protein comprises, or consists essentially or, or yet further consists of the polypeptide as set forth in amino acid (aa) 13 to aa 685 of SEQ ID NO: 1 or an equivalent thereof. In some embodiments, the S2 protein comprises, or consists essentially or, or yet further consists of the polypeptide as set forth in amino acid (aa) 686 to aa 1273 of SEQ ID NO: 1 or an equivalent thereof. In some embodiments, the S2 protein comprises, or consists essentially or, or yet further consists of the polypeptide as set forth in amino acid (aa) 816 to aa 1273 of SEQ ID NO: 1 or an equivalent thereof. Further non-limiting exemplary sequences of an S protein or the underlying gene may be found under Gene ID: 43740568 (retrieved from www.ncbi.nlm.nih.gov/gene/43740568, last accessed on Aug. 1, 2021), NCBI Reference Sequence: NC_045512.2 (retrieved from www.ncbi.nlm.nih.gov/nuccore/NC_045512.2/, last accessed on Aug. 1, 2021) or UniProtKB/Swiss-Prot: PODTC2 (retrieved from www.uniprot.org/uniprot/PODTC2, last accessed on Aug. 1, 2021), which are incorporated by reference herein.

In some embodiments, a fragment (such as an immunogenic fragment) of an S protein comprises, or consists essentially of, or yet further consists of a receptor binding domain (RBD) of the S protein. In some embodiments, a receptor-binding domain (RBD) refers to a short immunogenic fragment from a virus that binds to a specific endogenous receptor sequence to gain entry into target cells. In some embodiments, RBD refer to a part of the 'spike' glycoprotein (S-domain) which is needed to interact with endogenous receptors to facilitate membrane fusion and delivery to the cytoplasm. In some embodiments, the RBD as used herein comprises, or consists essentially of, or yet further consists of the polypeptide as set forth in aa 319 to aa 541 of SEQ ID NO: 1 or an equivalent thereof.

As used herein the term "angiotensin converting enzyme 2" or "ACE2" refers to an enzyme attached to the membrane of cells optionally located in the intestines, kidney, testis, gallbladder, and heart. ACE2 serves as the entry point into cells for some coronaviruses, including HCoV-NL63, SARS-CoV, and SARS-CoV-2. The SARS-CoV-2 spike protein itself is known to damage the epithelium via downregulation of ACE2. In some embodiments, the term "ACE2" refers to a human ACE2. Non-limiting exemplary sequences of this protein or the underlying gene may be found under Gene Cards ID: GC0XM015494 (retrieved from www.genecards.org/cgi-bin/carddisp.pl?gene=ACE2, last accessed on Aug. 1, 2021), HGNC: 13557 (retrieved from www.genenames.org/data/gene-symbol-report/#!/hgnc_id/13557, last accessed on Aug. 1, 2021), NCBI Entrez Gene: 59272 (retrieved from www.ncbi.nlm.nih.gov/gene/59272, last accessed on Aug. 1, 2021), Ensembl: ENSG00000130234 (retrieved from useast.ensembl.org/Homo_sapiens/Gene/Summary?g=ENSG00000130234;r=X:15494566-15607236, last accessed on Aug. 1, 2021), OMIM®: 300335 (retrieved from omim.org/entry/300335, last accessed on Aug. 1, 2021), or UniProtKB/Swiss-Prot: Q9BYF1 (retrieved from www.uniprot.org/uniprot/Q9BYF1, last accessed on Aug. 1, 2021), which are incorporated by reference herein.

As used herein the term "Transmembrane Serine Protease 2" or "TMPRSS2" refers to protein comprising a type II transmembrane domain, a receptor class A domain, a scavenger receptor cysteine-rich domain and a protease domain. This protein facilitates entry of viruses into host cells by proteolytically cleaving and activating viral envelope glycoproteins. Viruses found to use this protein for cell entry include Influenza virus and the human coronaviruses HCoV-229E, MERS-CoV, SARS-CoV and SARS-CoV-2. In some embodiments, the term "TMPRSS2" refers to a human TMPRSS2. Non-limiting exemplary sequences of this protein or the underlying gene may be found under Gene Cards ID GC21M041464 (retrieved from www.genecards.org/cgi-bin/carddisp.pl?gene=TMPRSS2, last accessed on Aug. 1, 2021), HGNC: 11876 (retrieved from www.genenames.org/data/gene-symbol-report/#!/hgnc_id/11876, last accessed on Aug. 1, 2021), NCBI Entrez Gene: 7113 (retrieved from www.ncbi.nlm.nih.gov/gene/7113, last accessed on Aug. 1, 2021), Ensembl: ENSG00000184012 (retrieved from useast.ensembl.org/Homo_sapiens/Gene/Summary?g=ENSG00000184012;r=21:41464300-41531116, last accessed on Aug. 1, 2021), OMIM®: 602060 (retrieved from omim.org/entry/602060, last accessed on Aug. 1, 2021), or UniProtKB/Swiss-Prot: O15393 (retrieved from www.uniprot.org/uniprot/O15393, last accessed on Aug. 1, 2021), which are incorporated by reference herein.

As used herein the term "Cathepsin L" or "CTSL" refers to a protein, which is a member of the peptidase C1 family, and a dimer composed of disulfide-linked heavy and light chains, both produced from a single protein precursor. Additionally, this protein cleaves the S1 subunit of the SARS-CoV-2 spike protein, which is necessary for entry of the virus into the cell. In some embodiments, the term "CTSL" refers to a human CTSL. Non-limiting exemplary sequences of this protein or the underlying gene may be found under Gene Cards ID GC09P087725 (retrieved from www.genecards.org/cgi-bin/carddisp.pl?gene=CTSL, last accessed on Aug. 1, 2021), HGNC: 2537 (retrieved from www.genenames.org/data/gene-symbol-report/#!/hgnc_id/2537, last accessed on Aug. 1, 2021), NCBI Entrez Gene: 1514 (retrieved from www.ncbi.nlm.nih.gov/gene/1514, last accessed on Aug. 1, 2021), Ensembl: ENSG00000135047 (retrieved from useast.ensembl.org/Homo_sapiens/Gene/Summary?g=ENSG00000135047;r=9:87724051-87731469, last accessed on Aug. 1, 2021), OMIM®: 116880 (retrieved from omim.org/entry/116880, last accessed on Aug. 1, 2021), or UniProtKB/Swiss-Prot: P07711 (retrieved from www.uniprot.org/uniprot/P07711, last accessed on Aug. 1, 2021), which are incorporated by reference herein.

As used herein the term "furin" refers to is a protease enzyme capable of cleavage at the RX(K/R)R, (RXR, RKR or RRR)) consensus motif, wherein X is any amino acid or alternatively K or R. It also facilitates SARS-CoV-2 infections by proteolytically cleaving the spike protein at the monobasic S1/S2 cleavage site, RRAR (SEQ ID NO: 48). This cleavage is essential for spike protein-mediated cell-cell fusion and entry into human lung cells. In some embodiments, the term furin refers to a mammal furin, such as a bovine furin, see for example UniProtKB Q28193 retrieved from www.uniprot.org/uniprot/Q28193 last accessed on Aug. 10, 2021. In some embodiments, the term "furin" refers to a human furin. Non-limiting exemplary sequences of this protein or the underlying gene may be found under Gene Cards ID: GC15P090868 (retrieved from www.genecards.org/cgi-bin/carddisp.pl?gene=FURIN, last accessed on Aug. 1, 2021), HGNC: 8568 (retrieved from www.genenames.org/data/gene-symbol-report/#!/hgnc_id/8568, last accessed on Aug. 1, 2021), NCBI Entrez Gene: 5045 (retrieved from www.ncbi.nlm.nih.gov/gene/5045, last accessed on Aug. 1, 2021), Ensembl: ENSG00000140564 (retrieved from useast.ensembl.org/Homo_sapiens/Gene/Summary?g=ENSG00000140564;r=15:90868588-90883564, last accessed on Aug. 1, 2021), OMIM®: 136950 (retrieved from omim.org/entry/136950, last accessed on Aug. 1, 2021), or UniProtKB/Swiss-Prot: P09958 (retrieved from www.uniprot.org/uniprot/P09958, last accessed on Aug. 1, 2021), which are incorporated by reference herein.

In some embodiments, a fragment of a protein can be an immunogenic fragment. As used herein, the term "immunogenic fragment" refers to such a polypeptide fragment, which at least partially retains the immunogenicity of the protein from which it is derived. In some embodiments, the immunogenic fragment is at least about 3 amino acid (aa) long, or at least about 4 aa long, or at least about 5 aa long, or at least about 6 aa long, or at least about 7 aa long, or at least about 8 aa long, or at least about 9 aa long, or at least about 10, aa long, or at least about 15, aa long, or at least about 20 aa long, or at least about 25 aa long, or at least about 30 aa long, or at least about 35 aa long, or at least about 40 aa long, or at least about 50 aa long, or at least about 60 aa long, or at least about 70 aa long, or at least about 80 aa long, or at least about 90 aa long, or at least about 100 aa long, or at least about 120 aa long, or at least about 150 aa long, or at least about 200, or longer. In some embodiments, an immunogenic fragment of an S protein comprises, or alternatively consists essentially of, or yet further consists of an RBD of the S protein.

As used herein, an amino acid (aa) or nucleotide (nt) residue position in a sequence of interest "corresponding to" an identified position in a reference sequence refers to that the residue position is aligned to the identified position in a sequence alignment between the sequence of interest and the reference sequence. Various programs are available for performing such sequence alignments, such as Clustal Omega and BLAST. In one aspect, equivalent polynucleotides, proteins and corresponding sequences can be determined using BLAST (accessible at blast.ncbi.nlm.nih.gov/Blast.cgi, last accessed on Aug. 1, 2021).

As used herein, an amino acid mutation is referred to herein as two letters separated by an integer, such as T19R. The first letter provides the one letter code of the original amino acid residue to be mutated; while the last letter provides the mutation, such as Δ indicating a deletion, or one letter code of the mutated amino acid residue. In some embodiments, the integer is the numbering of the to-be-mutated amino acid residue in the amino acid sequence free of the mutation, optionally counting from the N terminus to the C terminus. In some embodiments, the integer is the numbering of the mutated amino acid residue in the mutated amino acid sequence, optionally counting from the N terminus to the C terminus. In some embodiments, the integer is the numbering of the amino acid residue in SEQ ID NO: 1 that corresponds to (such as aligned to) the to-be-mutated residue or the mutated residue or both.

It is to be inferred without explicit recitation and unless otherwise intended, that when the present disclosure relates to a polypeptide, protein, polynucleotide, an equivalent or a biologically equivalent of such is intended within the scope of this disclosure. As used herein, the term "biological equivalent thereof" is intended to be synonymous with "equivalent thereof" when referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity, or at least about 85% homology or identity, or alternatively at least about 90% homology or identity, or alternatively at least about 95% homology or identity, or alternatively at least about 96% homology or identity, or alternatively at least about 97% homology or identity, or alternatively at least about 98% homology or identity, or alternatively at least about 99% homology or identity (in one aspect, as determined using the Clustal Omega alignment program) and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complementary sequence.

An equivalent of a reference polypeptide comprises, consists essentially of, or alternatively consists of an polypeptide having at least 80%, or at least 85%, or at least 90%, or at least 95%, or at least about 96%, or at least 97%, or at least 98%, or at least 99% amino acid identity to the reference polypeptide (as determined, in one aspect using the Clustal Omega alignment program or using BLAST (accessible at blast.ncbi.nlm.nih.gov/Blast.cgi, last accessed on Aug. 1, 2021)), or a polypeptide that is encoded by a polynucleotide that hybridizes under conditions of high stringency to the complementary sequence of a polynucleotide encoding the reference polypeptide, optionally wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, a first sequence (nucleic acid sequence or amino acid) is compared to a second sequence, and the identity percentage between the two sequences can be calculated. In further embodiments, the first sequence can be referred to herein as an equivalent and the second sequence can be referred to herein as a reference sequence. In yet further embodiments, the identity percentage is calculated based on the full-length sequence of the first sequence. In other embodiments, the identity percentage is calculated based on the full-length sequence of the second sequence.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "RNA" as used herein refers to its generally accepted meaning in the art. Generally, the term RNA refers to a polynucleotide comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, for example at one or more nucleotides of the RNA. Nucleotides in the nucleic acid molecules can also comprise non-standard nucleotides, such as non-naturally occurring nucleotides or chemically synthesized nucleotides or deoxynucleotides. These altered RNAs can be referred to as analogs or analogs of naturally-occurring RNA. In some embodiments, the RNA is a messenger RNA (mRNA).

"Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. In some embodiments, an mRNA as disclosed herein comprises, or consists essentially of, or yet further consists of at least one coding region, a 5' untranslated region (UTR), a 3' UTR, a 5' cap and a poly-A tail.

Vaccination is the most successful medical approach to disease prevention and control. The successful development and use of vaccines has saved thousands of lives and large amounts of money. A key advantage of RNA vaccines is that RNA can be produced in the laboratory from a DNA template using readily available materials, less expensively and faster than conventional vaccine production, which can require the use of chicken eggs or other mammalian cells. In addition, mRNA vaccines have the potential to streamline vaccine discovery and development, and facilitate a rapid response to emerging infectious diseases, see, for example, Maruggi et al., *Mol Ther.* 2019; 27(4):757-772.

Preclinical and clinical trials have shown that mRNA vaccines provide a safe and long-lasting immune response in animal models and humans. mRNA vaccines against infectious diseases may be developed as prophylactic or therapeutic treatments. mRNA vaccines expressing antigens of infectious pathogens have been shown to induce potent T cell and humoral immune responses. See, for example, Pardi et al., *Nat Rev Drug Discov.* 2018; 17:261-279. The production procedure to generate mRNA vaccines is cell-free, simple, and rapid, compared to production of whole microbe, live attenuated, and subunit vaccines. This fast and simple manufacturing process makes mRNA a promising bio-product that can potentially fill the gap between emerging infectious disease and the desperate need for effective vaccines.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, or protein, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, or protein, does not require "isolation" to distinguish it from its naturally occurring counterpart.

In some embodiments, the term "engineered" or "recombinant" refers to having at least one modification not normally found in a naturally occurring protein, polypeptide, polynucleotide, strain, wild-type strain or the parental host strain of the referenced species. In some embodiments, the term "engineered" or "recombinant" refers to being synthetized by human intervention. As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "complementary" sequences refer to two nucleotide sequences which, when aligned anti-parallel to each other, contain multiple individual nucleotide bases which pair with each other. Paring of nucleotide bases forms hydrogen bonds and thus stabilizes the double strand structure formed by the complementary sequences. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In some embodiments, the term complementary refers to 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide. Nucleotide bases paring is known in the field, such as in DNA, the purine adenine (A) pairs with the pyrimidine thymine (T) and the pyrimidine cytosine (C) always pairs with the purine guanine (G); while in RNA, adenine (A) pairs with uracil (U) and guanine (G) pairs with cytosine (C). Further, the nucleotide bases aligned anti-parallel to each other in two complementary sequences, but not a pair, are referred to herein as a mismatch.

A "gene" refers to a polynucleotide containing at least one open reading frame (ORF) that is capable of encoding a particular polypeptide or protein after being transcribed and translated.

The term "express" refers to the production of a gene product, such as mRNA, peptides, polypeptides or proteins. As used herein, "expression" refers to the process by which polynucleotides are transcribed into mRNA or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated. In some embodiments, the gene product may refer to an mRNA or other RNA, such as an interfering RNA, generated when a gene is transcribed.

The term "encode" as it is applied to polynucleotides refers to a polynucleotide which is said to "encode" a polypeptide if, in its native state or when manipulated by methods well known to those skilled in the art, it can be transcribed to produce the mRNA for the polypeptide or a fragment thereof, and optionally translated to produce the polypeptide or a fragment thereof. The antisense strand is the complement of such a nucleic acid, and the encoding sequence can be deduced therefrom. Further, as used herein an amino acid sequence coding sequence refers to a nucleotide sequence encoding the amino acid sequence.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. In some embodiments, the term refers to the ribonucleotide modifications in naturally occurring 5'-terminal mRNA cap moieties. In further embodiments, the chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, or 2'-O-methyl uridine. In some embodiments the extent of incorporation of chemically modified nucleotides has been optimized for improved immune responses to the vaccine formulation. In other embodiments, the term excludes the ribonucleotide modifications in naturally occurring 5'-terminal mRNA cap moieties.

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified by one or more of modifications as disclosed herein. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified by one or more of modifications as disclosed herein.

In some embodiments, an RNA as disclosed herein is optimized. Optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide.

A “3' untranslated region” (3' UTR) refers to a region of an mRNA that is directly downstream (i.e., 3') from the stop codon (i.e., the codon of an mRNA transcript that signals a termination of translation) that does not encode a polypeptide. In some embodiments, a 3' UTR as used herein comprises, or consists essentially of, or yet further consists of one or more of SEQ ID NOs: 18, 22, or 24.

A “5' untranslated region” (5' UTR) refers to a region of an RNA that is directly upstream (i.e., 5') from the start codon (i.e., the first codon of an mRNA transcript translated by a ribosome) that does not encode a polypeptide. In some embodiments, a 5' UTR as used herein comprises, or consists essentially of, or yet further consists of one or both of SEQ ID NO: 20 or 26.

A “polyA tail” is a region of mRNA that is downstream, e.g., directly downstream (i.e., 3'), from the 3' UTR that contains multiple, consecutive adenosine monophosphates. A polyA tail may contain 10 to 300 adenosine monophosphates (SEQ ID NO: 59). Additionally or alternatively, in a relevant biological setting (e.g., in cells, in vivo) the polyA tail functions to protect mRNA from enzymatic degradation, e.g., in the cytoplasm, and aids in transcription termination, export of the mRNA from the nucleus and translation. In some embodiments, a polyA tail as used herein comprises, or consists essentially of, or yet further consists of one or more of: SEQ ID NOs: 27, 28, 30, 53 or 54.

In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., *Methods Mol Biol.* 703:29-41(2011); Rio et al. RNA: A Laboratory Manual. Cold Spring Harbor: Cold Spring Harbor Laboratory Press, 2011, 205-220; and Cooper, Geoffery M. The Cell: A Molecular Approach. 4th ed. Washington D.C.: ASM Press, 2007, 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

It will be appreciated that an RNA as disclosed herein can be made using any appropriate synthesis method. For example, in some embodiments, an RNA is made using IVT from a single bottom strand DNA as a template and complementary oligonucleotide that serves as promotor. The single bottom strand DNA may act as a DNA template for in vitro transcription of RNA, and may be obtained from, for example, a plasmid, a PCR product, or chemical synthesis. In some embodiments, the single bottom strand DNA is linearized from a circular template. The single bottom strand DNA template generally includes a promoter sequence, e.g., a bacteriophage promoter sequence, to facilitate IVT. Methods of making RNA using a single bottom strand DNA and a top strand promoter complementary oligonucleotide are known in the art. An exemplary method includes, but is not limited to, annealing the DNA bottom strand template with the top strand promoter complementary oligonucleotide (e.g., T7 promoter complementary oligonucleotide, T3 promoter complementary oligonucleotide, or SP6 promoter complementary oligonucleotide), followed by IVT using an RNA polymerase corresponding to the promoter sequence, e.g., a T7 RNA polymerase, a T3 RNA polymerase, or an SP6 RNA polymerase.

IVT methods can also be performed using a double-stranded DNA template. For example, in some embodiments, the double-stranded DNA template is made by extending a complementary oligonucleotide to generate a complementary DNA strand using strand extension techniques available in the art. In some embodiments, a single bottom strand DNA template containing a promoter sequence and sequence encoding one or more epitopes of interest is annealed to a top strand promoter complementary oligonucleotide and subjected to a PCR-like process to extend the top strand to generate a double-stranded DNA template. Alternatively or additionally, a top strand DNA containing a sequence complementary to the bottom strand promoter sequence and complementary to the sequence encoding one or more epitopes of interest is annealed to a bottom strand promoter oligonucleotide and subjected to a PCR-like process to extend the bottom strand to generate a double-stranded DNA template. In some embodiments, the number of PCR-like cycles ranges from 1 to 20 cycles, e.g., 3 to 10 cycles. In some embodiments, a double-stranded DNA template is synthesized wholly or in part by chemical synthesis methods. The double-stranded DNA template can be subjected to in vitro transcription as described herein.

“Under transcriptional control”, which is also used herein as “directing expression of” or any grammatical variation thereof, is a term well understood in the art and indicates that transcription and optionally translation of a polynucleotide sequence, usually a DNA sequence, depends on its being operatively linked to an element which contributes to the initiation of, or promotes, transcription.

“Operatively linked” intends the polynucleotides are arranged in a manner that allows them to function in a cell.

The term “a regulatory sequence”, “an expression control element” or “promoter” as used herein, intends a polynucleotide that is operatively linked to a target polynucleotide to be transcribed or replicated, and facilitates the expression or replication of the target polynucleotide.

A promoter is an example of an expression control element or a regulatory sequence. Promoters can be located 5' or upstream of a gene or other polynucleotide, that provides a control point for regulated gene transcription. In some embodiments, a promoter as used herein is corresponding to the RNA polymerase. In further embodiments, a promoter as sued herein comprises, or consists essentially of, or yet further consists of a T7 promoter, or a SP6 promoter, or a T3 promoter. Non-limiting examples of suitable promoters are provided in WO2001009377A1.

An "RNA polymerase" refers to an enzyme that produces a polyribonucleotide sequence, complementary to a pre-existing template polynucleotide (DNA or RNA). In some embodiments, the RNA polymerase is a bacteriophage RNA polymerase, optionally a T7 RNA polymerase, or a SP6 RNA polymerase, or a T3 RNA polymerase. Non-limiting examples of suitable polymerase are further detailed in U.S. Ser. No. 10/526,629B2.

In some embodiments, the term "vector" intends a recombinant vector that retains the ability to infect and transduce non-dividing and/or slowly-dividing cells and optionally integrate into the target cell's genome. Non-limiting examples of vectors include a plasmid, a nanoparticle, a liposome, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. In one embodiment, the viral vector is a retroviral vector. In one embodiment, the vector is a plasmid. In one embodiment, the vector is a nanoparticle, optionally a polymeric nanoparticle or a lipid nanoparticle.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances. Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "viral vector" is defined as a recombinantly produced virus or viral particle that comprises a polynucleotide to be delivered into a host cell, either in vivo, ex vivo or in vitro. As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. As used herein, Multiplicity of infection (MOI) refers to the number of viral particles that are added per cell during infection.

A retrovirus such as a gammaretrovirus and/or a lentivirus comprises (a) envelope comprising lipids and glycoprotein, (b) a vector genome, which is a RNA (usually a dimer RNA comprising a cap at the 5' end and a polyA tail at the 3' end flanked by LTRs) derived to the target cell, (c) a capsid, and (d) proteins, such as a protease. U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11 sequentially numbered, AAV serotypes are known in the art. Non-limiting exemplary serotypes useful in the methods disclosed herein include any of the 11 serotypes, e.g., AAV2, AAV8, AAV9, or variant or synthetic serotypes, e.g., AAV-DJ and AAV PHP.B. The AAV particle comprises, alternatively consists essentially of, or yet further consists of three major viral proteins: VP1, VP2 and VP3. In one embodiment, the AAV refers to of the serotype AAV1, AAV2, AAV4, AAV5, AAV6, AAV7, AAV8, AAV9, AAV10, AAV 11, AAV12, AAV13, AAV PHP.B, or AAV rh74. These vectors are commercially available or have been described in the patent or technical literature.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

The term "a regulatory sequence" "an expression control element" or "promoter" as used herein, intends a polynucleotide that is operatively linked to a target polynucleotide to be transcribed and/or replicated, and facilitates the expression and/or replication of the target polynucleotide. A promoter is an example of an expression control element or a regulatory sequence. Promoters can be located 5' or upstream of a gene or other polynucleotide, that provides a control point for regulated gene transcription. Polymerase II and III are examples of promoters.

A polymerase II or "pol II" promoter catalyzes the transcription of DNA to synthesize precursors of mRNA, and most shRNA and microRNA. Examples of pol II promoters are known in the art and include without limitation, the phosphoglycerate kinase ("PGK") promoter; EF1-alpha; CMV (minimal cytomegalovirus promoter); and LTRs from retroviral and lentiviral vectors.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure. In some embodiments, the identity is calculated between two peptides or polynucleotides over their full-length, or over the shorter sequence of the two, or over the longer sequence of the two.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: blast.ncbi.nlm.nih.gov/Blast.cgi, last accessed on Aug. 1, 2021.

In some embodiments, the polynucleotide as disclosed herein is a RNA or an analog thereof. In some embodiments, the polynucleotide as disclosed herein is a DNA or an analog thereof. In some embodiments, the polynucleotide as disclosed herein is a hybrid of DNA and RNA or an analog thereof.

In some embodiments, an equivalent to a reference nucleic acid, polynucleotide or oligonucleotide encodes the same sequence encoded by the reference. In some embodiments, an equivalent to a reference nucleic acid, polynucleotide or oligonucleotide hybridizes to the reference, a complement reference, a reverse reference, or a reverse-complement reference, optionally under conditions of high stringency.

Additionally or alternatively, an equivalent nucleic acid, polynucleotide or oligonucleotide is one having at least 70% sequence identity, or at least 75% sequence identity, or at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence, or alternatively at least 99% sequence identity to the reference nucleic acid, polynucleotide, or oligonucleotide, or alternatively an equivalent nucleic acid hybridizes under conditions of high stringency to a reference polynucleotide or its complementary. In one aspect, the equivalent must encode the same protein or a functional equivalent of the protein that optionally can be identified through one or more assays described herein. In addition or alternatively, the equivalent of a polynucleotide would encode a protein or polypeptide of the same or similar function as the reference or parent polynucleotide.

The term "transduce" or "transduction" refers to the process whereby a foreign nucleotide sequence is introduced into a cell. In some embodiments, this transduction is done via a vector, viral or non-viral.

"Detectable label", "label", "detectable marker" or "marker" are used interchangeably, including, but not limited to radioisotopes, fluorochromes, chemiluminescent compounds, dyes, and proteins, including enzymes. Detectable labels can also be attached to a polynucleotide, polypeptide, protein or composition described herein.

As used herein, the term "label" or a detectable label intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In some embodiments, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, a purification label or maker refers to a label that may be used in purifying the molecule or component that the label is conjugated to, such as an epitope tag (including but not limited to a Myc tag, a human influenza hemagglutinin (HA) tag, a FLAG tag), an affinity tag (including but not limited to a glutathione-S transferase (GST), a poly-Histidine (His) tag, Calmodulin Binding Protein (CBP), or Maltose-binding protein (MBP)), or a fluorescent tag.

A "selection marker" refers to a protein or a gene encoding the protein necessary for survival or growth of a cell grown in a selective culture regimen. Typical selection markers include sequences that encode proteins, which confer resistance to selective agents, such as antibiotics, herbicides, or other toxins. Examples of selection markers include genes for conferring resistance to antibiotics, such as spectinomycin, streptomycin, tetracycline, ampicillin, kanamycin, G 418, neomycin, bleomycin, hygromycin, methotrexate, dicamba, glufosinate, or glyphosate.

The term "culturing" refers to the in vitro or ex vivo propagation of cells or organisms on or in media of various kinds. It is understood that the descendants of a cell grown in culture may not be completely identical (i.e., morphologically, genetically, or phenotypically) to the parent cell.

In some embodiments, the cell as disclosed herein is a eukaryotic cell or a prokaryotic cell. In some embodiments, the cell is a human cell. In some embodiments, the cell is a cell line, such as a human embryonic kidney 293 cell (HEK 293 cell or 293 cell), a 293T cell, or an a549 cell.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The host cell can be a prokaryotic or a eukaryotic cell. In some embodiments, the host cell is a cell line, such as a human embryonic kidney 293 cell (HEK 293 cell or 293 cell), a 293T cell, or an a549 cell.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, canine, bovine, porcine, murine, rat, avian, reptilian and human.

"Prokaryotic cells" that usually lack a nucleus or any other membrane-bound organelles and are divided into two domains, bacteria and archaea. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers.

Carriers also include pharmaceutical excipients and additives proteins, peptides, amino acids, lipids, lipid nanoparticle and the like, HK polymers, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A composition as disclosed herein can be a pharmaceutical composition. A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include lipid nanoparticles, HK polymers, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

As used herein, the term "excipient" refers to a natural or synthetic substance formulated alongside the active ingredient of a medication, included for the purpose of long-term stabilization, bulking up solid formulations, or to confer a therapeutic enhancement on the active ingredient in the final dosage form, such as facilitating drug absorption, reducing viscosity, or enhancing solubility.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

A unit dose, dosage, or regimen can be determined from the IC50 of a given polynucleotide, vector, cell, composition, or kit, for neutralizing activity against a SARS-CoV-2 polypeptide or polynucleotide, preferably a SARS-CoV-2 spike protein. "IC50" means the concentration of polynucleotide, vector, cell, composition, or kit required for 50% inhibition. Alternatively, the effective amount can be determined from the EC50 of a given polynucleotide, vector, cell, composition, or kit. "EC50" means the plasma concentration required to obtain 50% of the maximum neutralizing effect in vivo.

A combination as used herein intends that the individual active ingredients of the compositions are separately formulated for use in combination, and can be separately packaged with or without specific dosages. The active ingredients of the combination can be administered concurrently or sequentially.

The four-branched histidine-lysine (HK) peptide polymer H2K4b has been shown to be a good carrier of large molecular weight DNA plasmids (Leng et al. *Nucleic Acids Res* 2005; 33:e40.), but a poor carrier of relatively low molecular weight siRNA (Leng et al. *J Gene Med* 2005; 7:977-986.). Two histidine-rich peptides analogs of H2K4b, namely H3K4b and H3K(+H)4b, were shown to be effective carriers of siRNA (Leng et al. *J Gene Med* 2005; 7: 977-986. Chou et al. *Biomaterials* 2014; 35:846-855.), although H3K(+H)4b appeared to be modestly more effective (Leng et al. *Mol Ther* 2012; 20:2282-2290.). Moreover, the H3K4b carrier of siRNA induced cytokines to a significantly greater degree in vitro and in vivo than H3K(+H)4b siRNA polyplexes (Leng et al. *Mol Ther* 2012; 20:2282-2290.). Suitable HK polypeptides are described in WO/2001/047496, WO/2003/090719, and WO/2006/060182, the contents of each of which are incorporated herein in their entireties. These polypeptides have a lysine backbone (three lysine residues) where the lysine side chain F-amino groups and the N-terminus are coupled to various HK sequences. HK polypeptide carriers can be synthesized by methods that are well-known in the art including, for example, solid-phase synthesis.

It was found that such histidine-lysine peptide polymers ("HK polymers" or "HKP") were surprisingly effective as mRNA carriers, and that they can be used, alone or in combination with liposomes, to provide effective delivery of mRNA into target cells. Similar to PEI and other carriers, initial results suggested HK polymers differ in their ability to carry and release nucleic acids. However, because HK polymers can be reproducibly made on a peptide synthesizer, their amino acid sequence can be easily varied, thereby allowing fine control of the binding and release of RNAs, as well as the stability of polyplexes containing the HK polymers and RNA (Chou et al. *Biomaterials* 2014; 35:846-855. Midoux et al. *Bioconjug Chem* 1999; 10:406-411. Henig et al. *Journal of American Chemical Society* 1999; 121:5123-5126.). When mRNA molecules are admixed with one or more HKP carriers the components self-assemble into nanoparticles.

As described herein, advantageously the HK polymer comprises four short peptide branches linked to a three-lysine amino acid core. The peptide branches consist of histidine and lysine amino acids, in different configurations. The general structure of these histidine-lysine peptide polymers (HK polymers) is shown in Formula I, where R represents the peptide branches and K is the amino acid L-lysine.

Formula I

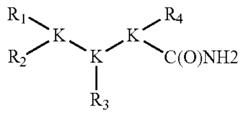

In Formula I where K is L-lysine and each of $R_1$, $R_2$, $R_3$ and $R_4$ is independently a histidine-lysine peptide. The $R_{1-4}$ branches may be the same or different in the HK polymers of the invention. When a R branch is "different", the amino acid sequence of that branch differs from each of the other R branches in the polymer. Suitable R branches used in the HK polymers of the invention shown in Formula I include, but are not limited to, the following R branches $R_A$-$R_{-J}$:

(SEQ ID NO: 38)
$R_A$ = KHKHHKHHKHHKHHKHHKHK- (SEQ ID NO: 39)
$R_B$ = KHHHKHHHKHHHKHHHK- (SEQ ID NO: 40)
$R_C$ = KHHHKHHHKHHHHKHHHK- (SEQ ID NO: 41)
$R_D$ = kHHHkHHHkHHHHkHHHk- (SEQ ID NO: 42)
$R_E$ = HKHHHKHHHKHHHHKHHHK- (SEQ ID NO: 43)
$R_F$ = HHKHHHKHHHKHHHHKHHHK- (SEQ ID NO: 44)
$R_G$ = KHHHHKHHHHKHHHHKHHHHK- (SEQ ID NO: 45)
$R_H$ = KHHHKHHHKHHHKHHHHK- (SEQ ID NO: 46)
$R_I$ = KHHHKHHHHKHHHKHHHK- (SEQ ID NO: 47)
$R_J$ = KHHHKHHHHKHHHKHHHHK-

Specific HK polymers that may be used in the mRNA compositions include, but are not limited to, HK polymers where each of $R_1$, $R_2$, $R_3$ and $R_4$ is the same and selected from $R_A$-$R_J$ (Table 1). These HK polymers are termed H2K4b, H3K4b, H3K(+H)4b, H3k(+H)4b, H-H3K(+H)4b, HH-H3K(+H)4b, H4K4b, H3K(1+H)4b, H3K(3+H)4b and H3K(1,3+H)4b, respectively. In each of these 10 examples, upper case "K" represents a L-lysine, and lower case "k" represents D-lysine. Extra histidine residues, in comparison to H3K4b, are underlined within the branch sequences. Nomenclature of the HK polymers is as follows:

1) for H3K4b, the dominant repeating sequence in the branches is -HHHK- (SEQ ID NO: 49), thus "H3K" is part of the name; the "4b" refers to the number of branches;
2) there are four -HHHK- (SEQ ID NO: 49) motifs in each branch of H3K4b and analogues; the first -HHHK- motif (SEQ ID NO: 49) ("1") is closest to the lysine core;
3) H3K(+H)4b is an analogue of H3K4b in which one extra histidine is inserted in the second -HHHK- motif (SEQ ID NO: 49) (motif 2) of H3K4b;
4) for H3K(1+H)4b and H3K(3+H)4b peptides, there is an extra histidine in the first (motif 1) and third (motif 3) motifs, respectively;
5) for H3K(1,3+H)4b, there are two extra histidines in both the first and the third motifs of the branches.

ingly was synergistic in its ability to carry mRNA into MDA-MB-231 cells (H3K(+H)4b/liposomes vs liposomes, P<0.0001). The combination was about 3-fold and 8-fold more effective as carriers of mRNA than the polymer alone and the cationic lipid carrier, respectively. Not all HK peptides demonstrated the synergistic activity with DOTAP lipid. For example, the combination of H3K4b and DOTAP was less effective than the DOTAP liposomes as carriers of luciferase mRNA. Besides DOTAP, other cationic lipids that may be used with HK peptides include Lipofectin (ThermoFisher), Lipofectamine (ThermoFisher), and DOSPER.

In the luciferase model as described above, the D-isomer of H3k (+H)4b, in which the L-lysines in the branches are replaced with D-lysines, was the most effective polymeric carrier (H3k(+H)4b vs. H3K(+H)4b, P<0.05). The D-isomer/liposome carrier of mRNA was nearly 4-fold and 10-fold more effective than the H3k(+H)4b alone and liposome carrier, respectively. Although the D-H3k(+H)4b/lipid combination was modestly more effective than the L-H3K (+H)4b/lipidmbination, this comparison was not statistically different.

TABLE 1

| Polymer | Branch Sequence | Sequence Identifier |
|---|---|---|
| H2K 4b | $R_A$ = KHKHHKHHKHHKHHKHHKHK- | (SEQ ID NO: 38) |
| H3K 4b | 4 3 2 1<br>$R_B$ = KHHHKHHHKHHHKHHHK- | (SEQ ID NO: 39) |
| H3K(+H)4b | $R_c$ = KHHHKHHHKHHHHKHHHK- | (SEQ ID NO: 40) |
| H3k(+H)4b | $R_D$ = kHHHkHHHkHHHHkHHHk- | (SEQ ID NO: 41) |
| H-H3K(+H)4b | $R_E$ = HKHHHKHHHKHHHHKHHHK- | (SEQ ID NO: 42) |
| HH-H3K(+H)4b | $R_F$ = HHKHHHKHHHKHHHHKHHHK- | (SEQ ID NO: 43) |
| H4K 4b | $R_G$ = KHHHHKHHHHKHHHHKHHHHK- | (SEQ ID NO: 44) |
| H3K(1+H)4b | $R_H$ = KHHHKHHHKHHHKHHHHK- | (SEQ ID NO: 45) |
| H3K(3+H)4b | $R_I$ = KHHHKHHHHKHHHKHHHK- | (SEQ ID NO: 46) |
| H3K(1,3+H)4b | $R_J$ = KHHHKHHHHKHHHKHHHHK- | (SEQ ID NO: 47) |

Methods well known in the art, including gel retardation assays, heparin displacement assays and flow cytometry can be performed to assess performance of different formulations containing HK polymer plus liposome in successfully delivering mRNA. Suitable methods are described in, for example, Gujrati et al, *Mol. Pharmaceutics* 11:2734-2744 (2014), and Pärnaste et al., *Mol Ther Nucleic Acids.* 7: 1-10 (2017).

Detection of mRNA uptake into cells can also be achieved using SMARTFLARE® technology (Millipore Sigma). These smart flares are beads that have a sequence attached that, when recognizing the RNA sequence in the cell, produce an increase in fluorescence that can be analyzed with a fluorescent microscope.

Other methods include measuring protein expressions from an mRNA, for example, an mRNA encoding luciferase can be used to measure the efficiency of transfection. See, for example, He et al (*J Gene Med.* 2021 February; 23(2): e3295) demonstrating the efficacy of delivering mRNA using a luciferase model HKP and liposome formulation.

In the luciferase model as described above, the combination of H3K(+H)4b and DOTAP (a cationic lipid) surpris- Both H3K4b and H3K(+H)4b can be used as carriers of nucleic acids in vitro See, for example, Leng et al. *J Gene Med* 2005; 7: 977-986; and Chou et al., *Cancer Gene Ther* 2011; 18: 707-716. Despite these previous findings, H3K(+H)4b was markedly better as a carrier of mRNA compared to other similar analogues in the luciferase model (Table 2).

TABLE 2

| Polymer | Ratio(wt:wt; mRNA:Polymer) | RLU/ug-Protein |
|---|---|---|
| H3K(+H)4b | 1:4 | 1532.9 ± 122.9 |
| | 1:8 | 1656.3 ± 202.5 |
| | 1:12 | 1033.4 ± 197 |
| H3k(+H)4b | 1:4 | 1851.6 ± 138.3 |
| | 1:8 | 1787.2 ± 195.2 |
| | 1:12 | 1982.3 ± 210.7 |
| H3K4b | 1:4 | 156.8 ± 41.8 |
| | 1:8 | 62.1 ± 13.2 |
| | 1:12 | 18.1 ± 4.0 |
| H3K(3 + H)4b | 1:4 | 61.7 ± 5.7 |
| | 1:8 | 68.7 ± 3.1 |
| | 1:12 | 59.0 ± 7.5 |

TABLE 2-continued

| Polymer | Ratio(wt:wt; mRNA:Polymer) | RLU/ug-Protein |
|---|---|---|
| H3K(1 + H)4b | 1:4 | 24.3 ± 4.5 |
| | 1:8 | 15.0 ± 3.6 |
| | 1:12 | 7.3 ± 2.5 |
| H-H3K(+H)4b | 1:4 | 1107.5 ± 140.4 |
| | 1:8 | 874.6 ± 65.2 |
| | 1:12 | 676.4 ± 25.7 |
| HH-H3K(+H)4b | 1:4 | 1101.9 ± 106.6 |
| | 1:8 | 832.2 ± 75.3 |
| | 1:12 | 739.8 ± 105.4 |
| H4K4b | 1:4 | 896.4 ± 112.6 |
| | 1:8 | 821.8 ± 115.6 |
| | 1:12 | 522.4 ± 69.2 |
| H3K(1,3 + H)4b | 1:4 | 518.3 ± 134.7 |
| | 1:8 | 427.7 ± 18.1 |
| | 1:12 | 378 ± 5.2 |
| H2K4b | 1:4 | 546.7 ± 70.1 |
| | 1:8 | 132.3 ± 58.5 |
| | 1:12 | 194.7 ± 18.4 |

Especially, it has higher mRNA transfection efficiency than H3K4b in various weight:weight (HK:mRNA) ratios. At a 4:1 ratio, luciferase expression was 10-fold higher with H3K(+H)4b than H3K4b in MDA-MB-231 cells without significant cytotoxicity. Moreover, the buffering capacity does not seem to be an essential factor in their transfection differences since the percent of histidines (by weight) in H3K4b and H3K(+H)4b is 68.9 and 70.6%, respectively.

Gel retardation assays show that the electrophoretic mobility of mRNA was delayed by the HK polymers. The retardation effect increased with higher peptide to mRNA weight ratios. However, mRNA was completely retarded in 2:1 ratio of H3K(+H)4b, whereas it was not completely retarded by H3K4b. This suggested that H3K(+H)4b could form a more stable polyplex, which was advantageous for its ability to be a suitable carrier for mRNA delivery.

Further confirmation that the H3K(+H)4b peptide binds more tightly to mRNA was demonstrated with a heparin-displacement assay. Various concentrations of heparin was added into the polyplexes formed with mRNA and HK and it was observed that, particularly at the lower concentrations of heparin, mRNA was released by the H3K4b polymer more readily than the H3K(+H)4b polymer. These data suggest H3K(+H)4b could bind to mRNA and form a more stable polyplex than H3K4b.

With the luciferase mRNA labeled with cyanine-5, the uptake of H3K4b and H3K(+H)4b polyplexes into MDA-MB-231 cells was compared using flow cytometry. At different time points (1, 2, and 4 h), the H3K(+H)4b polyplexes were imported into the cells more efficiently than H3K4b polyplexes. Similar to these results, fluorescent microscopy indicated that H3K(+H)4b polyplexes localized within the acidic endosomal vesicles significantly more than H3K4b polyplexes (H3K4b vs. H3K(+H)4b, $P<0.001$). Interestingly, irregularly-shaped H3K4b polyplexes, which did not overlap endocytic vesicles, were likely extracellular and were not observed with H3K(+H)4b polyplexes.

It is known both that HK polymers and cationic lipids (i.e., DOTAP) significantly and independently increase transfection with plasmids. See, for example, Chen et al. *Gene Ther* 2000; 7: 1698-1705. Consequently, whether these lipids together with HK polymers enhanced mRNA transfection was investigated. Notably, the H3K(+H)4b and H3k(+H)4b carriers were significantly better carriers of mRNA than the DOTAP liposomes. The combination of H3K(+H)4b and DOTAP lipid was synergistic in the ability to carry mRNA into MDA-MB-231 cells. The combination was about 3-fold and 8-fold more effective as carriers of mRNA than the polymer alone and the liposome carrier, respectively (H3K(+H)4b/lipid vs. liposomes or H3K(+H)4b). Notably, not all HK peptides demonstrated improved activity with DOTAP lipid. The combination of H3K4b and DOTAP carriers was less effective than the DOTAP liposomes as carriers of luciferase mRNA. The combination of DOTAP and H3K(+H)4b carriers were found to be synergistic in their ability to carry mRNA into cells. See, for example, He et al. *J Gene Med.* 2020 Nov. 10:e3295.

In some embodiments, the carrier, such as the NKP nanoparticle, further comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA, or MC3), and di((Z)-non-2-en-1-yl) 9-((4-(dimethylamino)butanoyl)oxy) heptadecanedioate (L319).

In some embodiments, the carrier is a lipid nanoparticle (LNP). In some embodiments, the LNP has a mean diameter of about 50 nm to about 200 nm. In some embodiments, Lipid nanoparticle carriers/formulations typically comprise, or alternatively consist essentially of, or yet further consist of a lipid, in particular, an ionizable cationic lipid, for example, SM-102 as disclosed herein, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy)heptadecanedioate (L319). In some embodiments, the LNP carriers/formulations further comprise a neutral lipid, a sterol (such as a cholesterol) and a molecule capable of reducing particle aggregation, for example a PEG or PEG-modified lipid (also referred to herein as PEGylated lipid). Additional exemplary lipid nanoparticle compositions and methods of making same are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21:1570-1578, the contents of each of which are incorporated herein by reference in their entirety.

In one embodiment, the term "disease" or "disorder" as used herein refers to a SARS-CoV-2 infection, a status of being diagnosed with a SARS-CoV-2 infection, a status of being suspect of having a SARS-CoV-2 infection, or a status of at high risk of having a SARS-CoV-2 infection. In one embodiment, the term "disease" or "disorder" as used herein refers to a symptomatic SARS-CoV-2 infection, a status of being diagnosed with a symptomatic SARS-CoV-2 infection, a status of being suspect of having a symptomatic SARS-CoV-2 infection, or a status of at high risk of having a symptomatic SARS-CoV-2 infection.

In one embodiment, the term "disease" or "disorder" as used herein refers to COVID-19, a status of being diagnosed with COVID-19, a status of being suspect of having COVID-19, or a status of at high risk of having COVID-19. In one embodiment, the term "disease" or "disorder" as used herein refers to a symptomatic COVID-19, a status of being diagnosed with a symptomatic COVID-19, a status of being suspect of having a symptomatic COVID-19, or a status of at high risk of having a symptomatic COVID-19.

As used herein, the term "animal" refers to living multicellular vertebrate organisms, a category that includes, for example, mammals and birds. The term "mammal" includes both human and non-human mammals such as non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, bat, rat, rabbit, guinea pig).

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, bat, rabbit, guinea pig). In some embodiments, a mammal is a human. A mammal can be any age or at any stage of development (e.g., an adult, teen, child, infant, or a mammal in utero). A mammal can be male or female. In some embodiments, a subject is a human. In some embodiments, a subject has or is diagnosed of having or is suspected of having a disease.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

In some embodiments, the terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

As used herein, "viral load", also known as "viral burden," "viral titer", "viral level" or "viral expression" in some embodiments, is a measure of the severity of a viral infection, and can be calculated by estimating the amount of virus in an infected organism, an involved body fluid, or a biological sample.

As used herein, a biological sample, or a sample, is obtained from a subject. Exemplary samples include, but are not limited to, cell sample, tissue sample, biopsy, liquid samples such as blood and other liquid samples of biological origin, including, but not limited to, anterior nasal swab, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood.

In some embodiments, the sample may be an upper respiratory specimen, such as a nasopharyngeal (NP) specimen, an oropharyngeal (OP) specimen, a nasal mid-turbinate swab, an anterior nares (nasal swab) specimen, or nasopharyngeal wash/aspirate or nasal wash/aspirate (NW) specimen.

In some embodiments, the samples include fluid from a subject, including, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, ear, arthroscopic), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a liquid biological sample is a blood plasma or serum sample. The term "blood" as used herein refers to a blood sample or preparation from a subject. The term encompasses whole blood, blood product or any fraction of blood, such as serum, plasma, buffy coat, or the like as conventionally defined. In some embodiments, the term "blood" refers to peripheral blood. Blood plasma refers to the fraction of whole blood resulting from centrifugation of blood treated with anticoagulants. Blood serum refers to the watery portion of fluid remaining after a blood sample has coagulated. Fluid samples often are collected in accordance with standard protocols hospitals or clinics generally follow. For blood, an appropriate amount of peripheral blood (e.g., between 3-40 milliliters) often is collected and can be stored according to standard procedures prior to or after preparation.

The term "adjuvant" refers to a substance or mixture that enhances the immune response to an antigen. As non-limiting example, the adjuvant can comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g., U.S. Pat. No. 8,241, 610). In another embodiment, the synthetic nanocarrier may comprise at least one polynucleotide and an adjuvant. As a non-limiting example, the synthetic nanocarrier comprising and adjuvant can be formulated by the methods described in WO2011150240 and US20110293700, each of which is herein incorporated by reference in its entirety.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

"Administration" or "delivery" of a polynucleotide, vector, cell or vector or other agent and compositions containing same can be performed in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician or in the case of animals, by the treating veterinarian. In some embodiments, administering or a grammatical variation thereof also refers to more than one doses with certain interval. In some embodiments, the interval is 1 day, 2 days, 3 days, 4 days, 5 days, 6 days, 1 week, 10 days, 2 weeks, 3 weeks, 1 month, 2 months, 3 months, 4 months, 5 months, 6 months, 1 year or longer. In some embodiments, one dose is repeated for once, twice, three times, four times, five times, six times, seven times, eight times, nine times, ten times or more. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include inhalation, intramuscular administration, nasal administration, oral administration, intraperitoneal, infusion, injection, and topical application. In preferred embodiments, the route of administration is inhalation or intramuscular administration. In some embodiments, the administration is an infusion (for example to peripheral blood of a subject) over a certain period of time, such as about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours or longer.

The term administration shall include without limitation, administration by oral, parenteral (e.g., intramuscular, intraperitoneal, intravenous, intracerebroventricular (ICV), intrathecal, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The disclosure is not limited by the route of administration, the formulation or dosing schedule.

In some embodiments, an RNA, polynucleotide, vector, cell or composition as disclosed herein is administered in an effective amount. An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific agent employed, bioavailability of the agent, the route of administration, the age of the animal and its body weight, general health, sex, the diet of the animal, the time of administration, the rate of excretion, the drug combination, and the severity of the particular disorder being treated and form of administration. In general, one will desire to administer an amount of the agent that is effective to achieve a serum level commensurate with the concentrations found to be effective in vivo. These considerations, as well as effective formulations and administration procedures are well known in the art and are described in standard textbooks.

As used herein, the term "RL-007" and RL007" refers to an lipid nanoparticle formulation or mix that is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). The Terms "RL-007 vaccine", "RL007 vaccine", "RL-007 mRNA vaccine", or "RL007 mRNA vaccine" refer to a vaccine which comprises, or alternatively consists essentially of, or yet further consists of an RL-007 carrier. In some embodiments, the pharmaceutically acceptable carrier comprises, or alternatively consists essentially of, or yet further consists of RL-007.

MODES FOR CARRYING OUT THE DISCLOSURE

RNA

The disclosure herein provides a ribonucleic acid (RNA) or DNA encoding a spike (S) protein or a fragment thereof (such as an immunogenic fragment) of a severe acute respiratory syndrome coronavirus 2 (SARS-CoV-2). The S protein or fragment comprises, or consists essentially of, or yet further consists of, at least one non-naturally occurring amino acid mutation.

In some embodiments, the fragment or immunogenic fragment comprises, or alternatively consists essentially of, or yet further consists of a receptor binding domain (RBD) of the S protein or an equivalent thereof, such as a fragment corresponding (such as aligning) to aa 319 to aa 541 of SEQ ID NO: 1. In some embodiments, a receptor-binding domain (RBD) refers to a short immunogenic fragment from a virus that binds to a specific endogenous receptor sequence to gain entry into target cells. In some embodiments, RBD refer to a part of the 'spike' glycoprotein which is needed to interact with endogenous receptors to facilitate membrane fusion and delivery to the cytoplasm. In some embodiments, the RBD as used herein comprises, or consists essentially of, or yet further consists of the polypeptide as set forth in aa 319 to aa 541 of SEQ ID NO: 1 or an equivalent thereof. In some embodiments, the fragment or immunogenic fragment is at least about 5 amino acids long, or at least about 8 amino acids long, or at least about 10 amino acids long, or at least about 15 amino acids long, or at least about 20 amino acids long, or at least about 25 amino acids long, or at least about 30 amino acids long, or at least about 40 amino acids long, or at least about 50 amino acids long, or at least about 60 amino acids long, or at least about 70 amino acids long, or at least about 80 amino acids long, or at least about 100 amino acids long, or at least about 125 amino acids long, or at least about 150 amino acids long, or at least about 160 amino acids long, or at least about 170 amino acids long, or at least about 180 amino acids long, or at least about 190 amino acids long, or at least about 200 amino acids long, or at least about 250 amino acids long, or at least about 300, or longer; and optionally comprises, consists essentially of, or yet further consists of a RBD of the S protein or an equivalent thereof. The immunogenic fragment is useful for inducing an immune response to the SARS-CoV-2, or reducing or inhibiting the binding of SARS-CoV-2 to its receptor, such as ACE2, or both and a fragment that is non-immunogenic is useful as a control in the assays as provided herein.

In some embodiments, the at least one non-naturally occurring amino acid mutation comprises, or alternatively consists essentially of, or yet further consists of a mutation in a furin-like cleavage site. In further embodiments, the furin-like cleavage site comprises, or alternatively consists of, or yet further consists of RRAR (SEQ ID NO: 48). In yet further embodiments, a furin-like cleavage site in an S protein or a fragment thereof as disclosed herein corresponds to (e.g., aligns to) amino acid (aa) 682 to aa 685 of SEQ ID NO: 1. In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), an S as the amino acid corresponding to R683 of SEQ ID NO: 1 (R683S), a glycine (G) as the amino acid corresponding to R685 of SEQ ID NO: 1 (R685G), or a G as the amino acid corresponding to R682 of SEQ ID NO: 1 (R682G). In some embodiments, the at least one non-naturally occurring amino acid mutation comprises, or alternatively consists essentially of, or yet further consists R682S and R685G. In some embodiments, a mutated furin-like cleavage site stabilize the S protein or fragment thereof as disclosed herein.

Additionally or alternatively, the at least one non-naturally occurring amino acid mutation comprises, or alternatively consists essentially of, or yet further consists of a proline (P) as the amino acid corresponding to any one or more (such as any two, or any three, or any four, or any five, or all six) of F817 of SEQ ID NO: 1 (F817P), A892 of SEQ ID NO: 1 (A892P), A899 of SEQ ID NO: 1 (A899P), A942 of SEQ ID NO: 1 (A942P), K986 of SEQ ID NO: 1 (K986P), and/or V987 of SEQ ID NO: 1 (V987P). In some embodiments, the at least one non-naturally occurring amino acid mutation comprises, or alternatively consists essentially of, yet further consists of K986P and/or V987P. These two mutations are referred to herein as S2P. In some embodiments, the at least one non-naturally occurring amino acid mutation comprises, or alternatively consists essentially of, yet further consists of F817P, A892P, A899P, A942P, K986P, and/or V987P. These six mutations are referred to herein as "S-HexaPro" or "S6P". In some embodiments, an S protein or a fragment (such as an immunogenic fragment thereof) comprising the S2P or S6P mutations has one or more of the following properties compared to those without the S2P or S6P mutations: increased expression level in vivo or in vitro or both; higher stability, such as room temperature, under heat, or after freeze-thaws; or maintaining the protein conformation.

In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), a glycine (G) as the amino acid corresponding to R685 of SEQ ID NO: 1 (R685G), a proline (P) as the amino acid corresponding to F817 of SEQ ID NO: 1 (F817P), a P as the amino acid corresponding to A892 of SEQ ID NO: 1 (A892P), a P as the amino acid corresponding to A899 of SEQ ID NO: 1 (A899P), a P as the amino acid corresponding to A942 of SEQ ID NO: 1 (A942P), a P as the amino acid corresponding to K986 of SEQ ID NO: 1 (K986P), or a P as the amino acid corresponding to V987 of SEQ ID NO: 1 (V987P).

Without wishing to be bound by the theory, an S protein or a fragment thereof comprises a mutated furin-like cleavage site and S2P or S6P mutations shows an advantage (such as an higher expression level in vivo and in vitro, or a better stability, or both) over those free of these mutations, or comprising a mutated furin-like cleavage site alone, or comprising S2P or S6P alone. In some embodiments, the advantage of comprising both mutation sets is synergistic.

In some embodiments, the S protein or fragment thereof is derived from a naturally occurring SARS-CoV-2 variant, such as an Omicron variant. For example, the at least one non-naturally occurring amino acid mutations as disclosed herein can be engineered to a S protein variant or a fragment thereof, such as an Omicron variant, thus arriving at a mutated S protein or a fragment thereof.

In further embodiments, the S protein or fragment thereof is derived from a chimeric SARS-CoV-2 S protein. The chimeric S protein comprises, or alternatively consists essentially of, or yet further consists of a first naturally occurring S variant having one or more of its amino acids or continuous segments substituted with the corresponding amino acids or continuous segments of a second naturally occurring S variant.

In some embodiments, the S protein or fragment thereof further comprises one or more mutations, which was found in a naturally occurring SARS-CoV-2 variant, such as an Omicron variant. In some embodiments, the one or more mutations comprises, or alternatively consists essentially of, or yet further consists of one or more of: an isoleucine (I) as the amino acid corresponding to T19 of SEQ ID NO: 1, a deletion of amino acids corresponding to residues 24-26 of SEQ ID NO: 1, a serine (S) as the amino acid corresponding to A27 of SEQ ID NO: 1, a valine (V) at the amino acid corresponding to A67 of SEQ ID NO: 1, a deletion of the amino acids corresponding to residues 69 and 70 of SEQ ID NO: 1, an isoleucine (I) at the amino acid corresponding to SEQ ID NO: 1, a aspartic acid (D) as the amino acid corresponding to G142 of SEQ ID NO: 1, a deletion of the amino acids corresponding to residues 143-145 of SEQ ID NO: 1, a glutamic acid (E) at the amino acid corresponding to position K147 of SEQ ID NO: 1, an arginine (R) at the amino acid corresponding to position W152 of SEQ ID NO: 1, a leucine (L) at the amino acid corresponding to position F157 of SEQ ID NO: 1, a valine (V) at the amino acid corresponding to position I210 of SEQ ID NO: 1, an isoleucine (I) at the amino acid corresponding to position V211 of SEQ ID NO: 1, a deletion at the amino acid corresponding to residue 212 of SEQ ID NO: 1, a glycine (G) as the amino acid corresponding to V213 of SEQ ID NO: 1, an insertion of glutamic acid-proline-glutamic acid (EPE)

at the amino acid corresponding to residue 214 of SEQ ID NO: 1, a serine (S) at the amino acid corresponding to position G257 of SEQ ID NO: 1, a aspartic acid (D) at the amino acid corresponding to G339 of SEQ ID NO: 1, a thymine (T) at the amino acid corresponding to R346 of SEQ ID NO: 1, a phenylalanine (F) at the amino acid corresponding to S371 of SEQ ID NO: 1, a leucine (L) at the amino acid corresponding to S371 of SEQ ID NO: 1, a proline (P) at the amino acid corresponding to S373 of SEQ ID NO: 1, a phenylalanine (F) at the amino acid corresponding to S375 of SEQ ID NO: 1, an alanine (A) at the amino acid corresponding to T376 of SEQ ID NO: 1, an asparagine (N) at the amino acid corresponding to D405 of SEQ ID NO: 1, a serine (S) at the amino acid corresponding to R408 of SEQ ID NO: 1, an asparagine (N) at the amino acid corresponding to K417 of SEQ ID NO: 1, a lysine (K) at the amino acid corresponding to N440 of SEQ ID NO: 1, a serine (S) at the amino acid corresponding to position G446 of SEQ ID NO: 1, an arginine (R) at the amino acid corresponding to L452 of SEQ ID NO: 1, a glutamine (Q) at the amino acid corresponding to L452 of SEQ ID NO: 1, a lysine (K) at the amino acid corresponding to position N460 of SEQ ID NO: 1, an asparagine (N) at the amino acid corresponding to S477 of SEQ ID NO: 1, a lysine (K) at the amino acid corresponding to T478 of SEQ ID NO: 1, an alanine (A) at the amino acid corresponding to E484 of SEQ ID NO: 1, a valine (V) at the amino acid corresponding to F486 of SEQ ID NO: 1, an arginine (R) at the amino acid corresponding to Q493 of SEQ ID NO: 1, a serine (S) at the amino acid corresponding to position G496 of SEQ ID NO: 1, an arginine (R) at the amino acid corresponding to Q498 of SEQ ID NO: 1, a tyrosine (Y) at the amino acid corresponding to N501 of SEQ ID NO: 1, a histidine (H) at the amino acid corresponding to Y505 of SEQ ID NO: 1, a lysine at the amino acid corresponding to T547 of SEQ ID NO: 1, a glycine (G) at the amino acid corresponding to D614 of SEQ ID NO: 1, a tyrosine (Y) at the amino acid corresponding to H655 of SEQ ID NO: 1, a lysine (K) at the amino acid corresponding to N679 of SEQ ID NO: 1, a histidine (H) at the amino acid corresponding to P681 of SEQ ID NO: 1, a leucine (L) at the amino acid corresponding to S704 of SEQ ID NO: 1, a lysine (K) at the amino acid corresponding to N764 of SEQ ID NO: 1, a tyrosine (Y) at the amino acid corresponding to D796 of SEQ ID NO: 1, a lysine (K) at the amino acid corresponding to N856 of SEQ ID NO: 1, a histidine (H) at the amino acid corresponding to Q954 of SEQ ID NO: 1, a lysine (K) at the amino acid corresponding to N969 of SEQ ID NO: 1, and/or a phenylalanine (F) at the amino acid corresponding to L981 of SEQ ID NO: 1. In some embodiments, the one or more mutations comprises, or alternatively consists essentially of, or yet further consists of one or more of: T19I, Δ24-26, A27S, A67V, Δ69/70, T95I, G142D, Δ143-145, N211I, Δ212, V213G, ins214EPE, G339D, S371F, S371L, S373P, S375F, T376A, D405N, R408S, K417N, N440K, G446S L452R, L452Q, S477N, T478K, E484A, F486V, Q493R, G496S, Q498R, N501Y, Y505H, D614G, T547K, H655Y, N679K, P681H, S704L, N764K, D796Y, N856K, Q954H, N969K, and/or L981F. In some embodiments, the one or more mutations comprises, or alternatively consists essentially of, or yet further consists of one or more of: T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, and/or N969K. In some embodiments, the one or more mutations comprises, or alternatively consists essentially of, or yet further consists of one or more of: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and/or N969K. In some embodiments, the one or more mutations comprises, or alternatively consists essentially of, or yet further consists of one or more of: A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K. In some embodiments, the one or more mutations comprises, or alternatively consists essentially of, or yet further consists of one or more of: T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K. In some embodiments, the one or more mutations comprises, or alternatively consists essentially of, or yet further consists of one or more of: T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K.

In some embodiments, the S protein comprises, or alternatively consists essentially of, or yet further consists of the polypeptide of SEQ ID NO: 5 or an equivalent thereof. In some embodiments, the equivalent of SEQ ID NO: 5 retains the mutations of SEQ ID NO: 5, i.e., T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, R682S, R685G, N764K, D796Y, Q954H, and/or N969K; S6P mutations (F817P, A892P, A899P, A942P, K986P and V987P); and furin-like cleavage site mutations (R682S and R685G). In further embodiments, the RNA or DNA comprises, or alternatively consists essentially of, or yet further consists of a polynucleotide encoding SEQ ID NO: 5 or an equivalent thereof. In further embodiments, the RNA or DNA comprises, or alternatively consists essentially of, or yet further consists of the polynucleotide of SEQ ID NO: 6 or an equivalent thereof. In further embodiments, the RNA or DNA comprises, or alternatively consists essentially of, or yet further consists of the polynucleotide of SEQ ID NO: 7 or an equivalent thereof. In some embodiments, the equivalent of SEQ ID NOs: 6-7 still encodes SEQ ID NO: 11 or an equivalent thereof.

In some embodiments, the S protein comprises, or alternatively consists essentially of, or yet further consists of the polypeptide of SEQ ID NO: 8 or an equivalent thereof. In some embodiments, the equivalent of SEQ ID NO: 8 retains the mutations of SEQ ID NO: 8, i.e., T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and/or N969K; S6P mutations (F817P, A892P, A899P, A942P, K986P and V987P); and furin-like cleavage site mutations (R682S and R685G). In further embodiments, the RNA or DNA comprises, or alternatively consists essentially of, or yet further consists of a polynucleotide encoding SEQ ID NO: 8 or an equivalent thereof. In further embodiments, the RNA or DNA comprises, or alternatively consists essentially of, or yet further consists of the polynucleotide of SEQ ID NO: 9 or an equivalent thereof. In further embodiments, the RNA or DNA comprises, or alternatively consists essentially of, or yet further consists of the polynucleotide of SEQ ID NO: 10 or an equivalent thereof. In some embodiments, the equivalent of SEQ ID NOs: 9-10 still encodes SEQ ID NO: 11 or an equivalent thereof.

In some embodiments, the S protein comprises, or alternatively consists essentially of, or yet further consists of the polypeptide of SEQ ID NO: 11 or an equivalent thereof. In some embodiments, the equivalent of SEQ ID NO: 11 retains the mutations of SEQ ID NO: 11, i.e., A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and/or L981F; S6P mutations (F817P, A892P, A899P, A942P, K986P and V987P); and furin-like cleavage site mutation (R682S and R685G). In further embodiments, the RNA or DNA comprises, or alternatively consists essentially of, or yet further consists of a polynucleotide encoding SEQ ID NO: 11 or an equivalent thereof. In further embodiments, the RNA or DNA comprises, or alternatively consists essentially of, or yet further consists of the polynucleotide of SEQ ID NO: 12 or an equivalent thereof. In further embodiments, the RNA or DNA comprises, or alternatively consists essentially of, or yet further consists of the polynucleotide of SEQ ID NO: 13 or an equivalent thereof. In further embodiments, the RNA or DNA comprises, or alternatively consists essentially of, or yet further consists of the polynucleotide of SEQ ID NO: 14 or an equivalent thereof. In further embodiments, the RNA or DNA comprises, or alternatively consists essentially of, or yet further consists of the polynucleotide of SEQ ID NO: 15 or an equivalent thereof. In some embodiments, the equivalent of SEQ ID NOs: 12-15 still encodes SEQ ID NO: 11 or an equivalent thereof.

In some embodiments, the S protein comprises, or alternatively consists essentially of, or yet further consists of the polypeptide of SEQ ID NO: 55 or an equivalent thereof. In some embodiments, the equivalent of SEQ ID NO: 55 retains the mutations of SEQ ID NO: 55, i.e., T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K; S6P mutations (F817P, A892P, A899P, A942P, K986P and V987P); and furin-like cleavage site mutation (R682S and R685G). In further embodiments, the RNA or DNA comprises, or alternatively consists essentially of, or yet further consists of a polynucleotide encoding SEQ ID NO: 55 or an equivalent thereof. In further embodiments, the RNA or DNA comprises, or alternatively consists essentially of, or yet further consists of the polynucleotide of SEQ ID NO: 56 or an equivalent thereof. In some embodiments, the equivalent of SEQ ID NO: 56 still encodes SEQ ID NO: 55 or an equivalent thereof.

In some embodiments, the S protein comprises, or alternatively consists essentially of, or yet further consists of the polypeptide of SEQ ID NO: 57 or an equivalent thereof. In some embodiments, the equivalent of SEQ ID NO: 57 retains the mutations of SEQ ID NO: 55, i.e., T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K; S6P mutations (F817P, A892P, A899P, A942P, K986P and V987P); and furin-like cleavage site mutation (R682S and R685G). In further embodiments, the RNA or DNA comprises, or alternatively consists essentially of, or yet further consists of a polynucleotide encoding SEQ ID NO: 57 or an equivalent thereof. In further embodiments, the RNA or DNA comprises, or alternatively consists essentially of, or yet further consists of the polynucleotide of SEQ ID NO: 58 or an equivalent thereof. In some embodiments, the equivalent of SEQ ID NO: 58 still encodes SEQ ID NO: 57 or an equivalent thereof.

In some embodiments, the equivalent of any one of SEQ ID NOs: 6, 9, 12, 56, or 58 consists of an GC content of about 35% to about 70% across the full length of the equivalent.

In some embodiments, the equivalent is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence, wherein the percent identity is determined using a programs such as BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: blast.ncbi.nlm.nih.gov/Blast.cgi, last accessed on Aug. 1, 2021.

In some embodiments, the RNA further comprises a 3' UTR. In further embodiments, the 3'UTR comprises, or alternatively consists essentially of, or consists of any one of SEQ ID NOs: 18, 22, or 24.

In some embodiments, the RNA further comprises a 5' UTR. In further embodiments, the 5' UTR comprises, or alternatively consists essentially of, or consists of SEQ ID NO: 20 or 26.

In some embodiments, the RNA further comprises a polyA tail. In further embodiments, the polyA tail comprises any one of SEQ ID NOs: 27, 28, 30, 53, or 54.

In some embodiments, the RNA further comprises a 5' cap. In further embodiments, the 5' cap comprises, or alternatively consists of, or yet further consists of a 5' CleanCap. This structure uses an initiating capped trimer to yield a naturally occurring 5' cap structure.

In some embodiments, the RNA comprises, or alternatively consists essentially of, or consist of, optionally from 5' to 3', a 5'UTR, a coding sequence encoding an S protein or a fragment as disclosed herein, a 3'UTR and a polyA. In further embodiments, the RNA comprises, or alternatively consists essentially of, or consists of SEQ ID NO: 32 or 52.

In some embodiments, the RNA is a messenger RNA (mRNA). Further provided are DNA molecules encoding these RNA as well as the complements thereof.

In some embodiments, the RNA is chemically modified. In further embodiments, the modification comprises, or alternatively consists essentially of, or consists of modifying a uridine (U) residue to an N1-methyl-pseudouridine residue. Additionally or alternatively, the modification comprises, or alternatively consists essentially of, or consist of modifying a U residue to a pseudouridine residue.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified, optionally to N1-methyl pseudouridine or pseudouridine. In further embodiments, at least about 50%, or at least about 70%, or about 100% of the uridine residues in the RNA are N1-methyl pseudouridine or pseudouridine.

In some embodiments, all or some of uridine residues are replaced by pseudouridines during in vitro transcription. This modification stabilizes the mRNA against enzymatic degradation in the cell, leading to enhanced translation efficiency of the mRNA. The pseudouridines used can be N1-methyl-pseudouridine, or other modifications that are well known in the art such as N6m -ethyladenosine (m6A), inosine, pseudouridine, 5-methylcytidine (m5C), 5-hydroxymethylcytidine (hm5C), and N1-methyladenosine (m1A). The modification optionally is made throughout the entire mRNA. The skilled artisan will recognize that other modified RNA residues can be used to stabilize the protein's 3 dimensional structure and increase protein translation.

Without wishing to be bound by the theory, an RNA encoding a naturally occurring S protein activates an endosomal RNA sensing pathway such as TLR3, TLR7, and TLR8 (Toll-like receptor), thereby induces innate immunity which in turn inhibits spike protein translation. In addition, a secreted IFN-β provokes tumor cell death upon binding of cognate receptor expressed on the cell surface by activation of the downstream apoptotic pathway. However, an optimized RNA expressing a mutated S protein as disclosed herein avoids this disadvantage, and thus presents an improved translation efficiency (innate immunity) which in turn inhibits spike protein translation. In some embodiments, the optimized RNA can be administered to a subject in need thereof, expressing the mutated S protein in vivo. In further embodiments, the expressed S protein can induce an immune response in the subject, which in turns preventing or treating a SARS-CoV-2 infection as disclosed herein. Additionally or alternatively, the optimized RNA expresses the mutated S protein in vitro and optionally such expressed S protein can activate an immune cell in vitro. The activated immune cells can then be used to treat a subject in need thereof.

In another aspect, provided is a method of producing a spike (S) protein or an immunogenic fragment thereof of a severe acute respiratory syndrome coronavirus 2 (SARS-CoV-2). In some embodiments, the method is an in vitro method. The method comprises, or alternatively consists essentially of, or yet further consists of culturing a cell as disclosed herein under conditions suitable for expressing the S protein or immunogenic fragment thereof. In further embodiments, the method herein further comprises isolating the S protein or immunogenic fragment thereof. In some embodiments, the cell is a host cell as disclosed herein.

Additionally, provided is a method for screening a candidate agent reducing or inhibiting the binding of SARS-CoV-2 and its receptor, such as ACE2, optionally in a subject or on a cell of the subject or both. The method comprises, or alternatively consist essentially of, or yet further consists of expressing a spike (S) protein or an immunogenic fragment thereof from an RNA as disclosed herein, and measuring the binding between the expressed S protein or immunogenic fragment thereof and the SARS-CoV-2 receptor, such as ACE2, with or without the presence of the candidate agent or with different concentrations of the candidate agent. In some embodiments, less binding between the expressed S protein or immunogenic fragment thereof and the SARS-CoV-2 receptor with the presence of the candidate agent compared to without the candidate agent, indicates that the candidate agent reduces or inhibits the binding of SARS-CoV-2 and its receptor. In some embodiments, decreased binding between the expressed S protein or immunogenic fragment thereof and the SARS-CoV-2 receptor while increasing the concentration of the candidate agent indicates the candidate agent reduces or inhibits the binding of SARS-CoV-2 and its receptor. In some embodiments, the S protein or immunogenic fragment thereof is expressed in a host cell in the measuring step. Additionally or alternatively, the receptor, such as ACE2, is expressed in a host cell in the measuring step. In some embodiments, the receptor, such as ACE2, is isolated from a host cell in the measuring step, In other embodiments, the S protein or immunogenic fragment thereof is isolated from a host cell in the measuring step. In some embodiments, the isolated S protein or immunogenic fragment thereof or the isolated receptor further comprises a detectable label, such as a fluorescent protein. In further embodiments, the binding between the S protein or immunogenic fragment thereof and the receptor is performed using a fluorescence-based assay, such as fluorescent microscopy or Fluorescence-Activated Cell Sorting (FACS)

In yet a further aspect, provided is a method for selecting an RNA encoding a spike (S) protein or an immunogenic fragment thereof of a severe acute respiratory syndrome coronavirus 2 (SARS-CoV-2). The method comprises, or alternatively consists essentially of, or yet further consists of transducing the RNA into a cell, culturing the cell under conditions suitable for expressing the RNA, and measuring IFN-α or IFN-β or both secreted by the cell. In some embodiments, the method further comprises selecting the RNA if no secretion of IFN-α or IFN-β or both or less secretion of IFN-α or IFN-β or both compared to an RNA encoding a wild type S protein or an immunogenic fragment thereof. In some embodiments, the IFN-α or IFN-β or both is measured using enzyme-linked immunosorbent assay.

Polynucleotides, Vectors, Cells and Related Methods

In one aspect, provided is a polynucleotide encoding an RNA as disclosed herein, or a polynucleotide complementary thereto. In some embodiments, the polynucleotide is selected from the group of: a deoxyribonucleic acid (DNA), an RNA, a hybrid of DNA and RNA, or an analog of each thereof.

In some embodiments, the disclosure provides a polynucleotide encoding a spike (S) protein or an immunogenic fragment thereof of a severe acute respiratory syndrome coronavirus 2 (SARS-CoV-2) the S protein or immunogenic fragment thereof comprising at least one non-naturally occurring amino acid mutation. A non-limiting example of such polynucleotide comprises, or alternatively consists essentially of, or consists of the sequence of SEQ ID NOs:

12-15. In some embodiments, the disclosure provides a polynucleotide encoding a spike (S) protein or an immunogenic fragment thereof of a severe acute respiratory syndrome coronavirus 2 (SARS-CoV-2) comprising at least one non-naturally occurring amino acid mutation, wherein the polynucleotide comprises, or alternatively consists essentially of, or consists of the sequence of SEQ ID NOs: 6, 7, 9, 10, or 12-15.

In a further aspect, provided is a vector comprising, or alternatively consisting essentially of, or consisting of a polynucleotide as disclosed herein.

In some embodiments, the vector further comprises a regulatory sequence operatively linked to the polynucleotide to direct the transcription thereof. In some embodiments, the regulatory sequence is suitable for use in an in vitro transcription system. In further embodiments, the regulatory sequence comprises, or alternatively consists essentially of, or consists of a promotor. In yet further embodiments, the promoter is an RNA polymerase promoter, optionally a bacteriophage RNA polymerase promoter. In some embodiment, the promoter comprises, or consists essentially of, or further consists of a T7 promoter, or a SP6 promoter, or a T3 promoter. In some embodiments, the T7 promoter comprises, or consists essentially of, or yet further consists of TAATACGACTCACTATAA (SEQ ID NO: 51). In some embodiments, the regulatory sequence is suitable for use in a cell to expressing an RNA as disclosed herein. In further embodiments, the regulatory sequence comprises, or alternatively consists essentially of, or yet further consists of a promotor, or an enhancer or both.

In some embodiments, the vector further comprises a regulatory sequence operatively linked to the polynucleotide to direct the replication thereof. In further embodiments, the regulatory sequence comprises, or alternatively consists essentially of, or yet further consists of one or more of the following: an origin of replication or a primer annealing site, a promoter, or an enhancer.

In some embodiments, an RNA, or a polynucleotide, or a vector further comprises a marker selected from a detectable marker, a purification marker, or a selection marker.

In some embodiments, the vector is a non-viral vector, optionally a plasmid, or a liposome, or a micelle. In some embodiments, the plasmid comprises, or alternatively consists essentially of, or consists of SEQ ID NO: 33 or an equivalent thereof. In some embodiments, the vector is a viral vector, optionally an adenoviral vector, or an adeno-associated viral vector, or a retroviral vector, or a lentiviral vector, or a plant viral vector.

In some embodiments, a polynucleotide or a vector as disclosed herein is suitable for producing (such as transcribing or expressing or replicating) an RNA as disclosed herein. Such production can be in vivo or in vitro. For example, the polynucleotide or vector can be used to produce or replicate the RNA in vitro. Such RNA is then administrated to a subject in need thereof optionally with a suitable pharmaceutical acceptable carrier. Alternatively, the polynucleotide or vector can be used as a gene therapy and directly administrated to a subject in need thereof optionally with a suitable pharmaceutical acceptable carrier. In further embodiments, the gene therapy can additionally deliver other prophylactic or therapeutic agent to the subject.

In another aspect, a cell comprising one or more of: an RNA as disclosed herein, a polynucleotide as disclosed herein, or a vector as disclosed herein. In some embodiments, the cell is a prokaryotic cell, optionally an *Escherichia coli* cell. In some embodiments, the cell is a eukaryotic cell, optionally a mammal cell, an insect cell, or a yeast cell. In some embodiments, the cell is a human embryonic kidney 293 cell (HEK 293 cell or 293 cell) or a 293T cell.

In some embodiments, a cell as disclosed herein is suitable for producing (such as transcribing or expressing) an RNA as disclosed herein. Such production can be in vivo or in vitro. For example, the cell can be used to produce the RNA in vitro. Such RNA is then administrated to a subject in need thereof optionally with a suitable pharmaceutical acceptable carrier. Alternatively, the cell can be used as a cell therapy and directly administrated to a subject in need thereof optionally with a suitable pharmaceutical acceptable carrier. In further embodiments, the cell therapy can additionally deliver other prophylactic or therapeutic agent to the subject.

In yet another aspect, provided is a composition comprising, or alternatively consisting essentially of, or yet further consisting of a carrier, optionally a pharmaceutically acceptable carrier, and one or more of: an RNA as disclosed herein, a polynucleotide as disclosed herein, a vector as disclosed herein, or a cell as disclosed herein.

In some embodiments, the composition further comprises an additional prophylactic or therapeutic agent.

In some embodiments, the additional prophylactic or therapeutic agent is suitable for preventing or treating a SARS-CoV-2 related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic agent is suitable for preventing a disease that is not related to SARS-CoV-2. For example, the additional prophylactic agent comprises, or alternatively consists essentially of, or yet further consists of a vaccine for another coronavirus, such as SARS-CoV or MERS-CoV. Additionally or alternatively, the additional prophylactic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the composition further comprises an adjuvant.

In one aspect, provided is a method of producing an RNA as disclosed herein. In some embodiments, the method comprises, or alternatively consists essentially of, or yet further consists of culturing a cell as disclosure herein under conditions suitable for expressing and/or replicating the RNA. In further embodiments, the RNA is produced by a plasmid DNA (pDNA) vector delivery system. In yet further embodiments, the plasmid vectors can be adapted for mRNA vaccine production. Commonly used plasmids include pSFV1, pcDNA3 and pTK126, which are all commercially available. One unique mRNA expression system is pEVL (see, Grier et al. *Mol Ther Nucleic Acids.* 19; 5:e306 (2016)).

In some embodiments, the method comprises, or alternatively consists essentially of, or yet further consists of contacting a polynucleotide as disclosed herein or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA. In some embodiments, the RNA is produced in a linear in vitro transcription (IVT) system from a linear DNA template comprising a bacteriophage promoter, UTRs and a coding sequence, by using a RNA polymerase (T7, T3 or SP6) and a mix of the different nucleosides. In some embodiments, the method further comprises isolating the RNA. In further embodiments, the method further comprises storing the RNA.

Formulation and Related Methods

In one aspect, provided is a composition comprising, or alternatively consisting essentially of, or yet further consisting of an RNA as disclosed herein and a pharmaceutically acceptable carrier.

In some embodiments, the pharmaceutically acceptable carrier comprises, or alternatively consists essentially of, or yet further consists of a polymeric nanoparticle. In some embodiments, the polymeric nanoparticle comprises, or alternatively consists essentially of, or yet further consists of a Histidine-Lysine co-polymer (HKP). In some embodiments, the HKP comprises a side chain selected from SEQ ID NOs: 34-47. Without wishing to be bound by the theory, RNA in the composition has a higher stability compared to the RNA free of a nanoparticle.

In some embodiments, the pharmaceutically acceptable carrier further comprises a lipid. In further embodiments, the lipid comprises a cationic lipid, optionally ionizable. In yet further embodiments, the cationic lipid comprises Dlin-MC3-DMA (MC3) or dioleoyloxy-3-(trimethylammonio) propane (DOTAP) or both. In some embodiments, the lipid further comprises one or more of: a helper lipid, a cholesterol, or a PEGylated lipid.

In some embodiments, the pharmaceutically acceptable carrier comprises, or alternatively consists essentially of, or yet further consists of a lipid nanoparticle (LNP). In further embodiments, the LNP comprises, or alternatively consists essentially of, or yet further consists of one or more of: 9-Heptadecanyl 8-{(2-hydroxyethyl)[6-oxo-6-(undecyloxy) hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), or an equivalent of each thereof. In yet further embodiments, the LNP further comprises one or more of: a helper lipid, a cholesterol, or a PEGylated lipid.

In some embodiments, the helper lipid comprises, or alternatively consists essentially of, or yet further consists of one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE).

As used herein, the term "RL-007" and RL007" refers to an ionizable lipid equivalent that is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). The Terms "RL-007 vaccine", "RL007 vaccine", "RL-007 mRNA vaccine", or "RL007 mRNA vaccine" refer to a vaccine which comprises, or alternatively consists essentially of, or yet further consists of an RL-007 carrier. In some embodiments, the pharmaceutically acceptable carrier comprises, or alternatively consists essentially of, or yet further consists of RL-007.

In some embodiments, wherein the cholesterol comprises, or alternatively consists essentially of, or yet further consists of a plant cholesterol or an animal cholesterol or both.

In some embodiments, the PEGylated lipid comprises, or alternatively consists essentially of, or yet further consists of one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dim-yristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

In a further aspect, provided is a method of producing a composition comprising, or alternatively consisting essentially of, or yet further consisting of an RNA as disclosed herein and an HKP. The method comprises, or alternatively consists essentially of, or yet further consists of contacting the RNA with an HKP, thereby the RNA and the HKP are self-assembled into nanoparticles.

In some embodiments, the mass ratio of HKP and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of HKP and the RNA in the contacting step is about 2.5:1. In another embodiment, the mass ratio of HKP and the RNA in the contacting step is about 4:1.

In some embodiments, the method further comprises contacting the HKP and RNA with a cationic lipid. In further embodiments, the cationic lipid comprises, or consists essentially of, or yet further consists of Dlin-MC3-DMA (MC3) or DOTAP (dioleoyloxy-3-(trimethylammonio)propane) or both. In yet further embodiments, the mass ratio of the cationic lipid and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the RNA and the cationic lipid in the contacting step is about 1:1. Accordingly, the mass ratio of the HKP, the RNA and the cationic lipid in the contacting step can be calculated based on the ratio between the HKP and the RNA and the ratio between the RNA and the cationic lipid. For example, if the ratio of the HKP to the RNA is about 4:1 and the ratio of the RNA to the cationic lipid is about 1:1, the ratio of the HKP to the RNA to the cationic lipid is about 4:1:1.

In one embodiments, HKP(+H) stock solution (10 mg/mL) was prepared in nuclease free water. A concentrated stock solution was diluted to 2.5 mg/mL in water. mRNA working solution (1 mg/mL) was prepared in 1 mM citrate buffer (pH 6.0). The mRNA/HKP(+H) polyplex was formed by mixing equal volumes of 2.5 mg/mL HKP(+H) and 1 mg/mL mRNA using microfluidics. The mass ratio of HKP (+H) to mRNA is 2.5:1. The mRNA/HKP(+H) polyplex was incubated for 30 min at room temperature before use. For preparation of all peptide based polyplexes, the size was determined with the Zetasizer(Malvern Panalytical) prior to its transfection or injection.

In some embodiments, the pharmaceutical comprises, or consists essentially of or yet further consists of a polymeric nanoparticle or a lipid nanoparticle both of which comprises a cationic lipid (such as one or more of those as disclosed herein), a helper lipid (such as one or more of those as disclosed herein), a cholesterol (such as one or more of those as disclosed herein) and a PEGylated lipid (such as one or more of those as disclosed herein). In further embodiments, a polymeric nanoparticle further comprises HKP. In some embodiments, the mass ratio of the cationic lipid, helper lipid, cholesterol and PEGylated lipid is about 1:1:1:1:1.

In some embodiments, the mass ratio of the cationic lipid and the helper lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and the helper lipid is about 1:1.

In some embodiments, the mass ratio of the cationic lipid and cholesterol is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and cholesterol is about 1:1.

In some embodiments, the mass ratio of the cationic lipid and PEGylated lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and PEGylated lipid is about 1:1.

The mass ratio of the cationic lipid, helper lipid, cholesterol and PEGylated lipid can be calculated by one of skill in the art based on the ratios of the cationic lipid and the helper lipid, the cationic lipid and the cholesterol and the cationic lipid and the PEGylated lipid as disclosed herein.

In some embodiments, the LNPs comprise, or consists essentially of, or yet further consists of SM-102, DSPC, cholesterol and PEG2000-DMG. In one embodiment, the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5.

In some embodiments, a mass ratio as provided here can be substituted with another parameter, such as a molar ratio, a weight percentage over the total weight, a component's weight over the total volume, or a molar percentage over the total molar amount. Knowing the component and its molecular weight, one of skill in the art would have no difficulty in converting a mass ratio to a molar ratio or other equivalent parameters.

In a further aspect, provided is a method of producing a composition comprising, or alternatively consisting essentially of, or yet further consisting of an RNA as disclosed herein and an LNP. The method comprises, or alternatively consists essentially of, or yet further consists of contacting the RNA with the LNP, thereby the RNA and the LNP are self-assembled into nanoparticles.

In some embodiments, the contacting step is performed in a microfluidic mixer, optionally selected from a slit interdigitial micromixer, or a staggered herringbone micromixer (SHM). In one embodiment, the microfluidic mixer is NanoAssemblr Ignite.

In some embodiments, the composition further comprises an additional prophylactic or therapeutic agent, such as those as disclosed herein. As used herein, the term "prophylactic or therapeutic agent" comprises, consists essentially of, or further consists of a nucleic acid (e.g., an mRNA), compound, polypeptide, antibody, antigen-binding portion thereof, composition, vector, antigen, host cell, and/or any pharmaceutically acceptable compositions comprising antigens, host cells, and/or additional therapeutic agents (e.g., formulations). In some embodiments, the additional prophylactic or therapeutic agent is suitable for preventing or treating a SARS-CoV-2 related disease as disclosed herein. In some embodiments, the additional prophylactic or therapeutic agent comprises, or alternatively consists essentially of, or yet further consists of an anti-viral agent, vaccine, or effective dose of a nucleic acid for vaccination, prevention, and treatment against SARS-CoV-2. In some embodiments, the additional prophylactic or therapeutic agent is suitable for preventing or treating a SARS-CoV-2 naturally occurring variant, such as an Omicron variant. In some further embodiments, the additional prophylactic or therapeutic agent is suitable for preventing or treating a SARS-CoV-2 naturally occurring variant and its descendent lineages. As used herein, a descendent lineage of a SARS-CoV-2 naturally occurring variant is a group of closely related viruses with a common ancestor, all of which cause COVID-19. Descendent lineages of a SARS-CoV-2 naturally occurring variant include, but are not limited to Omicron BA.1, BA.1.1, BA.2, BA.2.12.1, BA.2.75, BF.7, BA.4, and BA.5; Alpha B.1.1.7 and Q lineages; Beta B.1.351; Gamma P.1; Delta B.1.617.2 and AY lineages; Epsilon B.1.427 and B.1.429; Eta B.1.525; Iota B.1.526; Kappa B.1.617.1; Mu B.1.621, B.1.621.1; and/or Zeta P.2.

In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic or therapeutic agent is suitable for preventing a disease that is not related to SARS-CoV-2. For example, the additional prophylactic or therapeutic agent comprises, or alternatively consists essentially of, or yet further consists of a vaccine for another coronavirus, such as SARS-CoV or MERS-CoV. Additionally or alternatively, the additional prophylactic or therapeutic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic or therapeutic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic or therapeutic agent comprises, or alternatively consists essentially of, or yet further consists of a vaccine for a non-infectious disease, such as a cancer.

Methods of Treatment

In one aspect, provided is a method for preventing or treating a disease as disclosed herein. Additionally or alternatively, provided is a method of one or more of: (a) preventing a subject from having a symptomatic SARS-CoV-2 infection; (b) preventing a subject from hospitalization after infection by SARS-CoV-2; (c) preventing a subject from requiring intensive care (such as in an intensive care unit (ICU)) or a ventilator or both after infection by a SARS-CoV; (d) inducing an immune response to SARS-CoV-2 in a subject in need thereof, (e) reducing the binding of a SARS-CoV-2 or an S protein thereof with its receptor, such as angiotensin converting enzyme 2 (ACE2), in a subject in need thereof; (f) treating a subject infected with SARS-CoV-2; or (g) reducing a SARS-CoV-2 viral load in a subject in need thereof.

Host neutralizing antibodies block the binding of a SARS-CoV-2 or an S protein thereof with its receptors, such as ACE2, resulting in neutralized virus and decreased SARS-CoV-2 viral loads. Viral load is a measure of the severity of a viral infection, and can be calculated directly by estimating the amount of virus in an infected organism, an involved body fluid, or a biological sample. Quantification of viral load can generally be performed by utilizing a Plaque Reduction Neutralization Assay (PRNT). PRNT is a serological test which utilizes the ability of a specific antibody to neutralize a virus, in turn, preventing the virus from causing the formation of plaques in a cell monolayer. The assay involves mixing a constant amount of virus with dilutions of the serum specimen being tested, followed by plating of the mixture onto cells of an appropriate cell line for the individual virus. The concentration of plaque forming units can be determined by the number of plaques formed after a few days. A dye is added for visualization of the plaques, and the number of plaques in an individual plate is divided by the original number of virons to calculate the percentage neutralization. Depending on the virus, the plaque forming units (p.f.u.) are measured by microscopic observations, fluorescent antibodies, or specific dyes that react with the infected cell. Neutralizing titers can be calculated as the reciprocal of the lowest dilution that resulted in a greater than 50% reduction (PRNT50) or 90% reduction (PRNT90) in p.f.u. (plaque forming units) relative to negative control sera. Sera collected from two fully vaccinated subjects and serum from unvaccinated subjects can be used as a positive and negative controls, respectively.

An induced immune response in a subject therefore comprises inducing increased neutralizing antibody titers, increased splenocyte Th1-cytokine levels (IFN-7, IL-2, TNF-α) and Th2-cytokines levels (IL-4, IL-5, IL-13), and/or inducing decreased viral loads. The present disclosure provides a method of inducing an immune response in a subject against SARS-CoV-2. In some embodiments, the method comprises administering to the subject an effective dose of an RNA, or polynucleotide, or vector, or cell or composition as disclosed herein, thereby inducing in the subject an immune response specific to a SARS-CoV-2 antigen, wherein neutralizing antibody titers in the subject are increased following vaccination relative to neutralizing antibody titers in an unvaccinated subject. In some embodiments, the neutralizing antibody titers in the subject are increased 1 log to 10 log following vaccination relative to neutralizing antibody titers in an unvaccinated subject. In some embodiments, the neutralizing antibody titers in the subject are increased 1 log, 2 log, 3 log, 4 log, 5 log, or 10 log following vaccination relative to neutralizing antibody titers in an unvaccinated subject.

In other embodiments, the immune response is assessed by measuring splenocytes Th1-cytokine levels (IFN-7, IL-2, TNF-α) and Th2-cytokine levels (IL-4, IL-5, IL-13) in the subject. In some embodiments, the method comprises administering to the subject an effective dose of an RNA, or polynucleotide, or vector, or cell or composition as disclosed herein, thereby inducing in the subject an immune response specific to a SARS-CoV-2 antigen, wherein splenocytes Th1-cytokine levels (IFN-7, IL-2, TNF-α) and/or Th2-cytokine levels (IL-4, IL-5, IL-13) in the subject are increased following vaccination relative to neutralizing antibody titers in an unvaccinated subject.

The method comprises, or alternatively consists essentially of, or yet further consists of administering to the subject, optionally an effective amount of, one or more of: an RNA as disclosed herein, a polynucleotide as disclosed herein, a vector as disclosed herein, a cell as disclosed herein, or a composition as disclosed herein.

In some embodiments, the method further comprises treating the subject in need thereof, such as administering to the subject, an additional prophylactic or therapeutic agent.

In some embodiments, the additional prophylactic or therapeutic agent is suitable for preventing or treating a SARS-CoV-2 related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic agent is suitable for preventing a disease that is not related to SARS-CoV-2. For example, the additional prophylactic agent comprises, or alternatively consists essentially of, or yet further consists of a vaccine for another coronavirus, such as SARS-CoV or MERS-CoV. Additionally or alternatively, the additional prophylactic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the subject does not have a SARS-CoV-2 infection when administrated with the RNA or the composition. In some embodiments, a SARS-CoV-2 infection can be diagnosed using a conventional method, such as a nucleic acid amplification test (NAATs), an antigen test, or an antibody test. NAATs for SARS-CoV-2 specifically identify the RNA (ribonucleic acid) sequences that comprise the genetic material of the virus, including but not limited to reverse transcription polymerase chain reaction (RT-PCR), or an isothermal amplification (such as nicking endonuclease amplification reaction (NEAR), transcription mediated amplification (TMA), loop-mediated isothermal amplification (LAMP), helicase-dependent amplification (HDA), clustered regularly interspaced short palindromic repeats (CRISPR) or strand displacement amplification (SDA)). Antigen tests are immunoassays that detect the presence of a specific viral antigen, which implies current viral infection. More details are available at www.cdc.gov/coronavirus/2019-ncov/lab/resources/antigen-tests-guidelines.html assessed on Aug. 1, 2021. Antibody or serology tests look for antibodies in blood that fight SARS-CoV-2, and are commonly used to indicate a past infection or a successful vaccination. However, IgM antibody can persist for weeks to months following infection, though its persistence appears to be shorter than IgG; therefore, detection of IgM may suggest relatively recent infection. More details are available at www.cdc.gov/coronavirus/2019-ncov/lab/resources/antibody-tests-guidelines.html assessed on Aug. 1, 2021.

In some embodiments, the subject is at risk of having a disease as disclosed herein, such as SARS-CoV-2 infection. In some embodiments, the subject has not been exposed to SARS-CoV-2. In some embodiments, the subject is at risk of exposing to SARS-CoV-2.

In some embodiments, the subject is more likely than others to become severely ill after being infected by SARS-CoV-2. For example, they can require hospitalization, intensive care, or a ventilator, or die, after the infection. In some embodiments, the subject is over age 65. In some embodiments, the subject is over age 45. In some embodiments, the subject has one or more of the following medical conditions: a cancer, a chronic kidney disease, a chronic lung diseases (such as chronic obstructive pulmonary disease (COPD), asthma (moderate-to-severe), interstitial lung disease, cystic fibrosis, or pulmonary hypertension), dementia or other neurological conditions, diabetes (type 1 or type 2), Down syndrome, a heart condition (such as heart failure, coronary artery disease, cardiomyopathies or hypertension), an HIV infection, an immunocompromised state (weakened immune system), a liver disease, overweight, obesity, pregnancy, a sickle cell disease, thalassemia, smoking (current or former), a solid organ or blood stem cell transplant, stroke or cerebrovascular disease (such as those affecting blood flow to the brain), or a substance use disorder.

In some embodiments, the administrations is by inhalation. In further embodiments, the RNA or the composition is atomized by a nebulizer inhalation system prior to or during administration. In yet further embodiments, the nebulizer system is a portable nebulizer for whole respiratory tract drug delivery.

In some embodiments, the administration is by subcutaneous injection. In some embodiments, the administration is by intramuscular injection. In some embodiments, the administration is by intraperitoneal injection (i.p).

In some embodiment, a composition as disclosed herein can be in the form of an aerosol, dispersion, solution, or suspension and can be formulated for inhalation, intramuscular, oral, sublingual, buccal, parenteral, nasal, subcutaneous, intradermal, or topical administration. The term parenteral as used herein includes percutaneous, subcutaneous, intravascular (e.g., intravenous), intramuscular, or intrathecal injection or infusion techniques and the like.

As used herein, an effective dose of an RNA, or polynucleotide, or vector, or cell or composition as disclosed herein is the dose required to produce a protective immune response in the subject to be administered. A protective immune response in the present context is one that prevents or ameliorates disease in a subject challenged with SARS-CoV-2 or a pseudovirus thereof. The RNA, or polynucleotide, or vector, or cell or composition as disclosed herein can be administered one or more times. An initial measurement of an immune response to the vaccine may be made by measuring production of antibodies in the subject receiving the RNA, or polynucleotide, or vector, or cell, or composition. Methods of measuring antibody production in this manner are also well known in the art, is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the formulated composition. In some embodiments, an effective dose of an RNA, or polynucleotide, or vector, or cell or composition as disclosed herein is administered twice. In some embodiments, an effective dose of an RNA, or polynucleotide, or vector, or cell or composition as disclosed herein is administered twice at an interval of at least 21 days, at least 28 days, at least 35 days, at least 42 days, at least 49 days, at least 56 days, or at least 64 days In a further aspect, provided is an inhalation system comprising, or alternatively consisting essentially of, or yet further consisting of an RNA as disclosed herein, a polynucleotide as disclosed herein, a vector as disclosed herein, or a composition as disclosed herein and a nebulizer. In further embodiments, the nebulizer is a portable nebulizer for whole respiratory tract drug delivery.

In some embodiments, the RNA compositions can be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic or prophylactic effect. The desired dosage can be delivered three times a day, two times a day, once a day, every other day, every third day, every week, every two weeks, every three weeks, every four weeks, every 2 months, every three months, every 6 months, etc. In certain embodiments, the desired dosage can be delivered using multiple administrations (e.g., two, three, four, five, six, seven, eight, nine, ten, eleven, twelve, thirteen, fourteen, or more administrations). When multiple administrations are employed, split dosing regimens such as those described herein can be used. In some embodiments, the RNA compositions can be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg. In some embodiments, the RNA compositions can be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA compositions can be administered at an effective dosage level. The effective dose of the RNA, as provided herein, may range from about 10 μg-500 pg, administered as a single dose or as multiple (e.g., booster) doses. In some embodiments, a single dose of a vaccine composition (e.g., administered once, twice, three times, or more) comprises about 10 μg RNA. In some embodiments, a single dose of a vaccine composition (e.g., administered once, twice, three times, or more) comprises about g RNA. In some embodiments, a single dose of a vaccine composition (e.g., administered once, twice, three times, or more) comprises about 30 μg RNA. In some embodiments, a single dose of a vaccine composition (e.g., administered once, twice, three times, or more) comprises about 40 μg RNA. In some embodiments, a single dose of a vaccine composition (e.g., administered once, twice, three times, or more) comprises about 50 μg RNA. In some embodiments, a single dose of a vaccine composition (e.g., administered once, twice, three times, or more) comprises about 100 μg RNA. In some embodiments, a single dose of a vaccine composition (e.g., administered once, twice, three times, or more) comprises at least 25 pg RNA. In some embodiments, a single dose of a vaccine composition (e.g., administered once, twice, three times, or more) comprises less than 100 μg RNA. In some embodiments, a single dose of a vaccine composition (e.g., administered once, twice, three times, or more) comprises 100 μg or less RNA. In some embodiments, a single dose of a vaccine composition (e.g., administered once, twice, three times, or more) comprises about 250 μg RNA.

In some embodiments, a total amount of RNA administered to a subject is about 10 μg, about 20 μg, about 30 μg, about 40 μg, about 50 μg, about 100 μg, about 200 μg, about 250 μg, or about 500 μg mRNA. In some embodiments, a total amount of RNA administered to a subject is about 50 μg. In some embodiments, a total amount of RNA administered to a subject is about 100 μg. In some embodiments, a total amount of RNA administered to a subject is about 250 μg. In some embodiments, a total amount of RNA administered to a subject is about 500 μg.

In some embodiments, the RNA compositions can be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a the RNA composition can be administered three or four times.

Kits

In one aspect, provided is a kit for use in a method as disclosed herein.

In some embodiments, the kit comprises, or alternatively consists essentially of, or yet further consist of instructions for use and one or more of: a RNA as disclosed herein, a polynucleotide as disclosed herein, a vector as disclosed herein, a composition as disclosed herein, or an inhalation system as disclosed herein. In further embodiments, the kit is suitable for use in a method of treatment as disclosed herein.

In some embodiments, the kit comprises, or alternatively consists essentially of, or yet further consist of instructions for use and one or more of: an RNA as disclosed herein, a polynucleotide as disclosed herein, a vector as disclosed herein, a cell as disclosed herein, a composition as disclosed herein, an HKP, or a lipid optionally a cationic lipid. In further embodiments, the kit is suitable for use in a method producing an RNA or a composition as disclosed herein.

In some embodiments, the kit comprises, or alternatively consists essentially of, or yet further consist of instructions of use, a polynucleotide or a vector as disclosed herein, an RNA polymerase, ATP, CTP, GTP, and UTP or a chemically modified UTP. In further embodiments, the kit is suitable for use in an in vitro method producing an RNA or a composition as disclosed herein.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the invention.

EXAMPLES

Example 1: RNA Synthesis

A tested RNA as disclosed herein was synthesized, for example by in vitro transcription (IVT) using a vector as disclosed herein and an IVT kit available to one of skill in the art (such as MAXIscript™ T7 Transcription Kit from ThermoFisher Scientific), and then purified by selective binding of dsRNA to cellulose in an ethanol-containing chromatography buffer containing 10 mM HEPES (pH 7.2), 0.1 mM EDTA, 125 mM NaCl, 16% ethanol and cellulose fibers and centrifugation. Almost 90% of dsRNA could be removed after this procedure. See, for example, Baiersdorfer et. al, 2019, Mol Ther Nucleic Acids. 2019 Apr. 15; 15:26-35. Contaminants could be also eliminated using FPLC and HPLC, see, for example, Kariko et. al, 2011, Nucleic Acids Res. 2011 November; 39(21):e142.

Example 2: Peptides (HK Polymers) Preparation

The HK peptide polymers were synthesized on a Rainin Voyager synthesizer (Tucson, AZ) by the biopolymer core facility at the University of Maryland.

Example 3: In Vitro Formulation Preparation

PNI-Genvoy lipid nanoparticle (LNP) formulation: Lipid nanoparticles were formulated using the GenVoy Platform with PNI NanoAssemblr (Precision NanoSystems, Vancouver, British Columbia, Canada) as the positive control in both in vitro and in vivo assays.

HKP(+H) formulation version 1: HKP(+H) stock solution (10 mg/mL) was prepared in nuclease free water. A concentrated stock solution was diluted to 2.5 mg/mL in water. mRNA working solution (1 mg/mL) was prepared in 1 mM citrate buffer (pH 6.0). The mRNA/HKP(+H) polyplex was formed by mixing equal volumes of 2.5 mg/mL HKP(+H) and 1 mg/mL mRNA using microfluidics. The mass ratio of HKP(+H) to mRNA is 2.5:1. The mRNA/HKP(+H) polyplex was incubated for 30 min at room temperature before use. For preparation of all peptide based polyplexes, the size was determined with the Zetasizer (Malvern Panalytical) prior to its transfection or injection.

HKP(+H) formulation version 2: HKP(+H) stock solution (10 mg/mL) was prepared in nuclease free water. A concentrated stock solution was diluted to 4 mg/mL in water. mRNA working solution (1 mg/mL) was prepared in 1 mM citrate buffer (pH 6.0). The mRNA/HKP(+H) polyplex was formed by mixing equal volumes of 4 mg/mL HKP(+H) and 1 mg/mL mRNA. The mass ratio of HKP(+H) to mRNA is 4:1. The mRNA/HKP(+H) polyplex was incubated for 30 min at room temperature before use. The size of each peptide-based polyplex was determined with the Zetasizer (Malvern Panalytical) prior to transfection or injection.

HKP(+H)/DOTAP formulation (post-mixed DOTAP): HKP(+H) stock solution (10 mg/mL) was prepared in nuclease free water. A concentrated stock solution was diluted to 4 mg/mL in water. DOTAP (Sigma-Aldrich) is 1 mg/mL in aqueous buffered solution. mRNA working solution (1 mg/mL) was prepared in 1 mM citrate buffer (pH 6.0). First the mRNA/HKP(+H) polyplex was formed by mixing equal volumes of 4 mg/mL HKP(+H) and 1 mg/mL mRNA. The mRNA/HKP(+H) polyplex was incubated for 30 min at room temperature. Next, the same volume of DOTAP to HKP(+H) solution was added to the mRNA/HKP(+H) polyplex. The mass ratio of HKP(+H)/DOTAP to mRNA was 4:1:1. The mRNA/HKP(+H)/DOTAP nanoparticle was incubated for 30 min at room temperature before use.

HKP(+H)/MC3 or HKP(+H)/DOTAP formulations (pre-mixed MC3 or DOTAP): HKP(+H) stock solution (10 mg/mL) was prepared in nuclease-free water. A concentrated stock solution was diluted to 4 mg/mL in water. DOTAP or MC3 is 1 mg/mL in aqueous buffered solution. mRNA working solution (1 mg/mL) was prepared in 1 mM citrate buffer (pH 6.0). Equal volumes of HKP(+H) and MC3 were pre-mixed at a 4:1 mass ratio and the same volume of mRNA to HKP(+H) solution was added to a pre-mixed HKP(+H)/MC3. The mRNA/HKP(+H)/MC3 nanoparticle was formed by mixing pre-mixed 4 mg/mL HKP(+H)/1 mg/mL MC3 and 1 mg/mL mRNA. The mass ratio of HKP(+H)/MC3 to mRNA is 4:1:1. The mRNA/HKP(+H)/MC3 nanoparticle was incubated for 30 min at room temperature before use.

HKP(+H)/PLA NP formulation: HKP(+H) stock solution (10 mg/mL) was prepared in nuclease free water. A concentrated stock solution was diluted to 4 mg/mL in water. A poly-L-Lactic Acid (PLA) nanoparticle (5 mg/mL) was prepared in water. mRNA working solution (1 mg/mL) was prepared in 1 mM citrate buffer (pH 6.0). Equal volumes of HKP(+H) and mRNA were mixed at a 4:1 mass ratio. The mRNA/HKP(+H) polyplex was incubated for 30 min at room temperature, and then the same volume of PLA nanoparticle to HKP(+H) solution was added to the mRNA/HKP(+H) nanoparticle so that the mRNA/HKP(+H) polyplex was adsorbed on the surface of the PLA nanoparticle. The mass ratio of HKP(+H)/PLA to mRNA was 4:5:1. The mRNA/HKP(+H)/PLA nanoparticle was incubated for 30 min at room temperature before use.

TABLE 6

Lipids and RNA working solutions were prepared according to the Table below.

| | Molar ratio | M.W. | Final working solution(12.5 mM lipid) | 4x Stock(mM each) in 100% Ethanol | Supplier and Product Information |
|---|---|---|---|---|---|
| Ionizable lipid equivalent (e.g., SM-102) | 50 | | 6.25 | 25.00 | |
| DSPC | 10 | 790.145 | 1.25 | 5.00 | avantilipids.com/product/850365 (last accessed on Aug. 9th, 2021) |
| Cholesterol | 38.5 | 386.654 | 4.8125 | 19.25 | avantilipids.com/product/700100 (last accessed on Aug. 9th, 2021) |
| PEG2000-DMG | 1.5 | 2509.2 | 0.1875 | 0.75 | broadpharm.com/web/product.php?catalog = BP-25496 (last accessed on Aug. 9th, 2021) |
| mRNA | TriLink CleanCap mRNA | | in 50 mM Sodium Citrate | | www.trilinkbiotech.com/custom-mrna-synthesis (last accessed on Aug. 9th, 2021) |

Briefly, the working area was cleaned thoroughly with 70% ethanol. A 4× stock solution of each lipids was made in 100% Ethanol and stored at −20° C. until use. Lipid working solution was prepared by combining each of the following components in a ratio of 1:1:1:1 (final concentration 12.5 mM): Ionizable cationic lipid((heptadecan-9-yl 8-((2-hydroxyethyl) (6-oxo-6-(undecyloxy) hexyl) amino) octanoate}) SM-102 equivalent, a helper lipid (such as 1,2-Distearoyl-sn-glycero-3 phosphocholine (DSPC)), a cholesterol, and PEG2000-DMG (i.e., 1-monomethoxypolyethyleneglycol-2,3-dimyristylglycerol with polyethylene glycol of average molecular weight 2000). The RNA working solution was prepared in Formulation Buffer (50 mM Sodium Citrate pH4.0). RNA concentration depends on Lipid concentrations, the Flow Rate Ratio and the N/P ratio.

The RNA and lipid nanoparticle was prepared: The NanoAssemblr Ignite was turned on and "Quick Run" was selected from the Main Menu. The parameters were set as shown in FIG. 1 by selecting a field, selecting a value from the drop-down menu or entering the number with the on-screen keyboard and then tapping the check mark. The lid of the Ignite was open and the Cartridge Adaptor was ensured as installed over the "L" inlet of the cartridge slot with the arrow facing upwards, then a NxGen™ cartridge was removed from the package and inserted in the cartridge slot. The rotating block was raised until the cartridge luers were visible. At least 1.5 mL prepared RNA working solution was drawn into a 3 mL syringe. A blunt needle was used if necessary. The needle was removed, air bubbles were cleared from the syringe and the plunger was used to advance the liquid to the tip. Drips from the syringe tip were avoided. The syringe was inserted into the "C" inlet of the Ignite Cartridge and twisted clockwise to engage the Luer Lock. At least 0.5 mL prepared Lipid Working solution was drawn into a 1 mL syringe using a blunt needle if necessary. The needle was removed, air bubbles were cleared from the syringe and the plunger was used to advance the liquid to the tip. Drips from the syringe tip were avoided. The syringe was inserted into the "R" inlet of the Ignite Cartridge. The rotating block was returned to the downwards position. The sample switch arm for two 15 mL conical tubes was ensured as installed. A 15 mL conical collection tube was marked with "RNA-LNP" and pushed into the clip labeled "Sample". Another tube was marked with "waste" and pushed into the clip labeled "Waste". The Ignite lid was closed and "Next" on the screen was tapped. The parameters and the information in the dialog box were confirmed. The "Start" button was pressed. The pushers of the Ignite™ were then injecting the fluids into the microfluidic cartridge. The formulation was collected in the tube labeled "RNA-LNP". After the motors were positioned themselves back in the home position, the screen indicated when it was safe to open the lid. The lid was open once it was safe and the conical collection tube labeled "RNA-LNP" was removed and set aside for characterization and further processing immediately. The rotating block was raised and the syringes were removed from Ignite™ and discarded. The rotating block was returned to the downward position and the NxGen cartridge was removed and discarded. To make additional samples, the back "<" button was tapped to return to the Quick Run Screen and the steps described in this paragraph were repeated except the initial quick run setting step.

For the characterization of formulated lipid nanoparticles (LNPs), following preparation, 25-50 μL of the sample fraction was mixed with 650 μL of ultra pure water (Invitrogen) and the intensity-averaged particle size (Z-average) was measured on ZetaSizer (Malvern Instruments Inc.).

The sample fraction was transferred immediately to a Slide-a-lyzer G2 dialysis cassette (10000 MWCO, Thermo Fischer Scientific Inc.) and dialyzed over night at 4° C. against PBS (pH7.4).

The LNP formulations were concentrated using Amicon ultra-centrifugal filters (EMD Millipore, Billerica, MA, USA), passed through a 0.22-μm filter (Acrodisc) and stored at 4° C. (PBS).

The sample fraction was also collected and measured for the particle size (post dialysis particle size).

The final mRNA concentration and encapsulation efficiency (EE) were measured using Quant-it Ribogreen Assay Kit (Thermo Fischer Scientific).

Example 4: In-Vitro Transfection of mRNA

To verify the proper protein expression of RNAs, an EGFP mRNA or a tested RNA as disclosed herein is transiently transfected into human embryonic kidney 293T cells (293T cells). Briefly, $4.8\times10^5$ cells are plated into a 6 well plate containing 2 ml of DMEM (10% fetal bovine serum and 1% Penicillin-Streptomycin (ThermoFisher Scientific)). After 24 hr, when the cells are 70-90% confluent, the EGFR mRNA or the tested RNA is transfected into 293T cells using Lipofectamine MessengerMAX Transfection Reagent (ThermoFisher Scientific) according to the manual protocol. The transfected 293T cells are cultured for two day and then measured for in vitro protein expression.

Various formulations/carriers as disclosed herein are also examined for their ability to carry the EGFP mRNA or the tested RNA into a target host cell, such as human embryonic kidney 293 cells (HEK 293 cells). Briefly, $4.8\times10^5$ cells are plated into a 6 well plate containing 2 ml of DMEM (10% fetal bovine serum and Penicillin-Streptomycin (ThermoFisher Scientific)). After 24 hr, when the cells are 70-90% confluent, a formulation/carrier with the EGFP mRNA or the tested RNA as disclosed herein is added into each well. 293T cells are cultured for two day and then measured for in vitro protein expression.

Example 5: In Vitro Protein Expression Measurement

Immunofluorescence analysis: Two days post transfection, protein expression was measured by immunofluorescence imaging using a Cytation5 Cell Imaging Multi-Mode Reader (Biotek, Winooski, VT).

Cell lysate preparation: Two days post transfection, culture media is aspirated and cells are washed on ice with ice-cold PBS. Ice-cold lysis buffer (RIPA, ThermoFisher Scientific) with protease inhibitor (ThermoFisher Scientific) was added and the cells were incubated for 30 minutes at 4° C. Cells were then harvested using a cell scraper and lysed by sonication. The supernatant was transferred to a fresh microcentrifuge tube, following centrifugation at 10,000 g for 20 minutes at 4° C. pellets cell debris. The protein concentration of the lysate was determined by Bradford or BCA protein assay for Western blot.

Western blot: Briefly, in each well of a gel, 20-50 μg of protein was mixed with 4×SDS sample buffer (ThermoFisher Scientific), 10× Reducing buffer (ThermoFisher Scientific), and additional $ddH_2O$ (ThermoFisher Scientific) with a total loading volume of 25 μl/well. The mixture was denatured by heating at 95° C. for 5 minutes and cooled to room temperature and centrifuged before loading onto a NUPAGE™ 4 to 12%, Bis-Tris gel (ThermoFisher Scientific). After electrophoretic separation, the gel was removed from the cassette and transferred using an IBLOT™ 2 Dry Blotting System (ThermoFisher Scientific). The transferred membrane was blocked with 5% fat-free milk powder in TBST for 1 hr at room temperature (RT), incubated with primary antibody for overnight at 4° C., washed three times with TBST (0.05% Tween20 in TBS) buffer, and incubated with secondary antibody, which was HRP conjugated Mouse IgG (H+L) Secondary Antibody (ThermoFisher Scientific, A24512) for 1 hr at RT. Transferred membrane was then developed by Pierce ECL Western Blotting Substrate (ThermoFisher Scientific) and was imaged using chemiluminescent imaging system. A representative western blot demonstrating in vitro expression of Omicron BA. 1, Delta and UK (B.1.1.7) variant S proteins of SARS-CoV-2 is shown in FIG. 4.

In some embodiments, the primary antibody specifically recognizes and binds to an S protein of SARS-CoV-2 or a fragment thereof, such as an S2 protein or a RBD of the S protein or both. Accordingly, expression of a tested RNA to its protein product is assessed. In further embodiments, a loading control for the Western blot was performed. For example, the same sample was tested using Western blot as described above, except the primary antibody specifically recognizes and binds to β-actin. A substantially similar protein levels among groups are found in the loading control.

Figure 2A:
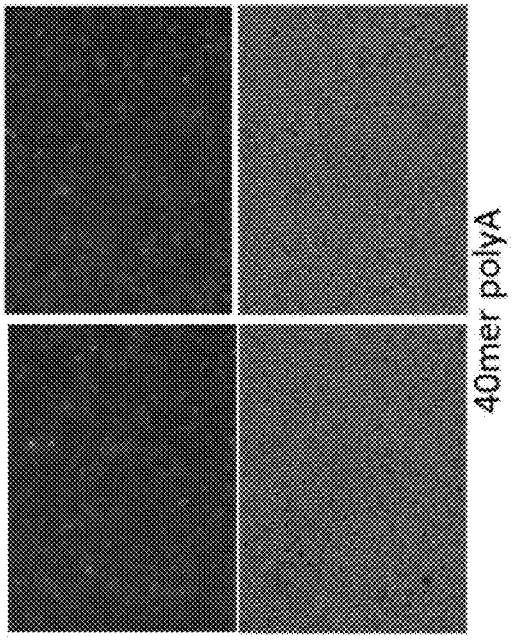
FIGS. 2A-2C provide representative images showing expression of a Blue Fluorescent Protein in cells transfected with RNAs encoding the Blue Fluorescent Protein and comprising various polyA tails (FIG. 2A, polyA 40.
Figure 2B:
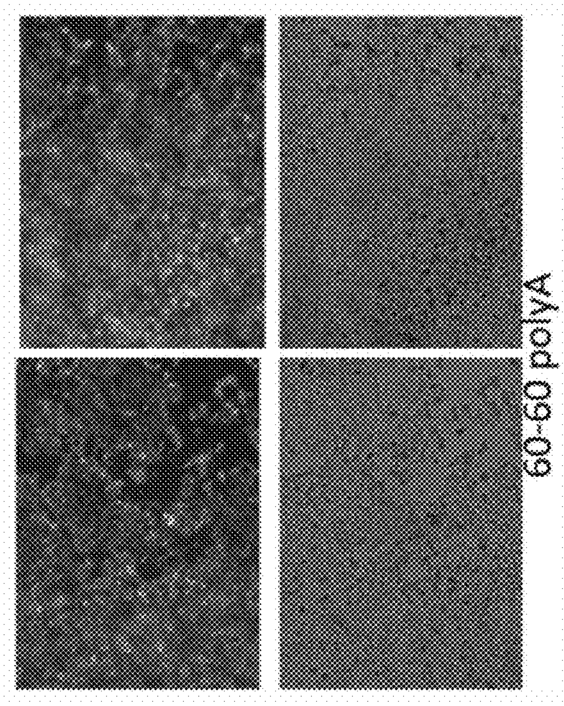
Figure 2C:
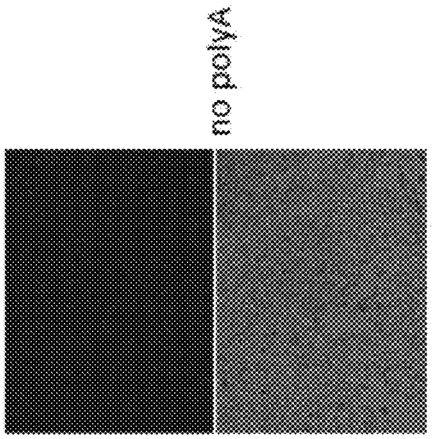

RNAs with different polyA tails, such as a 40 mer polyA (referred to herein as "polyA 40") or a 60-60 polyA (see "polyA 60"), were synthesized, purified, transfected to cells, and tested for protein expression. Briefly, DNA constructs comprising β-globulin 5' and 3' UTRs, Blue Fluorescent Protein 2 (BFP2) coding sequence, and different synthetic polyA tails were synthesized by Twist Bioscience. In further embodiments, the DNA constructs further comprise a plasmid backbone comprising, or consisting essentially of, or yet further consisting of a kanamycin selection marker, the pUC57 backbone, and a T7 promoter to make the plasmid in vitro transcription (IVT) competent. IVT was performed as described previously. RNA was transfected into HEK293T cells and Blue Fluorescent Protein (BFP) florescence intensity was observed using a Citation 5 microscope from BioTek. The results are shown in FIG. 2. A top panel of each of FIGS. 2A-2C provides a representative image showing the BFP fluorescence, while a bottom panel of each of FIGS. 2A-2C provides the corresponding bright filed image.

Figure 3:
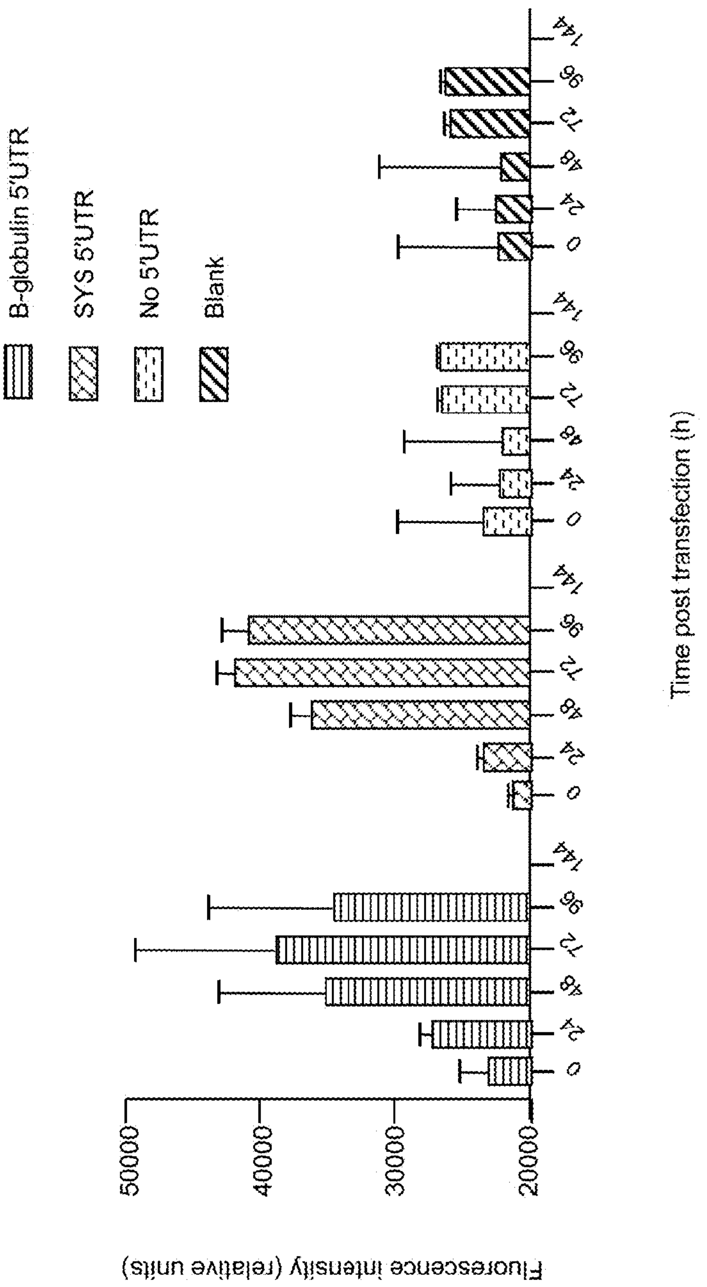
FIG. 3 provides a bar graph showing expression of a Blue Fluorescent Protein indicated by fluorescence intensity measured at various time points (0 hour, 24 hours, 48 hours, 72 hours, 96 hours and 144 hours) post transfection of RNAs encoding the Blue Fluorescent Protein and comprising different UTRs. The first set of bars from the left represents data acquired using β-globulin 5' UTR. The second set of bars from the left represents data acquired using SYS 5' UTR as disclosed herein. The third set of bars from the left represents data acquired using no 5' UTR. The fourth set of bars from the left represents data acquired from the blank control group. Error bars indicate the standard deviation of 3 replicates.
Figure 4A:
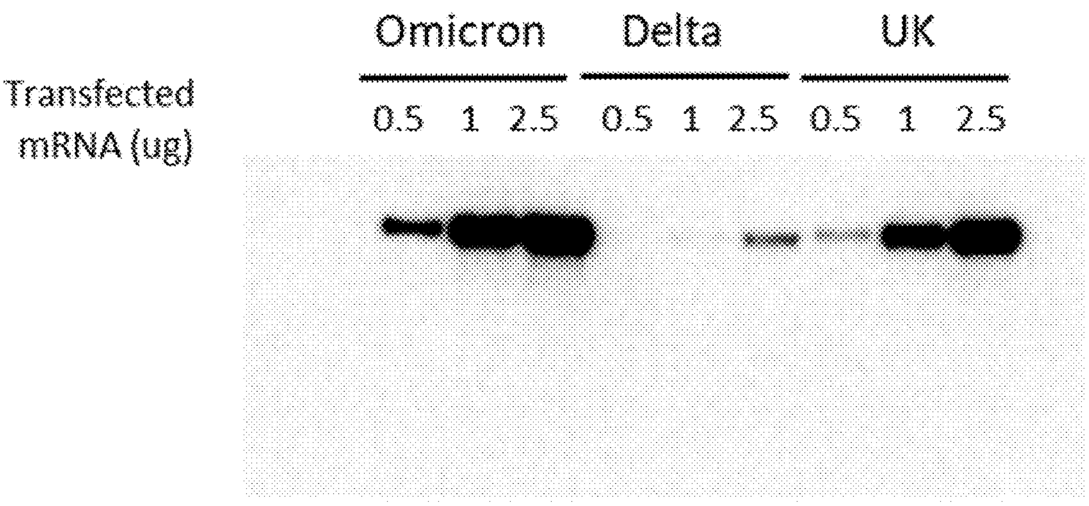
FIGS. 4A-4E provide representative western blot data demonstrating in vitro expression of Omicron BA.1, Delta, and UK variant S proteins of SARS-Cov2, as discussed in Example 5. 20-50 μg of protein was mixed with 4×SDS sample buffer (ThermoFisher Scientific), 10× Reducing buffer (ThermoFisher Scientific), and additional dd$H_2O$ (ThermoFisher Scientific) with a total loading volume of 25 μl/well. The mixture was denatured by heating at 95° C. for 5 minutes and cooled to room temperature and centrifuged before loading onto a NUPAGE™ 4 to 12%, Bis-Tris gel (ThermoFisher Scientific). After electrophoretic separation, the gel was removed from the cassette and transferred using an IBLOT™ 2 Dry Blotting System (ThermoFisher Scientific). The transferred membrane was blocked with 5% fat-free milk powder in TBST for 1 hr at room temperature (RT), incubated with primary antibody for overnight at 4° C., washed three times with TBST (0.05% Tween20 in TBS) buffer, and incubated with secondary antibody, which is HRP conjugated Mouse IgG (H+L) Secondary Antibody (ThermoFisher Scientific, A24512) for 1 hr at RT. The transferred membrane was imaged using a chemiluminescent imaging system. d Delta, were transfected into HEK293T cells using Lipofectamine MessengerMax Transfection Reagents. The amount of mRNA used is 0.5 μg, 1 μg, and 2.5 μg. The transfection was done in duplicate. Twenty-four hours post transfection, one set of transfected cells were collected for western blot analysis and the other set of transfected cells were used for FACS analysis.
Figure 4B:
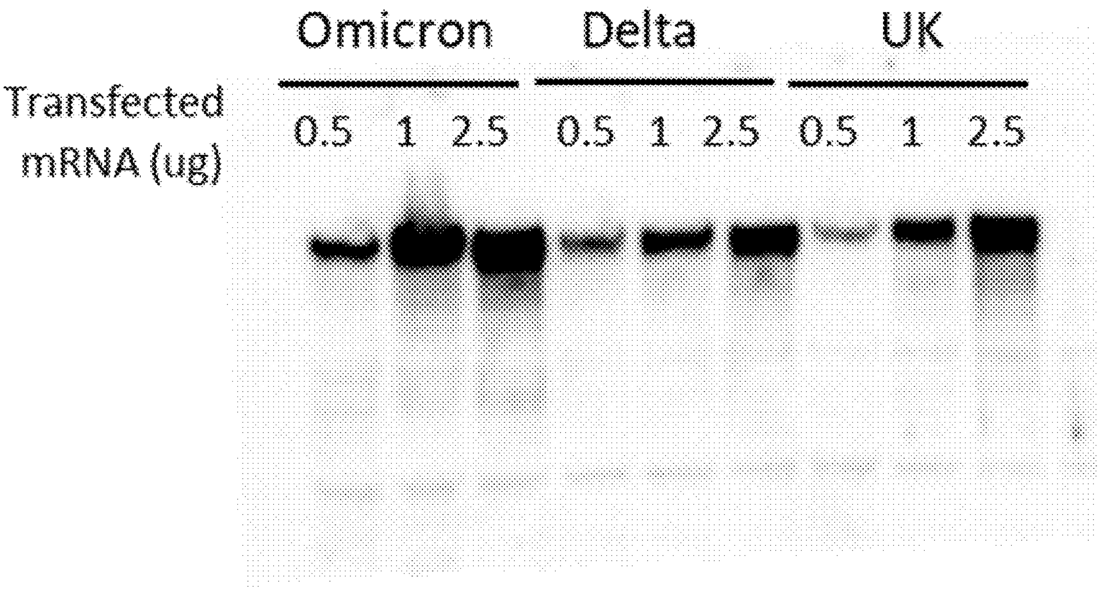
Figure 4C:
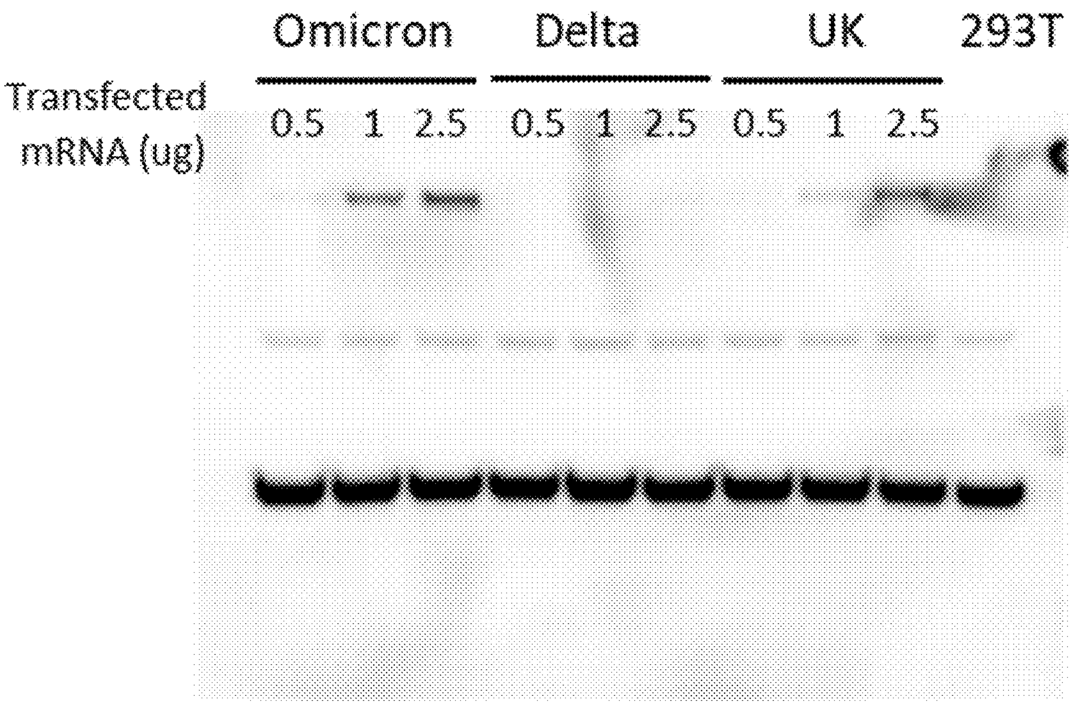
Figure 4D:
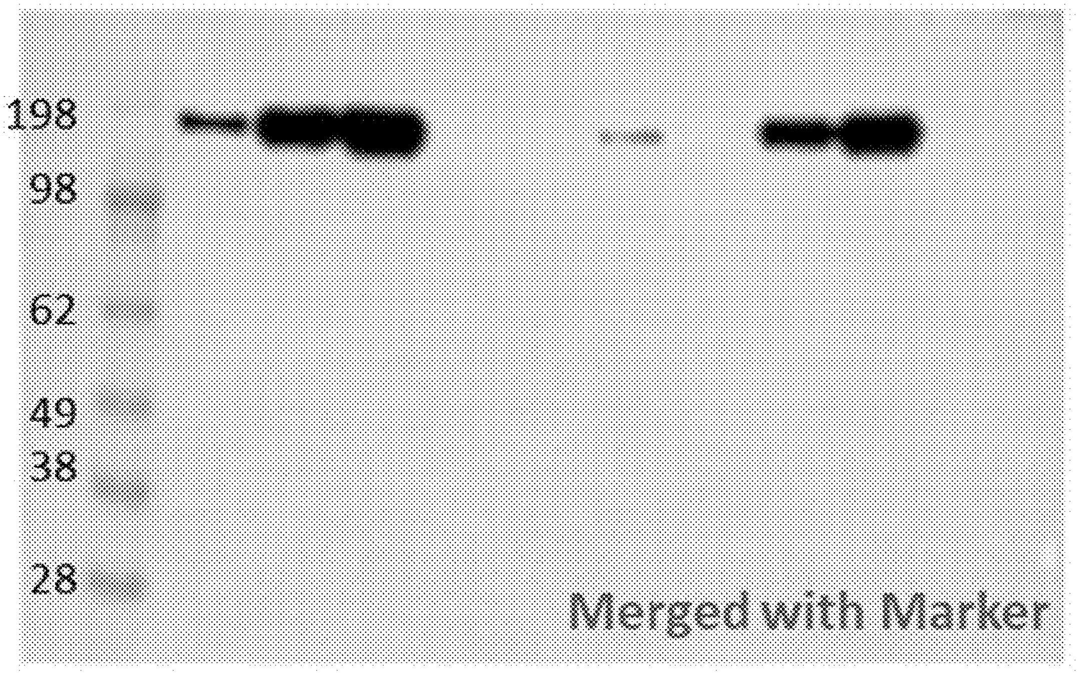
Figure 4E:
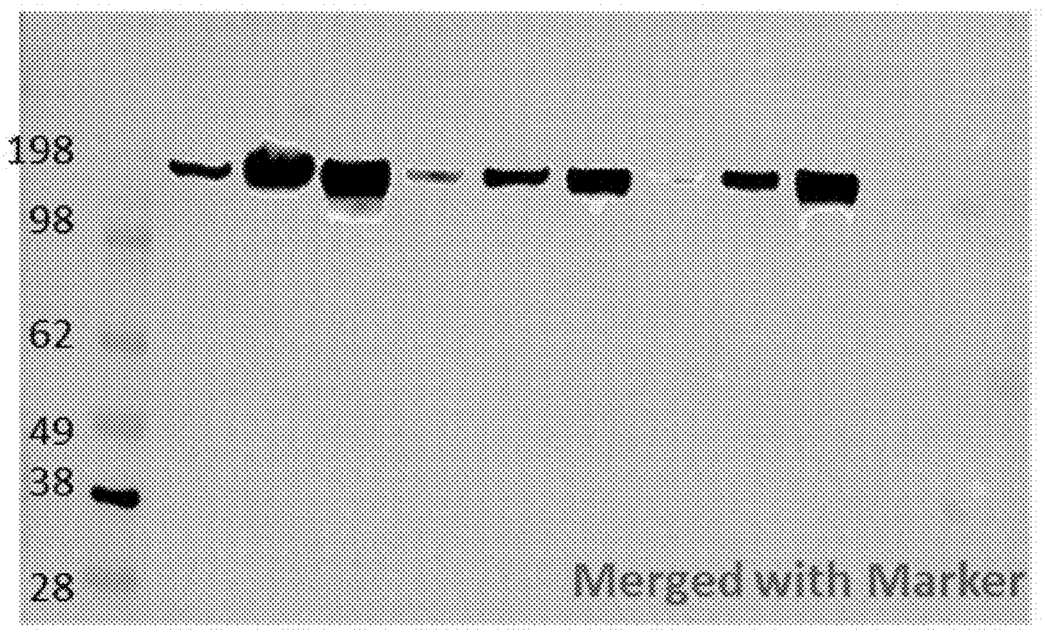

Additionally, RNAs with various UTRs, such as a β-globulin UTR or a SYS UTR as disclosed herein, were synthesized, purified, transfected to cells, and tested for protein expression. Briefly, DNA constructs comprising different 5'UTRs and BFP2 were synthesized by Twist Bioscience. The constructs further comprise a plasmid backbone comprising, or consisting essentially of, or yet further consisting of a kanamycin selection marker, the pUC57 backbone, and a T7 promoter to make the plasmid in vitro transcription (IVT) competent. Once plasmids were prepared and purified, IVT was performed as described previously. RNA was transfected into HEK293T cells using MessengerMax transfection reagent (Thermofisher) and BFP florescent intensity was measured using a Citation 5 microscope from BioTek. Different 5'UTRs were compared at various time points. See, FIG. 3. Error bars indicate the standard deviation of 3 replicates.

Example 6: Binding with Human ACE2

Figure 5:
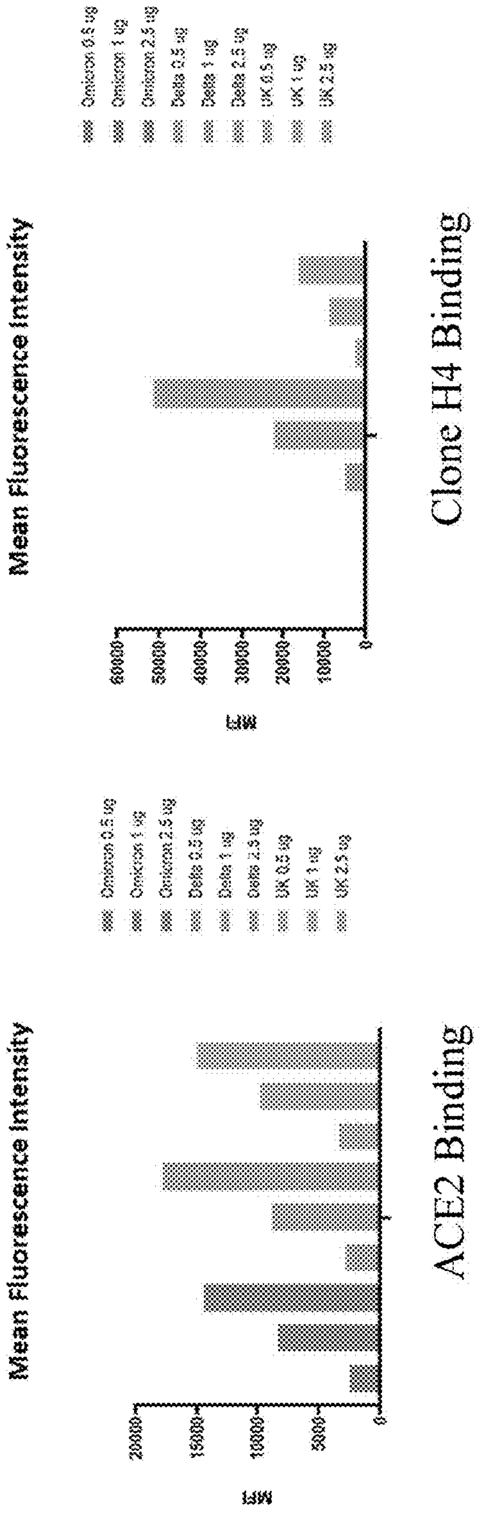
FIG. 5 (right and left panels) provides graphs of mean fluorescence intensity of ACE2 binding (left panel) or Clone H4 (right panel) binding to HEK293T and a549 cells in the presence of increasing doses of SARS-Cov2 S proteins, as discussed in Example 6. Cells (HEK293T (Cat #CRL-3216, ATCC) or a549 (Cat #CCL-185, ATCC)) transfected with RNA expressing the Omicron BA.1, Delta, or UK (B.1.1.7) variant SARS-Cov2 S protein, were incubated with a human ACE2 or Clone H4 directly or indirectly labeled with a fluorescent protein, such as FITC. Flow cytometry was performed and the mean fluorescence intensity (MFI) of each cell was measured.

Binding between the Omicron BA.1, delta, and UK (B.1.1.7) variant SARS-CoV-2 S proteins and their human ACE2 receptor was further tested. Cells (such as HEK293T (Cat #CRL-3216, ATCC) or a549 (Cat #CCL-185, ATCC)) transfected with the tested RNA expressing the S protein, were incubated with a human ACE2 or Clone H4 directly or indirectly labeled with a fluorescent protein, such as FITC. Clone H4 specifically targets the SARS-CoV-2 Spike receptor-binding domain (RBD), and the constant region of the human IgG1. The incubated cells were washed to remove the unbound ACE2. Flow cytometry was performed and the mean fluorescence intensity (MFI) of each cell was measured qualitatively. The higher the MFI is, the more ACE2 binds to the cell, indicating a stronger binding (such as showing a higher binding affinity) between ACE2 and the S protein, variant and/or mutant thereof expressed by the cell. ACE2 binding increased with increasing doses of Omicron BA.1, delta, and UK (B.1.1.7) variant SARS-CoV-2 S proteins. Clone H4 binding was significantly interrupted, but increased with escalating doses of the Delta and UK variant SARS-CoV-2 S proteins (FIG. 5).

Example 7: In Vivo Animal Model and Injection

Figure 6:
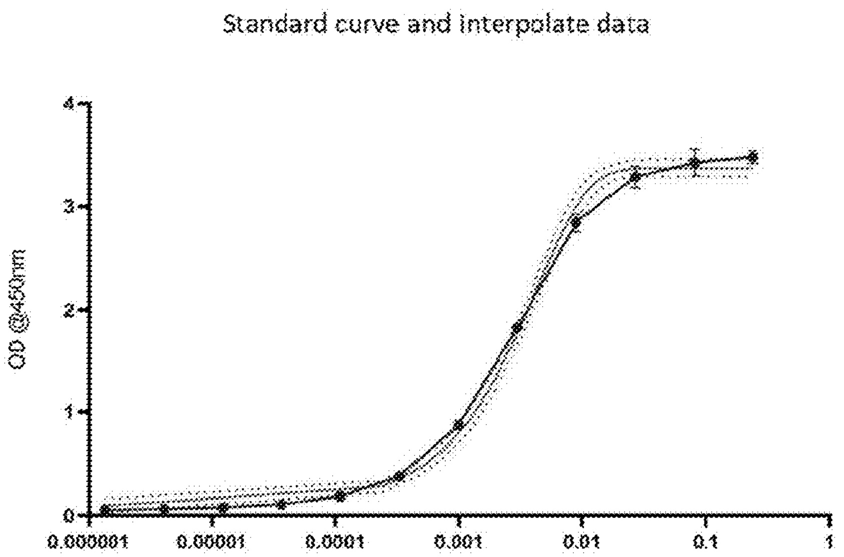
FIG. 6 shows a representative standard curve (left panel) and table (right panel) of antibody titer data for 6-8 week old female BALB/C randomized into dose groups of 4 mice per group and injected intramuscularly into the right flank with 30 μg of an EGFP mRNA Omicron BA.1 variant SARS-CoV-2 S protein, as discussed in Example 7. On day 28, a second booster injection was made. On day 35 serum was collected and analyzed by immunoassay (ELISA) for measurement of antibody titers in order to generate a standard curve for use in a neutralization assay.

An in vivo study was performed. Briefly, 6-8 week old female BALB/C were randomized into dose groups of 4 mice per group and injected intramuscularly into the right flank with 30 μg of an EGFP mRNA with different formulations of Omicron (BA.1 and BA.2), Delta, and 614D variant SARS-CoV-2 S protein. With the same formulation, the RNAs was prepared for in vivo analysis and antibody titer measurements and binding. On day 28, a second booster injection was made. On day 35 serum was collected and analyzed by immunoassay (ELISA) for measurement of antibody titers in order to generate a standard curve for use in a neutralization assay. A representative standard curve and table of antibody titer data is shown in FIG. 6.

Figure 7:
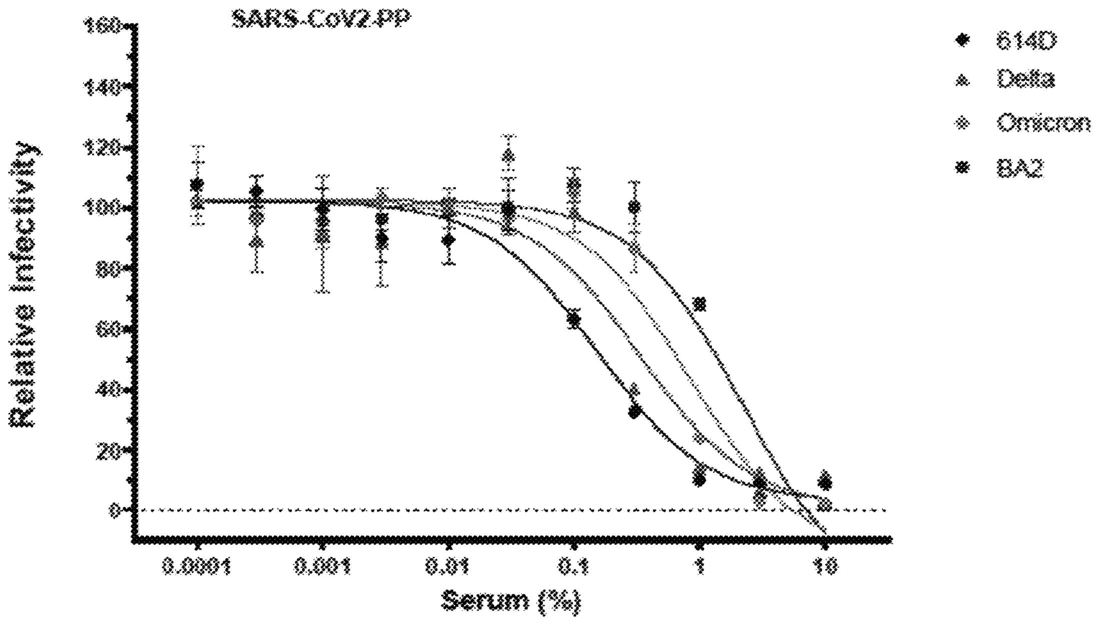
FIG. 7 shows neutralization antibody titer data against Omicron (BA.1 and BA.2), Delta, and 614D SARS-CoV-2 pseudovirus particles measured following first and second immunization doses, as discussed in Example 7. $IC_{50}$ values were calculated based on curve fitting for each of the neutralization assay conditions provided. $IC_{50}$ for each of the 614D, Delta, BA.1 and BA.2 variants was 0.338 μg/mL, 0.746 μg/mL, 1.903 μg/mL, and 4.812 μg/mL, respectively.

Neutralization antibody titers against Omicron SARS-CoV-2 pseudovirus particles was measured following first and second immunization doses. $IC_{50}$ values were calculated based on curve fitting. Strain-specific neutralization was observed. Curves (top panel) and $IC_{50}$ values (bottom panel) are shown and tabulated in FIG. 7 for each of the neutralization assay conditions provided. These data demonstrate that the Omicron SARS-CoV-2 spike mRNA vaccines provided herein are capable of inducing an immune response against SARS-CoV-2 variant spike proteins in a subject infected with SARS-CoV-2 by, e.g., increasing neutralizing antibody titers against SARS-CoV-2 following at least 14 or 35 days after first and second immunization doses.

Example 8: In Vivo Animal Models

Other suitable animal models can be used to investigate a tested RNA in a formulation/carrier as disclosed herein and assess its efficiency for use in a method as disclosed herein and for therapy alone or in combination with other possible therapies, such as anti-inflammatory therapies.

In one example, used herein is a genetically modified animal model expressing human ACE2 optionally under a tissue-specific promoter (for example, the Krt18 promoter for epithelial cells; K18-hACE2 mice), or a universal promoter (cytomegalovirus enhancer followed by the chicken β-actin promoter) or the endogenous mouse Ace2 promoter. All of these mice are susceptible to infection by SARS-CoV-2, but differences in their expression of human ACE2 result in a pathogenic range of mild to lethal disease. In some embodiments, the animal is mouse. Alternative animal models include syrian hamsters, whose ACE2 is significantly similar to human ones and considered as susceptible to infection with SARS-CoV-2; ferrets; and non-human primates.

A RNA composition, such as a tested RNA in a formulation/carrier as disclosed herein, is administered to the animal prior to or concurrently with a challenge with SARS-CoV-2 or a pseudovirus thereof. The administration of the RNA composition is repeated at least once or twice. A second administration of the RNA composition occurred about two or about three weeks apart. Animals not challenged with the SARS-CoV-2 or pseudovirus served as a negative control while those challenged with the SARS-CoV-2 or pseudovirus but not treated served as a positive control. Additional controls are used, such as animals treated with a SARS-CoV-2 vaccine as known in the art, such as BNT162b2 available from Pfizer-BioNTech, mRNA-1273 available from Moderna, or JNJ-78436735 from Johnson & Johnson's Janssen, and challenged with the SARS-CoV-2 or pseudovirus.

Viral load, lung pathology, immune cell infiltration to the lung, cytokine release, body weight, fur, posture, respiratory distress (such as laboured breathing), lethargy or not, nasal discharge, wheezing, oropharyngeal build-up of mucus, sneezing, loose stools and etc. are monitored after the administration of the RNA composition in order to assess the effects.

a serine (S) as the amino acid corresponding to R682 of SEQ ID NO: 1 (R682S), a glycine (G) as the amino acid corresponding to R685 of SEQ ID NO: 1 (R685G), a proline (P) as the amino acid corresponding to F817 of SEQ ID NO: 1 (F817P), a P as the amino acid corresponding to A892 of SEQ ID NO: 1 (A892P), a P as the amino acid corresponding to A899 of SEQ ID NO: 1 (A899P), a P as the amino acid corresponding to A942 of SEQ ID NO: 1 (A942P), a P as the amino acid corresponding to K986 of SEQ ID NO: 1 (K986P), or a P as the amino acid corresponding to V987 of SEQ ID NO: 1 (V987P), with the proviso that the RNA does not comprise SEQ ID NO: 2.

2. The RNA of embodiment 1, wherein the S protein or the fragment thereof further comprises at least one or more mutations comprising T19I, Δ24-26, A27S, A67V, Δ69/70, T95I, G142D, Δ143-145, N211I, Δ212, V213G, ins214EPE, G339D, S371F, S371L, S373P, S375F, T376A, D405N,

TABLE 8

SEQUENCES

| Designation | Amino Acid Sequence | DNA Sequence | RNA Sequence |
|---|---|---|---|
| S protein | SEQ ID NO: 1 | — | — |
| S protein D614G and S6P | SEQ ID NO: 2 | SEQ ID NO: 3 (non-optimized) | SEQ ID NO: 4 (non-optimized) |
| Omicron BA.4 | SEQ ID NO: 5 | SEQ ID NO: 6 (GC optimized) and SEQ ID NO: 7 (GS optimized) | |
| Omicron BA.5 | SEQ ID NO: 8 | SEQ ID NO: 9 (GC optimized) and SEQ ID NO: 10 (GS optimized) | |
| Omicron BA.2.12.1 | SEQ ID NO: 11 | SEQ ID NO: 12 (GC optimized), SEQ ID NO: 13 (GS optimized), SEQ ID NO: 14 (Fq optimized), and SEQ ID NO (Dp optimized): 15 | |
| Omicron BA.2.75 | SEQ ID NO: 55 | SEQ ID NO: 56 (GC optimized) | |
| Omicron BF.7 | SEQ ID NO: 57 | SEQ ID NO: 58 (GC optimized) | |
| 3'UTR | — | SEQ ID NO: 17 | SEQ ID NO: 18 |
| β-globulin 5'UTR | — | SEQ ID NO: 19 | SEQ ID NO: 20 |
| SYS UTR 2.0 | — | SEQ ID NO: 21 | SEQ ID NO: 22 |
| SYS UTR 1.0 | — | SEQ ID NO: 23 | SEQ ID NO: 24 |
| SYS4 5'UTR | — | SEQ ID NO: 25 | SEQ ID NO: 26 |
| poly A 40 | — | SEQ ID NO: 27 | SEQ ID NO: 53 |
| polyA 60 | — | SEQ ID NO: 28 | SEQ ID NO: 54 |
| poly A signal HSV | — | SEQ ID NO: 29 | SEQ ID NO: 30 |
| Plasmid | — | SEQ ID NO: 33 | — |
| Side chains of HKP | SEQ ID NO: 34 to 47 | — | — |

Embodiments

1. A ribonucleic acid (RNA) encoding a spike (S) protein or an immunogenic fragment thereof of a severe acute respiratory syndrome coronavirus 2 (SARS-CoV-2) comprising at least one non-naturally occurring amino acid mutation, wherein the at least one non-naturally occurring amino acid mutation comprises one or more of:

R408S, K417N, N440K, G446S L452R, L452Q, S477N, T478K, E484A, F486V, Q493R, G496S, Q498R, N501Y, Y505H, D614G, T547K, H655Y, N679K, P681H, S704L, N764K, D796Y, N856K, Q954H, N969K, and/or L981F, corresponding to the amino acid sequence of SEQ ID NO: 1.

3. The RNA of embodiment 1, wherein the S protein or the fragment thereof further comprises at least one or more mutations comprising:

a) T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, and/or N969K, corresponding to the amino acid sequence of SEQ ID NO: 1;

b) T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and/or N969K, corresponding to the amino acid sequence of SEQ ID NO: 1;

c) A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, and/or N969K corresponding to the amino acid sequence of SEQ ID NO: 1; d) T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K; or e) T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K.

4. The RNA of any one of embodiments 1-3, wherein the at least one or more non-naturally occurring amino acid mutation comprises R682S and/or R685G.

5. The RNA of any one of embodiments 1-4, wherein the at least one or more non-naturally occurring amino acid mutation comprises or further comprises any one, or any two, or any three, or any four, or any five of F817P, A892P, A899P, A942P, K986P, and/or V987P.

6. The RNA of embodiment 5, wherein the at least one or more non-naturally occurring amino acid mutation comprises or further comprises K986P and/or V987P.

7. The RNA of any one of embodiments 1-6, wherein the at least one or more non-naturally occurring amino acid mutation comprises or further comprises F817P, A892P, A899P, A942P, K986P, and/or V987P.

8. The RNA of any one of embodiments 1-6, wherein the S protein or fragment thereof comprises the polypeptide of SEQ ID NO: 5 or an equivalent thereof, wherein the equivalent of SEQ ID NO: 5 retains at least one or more of the mutations selected from T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, N969K, F817P, A892P, A899P, A942P, K986P, V987P, R682S and/or R685G, or all of the mutations selected from T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, N969K, F817P, A892P, A899P, A942P, K986P, V987P, R682S and R685G.

9. The RNA of embodiment 8, comprising a polynucleotide encoding SEQ ID NO: 5 or an equivalent thereof.

10. The RNA of any one of embodiments 1-6, wherein the S protein or fragment thereof comprises the polypeptide of SEQ ID NO: 8 or an equivalent thereof, wherein the equivalent of SEQ ID NO: 8 retains at least one or more of the mutations selected from T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, F817P, A892P, A899P, A942P, K986P, V987P, R682S and/or R685G, or all of the mutations selected from T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, F817P, A892P, A899P, A942P, K986P, V987P, R682S and R685G.

11. The RNA of embodiment 10, comprising a polynucleotide of encoding SEQ ID NO: 8 or an equivalent thereof.

12. The RNA of any one of embodiments 1-6, wherein the S protein or the fragment thereof comprises the polypeptide of SEQ ID NO: 11 or an equivalent thereof, wherein the equivalent of SEQ ID NO: 11 retains the mutations of A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, F817P, A892P, A899P, A942P, K986P, V987P, R682S and R685G.

13. The RNA of embodiment 12, comprising a polynucleotide of encoding SEQ ID NO: 11 or an equivalent thereof.

14. The RNA of any one of embodiments 1-6, wherein the S protein or fragment thereof comprises the polypeptide of SEQ ID NO: 55 or an equivalent thereof, wherein the equivalent of SEQ ID NO: 55 retains the at least one or more mutation selected from T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, N969K, F817P, A892P, A899P, A942P, K986P, V987P, R682S and/or R685G, or retains the mutations of T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, N969K, F817P, A892P, A899P, A942P, K986P, V987P, R682S and R685G.

15. The RNA of embodiment 14, comprising a polynucleotide of encoding SEQ ID NO: 55 or an equivalent thereof.

16. The RNA of any one of embodiments 1-6, wherein the S protein or fragment thereof comprises the polypeptide of SEQ ID NO: 57 or an equivalent thereof, wherein the equivalent of SEQ ID NO: 57 retains the at least one or more mutation selected from T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, N969K, F817P, A892P, A899P, A942P, K986P, V987P, R682S and/or R685G, or retains the mutations of T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, N969K, F817P, A892P, A899P, A942P, K986P, V987P, R682S and R685G.

17. The RNA of embodiment 16, comprising a polynucleotide of encoding SEQ ID NO: 57 or an equivalent thereof.

18. The RNA of any one of embodiments 1-17, wherein the equivalent of any one of SEQ ID NOs: 6, 9, 12, 56, or 58 consists of an GC content of about 35% to about 70% across the full length of the equivalent.

19. The RNA of any one of embodiments 8-18, wherein the equivalent is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence.

20. The RNA of any one of embodiments 1-19, further comprising a 3' UTR.

21. The RNA of embodiment 20, wherein the 3'UTR comprises any one of SEQ ID NOs: 18, 22, or 24.

22. The RNA of any one of embodiments 1-21, further comprising a 5' UTR.

23. The RNA of embodiment 22, wherein the 5' UTR comprises SEQ ID NO: 20 or 26.

24. The RNA of any one of embodiments 1-23, further comprising a polyA tail.

25. The RNA of embodiment 24, wherein the polyA tail comprises any one of SEQ ID NOs: 53, 54, or 30.

26. The RNA of any one of embodiments 1-25, wherein the RNA is chemically modified and optionally comprises one or more of: an N1-methyl-pseudouridine residue or a pseudouridine residue.

27. The RNA of embodiment 26, wherein at least about 50%, or at least about 70%, or about 100% of the uridine residues in the RNA are N1-methyl pseudouridine or pseudouridine.

28. A polynucleotide encoding the RNA of any one of embodiments 1-27, or a polynucleotide complementary thereto, optionally wherein the polynucleotide is selected from the group of: a deoxyribonucleic acid (DNA), an RNA, a hybrid of DNA and RNA, or an analog of each thereof.

29. A polynucleotide encoding a spike (S) protein or an immunogenic fragment thereof of a severe acute respiratory syndrome coronavirus 2 (SARS-CoV-2) comprising at least one non-naturally occurring amino acid mutation, wherein the polynucleotide comprises a polynucleotide sequence of SEQ ID NOs: 6, 7, 9, 10, 12-15, 56, or 58 or an equivalent of each thereof.

30. A vector comprising the polynucleotide of embodiment 28 or 29.

31. The vector of embodiment 30, further comprising a regulatory sequence operatively linked to the polynucleotide to direct the transcription thereof.

32. The vector of embodiment 31, wherein the regulatory sequence comprises a promotor.

33. The vector of embodiment 32, wherein the promoter comprises: a bacteriophage RNA polymerase promoter, optionally a T7 promoter, or a SP6 promoter, or a T3 promoter.

34. The vector of any one of embodiments 30-33, further comprising a marker selected from a detectable marker, a purification marker, or a selection marker.

35. The vector of any one of embodiments 30-34, wherein the vector is a non-viral vector, optionally a plasmid, or a liposome, or a micelle.

36. The vector of embodiment 31, wherein the plasmid comprises or consists of SEQ ID NO: 33, or an equivalent thereof.

37. The vector of any one of embodiments 26-32, wherein the vector is a viral vector, optionally an adenoviral vector, or an adeno-associated viral vector, or a retroviral vector, or a lentiviral vector, or a plant viral vector.

38. A polypeptide encoded by the RNA or polynucleotide of any of embodiments 1-29.

39. A cell comprising one or more of: the RNA of any one of embodiments 1-27, the polynucleotide of embodiment 28 or 29, or the vector of any one of embodiments 30-37, 40. The cell of embodiment 38, wherein the cell is: a eukaryotic cell, optionally a mammal cell, an insect cell, or a yeast cell; or prokaryotic cell, optionally an *Escherichia coli* cell.

41. A composition comprising a carrier and one or more of: the RNA of any one of embodiments 1-27, the polynucleotide of embodiment 28 or 29, or the vector of any one of embodiments 30-37, the cell of any one of embodiments 39-40 or the polypeptide of embodiment 38.

42. The composition of embodiment 41, wherein the carrier is a pharmaceutically acceptable carrier.

43. A method of producing the RNA of any one of embodiments 1-27, comprising introducing into the cell the RNA into a cell, and optionally culturing the cell under conditions suitable for expressing the RNA.

44. A method of producing the RNA of any one of embodiments 1-27, the polynucleotide of embodiment 28 or 29, or the vector of any one of embodiments 30-37 with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA.

45. The method of embodiment 43 or 44, further comprising isolating the RNA.

46. A composition comprising the RNA of any one of embodiments 1-27 and a pharmaceutically acceptable carrier.

47. The composition of embodiment 46, wherein the pharmaceutically acceptable carrier comprises a polymeric nanoparticle that comprises a Histidine-Lysine co-polymer (HKP).

48. The composition of embodiment 47, wherein the HKP comprises a side chain selected from SEQ ID NOs: 34-47.

49. The composition of embodiment 47 or 48, wherein the pharmaceutically acceptable carrier further comprises a lipid.

50. The composition of embodiment 49, wherein the lipid comprises a cationic lipid.

51. The composition of embodiment 50 wherein the cationic lipid is ionizable.

52. The composition of embodiment 50 or 51, wherein the cationic lipid comprises Dlin-MC3-DMA (MC3) or dioleoyloxy-3-(trimethylammonio)propane (DOTAP) or both.

53. The composition of any one of embodiments 49-52, wherein the lipid further comprises one or more of: a helper lipid, a cholesterol, or a PEGylated lipid.

54. The composition of embodiment 46, wherein the pharmaceutically acceptable carrier comprises a lipid nanoparticle (LNP).

55. The composition of embodiment 54, wherein the LNP comprises one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof.

56. The composition of embodiment 55, wherein the LNP further comprises one or more of: a helper lipid, a cholesterol, or a PEGylated lipid.

57. The composition of any one of embodiments 53-56, wherein the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE).

58. The composition of any one of embodiments 53-56, wherein the cholesterol comprises a plant cholesterol or an animal cholesterol or both.

59. The composition of any one of embodiments 54-58, wherein the PEGylated lipid comprises one or more of: PEG-c-DOMG (R-3-[(ω-methoxy-poly(ethyleneglycol) 2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

60. The composition of any one of embodiments 54-58, wherein the LNP comprises SM-102, DSPC, cholesterol and PEG2000-DMG.

61. The composition of embodiment 60, wherein the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5.

62. A method of producing the composition of any one of embodiments 46-61, comprising contacting the RNA of any one of embodiments 1-23 with an HKP, thereby the RNA and the HKP are self-assembled into nanoparticles.

63. The method of embodiment 62, wherein the mass ratio of HKP and the RNA in the contacting step is about 10:1 to about 1:10, optionally 2.5:1.

64. The method of embodiment 62 or 63, further comprising contacting the HKP and RNA with cationic lipid.

65. The method of embodiment 64, wherein the cationic lipid comprises Dlin-MC3-DMA (MC3) or DOTAP (dioleoyloxy-3-(trimethylammonio)propane) or both.

66. The method of embodiment 64 or 65, wherein the mass ratio of the cationic lipid and the RNA in the contacting step is about 10:1 to about 1:10, optionally 1:1.

67. The method of any one of embodiments 64-66, wherein the mass ratio of the HKP, the mRNA and the cationic lipid in the contacting step is about 4:1:1.

68. A method of producing the composition of any one of embodiments 46-67, comprising contacting the RNA of any one of embodiments 1-23 with a lipid, thereby the RNA and the lipid are self-assembled into lipid nanoparticles (LNPs).

69. The method of embodiment 68, wherein the LNPs comprise one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof.

70. The method of embodiment 69, wherein the LNPs further comprise one or more of: a helper lipid, a cholesterol, or a PEGylated lipid.

71. The method of embodiment 70, wherein the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE).

72. The method of embodiment 70 or 71, wherein the cholesterol comprises a plant cholesterol or an animal cholesterol or both.

73. The method of any one of embodiments 70-72, wherein the PEGylated lipid comprises one or more of: PEG-c-DOMG (R-3-[(ω-methoxy-poly(ethyleneglycol) 2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

74. The method of any one of embodiments 68-73, wherein the LNPs comprise SM-102, DSPC, cholesterol and PEG2000-DMG.

75. The method of embodiment 74, wherein the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5.

76. The method of any one of embodiments 68-73, wherein the contacting step is performed in a microfluidic mixer, optionally selected from a slit interdigitial micromixer, or a staggered herringbone micromixer (SHM).

77. A method of one or more of:

(a) preventing a subject from having a symptomatic SARS-CoV-2 infection,
(b) inducing an immune response to SARS-CoV-2 in a subject in need thereof,
(c) reducing the binding of a SARS-CoV-2 or an S protein thereof with angiotensin converting enzyme 2 (ACE2) in a subject in need thereof,
(d) treating a subject infected with SARS-CoV-2, or
(e) reducing a SARS-CoV-2 viral load in a subject in need thereof, comprising administering to the subject one or more of: the RNA of any one of embodiments 1-27 or the composition of any one of embodiments 46-61.

78. The method of embodiment 77, further comprising treating the subject with an additional therapeutic agent.

79. The method of embodiment 78, wherein the additional therapeutic agent comprises one or more of:

an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

80. The method of any one of embodiments 77-79, wherein the subject does not have a SARS-CoV-2 infection when administrated with the RNA or the composition.

81. The method of any one of embodiments 77-80, wherein the RNA or the composition is atomized by a nebulizer inhalation system prior to or during administration.

82. The method of embodiment 81, wherein the nebulizer system is a portable nebulizer for whole respiratory tract drug delivery.

83. The method of any one of embodiments 77-80, wherein the RNA or the composition is administered by subcutaneous injection.

84. The method of any one of embodiments 77-80, wherein the RNA or the composition is administered by intramuscular injection.

85. The method of any one of embodiments 77-80, wherein the RNA or the composition is administered by intraperitoneal injection (i.p).

86. The method of any one of embodiments 77-85, wherein the RNA or the composition is administered twice at an interval of at least 21 days, at least 28 days, at least 35 days, at least 42 days, at least 49 days, at least 56 days, or at least 64 days.

87. An inhalation system comprising the RNA of any one of embodiments 1-27 or the composition of any one of embodiments 46-61 and a nebulizer.

88. The inhalation system of embodiment 87, wherein the nebulizer is a portable nebulizer for whole respiratory tract drug delivery.

89. A kit for use in the method of any one of embodiments 77-86, comprising instructions for use and one or more of: the RNA of any one of embodiments 1-27, the composition of any one of embodiments 46-61, or the inhalation system of embodiment 87 or 88.

90. A kit for use in the method of any one of embodiments 77-86, comprising instructions of use and one or more of: the RNA of any one of embodiments 1-27, the polynucleotide of embodiment 28 or 29, the vector of any one of embodiments 30-37, the cell of any one of embodiments 39-40, the composition of embodiment 46-61, an HKP, or a lipid optionally a cationic lipid.

Partial Sequence Listing

SEQ ID NO: 1, amino acid sequence of S protein:

MFVFLVLLPLVSSQCVNLTTRTQLPPAYTNSFTRGVYYPDKVFRS

SVLHSTQDLFLPFFSNVTWFHAIHVSGTNGTKRFDNPVLPFNDGV

YFASTEKSNIIRGWIFGTTLDSKTQSLLIVNNATNVVIKVCEFQF

CNDPFLGVYYHKNNKSWMESEFRVYSSANNCTFEYVSQPFLMDLE

GKQGNFKNLREFVFKNIDGYFKIYSKHTPINLVRDLPQGFSALEP

LVDLPIGINITRFQTLLALHRSYLTPGDSSSGWTAGAAAYYVGYL

QPRTFLLKYNENGTITDAVDCALDPLSETKCTLKSFTVEKGIYQT

SNFRVQPTESIVRFPNITNLCPFGEVFNATRFASVYAWNRKRISN

CVADYSVLYNSASFSTFKCYGVSPTKLNDLCFTNVYADSFVIRGD

EVRQIAPGQTGKIADYNYKLPDDFTGCVIAWNSNNLDSKVGGNYN

YLYRLFRKSNLKPFERDISTEIYQAGSTPCNGVEGFNCYFPLQSY

GFQPTNGVGYQPYRVVVLSFELLHAPATVCGPKKSTNLVKNKCVN

FNFNGLTGTGVLTESNKKFLPFQQFGRDIADTTDAVRDPQTLEIL

DITPCSFGGVSVITPGTNTSNQVAVLYQDVNCTEVPVAIHADQLT

PTWRVYSTGSNVFQTRAGCLIGAEHVNNSYECDIPIGAGICASYQ

TQTNSPRRARSVASQSIIAYTMSLGAENSVAYSNNSIAIPTNFTI

SVTTEILPVSMTKTSVDCTMYICGDSTECSNLLLQYGSFCTQLNR

ALTGIAVEQDKNTQEVFAQVKQIYKTPPIKDFGGFNFSQILPDPS

KPSKRSFIEDLLFNKVTLADAGFIKQYGDCLGDIAARDLICAQKF

NGLTVLPPLLTDEMIAQYTSALLAGTITSGWTFGAGAALQIPFAM

-continued

QMAYRFNGIGVTQNVLYENQKLIANQFNSAIGKIQDSLSSTASAL

GKLQDVVNQNAQALNTLVKQLSSNFGAISSVLNDILSRLDKVEAE

VQIDRLITGRLQSLQTYVTQQLIRAAEIRASANLAATKMSECVLG

QSKRVDFCGKGYHLMSFPQSAPHGVVFLHVTYVPAQEKNFTTAPA

ICHDGKAHFPREGVFVSNGTHWFVTQRNFYEPQIITTDNTFVSGN

CDVVIGIVNNTVYDPLQPELDSFKEELDKYFKNHTSPDVDLGDIS

GINASVVNIQKEIDRLNEVAKNLNESLIDLQELGKYEQYIKWPWY

IWLGFIAGLIAIVMVTIMLCCMTSCCSCLKGCCSCGSCCKFDEDD

SEPVLKGVKLHYT

SEQ ID NO: 2, amino acid sequence of S protein comprising D614G (marked in bold font with underlines) and S6P mutations (F817P, A892P, A899P, A942P, K986P, and V987P, marked in bold and italic font with underlines):

MFVFLVLLPLVSSQCVNLTTRTQLPPAYTNSFTRGVYYPDKVFRS

SVLHSTQDLFLPFFSNVTWFHAIHVSGTNGTKRFDNPVLPFNDGV

YFASTEKSNIIRGWIFGTTLDSKTQSLLIVNNATNVVIKVCEFQF

CNDPFLGVYYHKNNKSWMESEFRVYSSANNCTFEYVSQPFLMDLE

GKQGNFKNLREFVFKNIDGYFKIYSKHTPINLVRDLPQGFSALEP

LVDLPIGINITRFQTLLALHRSYLTPGDSSSGWTAGAAAYYVGYL

QPRTFLLKYNENGTITDAVDCALDPLSETKCTLKSFTVEKGIYQT

SNFRVQPTESIVRFPNITNLCPFGEVFNATRFASVYAWNRKRISN

CVADYSVLYNSASFSTFKCYGVSPTKLNDLCFTNVYADSFVIRGD

EVRQIAPGQTGKIADYNYKLPDDFTGCVIAWNSNNLDSKVGGNYN

YLYRLFRKSNLKPFERDISTEIYQAGSTPCNGVEGENCYFPLQSY

GFQPTNGVGYQPYRVVVLSFELLHAPATVCGPKKSTNLVKNKCVN

FNFNGLTGTGVLTESNKKFLPFQQFGRDIADTTDAVRDPQTLEIL

DITPCSFGGVSVITPGTNTSNQVAVLYQGVNCTEVPVAIHA

DQLTPTWRVYSTGSNVFQTRAGCLIGAEHVNNSYECDIPIGAGIC

ASYQTQTNSPSRAGSVASQSIIAYTMSLGAENSVAYSNNSIAIPT

NFTISVTTEILPVSMTKTSVDCTMYICGDSTECSNLLLQYGSFCT

QLNRALTGIAVEQDKNTQEVFAQVKQIYKTPPIKDFGGFNFSQIL

PDPSKPSKRS*P*IEDLLFNKVTLADAGFIKQYGDCLGDIAARDLIC

AQKFNGLTVLPPLLTDEMIAQYTSALLAGTITSGWTFGAG*P*ALQI

PF*P*MQMAYRFNGIGVTQNVLYENQKLIANQFNSAIGKIQDSLSST

*P*SALGKLQDVVNQNAQALNTLVKQLSSNFGAISSVLNDILSRLD

*PP*EAEVQIDRLITGRLQSLQTYVTQQLIRAAEIRASANLAATKM

SECVLGQSKRVDFCGKGYHLMSFPQSAPHGVVFLHVTYVPAQEKN

FTTAPAICHDGKAHFPREGVFVSNGTHWFVTQRNFYEPQIITTDN

TFVSGNCDVVIGIVNNTVYDPLQPELDSFKEELDKYFKNHTSPDV

DLGDISGINASVVNIQKEIDRLNEVAKNLNESLIDLQELGKYEQY

IKWPWYIWLGFIAGLIAIVMVTIMLCCMTSCCSCLKGCCSCGSCC

KFDEDDSEPVLKGVKLHYT

-continued

SEQ ID NO: 3,
DNA sequence encoding SEQ ID NO: 2:

ATGTTTGTTTTTCTTGTTTTATTGCCACTAGTCTCTAGTCAGTGT

GTTAATCTTACAACCAGAACTCAATTACCCCCTGCATACACTAAT

TCTTTCACACGTGGTGTTTATTACCCTGACAAAGTTTTCAGATCC

TCAGTTTTACATTCAACTCAGGACTTGTTCTTACCTTTCTTTTCC

AATGTTACTTGGTTCCATGCTATACATGTCTCTGGGACCAATGGT

ACTAAGAGGTTTGATAACCCTGTCCTACCATTTAATGATGGTGTT

TATTTTGCTTCCACTGAGAAGTCTAACATAATAAGAGGCTGGATT

TTTGGTACTACTTTAGATTCGAAGACCCAGTCCCTACTTATTGTT

AATAACGCTACTAATGTTGTTATTAAAGTCTGTGAATTTCAATTT

TGTAATGATCCATTTTTGGGTGTTTATTACCACAAAAACAACAAA

AGTTGGATGGAAAGTGAGTTCAGAGTTTATTCTAGTGCGAATAAT

TGCACTTTTGAATATGTCTCTCAGCCTTTTCTTATGGACCTTGAA

GGAAAACAGGGTAATTTCAAAAATCTTAGGGAATTTGTGTTTAAG

AATATTGATGGTTATTTTAAAATATATTCTAAGCACACGCCTATT

AATTTAGTGCGTGATCTCCCTCAGGGTTTTTCGGCTTTAGAACCA

TTGGTAGATTTGCCAATAGGTATTAACATCACTAGGTTTCAAACT

TTACTTGCTTTACATAGAAGTTATTTGACTCCTGGTGATTCTTCT

TCAGGTTGGACAGCTGGTGCTGCAGCTTATTATGTGGGTTATCTT

CAACCTAGGACTTTTCTATTAAAATATAATGAAAATGGAACCATT

ACAGATGCTGTAGACTGTGCACTTGACCCTCTCTCAGAAACAAAG

TGTACGTTGAAATCCTTCACTGTAGAAAAAGGAATCTATCAAACT

TCTAACTTTAGAGTCCAACCAACAGAATCTATTGTTAGATTTCCT

AATATTACAAACTTGTGCCCTTTTGGTGAAGTTTTTAACGCCACC

AGATTTGCATCTGTTTATGCTTGGAACAGGAAGAGAATCAGCAAC

TGTGTTGCTGATTATTCTGTCCTATATAATTCCGCATCATTTTCC

ACTTTTAAGTGTTATGGAGTGTCTCCTACTAAATTAAATGATCTC

TGCTTTACTAATGTCTATGCAGATTCATTTGTAATTAGAGGTGAT

GAAGTCAGACAAATCGCTCCAGGGCAAACTGGAAAGATTGCTGAT

TATAATTATAAATTACCAGATGATTTTACAGGCTGCGTTATAGCT

TGGAATTCTAACAATCTTGATTCTAAGGTTGGTGGTAATTATAAT

TACCTGTATAGATTGTTTAGGAAGTCTAATCTCAAACCTTTTGAG

AGAGATATTTCAACTGAAATCTATCAGGCCGGTAGCACACCTTGT

AATGGTGTTGAAGGTTTTAATTGTTACTTTCCTTTACAATCATAT

GGTTTCCAACCCACTAATGGTGTTGGTTACCAACCATACAGAGTA

GTAGTACTTTCTTTTGAACTTCTACATGCACCAGCAACTGTTTGT

GGACCTAAAAAGTCTACTAATTTGGTTAAAAACAAATGTGTCAAT

TTCAACTTCAATGGTTTAACAGGCACAGGTGTTCTTACTGAGTCT

AACAAAAAGTTTCTGCCTTTCCAACAATTTGGCAGAGACATTGCT

GACACTACTGATGCTGTCCGTGATCCACAGACACTTGAGATTCTT

GACATTACACCATGTTCTTTTGGTGGTGTCAGTGTTATAACACCA

-continued

GGAACAAATACTTCTAACCAGGTTGCTGTTCTTTATCAGGGTGTT

AACTGCACAGAAGTCCCTGTTGCTATTCATGCAGATCAACTTACT

CCTACTTGGCGTGTTTATTCTACAGGTTCTAATGTTTTTCAAACA

CGTGCAGGCTGTTTAATAGGGGCTGAACATGTCAACAACTCATAT

GAGTGTGACATACCCATTGGTGCAGGTATATGCGCTAGTTATCAG

ACTCAGACTAATTCTCCTTCGCGGGCAGGTAGTGTAGCTAGTCAA

TCCATCATTGCCTACACTATGTCACTTGGTGCAGAAAATTCAGTT

GCTTACTCTAATAACTCTATTGCCATACCCACAAATTTTACTATT

AGTGTTACCACAGAAATTCTACCAGTGTCTATGACCAAGACATCA

GTAGATTGTACAATGTACATTTGTGGTGATTCAACTGAATGCAGC

AATCTTTTGTTGCAATATGGCAGTTTTTGTACACAATTAAACCGT

GCTTTAACTGGAATAGCTGTTGAACAAGACAAAAACACCCAAGAA

GTTTTTGCACAAGTCAAACAAATTTACAAAACACCACCAATTAAA

GATTTTGGTGGTTTTAATTTTTCACAAATATTACCAGATCCATCA

AAACCAAGCAAGAGGTCACCTATTGAAGATCTACTTTTCAACAAA

GTGACACTTGCAGATGCTGGCTTCATCAAACAATATGGTGATTGC

CTTGGTGATATTGCTGCTAGAGACCTCATTTGTGCACAAAAGTTT

AACGGCCTTACTGTTTTGCCACCTTTGCTCACAGATGAAATGATT

GCTCAATACACTTCTGCACTGTTAGCGGGTACAATCACTTCTGGT

TGGACCTTTGGTGCAGGTCCTGCATTACAAATACCATTTCCTATG

CAAATGGCTTATAGGTTTAATGGTATTGGAGTTACACAGAATGTT

CTCTATGAGAACCAAAAATTGATTGCCAACCAATTTAATAGTGCT

ATTGGCAAAATTCAAGACTCACTTTCTTCCACACCAAGTGCACTT

GGAAAACTTCAAGATGTGGTCAACCAAAATGCACAAGCTTTAAAC

ACGCTTGTTAAACAACTTAGCTCCAATTTTGGTGCAATTTCAAGT

GTTTTAAATGATATCCTTTCACGTCTTGACCCACCTGAGGCTGAA

GTGCAAATTGATAGGTTGATCACAGGCAGACTTCAAAGTTTGCAG

ACATATGTGACTCAACAATTAATTAGAGCTGCAGAAATCAGAGCT

TCTGCTAATCTTGCTGCTACTAAAATGTCAGAGTGTGTACTTGGA

CAATCAAAAAGAGTTGATTTTTGTGGAAAGGGCTATCATCTTATG

TCCTTCCCTCAGTCAGCACCTCATGGTGTAGTCTTCTTGCATGTG

ACTTATGTCCCTGCACAAGAAAAGAACTTCACAACTGCTCCTGCC

ATTTGTCATGATGGAAAAGCACACTTTCCTCGTGAAGGTGTCTTT

GTTTCAAATGGCACACACTGGTTTGTAACACAAAGGAATTTTTAT

GAACCACAAATCATTACTACAGACAACACATTTGTGTCTGGTAAC

TGTGATGTTGTAATAGGAATTGTCAACAACACAGTTTATGATCCT

TTGCAACCTGAATTAGACTCATTCAAGGAGGAGTTAGATAAATAT

TTTAAGAATCATACATCACCAGATGTTGATTTAGGTGACATCTCT

GGCATTAATGCTTCAGTTGTAAACATTCAAAAAGAAATTGACCGC

CTCAATGAGGTTGCCAAGAATTTAAATGAATCTCTCATCGATCTC

-continued

CAAGAACTTGGAAAGTATGAGCAGTATATAAAATGGCCATGGTAC

ATTTGGCTAGGTTTTATAGCTGGCTTGATTGCCATAGTAATGGTG

ACAATTATGCTTTGCTGTATGACCAGTTGCTGTAGTTGTCTCAAG

GGCTGTTGTTCTTGTGGATCCTGCTGCAAATTTGATGAAGACGAC

TCTGAGCCAGTGCTCAAAGGAGTCAAATTACATTACACATAA

SEQ ID NO: 4, RNA sequence
encoding SEQ ID NO: 2:
AUGUUUGUUUUUCUUGUUUUAUUGCCACUAGUCUCUAGUCAGUGU

GUUAAUCUUACAACCAGAACUCAAUUACCCCCUGCAUACACUAAU

UCUUUCACACGUGGUGUUUAUUACCCUGACAAAGUUUUCAGAUCC

UCAGUUUUACAUUCAACUCAGGACUUGUUCUUACCUUUCUUUUCC

AAUGUUACUUGGUUCCAUGCUAUACAUGUCUCUGGGACCAAUGGU

ACUAAGAGGUUUGAUAACCCUGUCCUACCAUUUAAUGAUGGUGUU

UAUUUUGCUUCCACUGAGAAGUCUAACAUAAUAAGAGGCUGGAUU

UUUGGUACUACUUUAGAUUCGAAGACCCAGUCCCUACUUAUUGUU

AAUAACGCUACUAAUGUUGUUAUUAAAGUCUGUGAAUUUCAAUUU

UGUAAUGAUCCAUUUUUGGGUGUUUAUUACCACAAAAACAACAAA

AGUUGGAUGGAAAGUGAGUUCAGAGUUUAUUCUAGUGCGAAUAAU

UGCACUUUUGAAUAUGUCUCUCAGCCUUUUCUUAUGGACCUUGAA

GGAAAACAGGGUAAUUUCAAAAAUCUUAGGGAAUUUGUGUUUAAG

AAUAUUGAUGGUUAUUUUAAAAUAUAUUCUAAGCACACGCCUAUU

AAUUUAGUGCGUGAUCUCCCUCAGGGUUUUUCGGCUUUAGAACCA

UUGGUAGAUUUGCCAAUAGGUAUUAACAUCACUAGGUUUCAAACU

UUACUUGCUUUACAUAGAAGUUAUUUGACUCCUGGUGAUUCUUCU

UCAGGUUGGACAGCUGGUGCUGCAGCUUAUUAUGUGGGUUAUCUU

CAACCUAGGACUUUUCUAUUAAAAUAUAAUGAAAAUGGAACCAUU

ACAGAUGCUGUAGACUGUGCACUUGACCCUCUCUCAGAAACAAAG

UGUACGUUGAAAUCCUUCACUGUAGAAAAAGGAAUCUAUCAAACU

UCUAACUUUAGAGUCCAACCAACAGAAUCUAUUGUUAGAUUUCCU

AAUAUUACAAACUUGUGCCCUUUUGGUGAAGUUUUUAACGCCACC

AGAUUUGCAUCUGUUUAUGCUUGGAACAGGAAGAGAAUCAGCAAC

UGUGUUGCUGAUUAUUCUGUCCUAUAUAAUUCCGCAUCAUUUUCC

ACUUUUAAGUGUUAUGGAGUGUCUCCUACUAAAUUAAAUGAUCUC

UGCUUUACUAAUGUCUAUGCAGAUUCAUUUGUAAUUAGAGGUGAU

GAAGUCAGACAAAUCGCUCCAGGGCAAACUGGAAAGAUUGCUGAU

UAUAAUUAUAAAUUACCAGAUGAUUUUACAGGCUGCGUUAUAGCU

UGGAAUUCUAACAAUCUUGAUUCUAAGGUUGGUGGUAAUUAUAAU

UACCUGUAUAGAUUGUUUAGGAAGUCUAAUCUCAAACCUUUUGAG

AGAGAUAUUUCAACUGAAAUCUAUCAGGCCGGUAGCACACCUUGU

AAUGGUGUUGAAGGUUUUAAUUGUUACUUUCCUUUACAAUCAUAU

GGUUUCCAACCCACUAAUGGUGUUGGUUACCAACCAUACAGAGUA

GUAGUACUUUCUUUUGAACUUCUACAUGCACCAGCAACUGUUUGU

-continued

GGACCUAAAAAGUCUACUAAUUUGGUUAAAAACAAAUGUGUCAAU

UUCAACUUCAAUGGUUUAACAGGCACAGGUGUUCUUACUGAGUCU

AACAAAAAGUUUCUGCCUUUCCAACAAUUUGGCAGAGACAUUGCU

GACACUACUGAUGCUGUCCGUGAUCCACAGACACUUGAGAUUCUU

GACAUUACACCAUGUUCUUUUGGUGGUGUCAGUGUUAUAACACCA

GGAACAAAUACUUCUAACCAGGUUGCUGUUCUUUAUCAGGGUGUU

AACUGCACAGAAGUCCCUGUUGCUAUUCAUGCAGAUCAACUUACU

CCUACUUGGCGUGUUUAUUCUACAGGUUCUAAUGUUUUUCAAACA

CGUGCAGGCUGUUUAAUAGGGGCUGAACAUGUCAACAACUCAUAU

GAGUGUGACAUACCCAUUGGUGCAGGUAUAUGCGCUAGUUAUCAG

ACUCAGACUAAUUCUCCUUCGCGGGCAGGUAGUGUAGCUAGUCAA

UCCAUCAUUGCCUACACUAUGUCACUUGGUGCAGAAAAUUCAGUU

GCUUACUCUAAUAACUCUAUUGCCAUACCCACAAAUUUUACUAUU

AGUGUUACCACAGAAAUUCUACCAGUGUCUAUGACCAAGACAUCA

GUAGAUUGUACAAUGUACAUUUGUGGUGAUUCAACUGAAUGCAGC

AAUCUUUUGUUGCAAUAUGGCAGUUUUUGUACACAAUUAAACCGU

GCUUUAACUGGAAUAGCUGUUGAACAAGACAAAAACACCCAAGAA

GUUUUUGCACAAGUCAAACAAAUUUACAAAACACCACCAAUUAAA

GAUUUUGGUGGUUUUAAUUUUUCACAAAUAUUACCAGAUCCAUCA

AAACCAAGCAAGAGGUCACCUAUUGAAGAUCUACUUUUCAACAAA

GUGACACUUGCAGAUGCUGGCUUCAUCAAACAAUAUGGUGAUUGC

CUUGGUGAUAUUGCUGCUAGAGACCUCAUUUGUGCACAAAAGUUU

AACGGCCUUACUGUUUUGCCACCUUUGCUCACAGAUGAAAUGAUU

GCUCAAUACACUUCUGCACUGUUAGCGGGUACAAUCACUUCUGGU

UGGACCUUUGGUGCAGGUCCUGCAUUACAAAUACCAUUUCCUAUG

CAAAUGGCUUAUAGGUUUAAUGGUAUUGGAGUUACACAGAAUGUU

CUCUAUGAGAACCAAAAAUUGAUUGCCAACCAAUUUAAUAGUGCU

AUUGGCAAAAUUCAAGACUCACUUUCUUCCACACCAAGUGCACUU

GGAAAACUUCAAGAUGUGGUCAACCAAAAUGCACAAGCUUUAAAC

ACGCUUGUUAAACAACUUAGCUCCAAUUUUGGUGCAAUUUCAAGU

GUUUUAAAUGAUAUCCUUUCACGUCUUGACCCACCUGAGGCUGAA

GUGCAAAUUGAUAGGUUGAUCACAGGCAGACUUCAAAGUUUGCAG

ACAUAUGUGACUCAACAAUUAAUUAGAGCUGCAGAAAUCAGAGCU

UCUGCUAAUCUUGCUGCUACUAAAAUGUCAGAGUGUGUACUUGGA

CAAUCAAAAAGAGUUGAUUUUUGUGGAAAGGGCUAUCAUCUUAUG

UCCUUCCCUCAGUCAGCACCUCAUGGUGUAGUCUUCUUGCAUGUG

ACUUAUGUCCCUGCACAAGAAAAGAACUUCACAACUGCUCCUGCC

AUUUGUCAUGAUGGAAAAGCACACUUUCCUCGUGAAGGUGUCUUU

GUUUCAAAUGGCACACACUGGUUUGUAACACAAAGGAAUUUUUAU

GAACCACAAAUCAUUACUACAGACAACACAUUUGUGUCUGGUAAC

-continued

UGUGAUGUUGUAAUAGGAAUUGUCAACAACACAGUUUAUGAUCCU

UUGCAACCUGAAUUAGACUCAUUCAAGGAGGAGUUAGAUAAAUAU

UUUAAGAAUCAUACAUCACCAGAUGUUGAUUUAGGUGACAUCUCU

GGCAUUAAUGCUUCAGUUGUAAACAUUCAAAAAGAAAUUGACCGC

CUCAAUGAGGUUGCCAAGAAUUUAAAUGAAUCUCUCAUCGAUCUC

CAAGAACUUGGAAAGUAUGAGCAGUAUAUAAAAUGGCCAUGGUAC

AUUUGGCUAGGUUUUAUAGCUGGCUUGAUUGCCAUAGUAAUGGUG

ACAAUUAUGCUUUGCUGUAUGACCAGUUGCUGUAGUUGUCUCAAG

GGCUGUUGUUCUUGUGGAUCCUGCUGCAAAUUUGAUGAAGACGAC

UCUGAGCCAGUGCUCAAAGGAGUCAAAUUACAUUACACAUAA

SEQ ID NO: 5, amino acid sequence of S protein comprising the following mutations: omicron variant mutations of T19I, Δ24-26, A27S, Δ69/70, G142D, V213G, G339D, S371F, S373P, S375F, T376A, D405N, R408S, K417N, L452R, S477N, T478K, E484A, F486V, Q498R, N501Y, Y505H, D614G, H655Y, N658S, N679K, P681H, N764K, D796Y, Q954H, and/or N969K; S6P (F817P, A892P, A899P, A942P, K986P and V987P); and furin-like cleavage site mutations (R682S and R685G):

MFVFLVLLPLVSSQCVNLITRTQSYTNSFTRGVYYPDKVFRSSVL

HSTQDLFLPFFSNVTWFHAISGTNGTKRFDNPVLPFNDGVYFAST

EKSNIIRGWIFGTTLDSKTQSLLIVNNATNVVIKVCEFQFCNDPF

LDVYYHKNNKSWMESEFRVYSSANNCTFEYVSQPFLMDLEGKQGN

FKNLREFVFKNIDGYFKIYSKHTPINLGRDLPQGFSALEPLVDLP

IGINITRFQTLLALHRSYLTPGDSSSGWTAGAAAYYVGYLQPRTF

LLKYNENGTITDAVDCALDPLSETKCTLKSFTVEKGIYQTSNFRV

QPTESIVRFPNITNLCPFDEVFNATRFASVYAWNRKRISNCVADY

SVLYNFAPFFAFKCYGVSPTKLNDLCFTNVYADSFVIRGNEVSQI

APGQTGNIADYNYKLPDDFTGCVIAWNSNNLDSKVGGNYNYRYRL

FRKSNLKPFERDISTEIYQAGNKPCNGVAGVNCYFPLQSYGFRPT

YGVGHQPYRVVVLSFELLHAPATVCGPKKSTNLVKNKCVNFNFNG

LTGTGVLTESNKKFLPFQQFGRDIADTTDAVRDPQTLEILDITPC

SFGGVSVITPGTNTSNQVAVLYQGVNCTEVPVAIHADQLTPTWRV

YSTGSNVFQTRAGCLIGAEYVNSSYECDIPIGAGICASYQTQTKS

HSRAGSVASQSIIAYTMSLGAENSVAYSNNSIAIPTNFTISVTTE

ILPVSMTKTSVDCTMYICGDSTECSNLLLQYGSFCTQLKRALTGI

AVEQDKNTQEVFAQVKQIYKTPPIKYFGGFNFSQILPDPSKPSKR

SPIEDLLFNKVTLADAGFIKQYGDCLGDIAARDLICAQKFNGLTV

LPPLLTDEMIAQYTSALLAGTITSGWTFGAGPALQIPFPMQMAYR

FNGIGVTQNVLYENQKLIANQFNSAIGKIQDSLSSTPSALGKLQD

VVNHNAQALNTLVKQLSSKFGAISSVLNDILSRLDPPEAEVQIDR

LITGRLQSLQTYVTQQLIRAAEIRASANLAATKMSECVLGQSKRV

DFCGKGYHLMSFPQSAPHGVVFLHVTYVPAQEKNFTTAPAICHDG

KAHFPREGVFVSNGTHWFVTQRNFYEPQIITTDNTFVSGNCDVVI

-continued

GIVNNTVYDPLQPELDSFKEELDKYFKNHTSPDVDLGDISGINAS

VVNIQKEIDRLNEVAKNLNESLIDLQELGKYEQYIKWPWYIWLGF

IAGLIAIVMVTIMLCCMTSCCSCLKGCCSCGSCCKFDEDDSEPVL

KGVKLHYT.

SEQ ID NO: 6, DNA sequence encoding SEQ ID NO: 5:

ATGTTCGTATTCCTAGTACTACTACCCCTAGTAAGCAGCCAGTGC

GTAAACCTAATCACCCGGACCCAGAGCTACACCAACAGCTTCACC

CGGGGCGTATACTACCCCGACAAGGTATTCCGGAGCAGCGTACTA

CACAGCACCCAGGACCTATTCCTACCCTTCTTCAGCAACGTAACC

TGGTTCCACGCCATCAGCGGCACCAACGGCACCAAGCGGTTCGAC

AACCCCGTACTACCCTTCAACGACGGCGTATACTTCGCCAGCACC

GAGAAGAGCAACATCATCCGGGGCTGGATCTTCGGCACCACCCTA

GACAGCAAGACCCAGAGCCTACTAATCGTAAACAACGCCACCAAC

GTAGTAATCAAGGTATGCGAGTTCCAGTTCTGCAACGACCCCTTC

CTAGACGTATACTACCACAAGAACAACAAGAGCTGGATGGAGAGC

GAGTTCCGGGTATACAGCAGCGCCAACAACTGCACCTTCGAGTAC

GTAAGCCAGCCCTTCCTAATGGACCTAGAGGGCAAGCAGGGCAAC

TTCAAGAACCTACGGGAGTTCGTATTCAAGAACATCGACGGCTAC

TTCAAGATCTACAGCAAGCACACCCCCATCAACCTAGGCCGGGAC

CTACCCCAGGGCTTCAGCGCCCTAGAGCCCCTAGTAGACCTACCC

ATCGGCATCAACATCACCCGGTTCCAGACCCTACTAGCCCTACAC

CGGAGCTACCTAACCCCCGGCGACAGCAGCAGCGGCTGGACCGCC

GGCGCCGCCGCCTACTACGTAGGCTACCTACAGCCCCGGACCTTC

CTACTAAAGTACAACGAGAACGGCACCATCACCGACGCCGTAGAC

TGCGCCCTAGACCCCCTAAGCGAGACCAAGTGCACCCTAAAGAGC

TTCACCGTAGAGAAGGGCATCTACCAGACCAGCAACTTCCGGGTA

CAGCCCACCGAGAGCATCGTACGGTTCCCCAACATCACCAACCTA

TGCCCCTTCGACGAGGTATTCAACGCCACCCGGTTCGCCAGCGTA

TACGCCTGGAACCGGAAGCGGATCAGCAACTGCGTAGCCGACTAC

AGCGTACTATACAACTTCGCCCCCTTCTTCGCCTTCAAGTGCTAC

GGCGTAAGCCCCACCAAGCTAAACGACCTATGCTTCACCAACGTA

TACGCCGACAGCTTCGTAATCCGGGGCAACGAGGTAAGCCAGATC

GCCCCCGGCCAGACCGGCAACATCGCCGACTACAACTACAAGCTA

CCCGACGACTTCACCGGCTGCGTAATCGCCTGGAACAGCAACAAC

CTAGACAGCAAGGTAGGCGGCAACTACAACTACCGGTACCGGCTA

TTCCGGAAGAGCAACCTAAAGCCCTTCGAGCGGGACATCAGCACC

GAGATCTACCAGGCCGGCAACAAGCCCTGCAACGGCGTAGCCGGC

GTAAACTGCTACTTCCCCCTACAGAGCTACGGCTTCCGGCCCACC

TACGGCGTAGGCCACCAGCCCTACCGGGTGGTGGTGCTAAGCTTC

GAGCTACTACACGCCCCCGCCACCGTGTGCGGCCCCAAGAAGAGC

ACCAACCTAGTGAAGAACAAGTGCGTGAACTTCAACTTCAACGGC

-continued

CTAACCGGCACCGGCGTGCTAACCGAGAGCAACAAGAAGTTCCTA
CCCTTCCAGCAGTTCGGCCGGGACATCGCCGACACCACCGACGCC
GTGCGGGACCCCCAGACCCTAGAGATCCTAGACATCACCCCCTGC
AGCTTCGGCGGCGTGAGCGTGATCACCCCCGGCACCAACACCAGC
AACCAGGTGGCCGTGCTATACCAGGGCGTGAACTGCACCGAGGTG
CCCGTGGCCATCCACGCCGACCAGCTAACCCCCACCTGGCGGGTG
TACAGCACCGGCAGCAACGTGTTCCAGACCCGGGCCGGCTGCCTA
ATCGGCGCCGAGTACGTGAACAGCAGCTACGAGTGCGACATCCCC
ATCGGCGCCGGCATCTGCGCCAGCTACCAGACCCAGACCAAGAGC
CACAGCCGGGCCGGCAGCGTGGCCAGCCAGAGCATCATCGCCTAC
ACCATGAGCCTAGGCGCCGAGAACAGCGTGGCCTACAGCAACAAC
AGCATCGCCATCCCCACCAACTTCACCATCAGCGTGACCACCGAG
ATCCTACCCGTGAGCATGACCAAGACCAGCGTGGACTGCACCATG
TACATCTGCGGCGACAGCACCGAGTGCAGCAACCTACTACTACAG
TACGGCAGCTTCTGCACCCAGCTAAAGCGGGCCCTAACCGGCATC
GCCGTGGAGCAGGACAAGAACACCCAGGAGGTGTTCGCCCAGGTG
AAGCAGATCTACAAGACCCCCCCCATCAAGTACTTCGGCGGCTTC
AACTTCAGCCAGATCCTACCCGACCCCAGCAAGCCCAGCAAGCGG
AGCCCCATCGAGGACCTACTATTCAACAAGGTGACCCTAGCCGAC
GCCGGCTTCATCAAGCAGTACGGCGACTGCCTAGGCGACATCGCC
GCCCGGGACCTAATCTGCGCCCAGAAGTTCAACGGCCTAACCGTG
CTACCCCCCCTACTAACCGACGAGATGATCGCCCAGTACACCAGC
GCCCTACTAGCCGGCACCATCACCAGCGGCTGGACCTTCGGCGCC
GGCCCCGCCCTACAGATCCCCTTCCCCATGCAGATGGCCTACCGG
TTCAACGGCATCGGCGTGACCCAGAACGTGCTATACGAGAACCAG
AAGCTAATCGCCAACCAGTTCAACAGCGCCATCGGCAAGATCCAG
GACAGCCTAAGCAGCACCCCCAGCGCCCTAGGCAAGCTACAGGAC
GTGGTGAACCACAACGCCCAGGCCCTAAACACCCTAGTGAAGCAG
CTAAGCAGCAAGTTCGGCGCCATCAGCAGCGTGCTAAACGACATC
CTAAGCCGGCTAGACCCCCCCGAGGCCGAGGTGCAGATCGACCGG
CTAATCACCGGCCGGCTACAGAGCCTACAGACCTACGTGACCCAG
CAGCTAATCCGGGCCGCCGAGATCCGGGCCAGCGCCAACCTAGCC
GCCACCAAGATGAGCGAGTGCGTGCTAGGCCAGAGCAAGCGGGTG
GACTTCTGCGGCAAGGGCTACCACCTAATGAGCTTCCCCCAGAGC
GCCCCCCACGGCGTGGTGTTCCTACACGTGACCTACGTGCCCGCC
CAGGAGAAGAACTTCACCACCGCCCCCGCCATCTGCCACGACGGC
AAGGCCCACTTCCCCCGGGAGGGCGTGTTCGTGAGCAACGGCACC
CACTGGTTCGTGACCCAGCGGAACTTCTACGAGCCCCAGATCATC
ACCACCGACAACACCTTCGTGAGCGGCAACTGCGACGTGGTGATC
GGCATCGTGAACAACACCGTGTACGACCCCCTACAGCCCGAGCTA

-continued

GACAGCTTCAAGGAGGAGCTAGACAAGTACTTCAAGAACCACACC
AGCCCCGACGTGGACCTAGGCGACATCAGCGGCATCAACGCCAGC
GTGGTGAACATCCAGAAGGAGATCGACCGGCTAAACGAGGTGGCC
AAGAACCTAAACGAGAGCCTAATCGACCTACAGGAGCTAGGCAAG
TACGAGCAGTACATCAAGTGGCCCTGGTACATCTGGCTAGGCTTC
ATCGCCGGCCTAATCGCCATCGTGATGGTGACCATCATGCTATGC
TGCATGACCAGCTGCTGCAGCTGCCTAAAGGGCTGCTGCAGCTGC
GGCAGCTGCTGCAAGTTCGACGAGGACGACAGCGAGCCCGTGCTA
AAGGGCGTGAAGCTACACTACACCTAAAA.

SEQ ID NO: 7, DNA Sequence encoding SEQ ID NO: 5:
ATGTTCGTGTTCCTGGTGCTGCTGCCTCTCGTGTCTAGCCAGTGC
GTCAACCTGATCACCCGGACCCAGTCTTATACCAACAGCTTCACA
AGGGGCGTCTACTATCCTGACAAGGTATTCAGAAGCTCCGTGCTG
CATAGCACCCAAGACCTGTTCCTGCCTTTCTTCTCTAACGTGACG
TGGTTCCACGCCATCAGTGGAACCAATGGCACCAAAAGATTTGAT
AATCCCGTGCTGCCTTTTAATGACGGCGTCTACTTCGCCTCTACA
GAGAAGTCTAACATTATCCGGGGCTGGATCTTCGGCACCACCCTG
GACAGCAAAACCCAGAGCCTGCTGATCGTGAACAACGCAACCAAC
GTGGTTATCAAAGTGTGTGAGTTCCAGTTCTGTAATGATCCTTTT
CTGGACGTGTATTACCACAAGAATAATAAGAGCTGGATGGAATCT
GAGTTCAGAGTGTACAGTAGCGCCAATAACTGCACCTTCGAGTAC
GTCTCTCAGCCTTTTCTGATGGACCTGGAAGGCAAGCAGGGCAAC
TTCAAGAACCTGAGAGAATTCGTGTTCAAAAACATCGACGGCTAC
TTCAAGATCTACTCCAAGCACACCCCAATCAACCTGGGCAGAGAT
CTGCCTCAAGGCTTCAGCGCCCTGGAACCCCTAGTGGACTTACCA
ATCGGCATCAACATCACCAGATTCCAGACCCTGCTAGCTCTGCAT
AGATCTTATCTGACACCAGGCGACAGCAGCAGCGGCTGGACCGCC
GGCGCTGCTGCTTACTACGTGGGCTACCTGCAGCCTAGAACCTTC
CTGCTGAAGTACAACGAAAACGGCACCATCACCGACGCCGTGGAC
TGTGCCCTGGACCCTCTGAGCGAAACCAAATGCACACTGAAGTCC
TTCACCGTGGAAAAGGGCATCTACCAGACAAGCAACTTCAGGGTG
CAGCCTACAGAGTCTATCGTGCGGTTTCCAAACATCACAAACCTC
TGTCCTTTCGACGAGGTGTTCAACGCCACAAGATTCGCCAGCGTG
TACGCCTGGAATCGGAAGCGGATCAGCAACTGCGTGGCCGACTAC
AGCGTGCTGTACAACTTCGCCCCTTTTTTCGCTTTTAAGTGCTAC
GGCGTGAGCCCTACCAAGCTGAACGACCTGTGCTTCACAAACGTG
TACGCCGACAGCTTCGTGATCAGAGGCAATGAGGTATCCCAGATC
GCCCCTGGCCAGACAGGCAACATAGCCGATTACAACTACAAGCTG
CCTGATGACTTCACAGGCTGCGTGATCGCCTGGAACTCTAACAAC
CTCGATAGCAAGGTGGGCGGAAACTACAACTACAGGTACCGGCTG
TTCCGGAAGTCTAACCTGAAGCCTTTTGAGAGAGACATCTCTACA -continued

GAAATCTACCAGGCCGGGAACAAACCCTGCAACGGAGTGGCCGGG

GTGAATTGCTACTTCCCTCTGCAAAGCTACGGCTTCCGGCCCACA

TACGGCGTCGGCCACCAGCCCTACAGAGTGGTCGTGCTCTCTTTT

GAGCTGCTGCACGCCCCTGCTACCGTGTGTGGCCCCAAGAAGTCT

ACCAACCTGGTTAAGAACAAGTGTGTGAACTTCAACTTCAACGGG

CTGACCGGCACCGGAGTGCTGACCGAAAGCAATAAGAAGTTCCTG

CCCTTTCAGCAATTTGGCAGAGATATTGCTGACACCACAGACGCC

GTGCGCGACCCCCAGACTCTGGAAATCCTGGATATCACCCCATGT

AGCTTCGGCGGCGTTAGCGTGATCACCCCCGGAACCAATACCTCC

AATCAGGTGGCCGTGCTCTACCAGGGCGTGAACTGTACCGAGGTG

CCTGTGGCCATCCACGCAGATCAGCTGACTCCTACATGGCGGGTG

TACTCCACCGGCTCCAATGTGTTCCAGACACGGGCTGGCTGCCTG

ATCGGCGCCGAGTACGTGAATAGCAGCTATGAGTGCGACATTCCT

ATTGGAGCCGGCATCTGCGCCTCTTATCAAACACAGACAAAGAGC

CACAGCAGAGCCGGCAGCGTGGCCAGCCAGAGCATCATCGCCTAC

ACCATGAGCCTGGGTGCCGAGAACAGCGTGGCATACAGCAACAAC

AGCATCGCCATCCCCACAAACTTCACGATCAGTGTGACCACCGAG

ATCCTGCCTGTGTCCATGACAAAGACATCCGTGGATTGCACCATG

TACATCTGCGGCGATTCTACAGAATGCTCAAATCTGCTGCTGCAA

TATGGCAGCTTCTGCACCCAACTGAAAAGAGCCCTGACAGGAATC

GCTGTCGAGCAGGATAAGAACACCCAGGAGGTGTTTGCCCAGGTG

AAACAGATCTATAAGACCCCTCCAATCAAGTACTTTGGCGGATTC

AACTTCAGCCAGATTCTCCCCGATCCAAGCAAGCCCAGCAAGAGA

AGCCCTATCGAGGATCTGCTGTTCAACAAGGTGACGCTGGCCGAC

GCCGGCTTCATCAAGCAGTACGGAGACTGCCTGGGCGACATCGCC

GCCAGAGATCTGATCTGTGCCCAGAAGTTCAACGGGCTTACTGTG

CTGCCACCTCTGCTGACGGATGAAATGATCGCTCAGTACACAAGC

GCTCTGCTGGCCGGCACAATCACCTCTGGCTGGACTTTCGGAGCC

GGCCCCGCTCTGCAGATCCCTTTCCCTATGCAGATGGCCTACAGA

TTCAACGGCATCGGAGTGACCCAGAACGTGCTGTACGAGAACCAG

AAGCTGATAGCTAACCAGTTTAATAGCGCCATCGGCAAAATCCAG

GACAGCCTGAGCAGCACCCCTAGCGCTCTGGGAAAGCTGCAGGAC

GTGGTGAACCACAATGCCCAGGCCCTGAACACCCTGGTGAAGCAG

CTCTCCTCTAAATTTGGCGCCATTTCCTCCGTGCTGAATGATATC

CTGAGCAGACTGGACCCTCCCGAGGCCGAAGTGCAAATCGACAGG

CTGATCACCGGCAGACTACAGAGCCTGCAAACCTACGTTACCCAG

CAGCTGATCAGAGCCGCCGAGATCAGAGCCAGCGCCAACCTCGCC

GCCACCAAAATGAGCGAATGTGTTCTGGGGCAGTCCAAGAGAGTG

GATTTCTGCGGCAAGGGATACCACCTGATGTCTTTCCCCCAGAGC

GCTCCTCATGGCGTCGTATTCCTGCACGTGACCTACGTGCCCGCC

CAGGAGAAAAACTTCACCACTGCCCCTGCCATCTGCCACGACGGC

-continued

AAGGCCCACTTCCCTCGGGAAGGCGTTTTCGTGTCAAACGGCACC

CACTGGTTCGTGACCCAGAGAAACTTCTACGAACCTCAGATTATC

ACAACCGACAACACCTTCGTGTCCGGCAACTGTGACGTCGTGATC

GGAATCGTGAACAATACCGTGTACGACCCCCTGCAGCCTGAGCTG

GACAGCTTCAAGGAGGAACTGGACAAGTACTTCAAGAATCACACA

TCTCCTGACGTGGACCTAGGCGACATCTCAGGCATCAACGCTTCG

GTTGTGAACATCCAGAAAGAGATCGACCGGCTGAACGAGGTGGCC

AAGAACCTGAACGAGAGCCTGATCGACCTGCAGGAGCTGGGAAAA

TACGAGCAGTACATCAAGTGGCCTTGGTACATCTGGCTGGGCTTT

ATCGCCGGCCTGATCGCCATCGTGATGGTGACCATCATGCTGTGC

TGCATGACCAGCTGCTGTAGCTGTCTGAAGGGCTGTTGCAGCTGC

GGCTCTTGCTGCAAGTTCGACGAGGACGACTCCGAGCCTGTGCTG

AAAGGCGTGAAGCTGCACTACACATAAAA.

SEQ ID NO: 8, amino acid sequence of S protein comprising the following mutations: omicron variant mutations of T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and/or N969K; S6P mutations (F817P, A892P, A899P, A942P, K986P and V987P); and furin-like cleavage site mutations (R682S and R685G):

MFVFLVLLPLVSSQCVNLITRTQSYTNSFTRGVYYPDKVFRSSVL

HSTQDLFLPFFSNVTWFHAISGTNGTKRFDNPVLPFNDGVYFAST

EKSNIIRGWIFGTTLDSKTQSLLIVNNATNVVIKVCEFQFCNDPF

LDVYYHKNNKSWMESEFRVYSSANNCTFEYVSQPFLMDLEGKQGN

FKNLREFVFKNIDGYFKIYSKHTPINLGRDLPQGFSALEPLVDLP

IGINITRFQTLLALHRSYLTPGDSSSGWTAGAAAYYVGYLQPRTF

LLKYNENGTITDAVDCALDPLSETKCTLKSFTVEKGIYQTSNFRV

QPTESIVRFPNITNLCPFDEVFNATRFASVYAWNRKRISNCVADY

SVLYNFAPFFAFKCYGVSPTKLNDLCFTNVYADSFVIRGNEVSQI

APGQTGNIADYNYKLPDDFTGCVIAWNSNKLDSKVGGNYNYRYRL

FRKSNLKPFERDISTEIYQAGNKPCNGVAGVNCYFPLQSYGFRPT

YGVGHQPYRVVVLSFELLHAPATVCGPKKSTNLVKNKCVNFNFNG

LTGTGVLTESNKKFLPFQQFGRDIADTTDAVRDPQTLEILDITPC

SFGGVSVITPGTNTSNQVAVLYQGVNCTEVPVAIHADQLTPTWRV

YSTGSNVFQTRAGCLIGAEYVNNSYECDIPIGAGICASYQTQTKS

HRSAGSVASQSIIAYTMSLGAENSVAYSNNSIAIPTNFTISVTTE

ILPVSMTKTSVDCTMYICGDSTECSNLLLQYGSFCTQLKRALTGI

AVEQDKNTQEVFAQVKQIYKTPPIKYFGGFNFSQILPDPSKPSKR

SPIEDLLFNKVTLADAGFIKQYGDCLGDIAARDLICAQKFNGLTV

LPPLLTDEMIAQYTSALLAGTITSGWTFGAGPALQIPFPMQMAYR

FNGIGVTQNVLYENQKLIANQFNSAIGKIQDSLSSTPSALGKLQD

VVNHNAQALNTLVKQLSSKFGAISSVLNDILSRLDPPEAEVQIDR

-continued

LITGRLQSLQTYVTQQLIRAAEIRASANLAATKMSECVLGQSKRV

DFCGKGYHLMSFPQSAPHGVVFLHVTYVPAQEKNFTTAPAICHDG

KAHFPREGVFVSNGTHWFVTQRNFYEPQIITTDNTFVSGNCDVVI

GIVNNTVYDPLQPELDSFKEELDKYFKNHTSPDVDLGDISGINAS

VVNIQKEIDRLNEVAKNLNESLIDLQELGKYEQYIKWPWYIWLGF

IAGLIAIVMVTIMLCCMTSCCSCLKGCCSCGSCCKFDEDDSEPVL

KGVKLHYT

SEQ ID NO: 9, DNA sequence encoding SEQ ID NO: 8:
ATGTTCGTATTCCTAGTACTACTACCCCTAGTAAGCAGCCAGTGC

GTAAACCTAATCACCCGGACCCAGAGCTACACCAACAGCTTCACC

CGGGGCGTATACTACCCCGACAAGGTATTCCGGAGCAGCGTACTA

CACAGCACCCAGGACCTATTCCTACCCTTCTTCAGCAACGTAACC

TGGTTCCACGCCATCAGCGGCACCAACGGCACCAAGCGGTTCGAC

AACCCCGTACTACCCTTCAACGACGGCGTATACTTCGCCAGCACC

GAGAAGAGCAACATCATCCGGGGCTGGATCTTCGGCACCACCCTA

GACAGCAAGACCCAGAGCCTACTAATCGTAAACAACGCCACCAAC

GTAGTAATCAAGGTATGCGAGTTCCAGTTCTGCAACGACCCCTTC

CTAGACGTATACTACCACAAGAACAACAAGAGCTGGATGGAGAGC

GAGTTCCGGGTATACAGCAGCGCCAACAACTGCACCTTCGAGTAC

GTAAGCCAGCCCTTCCTAATGGACCTAGAGGGCAAGCAGGGCAAC

TTCAAGAACCTACGGGAGTTCGTATTCAAGAACATCGACGGCTAC

TTCAAGATCTACAGCAAGCACACCCCCATCAACCTAGGCCGGGAC

CTACCCCAGGGCTTCAGCGCCCTAGAGCCCCTAGTAGACCTACCC

ATCGGCATCAACATCACCCGGTTCCAGACCCTACTAGCCCTACAC

CGGAGCTACCTAACCCCCGGCGACAGCAGCAGCGGCTGGACCGCC

GGCGCCGCCGCCTACTACGTAGGCTACCTACAGCCCCGGACCTTC

CTACTAAAGTACAACGAGAACGGCACCATCACCGACGCCGTAGAC

TGCGCCCTAGACCCCCTAAGCGAGACCAAGTGCACCCTAAAGAGC

TTCACCGTAGAGAAGGGCATCTACCAGACCAGCAACTTCCGGGTA

CAGCCCACCGAGAGCATCGTACGGTTCCCCAACATCACCAACCTA

TGCCCCTTCGACGAGGTATTCAACGCCACCCGGTTCGCCAGCGTA

TACGCCTGGAACCGGAAGCGGATCAGCAACTGCGTAGCCGACTAC

AGCGTACTATACAACTTCGCCCCCTTCTTCGCCTTCAAGTGCTAC

GGCGTAAGCCCCACCAAGCTAAACGACCTATGCTTCACCAACGTA

TACGCCGACAGCTTCGTAATCCGGGGCAACGAGGTAAGCCAGATC

GCCCCCGGCCAGACCGGCAACATCGCCGACTACAACTACAAGCTA

CCCGACGACTTCACCGGCTGCGTAATCGCCTGGAACAGCAACAAG

CTAGACAGCAAGGTAGGCGGCAACTACAACTACCGGTACCGGCTA

TTCCGGAAGAGCAACCTAAAGCCCTTCGAGCGGGACATCAGCACC

GAGATCTACCAGGCCGGCAACAAGCCCTGCAACGGCGTAGCCGGC

GTAAACTGCTACTTCCCCCTACAGAGCTACGGCTTCCGGCCCACC

-continued

TACGGCGTGGGCCACCAGCCCTACCGGGTGGTGGTGCTAAGCTTC

GAGCTACTACACGCCCCCGCCACCGTGTGCGGCCCCAAGAAGAGC

ACCAACCTAGTGAAGAACAAGTGCGTGAACTTCAACTTCAACGGC

CTAACCGGCACCGGCGTGCTAACCGAGAGCAACAAGAAGTTCCTA

CCCTTCCAGCAGTTCGGCCGGGACATCGCCGACACCACCGACGCC

GTGCGGGACCCCCAGACCCTAGAGATCCTAGACATCACCCCCTGC

AGCTTCGGCGGCGTGAGCGTGATCACCCCCGGCACCAACACCAGC

AACCAGGTGGCCGTGCTATACCAGGGCGTGAACTGCACCGAGGTG

CCCGTGGCCATCCACGCCGACCAGCTAACCCCCACCTGGCGGGTG

TACAGCACCGGCAGCAACGTGTTCCAGACCCGGGCCGGCTGCCTA

ATCGGCGCCGAGTACGTGAACAACAGCTACGAGTGCGACATCCCC

ATCGGCGCCGGCATCTGCGCCAGCTACCAGACCCAGACCAAGAGC

CACCGGAGCGCCGGCAGCGTGGCCAGCCAGAGCATCATCGCCTAC

ACCATGAGCCTAGGCGCCGAGAACAGCGTGGCCTACAGCAACAAC

AGCATCGCCATCCCCACCAACTTCACCATCAGCGTGACCACCGAG

ATCCTACCCGTGAGCATGACCAAGACCAGCGTGGACTGCACCATG

TACATCTGCGGCGACAGCACCGAGTGCAGCAACCTACTACTACAG

TACGGCAGCTTCTGCACCCAGCTAAAGCGGGCCCTAACCGGCATC

GCCGTGGAGCAGGACAAGAACACCCAGGAGGTGTTCGCCCAGGTG

AAGCAGATCTACAAGACCCCCCCCATCAAGTACTTCGGCGGCTTC

AACTTCAGCCAGATCCTACCCGACCCCAGCAAGCCCAGCAAGCGG

AGCGCCATCGAGGACCTACTATTCAACAAGGTGACCCTAGCCGAC

GCCGGCTTCATCAAGCAGTACGGCGACTGCCTAGGCGACATCGCC

GCCCGGGACCTAATCTGCGCCCAGAAGTTCAACGGCCTAACCGTG

CTACCCCCCCTACTAACCGACGAGATGATCGCCCAGTACACCAGC

GCCCTACTAGCCGGCACCATCACCAGCGGCTGGACCTTCGGCGCC

GGCCCCGCCCTACAGATCCCCTTCCCCATGCAGATGGCCTACCGG

TTCAACGGCATCGGCGTGACCCAGAACGTGCTATACGAGAACCAG

AAGCTAATCGCCAACCAGTTCAACAGCGCCATCGGCAAGATCCAG

GACAGCCTAAGCAGCACCCCCAGCGCCCTAGGCAAGCTACAGGAC

GTGGTGAACCACAACGCCCAGGCCCTAAACACCCTAGTGAAGCAG

CTAAGCAGCAAGTTCGGCGCCATCAGCAGCGTGCTAAACGACATC

CTAAGCCGGCTAGACCCCCCCGAGGCCGAGGTGCAGATCGACCGG

CTAATCACCGGCCGGCTACAGAGCCTACAGACCTACGTGACCCAG

CAGCTAATCCGGGCCGCCGAGATCCGGGCCAGCGCCAACCTAGCC

GCCACCAAGATGAGCGAGTGCGTGCTAGGCCAGAGCAAGCGGGTG

GACTTCTGCGGCAAGGGCTACCACCTAATGAGCTTCCCCCAGAGC

GCCCCCCACGGCGTGGTGTTCCTACACGTGACCTACGTGCCCGCC

CAGGAGAAGAACTTCACCACCGCCCCCGCCATCTGCCACGACGGC

AAGGCCCACTTCCCCCGGGAGGGCGTGTTCGTGAGCAACGGCACC

CACTGGTTCGTGACCCAGCGGAACTTCTACGAGCCCCAGATCATC

-continued

ACCACCGACAACACCTTCGTGAGCGGCAACTGCGACGTGGTGATC

GGCATCGTGAACAACACCGTGTACGACCCCCTACAGCCCGAGCTA

GACAGCTTCAAGGAGGAGCTAGACAAGTACTTCAAGAACCACACC

AGCCCCGACGTGGACCTAGGCGACATCAGCGGCATCAACGCCAGC

GTGGTGAACATCCAGAAGGAGATCGACCGGCTAAACGAGGTGGCC

AAGAACCTAAACGAGAGCCTAATCGACCTACAGGAGCTAGGCAAG

TACGAGCAGTACATCAAGTGGCCCTGGTACATCTGGCTAGGCTTC

ATCGCCGGCCTAATCGCCATCGTGATGGTGACCATCATGCTATGC

TGCATGACCAGCTGCTGCAGCTGCCTAAAGGGCTGCTGCAGCTGC

GGCAGCTGCTGCAAGTTCGACGAGGACGACAGCGAGCCCGTGCTA

AAGGGCGTGAAGCTACACTACACCTAAAA

SEQ ID NO: 10, DNA sequence encoding SEQ ID NO: 8:
atgttcgtgttcctggtgctgttacccctggtctctagccaatgt gtgaacctgatcacccggacccagagctacaccaacagcttcacc agaggcgtgtactaccctgacaaggtgttcagaagctcagtgctg cattctacccaagacctgttcctgcctttttttagcaatgtgaca tggttccacgccatcagtggaacaaacggcaccaagcggtttgac aaccccgtgctgccttttaacgacggcgtgtacttcgccagcaca gaaaagtctaacattatccggggctggatcttcggcacaacactg gatagcaaaacgcagagcctgttaatcgtgaacaacgccacaaat gtcgtgatcaaggtgtgcgagtttcagttttgtaacgaccctttc ctggatgtgtactaccacaagaacaacaagagctggatggaatcc gaattcagagtgtactctagcgccaacaactgcaccttcgagtac gtaagccagccctttctgatggaccttgagggcaaacagggaaac ttcaagaacctgcgggaattcgtgttcaagaacatcgacggctac ttcaagatctatagcaagcacacccctatcaacctgggaagagac ctgccccagggcttctccgccctggaacctctggtcgatctgccc atcggcatcaatatcacaagatttcagaccctactggccctgcat agatcctacctgacccccggcgatagctcatctggctggaccgcc ggcgccgctgcctactacgtcggatacctgcaacctagaaccttt ctgctgaagtacaatgagaacggcaccattaccgatgccgtggat tgcgcattggacccccctgagcgagacaaagtgtacactgaagtct ttcaccgtggaaaaaggcatctaccagaccagcaacttcagggtg caaccaacagaatccatcgtgaggttccctaacataactaatctg tgtcctttcgacgaggtgttcaacgccacaagatttgcttctgtt tatgcctggaaccggaagagaatctcgaactgcgtggctgactac tccgtgctgtataacttcgctcccttcttcgccttcaagtgctac ggcgtttctccgaccaaactgaatgacctctgcttcacaaacgta tacgcggacagcttcgtgatcaggggcaacgaggtgagtcagatc gctcctggccagaccgggaacatcgccgattacaattataagctg cctgacgacttcaccggctgtgtgatcgcttggaacagcaataag -continued ctggactctaaggtgggcggcaactacaactaccggtatcggctg ttcagaaagagcaacctgaagcccttcgagagagacatcagcacc gagatctaccaggccggtaataagccttgtaacggcgtggctggc gtcaattgctactttcctctgcaaagctacggcttccggcctacc tacggcgtgggccaccagccttacagagtggtggtgctgtctttc gagctgctccacgcccctgccaccgtttgcggccccaagaagtcc accaacctggtcaagaacaagtgcgtgaacttcaacttcaacgga ctgaccggcacaggagtgctgaccgagagcaacaaaaagttcctg cctttccagcagttcggcagagatatcgcagacaccactgacgcc gtgggggacccgcagacactggaaatcctggacatcacccccctgca gcttcggcggagttagcgttatcacacctggcacaaataccagca accaggtggccgtgctgtaccagggtgtgaattgcaccgaggtgc ccgtggctatccacgccgaccagctgacccctacatggcgggtgt acagcaccggtagcaatgtctttcaaaccagagcgggatgtctga ttggagctgaatacgtgaacaattcttatgaatgcgatatcccta tcggcgccggcatctgtgcctcttaccagacccagaccaagtctc acagaagcgccggcagcgtggccagccagagcatcatcgcctaca ccatgagccttggcgccgagaactccgtggcctacagcaacaaca gcatcgccatcccaacaaacttcaccatcagcgtcaccaccgaga tcctgccagtcagcatgacaaaaaccagcgtggactgcaccatgt acatctgcggagattccaccgaatgcagcaatctgctactccagt acggcagcttctgcacacagctgaagagagccctgaccggcatcg ccgtggaacaggataagaacacacaggaggttttcgctcaggtga agcaaatctataagacaccccccatcaagtacttcggaggcttca acttctctcagatactgcctgaccctagcaagccttccaaacggt ccgctatcgaggacctgctgttcaacaaggtgaccctggctgatg ccgggttcatcaagcagtacggcgactgcctgggcgacatcgccg ctagagacttgatttgtgcccagaaatttaacggactgacagtgt tgcccccctctgctgacagatgagatgatcgcccagtacaccagtg ccctgctggccggcactattacaagcggttggacattcggcgcgg gccctgccctgcagatcccttttcctatgcagatggcctatagat tcaatggcatcggcgtgacccagaacgtactgtacgagaaccaaa agctgatcgccaatcagtttaacagcgccatcggcaagatccagg atagcctgagctctacccccagcgccctggggaaactgcaggacg tggtgaaccacaacgcccaagccctgaacactctggtgaaacagc tgtcctcgaagttcggcgccatcagctccgtgctgaacgacatcc tcagcagactggaccctcctgaggccgaggtgcaaatcgacagac tgatcacaggccggctgcagagcctgcagacatacgtgacccagc agctgatcagagccgccgagattcgggccagcgctaatctggccg ccacgaagatgagtgaatgcgtgctgggccagtctaagagagtgg -continued atttctgcggcaagggctatcacctgatgagctttcctcagagcg cccctcacggcgtggtctttctgcacgtgacctacgtgcccgctc aggagaagaactttaccacagcccctgctatctgccacgacggca aggctcacttccctagagaaggcgtgttcgtgtccaacggcaccc actggttcgtgacccagagaaacttctacgagccacagatcatca ccacagacaacaccttcgtgtcgggcaactgtgatgtggtgatcg gcatcgtcaacaacaccgtctacgaccctctgcagccagagctgg acagcttcaaagaggaactggacaaatacttcaagaatcacacca gcccggacgtggacctgggcgacatctccggcattaacgcctctg tggttaacatccagaaggaaatcgatagactgaatgaggtggcaa agaacctgaacgagagcctgatcgacctgcaggagctgggaaagt acgaacagtacatcaagtggccttggtacatctggctgggattca tcgccggcctgatcgccatcgtgatggtgaccatcatgctgtgct gcatgaccagctgctgtagttgcctgaagggctgctgcagctgcg gatcttgctgtaagttcgacgaggatgacagcgagcccgtgctca aaggcgtcaagctgcactacacctaaa.

SEQ ID NO: 11, amino acid sequence of S protein comprising the following mutations: omicron variant mutations of A67V, Δ69/70, T95I, G142D, Δ143-145, N211I, Δ212, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and/or L981F; S6P mutations (F817P, A892P, A899P, A942P, K986P and V987P); and furin-like cleavage site mutation (R682S and R685G):

MFVFLVLLPLVSSQCVNLRTRTQLPPAYTNSFTRGVYYPDKVFRS

SVLHSTQDLFLPFFSNVTWFHAIHFSGTNGTKRFDNPVLPFNDGV

YFASIEKSNIIRGWIFGTTLDSKTQSLLIVNNATNVVIKVCEFQF

CNDPFLDVYYHKNNKSWMESGVYSSANNCTFEYVSQPFLMDLEGK

QGNFKNLREFVFKNIDGYFKIYSKHTPINLVRDLPQGFSVLEPLV

DLPIGINITRFQTLLALHRSYLTPGDSSSGLTAGAAAYYVGYLQP

RTFLLKYNENGTITDAVDCALDPLSETKCTLKSFTVEKGIYQTSN

FRVQPTESIVRFPNITNLCPFGEVENATRFASVYAWNRKRISNCV

ADYSVLYNSASFSTFKCYGVSPTKLNDLCFTNVYADSFVIRGDEV

RQIAPGQTGNIADYNYKLPDDFTGCVIAWNSNNLDSKVGGNYNYR

YRLFRKSNLKPFERDISTEIYQAGSKPCNGVEGFNCYFPLQSYGF

QPTNGVGYQPYRVVVLSFELLHAPATVCGPKKSTNLVKNKCVNFN

FNGLTGTGVLTESNKKFLPFQQFGRDIADTTDAVRDPQTLEILDI

TPCSFGGVSVITPGTNTSNQVAVLYQGVNCTEVPVAIHADQLTPT

WRVYSTGSNVFQTRAGCLIGAEHVNNSYECDIPIGAGICASYQTQ

TNSRSRAGSVASQSIIAYTMSLGAENSVAYSNNSIAIPTNFTISV

TTEILPVSMTKTSVDCTMYICGDSTECSNLLLQYGSFCTQLNRAL

TGIAVEQDKNTQEVFAQVKQIYKTPPIKDFGGFNFSQILPDPSKP

SKRSPIEDLLFNKVTLADAGFIKQYGDCLGDIAARDLICAQKFNG

LTVLPPLLTDEMIAQYTSALLAGTITSGWTFGAGPALQIPFPMQM

-continued

AYRENGIGVTQNVLYENQKLIANQFNSAIGKIQDSLSSTPSALGK

LQNVVNQNAQALNTLVKQLSSNFGAISSVLNDILSRLDPPEAEVQ

IDRLITGRLQSLQTYVTQQLIRAAEIRASANLAATKMSECVLGQS

KRVDFCGKGYHLMSFPQSAPHGVVFLHVTYVPAQEKNFTTAPAIC

HDGKAHFPREGVFVSNGTHWFVTQRNFYEPQIITTDNTFVSGNCD

VVIGIVNNTVYDPLQPELDSFKEELDKYFKNHTSPDVDLGDISGI

NASVVNIQKEIDRLNEVAKNLNESLIDLQELGKYEQYIKWPWYIW

LGFIAGLIAIVMVTIMLCCMTSCCSCLKGCCSCGSCCKFDEDDSE

PVLKGVKLHYT.

SEQ ID NO: 12, DNA sequence encoding SEQ ID NO: 11:

atgttcgtattcctagtactactacccctagtaagcagccagtgc gtaaacctaatcacccggacccagagctacaccaacagcttcacc cggggcgtatactaccccgacaaggtattccggagcagcgtacta cacagcacccaggacctattcctacccttcttcagcaacgtaacc tggttccacgccatccacgtaagcggcaccaacggcaccaagcgg ttcgacaaccccgtactacccttcaacgacggcgtatacttcgcc agcaccgagaagagcaacatcatccggggctggatcttcggcacc accctagacagcaagacccagagcctactaatcgtaaacaacgcc accaacgtagtaatcaaggtatgcgagttccagttctgcaacgac cccttcctagacgtatactaccacaagaacaacaagagctggatg gagagcgagttccgggtatacagcagcgccaacaactgcaccttc gagtacgtaagccagcccttcctaatggacctagagggcaagcag ggcaacttcaagaacctacgggagttcgtattcaagaacatcgac ggctacttcaagatctacagcaagcacacccccatcaacctaggc cgggacctaccccagggcttcagcgccctagagcccctagtagac ctacccatcggcatcaacatcacccggttccagaccctactagcc ctacaccggagctacctaacccccggcgacagcagcagcggctgg accgccggcgccgccgcctactacgtaggctacctacagccccgg accttcctactaaagtacaacgagaacggcaccatcaccgacgcc gtagactgcgccctagacccccctaagcgagaccaagtgcaccctaaagagcttcaccgtagagaagggcatctaccagaccagcaacttc cgggtacagcccaccgagagcatcgtacggttccccaacatcacc aacctatgccccttcgacgaggtattcaacgccacccggttcgcc agcgtatacgcctggaaccggaagcggatcagcaactgcgtagcc gactacagcgtactatacaacttcgcccccttcttcgccttcaag tgctacggcgtaagccccaccaagctaaacgacctatgcttcacc aacgtatacgccgacagcttcgtaatccggggcaacgaggtacgg cagatcgcccccggccagaccggcaacatcgccgactacaactac aagctacccgacgacttcaccggctgcgtaatcgcctggaacagc aacaagctagacagcaaggtaggcggcaactacaactaccagtac -continued cggctattccggaagagcaacctaaagcccttcgagcgggacatc
agcaccgagatctaccaggccggcaacaagccctgcaacggcgta
gccggcttcaactgctacttcccctacggagctacggcttccgg
cccacctacggcgtgggccaccagccctaccgggtggtggtgcta
agcttcgagctactacacgcccccgccaccgtgtgcggccccaag
aagagcaccaacctagtgaagaacaagtgcgtgaacttcaacttc
aacggcctaaccggcaccggcgtgctaaccgagagcaacaagaag
ttcctacccttccagcagttcggccgggacatcgccgacaccacc
gacgccgtgcgggacccccagaccctagagatcctagacatcacc
ccctgcagcttcggcggcgtgagcgtgatcacccccggcaccaac
accagcaaccaggtggccgtgctataccagggcgtgaactgcacc
gaggtgcccgtggccatccacgccgaccagctaacccccacctgg
cgggtgtacagcaccggcagcaacgtgttccagacccgggccggc
tgcctaatcggcgccgagtacgtgaacaacagctacgagtgcgac
atccccatcggcgccggcatctgcgccagctaccagacccagacc
aagagccacagccgggccggcagcgtggccagccagagcatcatc
gcctacaccatgagcctaggcgccgagaacctagtggcctacagc
aacaacagcatcgccatccccaccaacttcaccatcagcgtgacc
accgagatcctacccgtgagcatgaccaagaccagcgtggactgc
accatgtacatctgcggcgacagcaccgagtgcagcaacctacta
ctacagtacggcagcttctgcacccagctaaagcgggccctaacc
ggcatcgccgtggagcaggacaagaacacccaggaggtgttcgcc
caggtgaagcagatctacaagaccccccccatcaagtacttcggc
ggcttcaacttcagccagatcctacccgaccccagcaagcccagc
aagcggagccccatcgaggacctactattcaacaaggtgacccta
gccgacgccggcttcatcaagcagtacggcgactgcctaggcgac
atcgccgcccgggacctaatctgcgcccagaagttcaacggccta
accgtgctaccccccctactaaccgacgagatgatcgcccagtac
accagcgccctactagccggcaccatcaccagcggctggaccttc
ggcgccggccccgccctacagatccccttccccatgcagatggcc
taccggttcaacggcatcggcgtgacccagaacgtgctatacgag
aaccagaagctaatcgccaaccagttcaacagcgccatcggcaag
atccaggacagcctaagcagcacccccagcgccctaggcaagcta
caggacgtggtgaaccacaacgcccaggccctaaacaccctagtg
aagcagctaagcagcaagttcggcgccatcagcagcgtgctaaac
gacatcctaagccggctagacccccccgaggccgaggtgcagatc
gaccggctaatcaccggccggctacagagcctacagacctacgtg
acccagcagctaatccgggccgccgagatccgggccagcgccaac
ctagccgccaccaagatgagcgagtgcgtgctaggccagagcaag
cgggtggacttctgcggcaagggctaccacctaatgagcttcccc
cagagcgcccccacggcgtggtgttcctacacgtgacctacgtg
cccgcccaggagaagaacttcaccaccgcccccgccatctgccac
gacggcaaggcccacttcccccgggagggcgtgttcgtgagcaac
ggcacccactggttcgtgacccagcggaacttctacgagccccag
atcatcaccaccgacaacaccttcgtgagcggcaactgcgacgtg
gtgatcggcatcgtgaacaacaccgtgtacgacccccctacagccc
gagctagacagcttcaaggaggagctagacaagtacttcaagaac
cacaccagccccgacgtggacctaggcgacatcagcggcatcaac
gccagcgtggtgaacatccagaaggagatcgaccggctaaacgag
gtggccaagaacctaaacgagagcctaatcgacctacaggagcta
ggcaagtacgagcagtacatcaagtggccctggtacatctggcta
ggcttcatcgccggcctaatcgccatcgtgatggtgaccatcatg
ctatgctgcatgaccagctgctgcagctgcctaaagggctgctgc
agctgcggcagctgctgcaagttcgacgaggacgacagcgagccc
gtgctaaagggcgtgaagctacactacacctaaaa SEQ ID NO: 13, DNA sequence encoding
SEQ ID NO: 11:
atgtttgtgttcctggtgctgctgccactggtgagctcacagtgc
gtgaatctgatcacacggacccaatcctacaccaacagcttcaca
agaggagtgtattaccctgacaaggtgtttagaagcagcgtgctg
catagcacccaagatctgttcctgcccttcttcagcaatgtaacc
tggttccacgccatccacgtgagcggcacaaacggcaccaagcgg
ttcgacaaccccgtcctgcctttcaatgacggcgtttattttgct
tccaccgagaagagtaacatcataaggggctggatctttggcacc
actctggacagcaagacccagtccctgctgatcgtgaacaacgcc
acaaacgtggtgatcaaggtgtgtgaattccagttttgcaacgac
cctttcctggacgtgtattaccataagaacaataaatcttggatg
gaaagcgagttcagagtgtacagctctgccaacaactgcacattc
gaatacgtgagccagccttttctgatggacctggaaggaaagcag
ggcaacttcaagaatctgagagaattcgtattcaagaatatcgac
ggctacttcaagatctacagcaagcacacccccatcaacctggga
agagacctgccccaaggcttcagcgccctggaacccttggtcgac
ctgcccatcggcatcaacatcacaagattccaaaccctgctggcc
ctgcacagatcctacctgacacctggcgattctagctctggctgg
acagccggagccgctgcttattacgtgggatatctgcaacctcga
acattcctgctgaagtacaatgaaaatggaaccatcacagatgcc
gtggattgcgctctggaccctctctctgaaacaaaatgcaccctg
aagtctttcaccgtggaaaaaggcatctaccagaccagtaacttc
agagtgcagcccaccgaatccatcgtgcggttccctaacatcact
aacctgtgtccctttcgatgaggtgttcaacgccacccggttcgcc
tctgtgtacgcctggaatagaaagaggatctctaactgcgttgca
gactactctgtgctgtacaacttcgccccatttttcgccttcaag -continued tgctacggagtgagccctaccaaactaaacgatctgtgcttcacc aacgtgtacgccgacagctttgtgatcagaggcaacgaggttagg cagatcgcccctggccagacgggcaatatcgccgattacaactac aagctgcctgatgacttcaccgggtgtgtgattgcttggaacagc aacaaactggatagcaaggtgggcggcaactacaactaccagtat agactgtttcggaaaagcaacctgaaaccctttgagagagacatc agcaccgagatctaccaggccggcaacaagccttgtaatggagtg gccggatttaactgctacttccctctgagatcttacggcttccgc cccacctacggtgtgggccaccagccctaccgggtcgtggtgctg agctttgagttactgcacgcccctgccacagtctgtggccctaaa aagtccaccaatctggtgaagaacaagtgcgtgaacttcaacttc aatggcctgaccggcacaggagtgctgaccgagtctaacaaaaag ttcctgccgttccagcagttcggcagagatatcgccgacaccacc gacgccgtgcgggaccctcagaccctggaaatcctggacatcacc ccttgttcatttggaggcgtgtccgtgatcacgcctggcaccaac accagcaaccaggtggctgtgctgtaccagggcgtgaactgcaca gaggtgcctgtggctatccacgccgaccagttgacccctacctgg cgggtgtacagcacaggcagcaatgtattccagactagagccggc tgcctgatcggagccgaatacgtgaacaacagctatgagtgtgac atccccatcggcgccggcatctgcgcctcctaccagacacagacc aagagccacagccgggccggcagcgttgctagccagtctatcatt gcctacaccatgagcctcggcgccgagaacctggtcgcctacagc aacaatagcatcgccatccctaccaactttacgatcagcgtgacc accgagatcctgccagtgtctatgacgaaaaccagcgtggattgc acaatgtacatctgtggcgactctaccgagtgcagcaacctgctg ctccaatacgggagcttttgtacacagctgaagcgggcgctgaca gggattgctgtggaacaggacaagaacacacaggaggtgttcgct caggtgaagcaaatctacaagaccccacctatcaaatacttcggc ggattcaacttttctcagatcctgcctgaccctagcaaacctagc aagcgatccccaatcgaggacctgctgttcaacaaggtgaccctg gccgatgccggcttcatcaagcagtacggcgactgcctgggcgat atcgccgccagagacctgatttgcgctcagaaattcaacggcctg acagtgctgcctcctctgctgaccgatgagatgatcgcccagtac accagcgccctgctggccggaacaatcaccagcggctggaccttc ggcgcaggccctgccctgcaaatcccattccccatgcagatggcc tacagattcaacggcatcggtgtcacccagaacgtgctgtacgag aaccaaaagctgatcgccaaccagttcaatagcgccataggcaag atccaggacagcctgagcagcaccccttctgccctgggcaagctg caggatgtggtaaaccacaacgcccaggctctgaacaccctggtg aagcagctgagctccaaatttggcgctatcagcagcgttctgaac gacatcctgtcaagactggaccctcccgaggccgaagtgcagatc -continued gaccggctgatcacaggacggctgcagagcctgcaaacctacgtg acccagcagttgatcagagccgctgaaatccgggcaagcgccaac ctcgccgccaccaaaatgagcgaatgtgtgctgggccagagcaag agagttgacttctgcggaaagggctaccacctgatgagcttcccc cagagtgctccccacggcgtggtgtttctgcacgtgacatatgtg cctgcccaggagaagaatttcaccaccgcccctgccatctgccac gacggaaaggcccacttccctcgcgagggcgtgttcgtgagcaat ggcactcactggttcgtaactcaaagaaacttctacgagcctcag atcatcaccaccgacaacaccttcgtgagcggaaactgcgacgta gtgatcggaatcgtcaacaacacagtctacgacccccctgcagcct gagctggacagcttcaaagaggagctggacaagtacttcaagaac cacacctctcctgatgtggacctgggcgacatctcgggcatcaac gccagcgtggtgaacatccagaaggaaatcgacagacttaacgag gtggcaaagaacctgaacgagagcctgatcgatcttcaggagctg ggcaagtacgaacagtacatcaaatggccctggtacatctggctg ggcttcatcgccggcctgatcgccatcgtgatggtgacaatcatg ctgtgctgcatgacctcctgctgcagctgcctgaagggatgctgc agctgtggctcctgctgtaagttcgatgaggacgattcagaacca gtgctcaagggcgttaaactgcactacacataaaa SEQ ID NO: 14, DNA sequence encoding
SEQ ID NO: 11:

atgttcgtgttcctggtgctgctgcccctggtgagcagccagtgc gtgaacctgatcacccggacccagagctacaccaacagcttcacc cggggcgtgtactaccccgacaaggtgttccggagcagcgtgctg cacagcacccaggacctgttcctgcccttcttcagcaacgtgacc tggttccacgccatccacgtgagcggcaccaacggcaccaagcgg ttcgacaaccccgtgctgcccttcaacgacggcgtgtacttcgcc agcaccgagaagagcaacatcatccggggctggatcttcggcacc accctggacagcaagacccagagcctgctgatcgtgaacaacgcc accaacgtggtgatcaaggtgtgcgagttccagttctgcaacgac cccttcctggacgtgtactaccacaagaacaacaagagctggatg gagagcgagttccgggtgtacagcagcgccaacaactgcaccttc gagtacgtgagccagcccttcctgatggacctggagggcaagcag ggcaacttcaagaacctgcgggagttcgtgttcaagaacatcgac ggctacttcaagatctacagcaagcacacccccatcaacctgggc cgggacctgccccagggcttcagcgccctggagcccctggtggac ctgcccatcggcatcaacatcacccggttccagaccctgctggcc ctgcaccggagctacctgacccccggcgacagcagcagcggctgg accgccggcgccgccgcctactacgtgggctacctgcagccccgg accttcctgctgaagtacaacgagaacggcaccatcaccgacgcc gtggactgcgccctggacccccctgagcgagaccaagtgcaccctg -continued aagagcttcaccgtggagaagggcatctaccagaccagcaacttc
cgggtgcagcccaccgagagcatcgtgcggttccccaacatcacc
aacctgtgccccttcgacgaggtgttcaacgccacccggttcgcc
agcgtgtacgcctggaaccggaagcggatcagcaactgcgtggcc
gactacagcgtgctgtacaacttcgcccccttcttcgccttcaag
tgctacggcgtgagccccaccaagctgaacgacctgtgcttcacc
aacgtgtacgccgacagcttcgtgatccggggcaacgaggtgcgg
cagatcgcccccggccagaccggcaacatcgccgactacaactac
aagctgcccgacgacttcaccggctgcgtgatcgcctggaacagc
aacaagctggacagcaaggtgggcggcaactacaactaccagtac
cggctgttccggaagagcaacctgaagcccttcgagcgggacatc
agcaccgagatctaccaggccggcaacaagccctgcaacggcgtg
gccggcttcaactgctacttccccctgcggagctacggcttccgg
cccacctacggcgtgggccaccagccctaccgggtggtggtgctg
agcttcgagctgctgcacgcccccgccaccgtgtgcggccccaag
aagagcaccaacctggtgaagaacaagtgcgtgaacttcaacttc
aacggcctgaccggcaccggcgtgctgaccgagagcaacaagaag
ttcctgcccttccagcagttcggccgggacatcgccgacaccacc
gacgccgtgcgggacccccagaccctggagatcctggacatcacc
ccctgcagcttcggcggcgtgagcgtgatcacccccggcaccaac
accagcaaccaggtggccgtgctgtaccagggcgtgaactgcacc
gaggtgcccgtggccatccacgccgaccagctgacccccacctgg
cgggtgtacagcaccggcagcaacgtgttccagacccgggccggc
tgcctgatcggcgccgagtacgtgaacaacagctacgagtgcgac
atccccatcggcgccggcatctgcgccagctaccagacccagacc
aagagccacagccgggccggcagcgtggccagccagagcatcatc
gcctacaccatgagcctgggcgccgagaacctggtggcctacagc
aacaacagcatcgccatccccaccaacttcaccatcagcgtgacc
accgagatcctgcccgtgagcatgaccaagaccagcgtggactgc
accatgtacatctgcggcgacagcaccgagtgcagcaacctgctg
ctgcagtacggcagcttctgcacccagctgaagcgggccctgacc
ggcatcgccgtggagcaggacaagaacacccaggaggtgttcgcc
caggtgaagcagatctacaagaccccccccatcaagtacttcggc
ggcttcaacttcagccagatcctgcccgaccccagcaagcccagc
aagcggagccccatcgaggacctgctgttcaacaaggtgaccctg
gccgacgccggcttcatcaagcagtacggcgactgcctgggcgac
atcgccgcccgggacctgatctgcgcccagaagttcaacggcctg
accgtgctgccccccctgctgaccgacgagatgatcgcccagtac
accagcgccctgctggccggcaccatcaccagcggctggaccttc
ggcgccggccccgccctgcagatccccttccccatgcagatggcc
taccggttcaacggcatcggcgtgacccagaacgtgctgtacgag -continued aaccagaagctgatcgccaaccagttcaacagcgccatcggcaag
atccaggacagcctgagcagcacccccagcgccctgggcaagctg
caggacgtggtgaaccacaacgcccaggccctgaacaccctggtg
aagcagctgagcagcaagttcggcgccatcagcagcgtgctgaac
gacatcctgagccggctggacccccccgaggccgaggtgcagatc
gaccggctgatcaccggccggctgcagagcctgcagacctacgtg
acccagcagctgatccgggccgccgagatccgggccagcgccaac
ctggccgccaccaagatgagcgagtgcgtgctgggccagagcaag
cgggtggacttctgcggcaagggctaccacctgatgagcttcccc
cagagcgccccccacggcgtggtgttcctgcacgtgacctacgtg
cccgcccaggagaagaacttcaccaccgcccccgccatctgccac
gacggcaaggcccacttcccccgggggcgtgttcgtgagcaacg
gcacccactggttcgtgacccagcggaacttctacgagccccaga
tcatcaccaccgacaacaccttcgtgagcggcaactgcgacgtgg
tgatcggcatcgtgaacaacaccgtgtacgaccccctgcagcccg
agctggacagcttcaaggaggagctggacaagtacttcaagaacc
acaccagccccgacgtggacctgggcgacatcagcggcatcaacg
ccagcgtggtgaacatccagaaggagatcgaccggctgaacgagg
tggccaagaacctgaacgagagcctgatcgacctgcaggagctgg
gcaagtacgagcagtacatcaagtggccctggtacatctggctgg
gcttcatcgccggcctgatcgccatcgtgatggtgaccatcatgc
tgtgctgcatgaccagctgctgcagctgcctgaagggctgctgca
gctgcggcagctgctgcaagttcgacgaggacgacagcgagcccg
tgctgaagggcgtgaagctgcactacacctaaaa.

SEQ ID NO: 15, DNA sequence encoding
SEQ ID NO: 11:
atgttcgtgttcctggtgctgctgcctctggtgtcctcccaatgt
gttaacctcaccacaagaacgcagctgcccccagcctataccaac
agcttcacgagaggcgtgtactaccccgacaaggtgttccgtagc
tccgtgctgcacagcacccaagatctgtttctgcctttcttcagc
aatgtgacctggttccacgtcatcagcggcaccaatgggaccaag
cggtttgataatcctgtcctgccctttaacgatggagtgtatttc
gccagtatcgaaaagtccaacatcatcagaggctggatcttcggc
accaccctggattctaagacacaaagtctgctgatcgtgaacaac
gcaacaaatgtggtgatcaaggtgtgtgaattccagttctgcaat
gaccctttcctagaccacaagaacaacaagagctggatggaaagc
gaattccgggtgtacagctctgccaacaactgtaccttcgaatac
gtttctcagccctttctgatggacctggaaggcaagcagggaaac
ttcaagaacctaagagaattcgtgttcaagaacatcgatggctac
ttcaagatctacagcaagcacacacctatcatcgtgcgggaacct
gaggacctgcctcaaggcttcagcgccctggagcccctggtggac -continued ctgcctatcgggatcaacatcacccggttccagaccctgctcgcc ctgcatagatcttatctgacaccaggcgattctagcagcggctgg accgccggcgccgctgcctactacgtgggctacctgcagcctaga acctttctcctgaagtacaacgagaacggcacaatcaccgacgcc gtggactgcgccctggaccctctgtccgagacaaagtgcaccctg aagtctttcaccgtggaaaagggcatctatcagacctctaacttc cgggtgcagcctaccgagagcatcgtgcgctttccaaacatcacc aacctgtgccctttcgacgaggtgttcaatgccaccagattcgcc tccgtgtacgcctggaacagaaagaggatctccaactgcgtcgct gattacagcgtcctctacaacctggccccttttttcaccttcaag tgctacggagtgtctcctaccaagctgaacgacctctgcttcacc aatgtgtatgccgatagctttgtgatccggggcgatgaggtgcgg cagatcgctcctgggcagaccggcaacattgctgactacaactac aagctgcccgacgacttcacgggctgcgtgatcgcttggaatagc aacaaacttgacagcaaggtgtccggaaattacaactacctgtac agactgttcaggaagtctaacctgaagcctttcgagcgggatatc agcacagagatctaccaagctggcaacaagccctgcaacggcgtg gccggattcaattgctacttcccactgagatcctacagcttccga cctacgtacggcgttggccaccagccttacagggtcgtggtgctg agcttcgagctcctgcacgcccctgccaccgtgtgcggcccaaag aagtctaccaatcttgttaaaaacaagtgcgtgaacttcaacttc aacggtctgaagggaaccggcgtgctgaccgagtctaacaagaaa ttcctgccctttcagcagttcgggagagacattgctgacaccacg gatgccgtgagagaccctcagacactggaaatcctggacatcacc ccttgtagctttggcggagtgagcgtgatcacccctggcacaaac accagcaatcaggttgctgtgctgtaccagggcgtgaactgcacc gaggtgcctgtggccatccacgccgatcagctgacccctacctgg cgcgtttacagcacaggctctaatgtctttcagacaagagccggc tgtctgatcggcgccgagtacgtaaataatagctatgaatgcgac atcccgatcggcgcaggcatttgtgccagctaccagacccagacc aaaagccacagcagagccggatctgtggcttctcagtccatcatc gcctacaccatgagcctgggtgctgagaactccgtggcctacagc aacaactctatcgccatccccaccaacttcacaatatccgtgacc accgaaattctgcctgtgtctatgaccaagaccagcgtggactgc accatgtacatttgcggcgactctactgagtgcagcaacctgctg ctccaatacggcagcttctgtacccagctcaaaagagccctgacc ggaatcgccgtggaacaggacaagaacacacaggaggtgttcgcc caggtgaagcaaatctacaagacacctcccatcaaatacttcggc ggctttaatttttctcagatcctgcctgatccctccaagcctagc aaacggagccccatcgaggacctgctgttcaacaaggtgacactg gctgacgccggattcatcaagcagtacggcgactgcctgggcgac -continued atcgccgcaagagacctgatctgcgcccagaaattcaagggcctg actgtgctgccgccgctgctgaccgacgagatgatcgcccagtac acctccgccctgctggccggaaccatcacatccggctggaccttc ggcgctgggcctgccctgcagatccctttccctatgcagatggcc taccggtttaacggaatcggcgtgacacagaacgtgctgtacgag aatcaaaagctgatcgccaaccagtttaacagcgctattggcaag attcaggactccctgagctctacccctctgccctgggcaagctg caggacgtggtgaaccacaacgcccaggccctgaacaccctggtg aagcagctgagctccaagttcggagctatcagctctgtcctgaac gacattttctccagactggaccctccagaagccgaggtccagatc gatcggctgatcaccggcagactgcaaagcctgcagacatatgtg acacagcagctgatcagagccgccgaaatcagagcgagcgccaat ctggccgccacaaagatgagcgaatgcgtgttgggccaaagtaaa agagtggatttctgcggcaaaggataccacctgatgagcttccca cagagtgcccctcacggcgtggtgttcctgcatgtgacctacgtg cccgcccaggagaagaacttcactacagcccctgcaatctgccac gacggcaaggcccacttccccagagagggtgtgtttgtgagcaat ggcactcactggttcgtcacccaaagaaacttctacgagccccag atcatcaccacagacaacacattcgtgagcggcaattgcgacgtg gtgatcggaatcgtgaacaacacagtgtacgacccccctgcagcca gagctggatagcttcaaagaggaactggacaagtacttcaagaac cacacctctcctgacgtggaccttggcgacatctctggaatcaac gccagcgtggtgaacatccagaaggaaatcgacagactcaacgag gtcgccaagaacctgaacgagagcctgatcgatctgcaggagctg ggcaagtacgagcagtacatcaaatggccttggtacatctggctg ggcttcatcgctggccttatcgccatcgtcatggtgacaatcatg ctgtgttgcatgacatcttgttgcagctgtctgaagggctgctgc agctgcggctcttgttgtaaattcgacgaggatgatagcgagcct gtgctgaagggagtgaaactgcactacacctaaa SEQ ID NO: 17, DNA sequence of 3′ UTR:
GCTCGCTTTCTTGCTGTCCAATTTCTATTAAAGGTTCCTTTGTT

CCCTAAGTCCAACTACTAAACTGGGGGATATTATGAAGGGCCTT

GAGCATCTGGATTCTGCCTAATAAAAAACATTTATTTTCATTGC

SEQ ID NO: 18, RNA sequence of 3′ UTR:
GCUCGCUUUCUUGCUGUCCAAUUUCUAUUAAAGGUUCCUUUGUU

CCCUAAGUCCAACUACUAAACUGGGGGAUAUUAUGAAGGGCCUU

GAGCAUCUGGAUUCUGCCUAAUAAAAAACAUUUAUUUUCAUUGC

SEQ ID NO: 19,
DNA sequence of ß-globulin 5′UTR:
ACATTTGCTTCTGACACAACTGTGTTCACTAGCAACCTCAAACA

GACACC

SEQ ID NO: 20,
RNA sequence of B-globulin 5′UTR:

-continued

ACAUUUGCUUCUGACACAACUGUGUUCACUAGCAACCUCAAAC

AGACACC

SEQ ID NO: 21,
DNA sequence of SYS UTR 2.0:
GGCGCTCGAGCAGGTTCAGAAGGAGATCAAAAACCCCCAAGGA

TCAAACGCCACC

SEQ ID NO: 22,
RNA sequence of SYS UTR 2.0:
GGCGCUCGAGCAGGUUCAGAAGGAGAUCAAAAAC

CCCCAAGGAUCAAACGCCACC

SEQ ID NO: 23,
DNA sequence of SYS UTR 1.0:
GGGCGCTCGAGCAGGTTCAGAAGGAGATCAAAAACCCC

CAAGGATCAAAC

SEQ ID NO: 24,
RNA sequence of SYS UTR 1.0:
GGGCGCUCGAGCAGGUUCAGAAGGAGAUCAAAAACCC

CCAAGGAUCAAAC

SEQ ID NO: 25,
DNA sequence of SYS4 5'UTR:
GGCGCACGAGCAGGGAGAGAAGGAGATCAAAAACCCCCA

AGGATCAAACGCCACC

SEQ ID NO: 26,
RNA sequence of SYS4 5'UTR:
GGCGCACGAGCAGGGAGAGAAGGAGAUCAAAAACCCCCA

AGGAUCAAACGCCACC

SEQ ID NO: 27,
DNA sequence of polyA 40:
AAAAAAAAAAAAAAAAAAAAAAAAAAAAAAAAAAAAAAAA SEQ ID NO: 28,
DNA sequence of polyA 60:
AAAAAAAAAAAAAAAAAAAAAAAAAAAAAAAAAAAAAAAAAAAAA

AAAAAAAAAAAAAAAGAAAAAAAAAAAAAAAAAAAAAAAAAAAAA

AAAAAAAAAAAAAAAAAAAAAAAAAAAAAAA

SEQ ID NO: 29,
DNA sequence of polyA signal HSV:
CGGCAATAAAAAGACAGAATAAAACGCACGGTGTTGGGTCGTTTG

TTC

SEQ ID NO: 30,
RNA sequence of polyA signal HSV:
CGGCAAUAAAAAGACAGAAUAAAACGCACGGUGUUGGG

UCGUUUGUUC

SEQ ID NO: 33, plasmid DNA sequence:
TCGCGCGTTTCGGTGATGACGGTGAAAACCTCTGACACATGCAGC

TCCCGGAGACGGTCACAGCTTGTCTGTAAGCGGATGCCGGGAGCA

GACAAGCCCGTCAGGGCGCGTCAGCGGGTGTTGGCGGGTGTCGGG

GCTGGCTTAACTATGCGGCATCAGAGCAGATTGTACTGAGAGTGC

ACCATATGCGGTGTGAAATACCGCACAGATGCGTAAGGAGAAAAT

ACCGCATCAGGCGCCATTCGCCATTCAGGCTGCGCAACTGTTGGG

AAGGGCGATCGGTGCGGGCCTCTTCGCTATTACGCCAGCTGGCGA

AAGGGGGATGTGCTGCAAGGCGATTAAGTTGGGTAACGCCAGGGT

-continued

TTTCCCAGTCACGACGTTGTAAAACGACGGCCAGTGAATTCGAGC

TCGGTACCTCGCGAATGCATCTAGATATCGGATCCCGGGCCCGTC

GACTGCAGAGGCCTGCATGCAAGCTTTAATACGACTCACTATAAG

GACATTTGCTTCTGACACAACTGTGTTCACTAGCAACCTCAAACA

GACACCGCCACCATGTTCGTGTTCCTGGTGCTGCTGCCTCTGGTC

AGCAGCCAGTGCGTGAACCTGAGAACAAGAACACAGCTTCCTCCA

GCCTACACAAACTCTTTTACACGGGGCGTGTACTATCCTGACAAG

GTGTTCCGGTCCAGCGTGCTGCACTCAACCCAAGACCTGTTCCTG

CCCTTCTTCAGCAACGTCACCTGGTTCCACGCCATCCACGTGTCT

GGCACCAATGGCACAAAGCGATTCGATAACCCCGTGCTGCCTTTC

AACGACGGCGTGTACTTTGCCTCCATCGAGAAGTCCAACATCATC

CGGGGCTGGATCTTCGGGACCACACTGGATAGCAAGACCCAGTCT

CTGCTGATCGTAAACAACGCCACCAACGTGGTCATCAAGGTGTGC

GAGTTCCAGTTCTGCAACGACCCTTTCCTCGATGTGTACTACCAC

AAGAACAACAAGTCTTGGATGGAATCGGGCGTGTATAGCAGCGCC

AACAACTGCACCTTCGAATACGTGAGCCAGCCTTTCCTGATGGAC

CTGGAAGGCAAACAAGGCAATTTTAAGAACCTGAGAGAATTCGTG

TTCAAAAATATAGACGGCTATTTCAAGATCTACAGCAAGCACACC

CCTATTAATCTGGTGCGGGATCTGCCTCAGGGCTTCAGCGCCCTC

GAACCTCTGGTGGACCTGCCAATCGGCATCAACATTACAAGATTC

CAGACGCTGCTCGCTCTGCACAGATCTTACCTGACCCCTGGCGAC

AGCAGCAGCGGCTGGACCGCCGGCGCCGCCGCTTACTACGTGGGC

TACCTGCAGCCTAGAACCTTTCTGCTGAAGTACAACGAGAACGGC

ACCATCACTGATGCCGTGGATTGCGCCCTGGACCCTCTGTCCGAA

ACCAAATGTACACTGAAGTCTTTTACCGTGGAAAAAGGAATCTAC

CAGACTTCCAACTTCCGGGTGCAGCCGACCGAGAGCATCGTGCGG

TTCCCTAACATCACAAACCTGTGCCCCTTTGGCGAGGTGTTCAAC

GCCACAAGATTTGCTAGCGTGTACGCCTGGAATAGAAAGAGAATC

AGCAACTGCGTGGCCGATTACAGCGTGCTGTACAATAGCGCCTCT

TTCAGCACCTTCAAATGCTACGGCGTGAGCCCCACCAAGCTGAAC

GATCTGTGTTTTACAAACGTGTATGCCGACTCATTCGTAATCAGG

GGCGATGAGGTGAGACAGATCGCTCCTGGACAGACAGGCAAAATC

GCGGACTACAACTATAAGCTGCCTGATGACTTCACAGGATGTGTG

ATCGCATGGAACTCCAATAACCTCGACAGCAAGGTGGGCGGAAAT

TACAATTACCGCTACAGACTGTTTAGAAAGAGCAATCTGAAACCT

TTCGAGAGAGACATCAGCACAGAGATCTACCAGGCCGGCAGCAAG

CCCTGTAACGGCGTCGAGGGCTTCAACTGCTACTTCCCCCTGCAG

AGCTACGGCTTCCAGCCTACCAACGGCGTGGGATACCAGCCTTAC

AGAGTGGTGGTGCTGAGCTTCGAGCTGCTGCATGCTCCTGCTACA

GTGTGTGGTCCTAAGAAGAGCACCAACCTGGTTAAGAACAAGTGC

GTGAATTTTAACTTCAATGGACTGACCGGAACCGGCGTGCTGACC

-continued

GAAAGCAACAAGAAATTCCTGCCTTTTCAGCAGTTTGGCAGAGAC

ATCGCCGACACCACCGACGCCGTGAGAGATCCACAAACCCTGGAA

ATCCTGGACATCACACCTTGCTCATTTGGAGGGGTGTCGGTGATC

ACACCTGGCACCAACACCAGCAACCAGGTGGCCGTGCTGTACCAG

GGAGTGAATTGTACCGAGGTCCCCGTGGCCATTCACGCCGACCAG

CTGACCCCTACCTGGCGGGTGTACTCCACCGGCTCTAACGTATTC

CAGACCAGAGCCGGCTGTCTGATCGGCGCAGAACACGTGAACAAT

AGCTACGAGTGCGACATCCCTATCGGAGCCGGGATCTGCGCTAGC

TACCAGACCCAGACAAACTCCAGAAGCAGAGCCGGAAGCGTGGCC

AGCCAGTCTATCATCGCCTACACCATGAGCCTGGGCGCCGAAAAC

AGCGTTGCCTACAGCAACAATTCTATCGCCATCCCTACAAACTTC

ACCATCTCCGTGACCACCGAGATCCTGCCTGTCAGCATGACAAAG

ACCAGCGTAGACTGCACAATGTACATCTGCGGAGATTCCACCGAG

TGTAGTAACCTCCTGCTGCAATACGGATCTTTCTGTACTCAGCTG

AACAGAGCCCTGACCGGCATCGCCGTTGAACAGGACAAGAACACC

CAGGAGGTTTTCGCCCAGGTTAAGCAGATCTACAAAACCCCTCCT

ATCAAGGACTTCGGAGGCTTTAACTTCTCCCAGATCCTGCCCGAC

CCCAGCAAGCCCAGCAAGCGGAGCCCCATCGAGGACCTGCTGTTC

AACAAGGTGACCCTGGCCGACGCCGGCTTCATCAAACAGTACGGC

GATTGCCTGGGAGACATCGCCGCTAGAGATCTAATTTGCGCCCAA

AAGTTTAACGGCCTGACAGTGCTGCCTCCACTGCTGACAGACGAG

ATGATCGCCCAGTACACATCTGCCCTGCTGGCTGGTACCATCACA

TCTGGCTGGACCTTTGGCGCCGGCCCCGCCCTCCAGATCCCTTTC

CCCATGCAGATGGCCTACCGGTTCAACGGCATCGGCGTGACCCAG

AACGTGCTGTACGAAAACCAGAAACTGATCGCCAACCAGTTCAAT

AGCGCGATCGGCAAAATCCAGGATAGCCTCAGCTCTACACCCAGC

GCTCTTGGCAAGCTGCAAAACGTGGTGAACCAGAATGCCCAGGCC

CTTAACACCCTGGTGAAGCAGCTATCCTCTAATTTCGGTGCCATC

AGCAGCGTGCTGAATGATATCCTGAGCAGACTGGACCCCCCTGAG

GCCGAAGTGCAGATCGACAGACTGATCACCGGAAGACTGCAGAGC

CTGCAAACCTACGTGACCCAGCAACTGATCCGGGCCGCAGAAATC

CGGGCCTCCGCTAACCTGGCCGCTACCAAGATGAGCGAGTGCGTG

CTGGGTCAAAGCAAGCGCGTGGACTTCTGTGGAAAAGGCTACCAC

CTGATGAGCTTCCCTCAGAGCGCTCCACACGGCGTGGTGTTCCTG

CATGTGACTTACGTGCCTGCCCAGGAAAAGAACTTCACCACCGCC

CCTGCCATTTGTCACGACGGCAAGGCCCACTTCCCCCGGGAAGGC

GTGTTTGTGTCTAACGGAACACACTGGTTTGTGACTCAAAGAAAC

TTCTACGAGCCACAGATCATCACCACAGATAACACCTTCGTCAGC

GGCAACTGCGACGTGGTGATCGGCATCGTGAACAATACTGTGTAC

GACCCCCTGCAGCCAGAGCTCGATTCTTTCAAAGAGGAACTGGAT

-continued

AAGTACTTCAAGAACCACACATCCCCCGACGTCGACCTGGGCGAT

ATCAGCGGCATTAACGCCAGCGTGGTGAACATCCAGAAGGAAATC

GATAGACTGAACGAGGTGGCAAAGAACCTGAATGAGTCCCTGATT

GACCTGCAAGAGCTCGGGAAGTACGAGCAGTATATCAAGTGGCCT

TGGTACATCTGGCTGGGCTTCATCGCGGGCCTGATCGCCATCGTT

ATGGTGACGATCATGCTGTGCTGCATGACCAGTTGCTGTAGCTGC

CTGAAGGGCTGCTGCAGCTGCGGCAGCTGTTGCAAGTTCGACGAG

GACGACAGCGAGCCTGTGCTGAAGGGCGTTAAGCTGCACTACACC

TGAGCTCGCTTTCTTGCTGTCCAATTTCTATTAAAGGTTCCTTTG

TTCCCTAAGTCCAACTACTAAACTGGGGGATATTATGAAGGGCCT

TGAGCATCTGGATTCTGCCTAATAAAAAACATTTATTTTCATTGC

CAATAGGCCGAAATCGGCAAGCGCGATCGCAAAAAAAAAAAAAAA

AAAAAAAAAAAAAAAAAAAAAAAAAAAAAAAAAAAGAAAAAAAAA

AAAAAAAAAAAAAAAAAAAAAAAAAAAAAAAAAAAAAAAAAAAAA

AAAAAAGAATTCCTCGAGATTTAAATTCGCGAGTACTATGCATAT

GGGCCCAATATTAATTAAGCGCTAGCACGCGTTTAAACAGGCCTC

GAGGCGCGCCCGCTTCCTCGCTCACTGACTCGCTGCGCTCGGTCG

TTCGGCTGCGGCGAGCGGTATCAGCTCACTCAAAGGCGGTAATAC

GGTTATCCACAGAATCAGGGGATAACGCAGGAAAGAACATGTGAG

CAAAAGGCCAGCAAAAGGCCAGGAACCGTAAAAAGGCCGCGTTGC

TGGCGTTTTTCCATAGGCTCCGCCCCCCTGACGAGCATCACAAAA

ATCGACGCTCAAGTCAGAGGTGGCGAAACCCGACAGGACTATAAA

GATACCAGGCGTTTCCCCCTGGAAGCTCCCTCGTGCGCTCTCCTG

TTCCGACCCTGCCGCTTACCGGATACCTGTCCGCCTTTCTCCCTT

CGGGAAGCGTGGCGCTTTCTCATAGCTCACGCTGTAGGTATCTCA

GTTCGGTGTAGGTCGTTCGCTCCAAGCTGGGCTGTGTGCACGAAC

CCCCCGTTCAGCCCGACCGCTGCGCCTTATCCGGTAACTATCGTC

TTGAGTCCAACCCGGTAAGACACGACTTATCGCCACTGGCAGCAG

CCACTGGTAACAGGATTAGCAGAGCGAGGTATGTAGGCGGTGCTA

CAGAGTTCTTGAAGTGGTGGCCTAACTACGGCTACACTAGAAGAA

CAGTATTTGGTATCTGCGCTCTGCTGAAGCCAGTTACCTTCGGAA

AAAGAGTTGGTAGCTCTTGATCCGGCAAACAAACCACCGCTGGTA

GCGGTGGTTTTTTTGTTTGCAAGCAGCAGATTACGCGCAGAAAAA

AAGGATCTCAAGAAGATCCTTTGATCTTTTCTACGGGGTCTGACG

CTCAGTGGAACGAAAACTCACGTTAAGGGATTTTGGTCATGAGAT

TATCAAAAAGGATCTTCACCTAGATCCTTTTAAATTAAAAATGAA

GTTTTAAATCAAGCCCAATCTGAATAATGTTACAACCAATTAACC

AATTCTGATTAGAAAAACTCATCGAGCATCAAATGAAACTGCAAT

TTATTCATATCAGGATTATCAATACCATATTTTTGAAAAAGCCGT

TTCTGTAATGAAGGAGAAAACTCACCGAGGCAGTTCCATAGGATG

GCAAGATCCTGGTATCGGTCTGCGATTCCGACTCGTCCAACATCA

-continued

ATACAACCTATTAATTTCCCCTCGTCAAAAATAAGGTTATCAAGT

GAGAAATCACCATGAGTGACGACTGAATCCGGTGAGAATGGCAAA

AGTTTATGCATTTCTTTCCAGACTTGTTCAACAGGCCAGCCATTA

CGCTCGTCATCAAAATCACTCGCATCAACCAAACCGTTATTCATT

CGTGATTGCGCCTGAGCGAGACGAAATACGCGATCGCTGTTAAAA

GGACAATTACAAACAGGAATCGAATGCAACCGGCGCAGGAACACT

GCCAGCGCATCAACAATATTTTCACCTGAATCAGGATATTCTTCT

AATACCTGGAATGCTGTTTTTCCGGGGATCGCAGTGGTGAGTAAC

CATGCATCATCAGGAGTACGGATAAAATGCTTGATGGTCGGAAGA

GGCATAAATTCCGTCAGCCAGTTTAGTCTGACCATCTCATCTGTA

ACATCATTGGCAACGCTACCTTTGCCATGTTTCAGAAACAACTCT

GGCGCATCGGGCTTCCCATACAAGCGATAGATTGTCGCACCTGAT

TGCCCGACATTATCGCGAGCCCATTTATACCCATATAAATCAGCA

TCCATGTTGGAATTTAATCGCGGCCTCGACGTTTCCCGTTGAATA

TGGCTCATAACACCCCTTGTATTACTGTTTATGTAAGCAGACAGT

TTTATTGTTCATGATGATATATTTTTATCTTGTGCAATGTAACA

TCAGAGATTTTGAGACACGGGCCAGAGCTGCA

SEQ ID NO: 34,
HKP side chain: KHKHKHKHK

SEQ ID NO: 35,
HKP side chain: HKHKHKHKHK

SEQ ID NO: 36,
HKP side chain: KHKHKHKHKH

SEQ ID NO: 37,
HKP side chain: HKHKHKHKHKH

SEQ ID NO: 38,
HKP side chain: KHKHHKHHKHHKHHKHHKHK

SEQ ID NO: 39,
HKP side chain: KHHHKHHHKHHHKHHHK

SEQ ID NO: 40,
HKP side chain: KHHHKHHHKHHHHKHHHK

SEQ ID NO: 41,
HKP side chain: KHHHKHHHKHHHHKHHHK
wherein
the 1st, 5th, 9th, 14th and 18th amino acids are D-amino acids.

SEQ ID NO: 42,
HKP side chain: HKHHHKHHHKHHHHKHHHK

SEQ ID NO: 43,
HKP side chain: HHKHHHKHHHKHHHHKHHHK

SEQ ID NO: 44,
HKP side chain: KHHHHKHHHHKHHHHKHHHHK

SEQ ID NO: 45,
HKP side chain: KHHHKHHHKHHHKHHHHK

SEQ ID NO: 46,
HKP side chain: KHHHKHHHHKHHHKHHHK

SEQ ID NO: 47,
HKP side chain: KHHHKHHHHKHHHKHHHHK

SEQ ID NO: 48,
furin-like cleavage site: RRAR

SEQ ID NO: 49:,
-HHHK-

SEQ ID NO: 51: TAATACGACTCACTATAA

SEQ ID NO: 53, RNA sequence of polyA 40:
AAAAAAAAAAAAAAAAAAAAAAAAAAAAAAAAAAAAAAAA SEQ ID NO: 54 RNA sequence of polyA 60:
AAAAAAAAAAAAAAAAAAAAAAAAAAAAAAAAAAAAAAAAA

AAAAAAAAAAAAAAAAAAAGAAAAAAAAAAAAAAAAAAAAA

AAAAAAAAAAAAAAAAAAAAAAAAAAAAAAAAAAAAAAA

SEQ ID NO: 55, amino acid sequence of S protein comprising the following mutations: omicron variant mutations of T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q493R, Q498R, N501Y, Y505H, D614G, H655Y, N679K, P681H, N764K, D796Y, Q954H, and/or N969K; S6P mutations (F817P, A892P, A899P, A942P, K986P, and V987P); and furin-like cleavage site mutation (R682S and R685G).
MFVFLVLLPLVSSQCVNLITRTQSYTNSFTRGVYYPDKVFRSSVL

HSTQDLFLPFFSNVTWFHAIHVSGTNGTKRFDNPVLPFNDGVYFA

STEKSNIIRGWIFGTTLDSKTQSLLIVNNATNVVIKVCEFQFCND

PFLDVYYHENNKSRMESELRVYSSANNCTFEYVSQPFLMDLEGKQ

GNFKNLREFVFKNIDGYFKIYSKHTPVNLGRDLPQGFSALEPLVD

LPIGINITRFQTLLALHRSYLTPGDSSSSWTAGAAAYYVGYLQPR

TFLLKYNENGTITDAVDCALDPLSETKCTLKSFTVEKGIYQTSNF

R+10VQPTESIVRFPNITNLCPFHEVFNATRFASVYAWNRKRISN

CVADYSVLYNFAPFFAFKCYGVSPTKLNDLCFTNVYADSFVIRGN

EVSQIAPGQTGNIADYNYKLPDDFTGCVIAWNSNKLDSKVSGNYN

YLYRLFRKSKLKPFERDISTEIYQAGNKPCNGVAGENCYFPLRSY

GFRPTYGVGHQPYRVVVLSFELLHAPATVCGPKKSTNLVKNKCVN

FNFNGLTGTGVLTESNKKFLPFQQFGRDIADTTDAVRDPQTLEIL

DITPCSFGGVSVITPGTNTSNQVAVLYQGVNCTEVPVAIHADQLT

PTWRVYSTGSNVFQTRAGCLIGAEYVNNSYECDIPIGAGICASYQ

TQTKSHSRAGSVASQSIIAYTMSLGAENSVAYSNNSIAIPTNFTI

SVTTEILPVSMTKTSVDCTMYICGDSTECSNLLLQYGSFCTQLKR

ALTGIAVEQDKNTQEVFAQVKQIYKTPPIKYFGGFNFSQILPDPS

KPSKRSPIEDLLFNKVTLADAGFIKQYGDCLGDIAARDLICAQKF

NGLTVLPPLLTDEMIAQYTSALLAGTITSGWTFGAGPALQIPFPM

QMAYRENGIGVTQNVLYENQKLIANQFNSAIGKIQDSLSSTPSAL

GKLQDVVNHNAQALNTLVKQLSSKFGAISSVLNDILSRLDPPEAE

VQIDRLITGRLQSLQTYVTQQLIRAAEIRASANLAATKMSECVLG

QSKRVDFCGKGYHLMSFPQSAPHGVVFLHVTYVPAQEKNFTTAPA

ICHDGKAHFPREGVFVSNGTHWFVTQRNFYEPQIITTDNTFVSGN

CDVVIGIVNNTVYDPLQPELDSFKEELDKYFKNHTSPDVDLGDIS

-continued

GINASVVNIQKEIDRLNEVAKNLNESLIDLQELGKYEQYIKWPWY

IWLGFIAGLIAIVMVTIMLCCMTSCCSCLKGCCSCGSCCKFDEDD

SEPVLKGVKLHYT

SEQ ID NO: 56, DNA sequence encoding
SEQ ID NO: 55
ATGTTCGTGTTCCTGGTGCTGCTGcctCTGGTGtcttctCAGTGC GTGaatCTGATCACCagaACCCAGtctTACACCaattctTTCACC agaGGCGTGTACTACcctgatAAGGTGTTCagatcttctGTGCTG CACtctACCCAGgatCTGTTCCTGcctTTCTTCtctaatGTGACC TGGTTCCACGCCATCCACGTGtctGGCACCaatGGCACCAAGaga TTCgataatcctGTGCTGcctTTCaatgatGGCGTGTACTTCGCC tctACCGAGAAGtctaatATCATCagaGGCTGGATCTTCGGCACC ACCCTGgattctAAGACCCAGtctCTGCTGATCGTGaataatGCC ACCaatGTGGTGATCAAGGTGTGCGAGTTCCAGTTCTGCaatgat cctTTCCTGgatGTGTACTACCACGAGaataatAAGagcagaATG GAGtctGAGCTGagaGTGTACtcttctGCCaataatTGCACCTTC GAGTACGTGtctCAGcctTTCCTGATGgatCTGGAGGGCAAGCAG GGCaatTTCAAGaatCTGagaGAGTTCGTGTTCAAGaatATCgat GGCTACTTCAAGATCTACtctAAGCACACCcctGTGaatCTGGGC agagatCTGcctCAGGGCTTCtctGCCCTGGAGcctCTGGTGgat CTGcctATCGGCATCaatATCACCagaTTCCAGACCCTGCTGGCC CTGCACagatctTACCTGACCcctGGCgattcttcttcttctTGG ACCGCCGGCGCCGCCGCCTACTACGTGGGCTACCTGCAGcctaga ACCTTCCTGCTGAAGTACaatGAGaatGGCACCATCACCgatGCC GTGgatTGCGCCCTGgatcctCTGtctGAGACCAAGTGCACCCTG AAGtctTTCACCGTGGAGAAGGGCATCTACCAGACCtctaatTTC agaGTGCAGcctACCGAGtctATCGTGagaTTCcctaatATCACC aatCTGTGCcctTTCCACGAGGTGTTCaatGCCACCagaTTCGCC tctGTGTACGCCTGGaatagaAAGagaATCtctaatTGCGTGGCC gatTACtctGTGCTGTACaatTTCGCCcctTTCTTCGCCTTCAAG TGCTACGGCGTGtctcctACCAAGCTGaatgatCTGTGCTTCACC AACGTGTACGCCgattctTTCGTGATCagaGGCAACGAGGTGtct CAGATCGCCcctGGCCAGACCGGCAACATCGCCgatTACAACTAC AAGCTGcctgatgatTTCACCGGCTGCGTGATCGCCTGGAACtct AACAAGCTGgattctAAGGTGtctGGCAACTACAACTACCTGTAC agaCTGTTCagaAAGtctAAGCTGAAGcctTTCGAGagagatATC tctACCGAGATCTACCAGGCCGGCAACAAGcctTGCAACGGCGTG GCCGGCTTCAACTGCTACTTCcctCTGCAGtctTACGGCTTCaga cctACCTACGGCGTGGGCCACCAGcctTACagaGTGGTGGTGCTG tctTTCGAGCTGCTGCACGCCcctGCCACCGTGTGCGGCcctAAG AAGtctACCAACCTGGTGAAGAACAAGTGCGTGAACTTCAACTTC -continued AACGGCCTGACCGGCACCGGCGTGCTGACCGAGtctAACAAGAAG TTCCTGcctTTCCAGCAGTTCGGCagagatATCGCCgatACCACC gatGCCGTGagagatcctCAGACCCTGGAGATCCTGgatATCACC cctTGCtctTTCGGCGGCGTGtctGTGATCACCcctGGCACCAAC ACCtctAACCAGGTGGCCGTGCTGTACCAGGGCGTGAACTGCACC GAGGTGcctGTGGCCATCCACGCCgatCAGCTGACCcctACCTGG agaGTGTACtctACCGGCtctAACGTGTTCCAGACCagaGCCGGC TGCCTGATCGGCGCCGAGTACGTGAACAACtctTACGAGTGCgat ATCcctATCGGCGCCGGCATCTGCGCCtctTACCAGACCCAGACC AAGtctCACagcagaGCCGGCtctGTGGCCtctCAGtctATCATC GCCTACACCATGtctCTGGGCGCCGAGAACtctGTGGCCTACtct AACAACtctATCGCCATCcctACCAACTTCACCATCtctGTGACC ACCGAGATCCTGcctGTGtctATGACCAAGACCtctGTGgatTGC ACCATGTACATCTGCGGCgattctACCGAGTGCtctAACCTGCTG CTGCAGTACGGCtctTTCTGCACCCAGCTGAAGagaGCCCTGACC GGCATCGCCGTGGAGCAGgatAAGAACACCCAGGAGGTGTTCGCC CAGGTGAAGCAGATCTACAAGACCcctcctATCAAGTACTTCGGC GGCTTCAACTTCtctCAGATCCTGcctgatccttctAAGccttct AAGagatctcctATCGAGgatCTGCTGTTCAACAAGGTGACCCTG GCCgatGCCGGCTTCATCAAGCAGTACGGCgatTGCCTGGGCgat ATCGCCGCCagagatCTGATCTGCGCCCAGAAGTTCAACGGCCTG ACCGTGCTGcctcctCTGCTGACCgatGAGATGATCGCCCAGTAC ACCtctGCCCTGCTGGCCGGCACCATCACCtctGGCTGGACCTTC GGCGCCGGCcctGCCCTGCAGATCcctTTCcctATGCAGATGGCC TACagaTTCAACGGCATCGGCGTGACCCAGAACGTGCTGTACGAG AACCAGAAGCTGATCGCCAACCAGTTCAACtctGCCATCGGCAAG ATCCAGgattctCTGtcttctACCccttctGCCCTGGGCAAGCTG CAGgatGTGGTGAACCACAACGCCCAGGCCCTGAACACCCTGGTG AAGCAGCTGtcttctAAGTTCGGCGCCATCtcttctGTGCTGAAC gatATCCTGagcagaCTGgatcctcctGAGGCCGAGGTGCAGATC gatagaCTGATCACCGGCagaCTGCAGtctCTGCAGACCTACGTG ACCCAGCAGCTGATCagaGCCGCCGAGATCagaGCCtctGCCAAC CTGGCCGCCACCAAGATGtctGAGTGCGTGCTGGGCCAGtctAAG agaGTGgatTTCTGCGGCAAGGGCTACCACCTGATGtctTTCcct CAGtctGCCcctCACGGCGTGGTGTTCCTGCACGTGACCTACGTG cctGCCCAGGAGAAGAACTTCACCACCGCCcctGCCATCTGCCAC gatGGCAAGGCCCACTTCcctagaGAGGGCGTGTTCGTGtctAAC GGCACCCACTGGTTCGTGACCCAGagaAACTTCTACGAGcctCAG ATCATCACCACCgatAACACCTTCGTGtctGGCAACTGCgatGTG GTGATCGGCATCGTGAACAACACCGTGTACgatcctCTGCAGcct GAGCTGgattctTTCAAGGAGGAGCTGgatAAGTACTTCAAGAAC -continued CACACCtctcctgatGTGgatCTGGGCgatATCtctGGCATCAAC GCCtctGTGGTGAACATCCAGAAGGAGATCgatagaCTGAACGAG GTGGCCAAGAACCTGAACGAGtctCTGATCgatCTGCAGGAGCTG GGCAAGTACGAGCAGTACATCAAGTGGcctTGGTACATCTGGCTG

GGCTTCATCGCCGGCCTGATCGCCATCGTGATGGTGACCATCATG

CTGTGCTGCATGACCtctTGCTGCtctTGCCTGAAGGGCTGCTGC tctTGCGGCtctTGCTGCAAGTTCgatGAGgatgattctGAGcct

GTGCTGAAGGGCGTGAAGCTGCACTACACCTAA

SEQ ID NO: 57, amino acid sequence of S protein comprising the following mutations: omicron variant mutations of T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, S704L, N764K, D796Y, Q954H, and/or N969K; S6P mutations (F817P, A892P, A899P, A942P, K986P, and V987P); and furin-like cleavage site mutation (R682S and R685G).

MFVFLVLLPLVSSQCVNLITRTQSYTNSFTRGVYYPDKVFRSSVL

HSTQDLFLPFFSNVTWFHAISGTNGTKRFDNPVLPFNDGVYFAST

EKSNIIRGWIFGTTLDSKTQSLLIVNNATNVVIKVCEFQFCNDPF

LDVYYHKNNKSWMESEFRVYSSANNCTFEYVSQPFLMDLEGKQGN

FKNLREFVFKNIDGYFKIYSKHTPINLGRDLPQGFSALEPLVDLP

IGINITRFQTLLALHRSYLTPGDSSSGWTAGAAAYYVGYLQPRTF

LLKYNENGTITDAVDCALDPLSETKCTLKSFTVEKGIYQTSNFR

VQPTESIVRFPNITNLCPFDEVFNATTFASVYAWNRKRISNCV

ADYSVLYNFAPFFAFKCYGVSPTKLNDLCFTNVYADSFVIRGNEV

SQIAPGQTGNIADYNYKLPDDFTGCVIAWNSNKLDSKVGGNYNYR

YRLFRKSNLKPFERDISTEIYQAGNKPCNGVAGVNCYFPLQSYGF

RPTYGVGHQPYRVVVLSFELLHAPATVCGPKKSTNLVKNKCVNFN

FNGLTGTGVLTESNKKFLPFQQFGRDIADTTDAVRDPQTLEILDI

TPCSFGGVSVITPGTNTSNQVAVLYQGVNCTEVPVAIHADQLTPT

WRVYSTGSNVFQTRAGCLIGAEYVNNSYECDIPIGAGICASYQTQ

TKSHSRAGSVASQSIIAYTMSLGAENSVAYSNNSIAIPTNFTISV

TTEILPVSMTKTSVDCTMYICGDSTECSNLLLQYGSFCTQLKRAL

TGIAVEQDKNTQEVFAQVKQIYKTPPIKYFGGFNFSQILPDPSKP

SKRSPIEDLLFNKVTLADAGFIKQYGDCLGDIAARDLICAQKFNG

LTVLPPLLTDEMIAQYTSALLAGTITSGWTFGAGPALQIPFPMQM

AYRENGIGVTQNVLYENQKLIANQFNSAIGKIQDSLSSTPSA

LGKLQDVVNHNAQALNTLVKQLSSKFGAISSVLNDILSRLDPPEA

EVQIDRLITGRLQSLQTYVTQQLIRAAEIRASANLAATKMSECVL

GQSKRVDFCGKGYHLMSFPQSAPHGVVFLHVTYVPAQEKNFTTAP

AICHDGKAHFPREGVFVSNGTHWFVTQRNFYEPQIITTDNTFVSG

NCDVVIGIVNNTVYDPLQPELDSFKEELDKYFKNHTSPDVDLGDI

SGINASVVNIQKEIDRLNEVAKNLNESLIDLQELGKYEQYIKWPW

-continued

YIWLGFIAGLIAIVMVTIMLCCMTSCCSCLKGCCSCGSCCKFDED

DSEPVLKGVKLHYT

SEQ ID NO: 58,
DNA sequence encoding SEQ ID NO: 57

ATGTTCGTGTTCCTGGTGCTGCTGcctCTGGTGtcttctCAGTGC

GTGaatCTGATCACCagaACCCAGtctTACACCaattctTTCACC agaGGCGTGTACTACcctgatAAGGTGTTCagatcttctGTGCTG CACtctACCCAGgatCTGTTCCTGcctTTCTTCtctaatGTGACC TGGTTCCACGCCATCtctGGCACCaatGGCACCAAGagaTTCgat aatcctGTGCTGcctTTCaatgatGGCGTGTACTTCGCCtctACC GAGAAGtctaatATCATCagaGGCTGGATCTTCGGCACCACCCTG gattctAAGACCCAGtctCTGCTGATCGTGaataatGCCACCaat GTGGTGATCAAGGTGTGCGAGTTCCAGTTCTGCaatgatcctTTC CTGgatGTGTACTACCACAAGaataatAAGtctTGGATGGAGtct GAGTTCagaGTGTACtcttctGCCaataatTGCACCTTCGAGTAC GTGtctCAGcctTTCCTGATGgatCTGGAGGGCAAGCAGGGCaat TTCAAGaatCTGagaGAGTTCGTGTTCAAGaatATCgatGGCTAC TTCAAGATCTACtctAAGCACACCcctATCaatCTGGGCagagat CTGcctCAGGGCTTCtctGCCCTGGAGcctCTGGTGgatCTGcct ATCGGCATCaatATCACCagaTTCCAGACCCTGCTGGCCCTGCAC agatctTACCTGACCcctGGCgattcttcttctGGCTGGACCGCC GGCGCCGCCGCCTACTACGTGGGCTACCTGCAGcctagaACCTTC CTGCTGAAGTACaatGAGaatGGCACCATCACCgatGCCGTGgat TGCGCCCTGgatcctCTGtctGAGACCAAGTGCACCCTGAAGtct TTCACCGTGGAGAAGGGCATCTACCAGACCtctaatTTCagaGTG CAGcctACCGAGtctATCGTGagaTTCcctaatATCACCaatCTG TGCcctTTCgatGAGGTGTTCaatGCCACCACCTTCGCCtctGTG TACGCCTGGaatagaAAGagaATCtctaatTGCGTGGCCgatTAC tctGTGCTGTACaatTTCGCCcctTTCTTCGCCTTCAAGTGCTAC GGCGTGtctcctACCAAGCTGaatgatCTGTGCTTCACCaatGTG TACGCCgattctTTCGTGATCagaGGCAACGAGGTGtctCAGATC GCCcctGGCCAGACCGGCAACATCGCCgatTACAACTACAAGCTG cctgatgatTTCACCGGCTGCGTGATCGCCTGGAACtctAACAAG CTGgattctAAGGTGGGCGGCAACTACAACTACagaTACagaCTG TTCagaAAGtctAACCTGAAGcctTTCGAGagagatATCtctACC GAGATCTACCAGGCCGGCAACAAGcctTGCAACGGCGTGGCCGGC GTGAACTGCTACTTCcctCTGCAGtctTACGGCTTCagacctACC TACGGCGTGGGCCACCAGcctTACagaGTGGTGGTGCTGtctTTC GAGCTGCTGCACGCCcctGCCACCGTGTGCGGCcctAAGAAGtct

ACCAACCTGGTGAAGAACAAGTGCGTGAACTTCAACTTCAACGGC

CTGACCGGCACCGGCGTGCTGACCGAGtctAACAAGAAGTTCCTG cctTTCCAGCAGTTCGGCagagatATCGCCgatACCACCgatGCC -continued

```
GTGagagatcctCAGACCCTGGAGATCCTGgatATCACCcctTGC
tctTTCGGCGGCGTGtctGTGATCACCcctGGCACCAACACCtct
AACCAGGTGGCCGTGCTGTACCAGGGCGTGAACTGCACCGAGGTG
cctGTGGCCATCCACGCCgatCAGCTGACCcctACCTGGagaGTG
TACtctACCGGCtctAACGTGTTCCAGACCagaGCCGGCTGCCTG
ATCGGCGCCGAGTACGTGAACAACtctTACGAGTGCgatATCcct
ATCGGCGCCGGCATCTGCGCCtctTACCAGACCCAGACCAAGtct
CACagcagaGCCGGCtctGTGGCCtctCAGtctATCATCGCCTAC
ACCATGtctCTGGGCGCCGAGAACtctGTGGCCTACtctAACAAC
tctATCGCCATCcctACCAACTTCACCATCtctGTGACCACCGAG
ATCCTGcctGTGtctATGACCAAGACCtctGTGgatTGCACCATG
TACATCTGCGGCgattctACCGAGTGCtctAACCTGCTGCTGCAG
TACGGCtctTTCTGCACCCAGCTGAAGagaGCCCTGACCGGCATC
GCCGTGGAGCAGgatAAGAACACCCAGGAGGTGTTCGCCCAGGTG
AAGCAGATCTACAAGACCcctectATCAAGTACTTCGGCGGCTTC
AACTTCtctCAGATCCTGcctgatccttctAAGccttctAAGaga
tctcctATCGAGgatCTGCTGTTCAACAAGGTGACCCTGGCCgat
GCCGGCTTCATCAAGCAGTACGGCgatTGCCTGGGCgatATCGCC
GCCagagatCTGATCTGCGCCCAGAAGTTCAACGGCCTGACCGTG
CTGcctcctCTGCTGACCgatGAGATGATCGCCCAGTACACCtct
GCCCTGCTGGCCGGCACCATCACCtctGGCTGGACCTTCGGCGCC
GGCcctGCCCTGCAGATCcctTTCcctATGCAGATGGCCTACaga
TTCAACGGCATCGGCGTGACCCAGAACGTGCTGTACGAGAACCAG
AAGCTGATCGCCAACCAGTTCAACtctGCCATCGGCAAGATCCAG
gattctCTGtcttctACCccttctGCCCTGGGCAAGCTGCAGgat
GTGGTGAACCACAACGCCCAGGCCCTGAACACCCTGGTGAAGCAG
CTGtcttctAAGTTCGGCGCCATCtcttctGTGCTGAACgatATC
CTGagcagaCTGgatcctcctGAGGCCGAGGTGCAGATCgataga
CTGATCACCGGCagaCTGCAGtctCTGCAGACCTACGTGACCCAG
CAGCTGATCagaGCCGCCGAGATCagaGCCtctGCCAACCTGGCC
GCCACCAAGATGtctGAGTGCGTGCTGGGCCAGtctAAGagaGTG
gaTTCTGCGGCAAGGGCTACCACCTGATGtctTTCcctCAGtctG
CCcctCACGGCGTGGTGTTCCTGCACGTGACCTACGTGcctGCCC
AGGAGAAGAACTTCACCACCGCCcctGCCATCTGCCACgatGGCA
AGGCCCACTTCcctagaGAGGGCGTGTTCGTGtctAACGGCACCC
ACTGGTTCGTGACCCAGagaAACTTCTACGAGcctCAGATCATCA
CCACCgatAACACCTTCGTGtctGGCAACTGCgatGTGGTGATCG
GCATCGTGAACAACACCGTGTACgatcctCTGCAGcctGAGCTGg
attctTTCAAGGAGGAGCTGgatAAGTACTTCAAGAACCACACCt
ctcctgatGTGgatCTGGGCgatATCtctGGCATCAACGCCtctG
```

-continued

```
TGGTGAACATCCAGAAGGAGATCgatagaCTGAACGAGGTGGCCA
AGAACCTGAACGAGtctCTGATCgatCTGCAGGAGCTGGGCAAGT
ACGAGCAGTACATCAAGTGGcctTGGTACATCTGGCTGGGCTTCA
TCGCCGGCCTGATCGCCATCGTGATGGTGACCATCATGCTGTGCT
GCATGACCtctTGCTGCtctTGCCTGAAGGGCTGCTGCtctTGCG
GCtctTGCTGCAAGTTCgatGAGgatgattctGAGcctGTGCTGA
AGGGCGTGAAGCTGCACTACACCTAA
```

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A ribonucleic acid (RNA) encoding a spike(S) protein or an immunogenic fragment thereof of a severe acute respiratory syndrome coronavirus 2 (SARS-CoV-2), wherein the S protein or immunogenic fragment thereof comprises the polypeptide of SEQ ID NO: 55.

2. The RNA of claim 1, further comprising a 3' UTR.

3. The RNA of claim 2, wherein the 3'UTR comprises any one of SEQ ID NOs: 18, 22, or 24.

4. The RNA of claim 1, further comprising a 5' UTR.

5. The RNA of claim 4, wherein the 5' UTR comprises SEQ ID NO: 20 or 26.

6. The RNA of claim 1, further comprising a poly A tail.

7. The RNA of claim 6, wherein the polyA tail comprises any one of SEQ ID NOs: 53, 54, or 30.

8. The RNA of claim 1, wherein the RNA is chemically modified and optionally comprises one or more of: an N1-methyl-pseudouridine residue or a pseudouridine residue.

9. The RNA of claim 8, wherein at least about 50%, or at least about 70%, or about 100% of the uridine residues in the RNA are N1-methyl pseudouridine or pseudouridine.

10. A polynucleotide encoding the RNA of claim 1, or a polynucleotide complementary thereto, optionally wherein the polynucleotide is selected from the group of: a deoxyribonucleic acid (DNA), an RNA, a hybrid of DNA and RNA.

11. A polynucleotide encoding a spike(S) protein or an immunogenic fragment thereof of a severe acute respiratory syndrome coronavirus 2 (SARS-CoV-2) comprising at least one non-naturally occurring amino acid mutation, wherein the polynucleotide comprises a polynucleotide sequence of SEQ ID NO: 56.

12. A vector comprising the polynucleotide of claim 10.

13. A method of producing the RNA of claim 1, comprising introducing the RNA into a cell, and optionally culturing the cell under conditions suitable for expressing the RNA.

14. A method of producing an RNA encoding an S protein or an immunogenic fragment thereof comprising the polypeptide of SEQ ID NO: 55, comprising contacting the polynucleotide of claim 10 with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA, and optionally further comprising isolating the RNA.

15. A composition comprising the RNA of claim 1, and a pharmaceutically acceptable carrier, and optionally wherein the pharmaceutically acceptable carrier comprises a lipid, a lipid nanoparticle, or a polymeric nanoparticle that comprises a Histidine-Lysine co-polymer (HKP), and further optionally wherein the HKP comprises a side chain selected from SEQ ID NOs: 34-47.

16. The composition of claim 15, wherein the HKP comprises a side chain selected from SEQ ID NOs: 34-47.

17. A method of producing a composition, comprising contacting the RNA of claim 1 with an HKP, thereby the RNA and the HKP are self-assembled into nanoparticles.

18. A method of producing a composition, comprising contacting the RNA of claim 1 with a lipid, thereby the RNA and the lipid are self-assembled into lipid nanoparticles (LNPs).

19. A method of one or more of:

(a) preventing a subject from having a symptomatic SARS-COV-2 infection, (b) inducing an immune response to SARS-COV-2 in a subject in need thereof, (c) reducing the binding of a SARS-COV-2 or an S protein thereof with angiotensin converting enzyme 2 (ACE2) in a subject in need thereof, or (d) reducing a SARS-COV-2 viral load in a subject in need thereof, comprising administering to the subject a composition comprising the RNA of claim 1 and pharmaceutically acceptable carrier that is a lipid nanoparticle.

20. The method of claim 19, further comprising treating the subject with an additional therapeutic agent, optionally wherein the additional therapeutic agent comprises one or more of:

an anti-viral agent, optionally remdesivir, lopinavir, ritonavir, ivermectin, tamiflu, or favipiravir;

an anti-inflammatory agent, optionally dexamethasone, tocilizumab, kevzara, colcrys, hydroxychloroquine, chloroquine, or a kinase inhibitor;

a covalescent plasma from a subject recovered from a SARS-COV-2 infection;

an antibody binding to SARS-COV-2, optionally bamlanivimab, etesevimab, casirivimab, or imdevimab; or an antibiotic agent, optionally azithromycin.

21. The RNA of claim 2, further comprising a 5' UTR and a poly A tail.

22. The RNA of claim 21, wherein the RNA is chemically modified and optionally comprises one or more of: an N1-methyl-pseudouridine residue or a pseudouridine residue.

23. The RNA of claim 22, wherein at least about 50%, or at least about 70%, or about 100% of the uridine residues in the RNA are N1-methyl pseudouridine or pseudouridine.

24. A polynucleotide encoding the RNA of claim 21, or a polynucleotide complementary thereto, optionally wherein the polynucleotide is selected from the group of: a deoxyribonucleic acid (DNA), an RNA, a hybrid of DNA and RNA.

25. The polynucleotide of claim 11, further comprising a 3' UTR.

26. The polynucleotide of claim 25, further comprising a 5' UTR.

27. The polynucleotide of claim 26, further comprising a polyA tail.

28. A method of producing an RNA encoding an S protein or an immunogenic fragment thereof comprising the polypeptide of SEQ ID NO: 55, comprising contacting the polynucleotide of claim 27 with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA, and optionally further comprising isolating the RNA.

29. A composition comprising the RNA of claim 22, and a pharmaceutically acceptable carrier, and optionally wherein the pharmaceutically acceptable carrier comprises a lipid, a lipid nanoparticle, or a polymeric nanoparticle that comprises a Histidine-Lysine co-polymer (HKP), and further optionally wherein the HKP comprises a side chain selected from SEQ ID NOs: 34-47.

30. A method of one or more of:

(a) preventing a subject from having a symptomatic SARS-COV-2 infection, (b) inducing an immune response to SARS-COV-2 in a subject in need thereof, (c) reducing the binding of a SARS-COV-2 or an S protein thereof with angiotensin converting enzyme 2 (ACE2) in a subject in need thereof, or (d) reducing a SARS-COV-2 viral load in a subject in need thereof, comprising administering to the subject a composition comprising the RNA of claim 22 and pharmaceutically acceptable carrier that is a lipid nanoparticle.

* * * * *